United States Patent [19]

Ranney

[11] Patent Number: 6,106,866
[45] Date of Patent: Aug. 22, 2000

[54] IN VIVO AGENTS COMPRISING CATIONIC DRUGS, PEPTIDES AND METAL CHELATORS WITH ACIDIC SACCHARIDES AND GLYCOSAMINOGLYCANS, GIVING IMPROVED SITE-SELECTIVE LOCALIZATION, UPTAKE MECHANISM, SENSITIVITY AND KINETIC-SPATIAL PROFILES, INCLUDING TUMOR SITES

[75] Inventor: David F. Ranney, Dallas, Tex.

[73] Assignee: Access Pharmaceuticals, Inc., Dallas, Tex.

[21] Appl. No.: 08/509,338

[22] Filed: Jul. 31, 1995

[51] Int. Cl.[7] .................................................. A61K 31/726
[52] U.S. Cl. .......................... 424/499; 424/489; 424/491; 424/493; 424/548; 514/54; 514/62; 530/322; 536/54
[58] Field of Search ............................. 530/322; 424/548, 424/489, 491, 493, 499; 536/54; 514/54, 62

[56] References Cited

U.S. PATENT DOCUMENTS

| | | | |
|---|---|---|---|
| 3,158,552 | 11/1964 | Gaeumann et al. | 195/80 |
| 3,957,435 | 5/1976 | Adams et al. | 23/230 B |
| 3,961,038 | 6/1976 | Benes | 424/1 |
| 4,024,073 | 5/1977 | Shimizu et al. | 252/316 |
| 4,115,534 | 9/1978 | Ithakissios | 424/1 |
| 4,182,330 | 1/1980 | Michaels | 128/260 |
| 4,239,754 | 12/1980 | Sache et al. | 424/183 |
| 4,385,046 | 5/1983 | Milbrath et al. | 424/1 |
| 4,397,867 | 8/1983 | Blake | 424/320 |
| 4,419,365 | 12/1983 | McLachlin | 424/320 |
| 4,425,319 | 1/1984 | Yokoyama et al. | 424/1.1 |
| 4,427,808 | 1/1984 | Stol et al. | 524/24 |
| 4,432,802 | 2/1984 | Harata et al. | 106/163 |

(List continued on next page.)

FOREIGN PATENT DOCUMENTS

| | | |
|---|---|---|
| 1168150 | 5/1984 | Canada. |
| 0055028 | 6/1982 | European Pat. Off. . |
| 0 071 564 A1 | 7/1982 | European Pat. Off. . |
| 0087786 | 9/1983 | European Pat. Off. . |
| WO83/03426 | 10/1983 | European Pat. Off. . |
| WO84/00294 | 2/1984 | European Pat. Off. . |
| 0 124 766 A2 | 4/1984 | European Pat. Off. . |
| 0137356 | 4/1985 | European Pat. Off. . |
| WO85/05554 | 12/1985 | European Pat. Off. . |
| 0167825 | 1/1986 | European Pat. Off. . |
| 0240424 | 10/1987 | European Pat. Off. . |
| PCT/US88/01096 | 10/1988 | European Pat. Off. . |
| WO88/07365 | 10/1988 | European Pat. Off. . |
| 0326226 | 8/1989 | European Pat. Off. . |
| 0361960 | 4/1990 | European Pat. Off. . |
| 0 392 487 A2 | 10/1990 | European Pat. Off. . |
| 0565930 | 10/1993 | European Pat. Off. . |
| 63-225601 | 9/1988 | Japan . |
| 1268167 | 11/1986 | U.S.S.R. . |
| 1516348 | 7/1978 | United Kingdom . |
| 2041517 | 9/1980 | United Kingdom . |
| 2 137 612 | 10/1984 | United Kingdom . |
| 2185397 | 7/1987 | United Kingdom . |
| WO 87/02893 | 5/1987 | WIPO . |
| WO 92/07259 | 4/1992 | WIPO . |
| WO 92/17214 | 10/1992 | WIPO . |
| WO 93/05074 | 3/1993 | WIPO . |
| WO 93/05075 | 3/1993 | WIPO . |
| WO 94/05203 | 3/1994 | WIPO . |
| WO 94/17829 | 8/1994 | WIPO . |

OTHER PUBLICATIONS

Lyubina et al., Biosis 96:797 59, 1995.
Kalishevaskaya et al., Biosis 89: 450–490, 1989.
Thorpe, Caplus ABS #1997:69602, Sep. 30, 1993.
Bernat et al. "Effect of Various Drugs on Adriamycin Enhanced Venous Thrombosis in the Rat:" Thromb. Res., V. 75 (1), pp. 91–97, 1994.
Shiro, "High Incidence of Atrial Thrombosis in Mile Given Doxorubilin" Caplus: 1997: 182656, 1993.
Ranney, "Drug Targeting to the Lungs" *Biochemical Pharmacology*, vol. 35, No. 7, pp. 1063–1069, (1986), published in Europe.
Lambe, et al., "Morphological stabilization of the glycocalyces of 23 strains of five Bacteroides species using specific antisera" *Can. J. Microbiol.*, vol. 30, pp. 809–819, (1984,) published in Canada.
Costerton, et al., "How Bacteria Stick" *Scientific American*, vol. 238:86, Jan. (1978,) published in U.S.A.
Epenetos et al., "Monoclonal antibodies for imaging and therapy" *Br. J. Cancer*, 59:152–155, (1989,) published in Europe.

(List continued on next page.)

*Primary Examiner*—Michael P. Woodward
*Attorney, Agent, or Firm*—Arnold, White & Durkee

[57] ABSTRACT

A drug carrier composition comprising a drug complexed with dermatan sulfate is disclosed. The drug is preferably an anti tumor drug and may be taxol, a peptide onco-agent or vincristine. The most preferred antitumor drug is doxorubicin. The dermatan sulfate is essentially purified dermatan sulfate with a sulfur content of up to 9% (w/w) and with selective oligosaccharide oversulfation. The compositions are administered in a fashion that allows efficient vascular access and induces the following in vivo effects: 1) rapid, partial or total endothelial envelopment of the drug (diagnostic) carrier; 2) sequestration of the carrier and protection of the entrapped agent from blood vascular clearance at an early time (2 minutes) when the endothelial pocket which envelops the carrier still invaginates into the vascular compartment; 3) acceleration of the carrier's transport across and/or through the vascular endothelium or subendothelial structures into the tissue compartment (interstitium); and 4) improvement of the efficiency with which the drug migrates across the endothelium, or epi-endothelial or subendothelial barriers, such that a lower total drug dose is required to obtain the desired effect relative to that required for standard agents. Analogous tissue uptake is described for transepithelial migration into the lungs, bladder and bowel.

23 Claims, 72 Drawing Sheets

U.S. PATENT DOCUMENTS

| | | | |
|---|---|---|---|
| 4,446,126 | 5/1984 | Jordan | 424/183 |
| 4,489,065 | 12/1984 | Walton et al. | 424/180 |
| 4,568,536 | 2/1986 | Kronenthal et al. | 424/22 |
| 4,613,616 | 9/1986 | Winston et al. | 514/507 |
| 4,619,913 | 10/1986 | Luck et al. | 514/2 |
| 4,624,846 | 11/1986 | Goldenberg | 424/1.1 |
| 4,647,447 | 3/1987 | Gries et al. | 424/9 |
| 4,671,958 | 6/1987 | Rodwell et al. | 424/85 |
| 4,673,754 | 6/1987 | Smith et al. | 556/137 |
| 4,683,142 | 7/1987 | Zimmerman et al. | 427/2 |
| 4,689,323 | 8/1987 | Mitra et al. | 514/56 |
| 4,703,108 | 10/1987 | Silver et al. | 530/356 |
| 4,710,493 | 12/1987 | Landsberger | 514/56 |
| 4,738,955 | 4/1988 | Landsberger | 514/56 |
| 4,745,180 | 5/1988 | Moreland et al. | 530/351 |
| 4,783,447 | 11/1988 | Del Bono et al. | 514/56 |
| 4,863,964 | 9/1989 | Hedlund et al. | 514/575 |
| 4,880,634 | 11/1989 | Speiser | 424/450 |
| 4,904,479 | 2/1990 | Illum | 424/490 |
| 4,925,678 | 5/1990 | Ranney | 424/493 |
| 4,957,939 | 9/1990 | Gries et al. | 514/492 |
| 4,963,344 | 10/1990 | Gries et al. | 424/9 |
| 4,973,580 | 11/1990 | Mascellani et al. | 514/54 |
| 5,021,236 | 6/1991 | Gries et al. | 424/9 |
| 5,021,404 | 6/1991 | Folkman et al. | 514/26 |
| 5,023,078 | 6/1991 | Halluin | 424/94.64 |
| 5,039,529 | 8/1991 | Bergendal et al. | 424/630 |
| 5,108,759 | 4/1992 | Ranney | 424/493 |
| 5,116,963 | 5/1992 | Del Bono et al. | 536/21 |
| 5,155,215 | 10/1992 | Ranney | 534/16 |
| 5,213,788 | 5/1993 | Ranney | 424/9 |
| 5,260,050 | 11/1993 | Ranney | 424/9 |
| 5,288,704 | 2/1994 | Ungheri et al. | 514/12 |
| 5,308,617 | 5/1994 | Halluin | 424/94.64 |
| 5,336,762 | 8/1994 | Ranney . | |
| 5,427,767 | 6/1995 | Kresse et al. | 424/9.32 |
| 5,474,765 | 12/1995 | Thorpe | 424/178.17 |
| 5,547,944 | 8/1996 | Mascellani et al. | 514/54 |

OTHER PUBLICATIONS

Mayberry–Carson et al., "Bacterial Adherence and Glycocalyx Formation in Osteomyelitis Experimentally Induced with *Staphylococcus aureus*", *Infection and Immunity*, 43:825–833, Mar., (1984), published in U.S.A.

Jain, "Delivery of Novel Therapeutic Agents in Tumors: Physiological Barriers and Strategies" *Journal of the National Cancer Institute*, 81:570–576, (1989), published in U.S.A.

Henneberry et al., "Immunocytochemical Localization of VP16–213 In Normal and Malignant Tissues" *Cancer Letters*, 37, (1987), pp. 225–233, published in Ireland.

Henneberry et al., Light Microscope Visualization of Tissue and Tumour Distributions of Anti–Cancer Drugs Using Immunocytochemistry. Abstract #1931, *Seventy–Ninth annual meeting of the American Association for Cancer Research May 25–28, 1988 Proceedings, Proceedings of AACR*, vol. 29, (Mar. 1988,) p. 486, published in U.S.A.

Dvorak et al., "Identification and Characterization of the Blood Vessels of Solid Tumors That Are Leaky to Circulating Macromolecules" *American Journal of Pathology*, vol. 133, No. 1, (Oct. 1988,) published in U.S.A.

Weinstein et al., "Selected Issues in the Pharmacology of Monoclonal Antibodies" *Site–Specific Drug Delivery*, (1986): pp. 81–91, published in U.S.A.

Mahadoo et al., "Vascular Sequestration of Heparin" *Thrombosis Research*, vol. 12, pp. 79–90, (1977,) published Europe.

Engel et al., "Intestinal Absorption of Heparin Facilitated by Sulfated or Sulfonated Surfactants" *Journal of Pharmaceutical Sciences*, vol. 58, No. 6, (Jun. 1969), pp. 706–710, published in U.S.A.

Smirnov et al., "Carrier–directed targeting of liposomes and erythrocytes to denuded areas of vessel wall" *Proc. Natl. Acad. Sci. USA*, vol. 83, pp. 6603–6607, Sep. 1986, published in U.S.A.

Ghitescu et al., "Specific Binding Sites for Albumin Restricted to Plasmalemmal Vesicles of Continuous Capillary Endothelium: Receptor–mediated Transcytosis" *The Journal of Cell Biology*, vol. 102, Apr. 1986, pp. 1304–1311, published in U.S.A.

Laurie et al., "Localization of Binding Sites for Laminin, Heparan Sulfate Proteoglycan and Fibronectin on Basement Membrane (Type IV) Collagen" *J. Mol. Biol.*, 1986:189, pp. 205–216, published in Europe.

Williams et al., "Micropinocytic ingestion of glycosylated albumin by isolated microvessels: Possible role in pathogenesis of diabetic microangiopathy" *Proc. Natl. Acad. Sci, USA*, vol. 78, No. 4, pp. 2393–2397, Apr. 1981, published in U.S.A.

Glimelius et al., "Binding of Heparin on the Surface of Cultured Human Endothelial Cells" *Thrombosis Research*, 1978, vol. 12, No., 5, pp. 773–782, published in Europe.

Jaques, "Drug Prophylaxis in Atherosclerosis" *Artery*, 14(4):209–215, 1987, place of publication is uncertain, possibly Canada.

Parsons et al., "Antibacterial Activity of Bladder Surface Mucin Duplicated in the Rabbit Bladder by Exogenous Glycosaminoglycan (Sodium Pentosanpolysulfate)" *Infection and Immunity*, vol. 27, No.3., Mar. 1980, p. 876–881, published in U.S.A.

Ryan et al., "New Substrates for the Radioassay of Angiotensin Converting Enzyme of Endothelial Cells in Culture" *Tissue & Cell*, 1978 10(3) :555–562, published in Europe.

Fransson, "Self–Association of Bovine Lung Heparan Sulphates Identification and Characterization of Contact Zones" *Eur. J. Biochem.* 120, 251–255, 1981, published in Europe.

Jaques et al., "Intrapulmonary Heparin A New Procedure for Anticoagulant Therapy" *The Lancet*, Nov. 27, 1976, pp. 1157–1161, published in Europe.

Wick et al., "In Vivo Localization and Pathological Effects of Passively Transferred Antibodies to Type IV Collagen and Laminin in Mice" *Clinical Immunology and Immunopathology*, 23:656–665, 1982, published in U.S.A.

Lopes et al., "Presence of Laminin Receptors in *Staphylococcus aureus*" *Science*, vol. 229, Jul. 1985, pp. 275–277, published in U.S.A.

Holthofer et al., "*Ulex europaeus* I Lectin as a Marker for Vascular Endothelium in Human Tissues" *Laboratory Investigation*, vol. 47, No. 1, pp. 60–65, 1982, published in U.S.A.

Loesberg et al., "The Effect of Calcium on the Secretion of Factor VIII–Related Antigen by Cultured Human Endothelial Cells," *Biochimica et Biophysica Acta*, 763:160–167, 1983, published in Europe.

Widder et al., "Magnetically Responsive Microspheres as a Carrier for Site–Specific Delivery of Adriamycin," *Proc. Am. Assn. Cancer. Res.*, 19:17, 1978, published in USA.

Libby et al., "Inducible Interleukin–1 Gene Expression in Adult Human Vascular Endothelial Cells," *Proc. Fed. Am. Soc. for Exp. Biol.*, 45:1074, 1986, published in USA.

Rofsky, et al., "Selective Tumor Enhancement of a Transplanted Mammary Carcinoma in Rat Livers: First Evaluation of Fe–Dermatan Sulfate, a New MR Contrast Agent," *Access Pharmaceuticals, Inc.*, Oct. 1993.

Dawson, et al., "Progress Toward the Synthesis of Polymerically Bound Chelating Agents for Iron (III) and the Development of a New Assay Method for Determining Iron Chelator Effectiveness," 201–209, 1981.

Duewell, et al., "Nonionic Polyethylene Glycol–Ferrioxamine as a Renal Magnetic Resonance Contrast Agent," *Investigative Radiology*, 26:50–57, 1991.

Ramirez and Andrade, "A Novel Iron–Cleaning Graft Copolymer", *J. Macromol. Sci.–Chem.*, A7:1035–1045, 1973.

Ramirez and Andrade, "Polymer–Drug Grafts for Iron Chelation," *Macromol. Sci.—Chem.*, A10(1&2): 309–365, 1976.

Dol et al., "Pharmacokinetics of Dermatan Sulfate in the Rabbit After Intravenous Injection," *Database Chemabs*, Chemical Abstracts Service, Columbus, Ohio, AN=109:31788 & Thromb. Haemostasis, 59(2):255–258, 1988.

Hallaway et al., "Modulation of Deferoxamine Toxicity and Clearance by Covalent Attachment to Biocompatible Polymers," *Proc. Natl. Acad. Sci. USA*, 86:10108–10112, 1989.

Kresse and Buddecke, "Chemistry of the Arterial Wall. XV. Metabolic Heterogeneity of Carbon–14 and Sulfur–35 Labeled Glycosaminoglycans (Acidic Mucopolysaccharides) when Incubated in Vitro," *Database Chemabs*, Chemical Abstracts Service, Columbus, Ohio, AN=72:97979 & Hoppe–Seyler's Z. Physiol. Chem., 351(2):151–156, 1970.

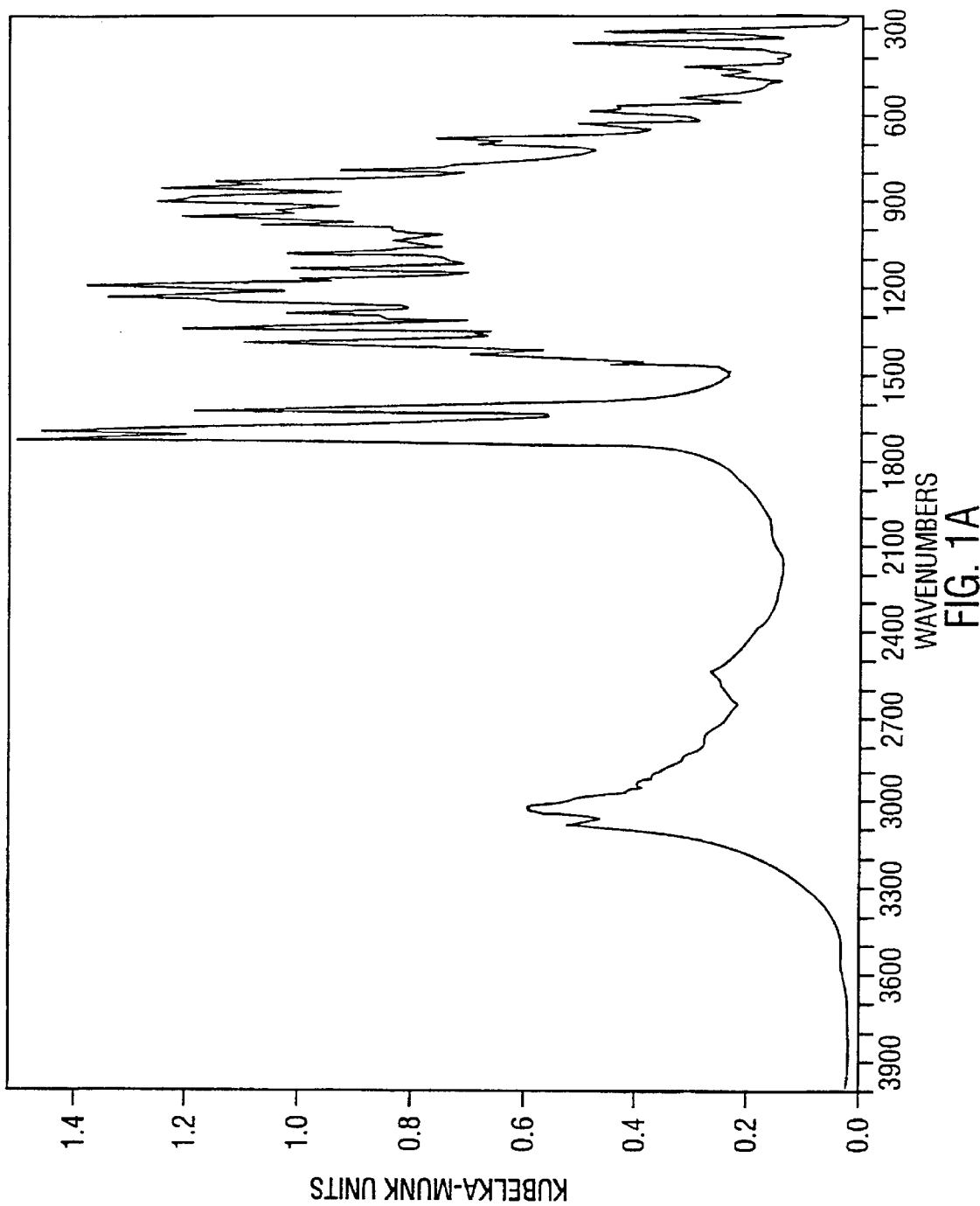

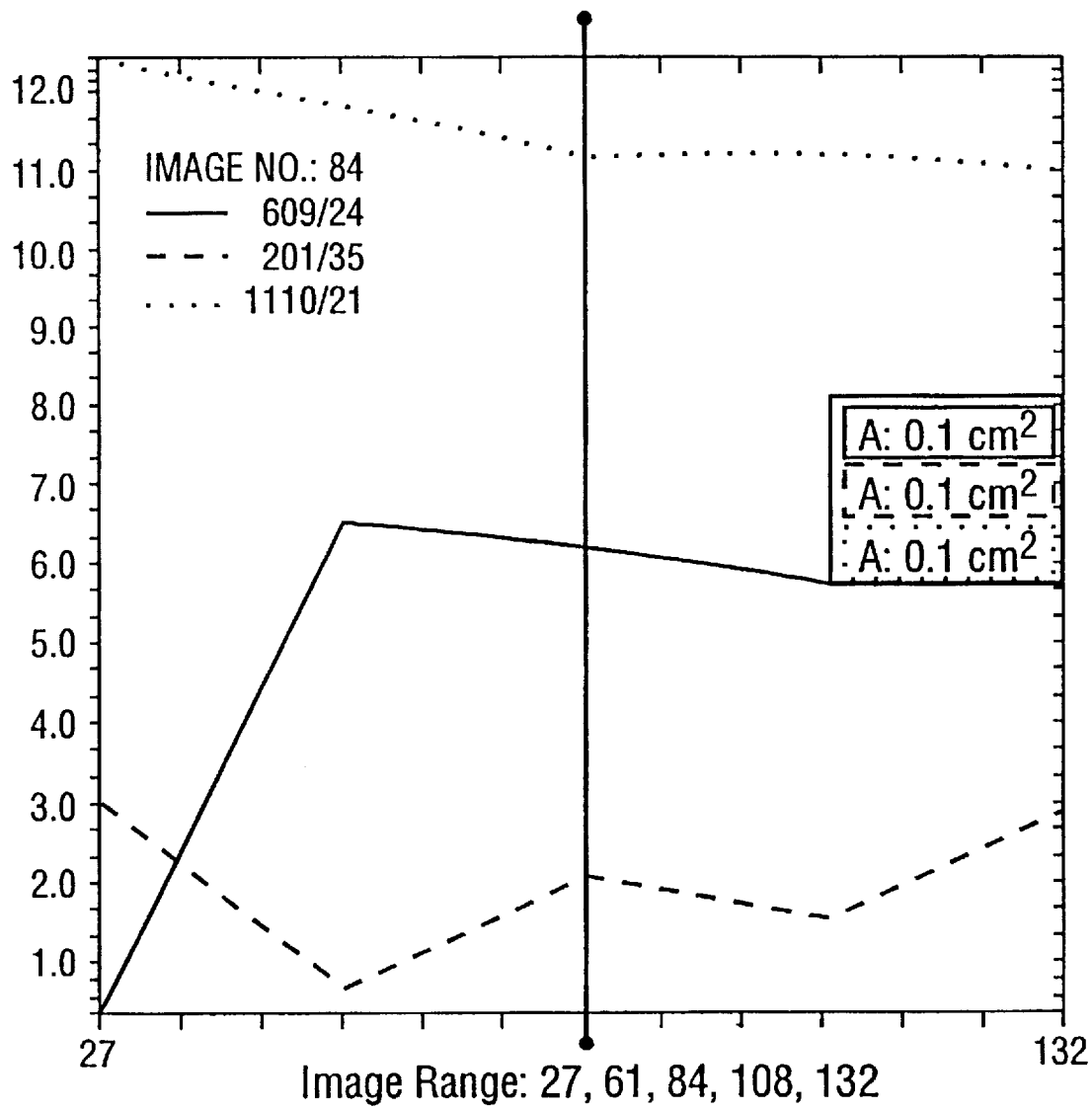

```
SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = N-formyl-met"

(xi) SEQUENCE DESCRIPTION: SEQ ID NO:1:

Xaa Leu Phe Lys
1

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Arg Pro Pro Gly Phe Ser Pro Phe Arg
1               5
```

IN VIVO AGENTS COMPRISING CATIONIC DRUGS, PEPTIDES AND METAL CHELATORS WITH ACIDIC SACCHARIDES AND GLYCOSAMINOGLYCANS, GIVING IMPROVED SITE-SELECTIVE LOCALIZATION, UPTAKE MECHANISM, SENSITIVITY AND KINETIC-SPATIAL PROFILES, INCLUDING TUMOR SITES

BACKGROUND OF THE INVENTION

Until recently the localization of intravascular drugs in body tissues has depended on chemical partitioning across microvascular barriers into the tissue compartments of multiple body organs. This resulted in only 0.01% to 0.001% of the injected dose actually reaching the intended targets. Approximately 20 years ago, drugs were entrapped in liposomes and microspheres. This modified the initial biodistributions and redirected them to phagocytes in the reticuloendothelial organs: liver, spleen and bone marrow.

In 1978, the present inventor and coworkers (Widder, et al., *Proc. Am. Assn. Cancer Res.*, V. 19, p 17 (1978)) developed a means to co-entrap drug plus magnetite in microspheres which could be injected intravenously and localized magnetically in the tissue compartments of non-reticuloendothelial target organs (e.g., lung and brain). Magnetic capture was accomplished by selective dragging of the particles through the vascular endothelium into normal tissues and tissue tumors positioned adjacent to an extracorporeal magnet of sufficient strength (0.5 to 0.8 Tesla) and gradient (0.1 Tesla/mm). Although this technique was highly efficient and deposited between 25% and 50% of an injected dose in the desired target tissue, it was also a very complicated approach which had the following major disadvantages: 1) restriction of use to specialized medical centers; 2) permanent disposition of magnetite in target tissue; 3) focal overdosing of drug due to inhomogeneity of the capturing magnetic field; and 4) application to a very limited number of therapeutic agents. In the process of studying magnetic targeting, however, it was learned that slow (controlled) release of toxic drugs from entrapment-type carriers (microspheres) protected the normal cells within the local tissue environment from drug toxicity and still gave effective treatment of tumor cells and microorganisms.

When monoclonal antibodies became generally available for animal and clinical research, it was hoped that antibody-drug conjugates would limit the biodistribution of toxic agents and cause them to become deposited in foci of disease (tumors and infections) which were located across the microvascular barrier within target tissues. Unfortunately, most monoclonal antibodies were (and are still) obtained from mice, making them immunologically foreign to human recipients. Conjugation of drugs at therapeutically relevant substitution ratios makes the monoclonal antibody derivatives even more foreign and impairs their binding specificities. Hence, antibody-drug conjugates are cleared substantially by the liver, as are liposomes. Importantly, their localization in most solid tumors is even further impaired by the presence of a partially intact microvascular barrier which separates the tumor tissue (interstitium) from the bloodstream. This allows only about 1% to 7% (at best) of the injected dose to reach nonreticuloendothelial targets. Selected lymphomas and leukemias provide exceptions to this rule because of a greater natural breakdown of this vascular barrier. However, for the vast majority of solid tumors and infections, a general-purpose method is still needed to deliver drugs efficiently across microvascular barriers in a depot (controlled release) form.

Such a form of drugs is necessary in order to protect the normal vascular endothelium, organs and tissue cells from the toxic effects of drugs, protect the drug from endothelial and tissue metabolism during transit and make the drug bioavailable at a controlled therapeutic rate selectively within the target tissues and tissue lesions, including solid tumors.

Active endothelial transport has been demonstrated for small molecules (e.g., glucose and insulin), however, no studies other those that of the present inventor have shown such transport for larger molecules or molecules carried in a cargo format. Present examples show that transendothelial migration of macromolecular conjugates and noncovalent paired-ion formulations of drugs and diagnostic agents with sulfated glycosaminoglycan, having a combined size of between about 8,000 daltons and about 500 nanometers, are accelerated by the inclusion of sulfated glycosaminoglycans, and in particular, dermatan sulfates, which bind multiply to receptors or antigens which are either synthesized by disease-induced endothelium or are synthesized at other sites, but become selectively bound to the induced endothelial receptors at sites of disease. (Ranney, *Biochem. Pharmacology*, V. 35, No. 7, pp. 1063–1069 (1986)).

The present invention describes improved novel compositions, carriers, agents and methods of in vivo use which give improved selectivity, efficacy, uptake mechanism and kinetic-spatial profiles at sites of disease. It further describes compositions, agents and methods of use for improved selectivity, sensitivity, uptake mechanism and kinetic-spatial profiles of in vivo selective drug localization, accumulation and action at sites of disease, including but not limited to solid tumors. Novel compositions are prepared by (a) unique non-covalent chemical binding, further enhanced by (b) physical stabilization. Other compositions are prepared by covalent chemical binding. Binding is of cationic or chemically basic metal chelators to carriers comprising anionic or chemically acidic saccharides, sulfatoids and glycosaminoglycans, typically and advantageously of a hydrophilic or essentially completely hydrophilic nature. Binding of the active and carrier may also be by a combination of non-covalent, physical, and covalent means. Non-covalent binding can be carried out by means including but not limited to admixing cationic or basic drugs and metal chelates at appropriate ratios with anionic or acidic saccharide carriers, thereby forming strong solution-state and dry-state paired-ion complexes and salts, respectively, based principally on electrostatic binding of cationic (basic) group or groups of the metal chelator to anionic (acidic) group or groups of the acidic carrier. Such binding may be further stabilized by hydrogen bonds and physical factors, including but not limited to concentration, viscosity, and various means of drying, including lyophilization.

Carrier substances useful in this invention may include, but are not limited to natural and synthetic, native and modified, anionic or acidic saccharides, disaccharides, oligosaccharides, polysaccharides and glycosaminoglycans (GAGs) and in particular, dermatan sulfates. It will be apparent to those skilled in the art that a wide variety of additional biologically compatible, water-soluble and water dispersable, anionic carrier substances can also be used. Due to an absence of water-diffusion barriers, favorable initial biodistribution and multivalent site-binding properties, oligomeric and polymeric, hydrophilic and substantially completely hydrophilic carrier substances are included among the preferred carriers for agents to be used for treating tumors, cardiovascular infarcts and other types of local disease. However, it will be apparent to those skilled in the art that amphoteric and hydrophobic carriers may be favored for certain therapeutic applications. Drugs and metal chelators most useful in this invention include those which contain cationic, basic and basic-amine groups for binding to the carrier, and which are effective to treat local disease conditions either directly or indirectly, including by chelation of metals and metal ions, transition elements and ions, and lanthanide series elements and ions. It will be apparent to those skilled in the art that essentially any single atomic element or ion amenable to chelation by a cationic, basic and amine-containing chelator, may also be useful in this invention.

For purposes of this invention, a cationic or basic metal chelator is defined and further distinguished from a metal-ion complex as follows: a cationic or basic metal chelator comprises an organic, covalent, bridge-ligand molecule, capable of partly or entirely surrounding a single metal atom or ion, wherein the resulting formation constant of chelator for appropriate metal or ion is at least about $10^{14}$. A chelator is further defined as cationic or basic if it or its functional group or groups which confer the cationic or basic property, and which include but are not limited to an amine or amines, is (are) completely or essentially completely electrophilic, positively charged or protonated at a typical pH employed for formulation. A formulation pH is characteristically selected to closely bracket the range of physiologic pH present in mammalian vertebrates. This typically includes, but is not limited to a pH in the range of pH 5 to 8. Amines may include primary, secondary, tertiary or quaternary amines or combinations thereof on the metal chelator. Herein, and as specified, a hydrophilic carrier is defined as a substance which is water soluble, partitions into the water phase of aqueous-organic solvent mixtures, or forms a translucent aqueous solution, complex, aggregate, or particulate dispersion under the conditions employed for formulation. A carrier is further defined as being anionic or acidic if it is completely or nearly completely nucleophilic, or if its functional group or groups are capable of interacting with cationic, basic or amine metal chelators, is (are) completely or nearly completely negatively charged, anionic or ionized at the pH employed for formulation. Such anionic and acidic groups include, but are not limited to sulfates, phosphates and carboxylates, or combinations thereof on the carrier.

Novel agent compositions include, but are not limited to the classes of cationic or basic, typically basic-amine metal chelator actives, or metal chelator actives including the chelated metal or metal ion, wherein these actives are further bound to anionic and acidic carriers comprising natural or synthetic carriers, including but not limited to hydrophilic anionic or acidic, natural or synthetic, native, modified, derivatized and fragmented, anionic or acidic saccharides, oligosaccharides, polysaccharides, sulfatoids, and glycosaminoglycans (GAGs).

Anionic and acidic saccharide and glycosaminoglycan carriers may contain monomeric units comprising glucose, glucuronic acid, iduronic acid, glucosamine, galactose, galactosamine, xylose, mannose, fucose, sialic acid, pentose, and other naturally occurring, semi-synthetic or synthetic monosaccharides or chemical derivatives thereof, comprising amine, sulfate, carboxylate, sialyl, phosphate, hydroxyl or other side groups. Glycosaminoglycans (GAGs) comprise essentially the carbohydrate portions of cell-surface and tissue matrix proteoglycans. They are derived from naturally occurring proteoglycans by chemical separation and extraction; and in certain instances, by enzymatic means [Lindahl et al. (1978), incorporated herein by reference]. They include, but are not limited to those of the following types: heparin, heparan sulfate, dermatan sulfate, chondroitin-4-sulfate, chondroitin-6-sulfate, keratan sulfate, syndecan, and hyaluronate, and over-sulfated, hyper-sulfated, and other chemical derivatives thereof, as described further below.

The strongly acidic, sulfated glycosaminoglycans include all of those classes listed just above, except for hyaluronate, which contains only the more weakly acidic carboxylate groups and not sulfate groups. Natural sources of glycosaminoglycans include, but are not limited to: pig and beef intestinal mucosa, lung, spleen, pancreas, and a variety of other solid and parenchymal organs and tissues.

Sulfatoids comprise a second class of sulfated saccharide substances which are derived principally but not exclusively from bacterial and non-mammalian sources. Sulfatoids are typically of shorter chain length and lower molecular weight than glycosaminoglycans, but may be synthetically modified to give (a) longer chain lengths, (b) increased sulfation per unit saccharide, (c) various other chemical side groups, or (d) other properties favorable to the desired ligand-binding property and site-selective binding, uptake and accumulation property (or properties) in vivo. Sucrose and other short-chain oligosaccharides may be obtained from natural and synthetic sources.

These oligosaccharides can be rendered anionic or acidic by chemical or enzymatic derivatization with carboxylate, phosphate, sulfate or silyl side groups, or combinations thereof, at substitution ratios of up to about eight anionic or acidic substituent groups per disaccharide unit. Modified glycosaminoglycans may be derived from any of the types and sources of native glycosaminoglycans described above, and include: (1) glycosaminoglycan fragments, further defined as glycosaminoglycans with chain lengths made shorter than the parental material as isolated directly from natural sources by standard ion-exchange separation and solvent fractionation methods; (2) glycosaminoglycans chemically modified to decrease their anticoagulant activities, thereby giving "non-anticoagulant" (NAC) GAGs, prepared typically but not exclusively by (a) periodate oxidation followed by borohydride reduction; (b) partial or complete desulfation; and (c) formation of non-covalent divalent or trivalent counterion salts, principally including but not limited to salts of the more highly acidic sulfate functional groups, with principally but not exclusively: calcium, magnesium, manganese, iron, gadolinium and aluminum ions.

For purposes of this invention, a special class of such solution complexes and salts includes those strong complexes and salts formed by electrostatic or paired-ion association between the acidic or sulfate groups of acidic saccharide or glycosaminoglycan carrier, and the basic or cationic group or groups of the metal chelator or metal chelator including metal, as described above. Derivatized acidic saccharides and glycosaminoglycans are typically prepared by derivatization of various chemical side groups to various sites on the saccharide units. This may be performed by chemical or enzymatic means.

Enzymatic means are used in certain instances where highly selective derivatization is desired. Resulting chemical and enzymatic derivatives include, but are not limited to acidic saccharides and glycosaminoglycans derivatized by: (1) esterification of (a) carboxylate groups, (b) hydroxyl groups, and (c) sulfate groups; (2) oversulfation by nonselective chemical or selective enzymatic means; (3) acetylation, and (4) formation of various other ligand derivatives, including but not limited to (a) addition of sialyl side groups, (b) addition of fucosyl side groups, and (c) treatment with various carbodiimide, anhydride and isothiocyanate linking groups, and (d) addition of various other ligands.

If and when present, sulfate and sialyl side groups may be present at any compatible position of saccharide monomer, and on any compatible position of glycosaminoglycan monomers [Lindahl et al. (1978), incorporated herein by reference]. Certain of the resulting derivatized acidic saccharides and glycosaminoglycans may have desired alterations of anticoagulant activities, site-localization patterns, clearance and other biological properties. As one example of this relationship between certain classes of glycosaminoglycans and biological properties, dermatan sulfates with a native sulfate/carboxylate ratio preferably in the range of from 0.7:1 to 1.8:1, more preferably between 0.9:1 and 1.5:1 and typically 1:1, are reported to have relatively low binding to normal endothelial cells, avoid displacement of endogenous heparan sulfate from endothelial-cell surfaces, have relatively high selectivity to induced endothelia at sites of disease, including thrombus, and have rapid plasma clearance, principally by the renal route; whereas heparins and oversulfated dermatan sulfates with higher sulfate/carboxylate ratios of between 2:1 and 3.7:1, are reported to have relatively higher binding for both normal and induced endothelia, to displace relatively more endogenous endothelial heparan sulfate, and to clear more slowly than dermatans [Boneu et al. (1992), incorporated herein by reference].

As newly described and used in the present invention, the dermatan sulfate class of glycosaminoglycans, and especially the new special class of dermatan sulfates which contain selectively oversulfated oligosaccharide sequences, have the further unique advantages of higher potency combined with very low toxicity as carrier substances of associated or bound actives (i.e., dermatan sulfate-actives, DS-actives). This is related to their (a) relatively low sulfate/carboxylate ratios which range between 0.7:1 and 1.8:1, most preferably lying between 0.9:1 and 1.5:1, and most typically being 1:1; (b) very low anticoagulant activities—related to very low factor Xa and USP heparin activity plus negligible binding to antithrombin III; (c) very low or absent platelet-aggregating, and hence thrombocytopenia-inducing properties—related to their relatively low $SO_3$—/COO- ratios in combination with a modal molecular weight of less than about 45,000 daltons and preferably less than about 25,000 daltons; (d) essentially complete absence of in vivo metabolism; and (e) very rapid blood and body clearance, all as further described below. These properties result in an extremely high in vivo safety profile with an absence of bleeding, metabolism and in vivo residua in normal tissues and organs. These properties and their resulting safety profiles clearly distinguish the dermatan sulfates from all other classes of glycosaminoglycans (GAGs) and other classes of acidic saccharides, oligosaccharides, polysaccharides and sulfatoid substances (taken together, comprising acidic and anionic saccharide substances), and they provide uniquely surprising and unexpected advantages for dermatan sulfates over these other classes of acidic and anionic saccharides. Most particularly, the dermatan sulfates show these surprising and unexpected advantages over other glycosaminoglycan polysulfates, with $SO_3$—/COO— ratios in the range of between 2:1 and 3.7:1 and sulfur contents of greater than or equal to 10% (weight basis—indicative of their much higher sulfate contents). Also, most particularly, the new special class of dermatan sulfates (as described at length below), which is enriched for selectively oversulfated oligosaccharide sequences without comprising oversulfated or polysulfated molecules overall throughout the entire chain length (the latter being characterized by $SO_3$—/COO— ratios greater than or equal to 2.0:1 and sulfur contents greater than or equal 10%), have the further surprising and unexpected advantage of more strongly binding to the selectively induced receptors of endothelium, tissue matrix and target-cells at sites of disease (including tumors) by means of the complementary, selectively oversulfated oligosaccharide sequences of these new special dermatan sulfates. Hence, these new special dermatan sulfates exhibit surprisingly and unexpectedly more potent site localization and site-targeting potencies than would otherwise be expected based on their moderately low overall $SO_3$—/COO— ratio and sulfation and on their related extremely low cellular and systemic toxicity properties and side-effect profiles.

In a special case unique to the present invention, derivatization of the acidic saccharide and glycosaminoglycan carriers may be accompanied by the basic metal chelator itself. Although the general classes of carriers described above are particularly suitable to the present invention, it will be apparent to those skilled in the art that a wide variety of additional native, derivatized and otherwise modified carriers and physical formulations thereof, may be particularly suitable for various applications of this invention. As one representative example, the source and type of glycosaminoglycans, its chain length and sulfate/carboxylate ratio can be optimized to (1) provide optimal formulation characteristics in combination with different small and macromolecular diagnostic agents and drugs; (2) modulate carrier localization on diseased versus normal endothelium; (3) minimize dose-related side effects; (4) optimize clearance rates and routes of the carrier and bound diagnostic and therapeutic actives.

Non-covalent formulations of active and carrier afford markedly higher active-to-carrier ratios than those possible for covalent chemical conjugates. In the present invention, non-covalent binding affords a minimum of 15% active to total agent by weight [active/(active+carrier), w/w]; typically greater than about 30% (w/w); preferably at least about 50% (w/w); and frequently between about 70–99% (w/w). Covalent binding characteristically limits the percent active to (a) less than about 12% for non-protein small and polymeric carriers, (b) less than about 7% for peptide and protein carriers, including antibodies, and (c) less than about 0.5–2.0% for antibody fragments. This limitation is based on the number of functional groups available on carrier molecules which are useful in agent formulation and in vivo site localization.

It will be apparent to those skilled in the art that covalent active-carrier agent compositions of low substitution ratio may be useful for certain in vivo applications of typically narrow range, and that non-covalent active-carrier agent compositions of high substitution ratio may be useful for other in vivo applications of typically broader range. Generally, but not exclusively, non-covalent agents may be particularly useful for the majority of diagnostic imaging applications and for most therapeutic applications, wherein high total-body and site-localized doses are needed, and rapid clearance of the non-localized fraction of administered agent is desired in order to accelerate plasma clearance and to achieve low background levels for purposes of maximizing image contrast and minimizing systemic drug toxicity.

These properties of the present formulations represent additional substantial improvements over prior, non-selective and covalently conjugated active-carrier agents. The resulting agents are broadly useful for: (a) site-selective drug localization, including tumors, infections and cardiovascular disease with an acute endothelial induction; (b) MRI contrast and spectral enhancement, Ultrasound contrast enhancement, and X-Ray contrast enhancement, where relatively high administered doses may be favored or required; (c) Nuclear Medical or Radionuclide imaging and therapy, where enhanced clearance of the non-targeted dose may be favored or required: and (d) certain high-dose, extended-release or sustained-effect therapy may be favored or required. Such therapeutic agents include but are not limited to those useful at a broad variety of organ sites and medical indications, for the treatment of: (a) acute vascular ischemia, acute infarct, acute vascular damage, shock, hypotension, restenosis, tumors and tumor angiogenesis and parenchymal-cell or other pathological proliferations; and (b) the following classes of disease: vascular, parenchymal, mesenchymal, endothelial, smooth muscle, striated muscle, adventitial, immune, inflammatory, bacterial, fungal, viral, degenerative, neoplastic, genetic and enzymatic.

MRI contrast enhancement and drug therapy are important indications for which high payload and controlled release of active agents are important unique advantages in addition to site selective localization (see below).

For purposes of this invention, potentially therapeutic metal ions generally useful for trans chelation at sites of disease may include divalent and trivalent cations selected from the group consisting of: iron, manganese, chromium, copper, aluminum, nickel, gallium, indium, gadolinium, erbium, europium, dysprosium and holmium. Chelated metal ions generally useful for radionuclide imaging and compositions and uses, and in radiotherapeutic compositions and uses, may include metals selected from the group consisting of: phosphorous, sulfur, gallium, iodine, germanium, cobalt, calcium, rubidium, yttrium, technetium, ruthenium, rhenium, indium, tin, iridium, platinum, thallium, strontium and samarium. Metal ions useful in neutron-capture radiation therapy may include boron and others with large nuclear cross sections. Metal ions useful in Ultrasound contrast and X-Ray contrast compositions and uses may, provided they achieve adequate site concentrations, include any of the metal ions listed above, and in particular, may include metal ions of atomic number at least equal to that of iron.

For purposes of this invention, agents for therapeutic composition and uses in chelating internal body iron, copper or both, in order to make these metals unavailable locally (1) which are typically required for neovascularization, or (2) which cause and amplify local tissue injury [Levine (1993), incorporated herein by reference], include the carrier with basic metal chelator in one or both of the following forms: (a) carrier plus chelator without metal ion; and (b) carrier plus chelator with metal ion added and chelated in the composition at a formation constant lower or equal to that of the internal body metal which is to be chelated by metal ion exchange into the respective basic metal chelator of the composition (see below). Such weakly chelated metal ions of the composition may include one selected from the group consisting of: calcium, manganese, magnesium, chromium, copper, zinc, nickel, iron, gallium, indium, aluminum, cobalt, gadolinium or other exchangeable ion. Metal ions useful for inclusion in compositions for other therapeutic uses may include the divalent and trivalent cations selected from the group consisting of magnesium, manganese, chromium, zinc and calcium, iron, copper and aluminum. It will be obvious to those skilled in the art that various ones of the preceding metal ions can be used in combination with basic metal chelators, for alternative indications than those specified above, and that metal ions other than those listed above may, under certain conditions, be useful in the uses and indications listed above.

The compositions described in this invention give surprising and unexpected improvements of performance and use which include:

(1) retained high association of active plus carrier during in vitro dialysis and in vivo targeting;
(2) selective binding of the active plus carrier to induced endothelia at sites of disease;
(3) following intravenous administration, very rapid (2–7 min) localization at the diseased site, due to rapid selective endothelial binding, envelopment and extravasation of the carrier plus metal chelator across disease-induced endothelia (including histologically non-porous endothelia);
(4) widespread uptake throughout the diseased tissue site;
(5) sustained retention (multiple hours to days) within the diseased site in combination with
(6) rapid plasma clearance (minutes) of the non-targeted fraction;
(7) moderately slower, polymeric backdiffusion rates into the plasma, affording prolonged disease-site retention;
(8) capacity to selectively treat and image solid tumors or acute vascular and myocardial infarcts at body sites, as well as at brain and central nervous system sites, with substantially improved selectivity and sensitivity, including small tumor metastases, in liver, lung and other organ sites.

Diagnostic and drug enhancement can be made to occur by a number of mechanisms, the principal ones being:
1. Effective TARGETING to tissue sites of disease;
2. STABILIZATION during both storage and plasma transit;
3. Prolonged RETENTION at the site of disease, giving a markedly increased area under the curve at the tissue site;
4. RAPID CLEARANCE of the non-TARGETED fraction, thereby reducing background signal in imaging applications and reducing normal organ exposure and systemic toxicity in therapeutic applications.

Five further significant advantages of the present compositions and uses are:

1. Simple formulations of active and carrier;
2. Stabilization of diagnostic and therapeutic actives on the shelf and during plasma transit;
3. Rapid site localization and sustained site retention;
4. Rapid clearance of the non-targeted fraction;
5. Availability of low toxicity carbohydrate and glycosaminoglycan carriers from natural sources and, where needed, modification or derivatization by straightforward synthetic means.

Acidic or anionic saccharides and glycosaminoglycans have unique mechanisms of site localization and retention in vivo. They bind to the body's endothelial determinants which are selectively induced on the microvascular barrier by underlying tissue disease. Previous approaches to site targeting were directed at antigenic determinants. However, because these determinants are typically located in sequestered sites within the tissues, in other words at sites across the endothelial barrier and not within the bloodstream and not on its endothelial surface, carriers and agents injected into the bloodstream had no effective means to recognize and localize in the region of these target antigens. Stated another way, previous approaches ignored the major problem of inappropriate carrier distribution which resulted from its failure to recognize the vascular access codes required for efficient extravasation at disease sites. Hence, these carriers failed to effectively load the relevant tissue sites with effective concentrations of their bound actives.

Acidic or anionic saccharides, including glycosaminoglycans, dermatan sulfates and the new special dermatan sulfates, localize at target sites by binding first to complementary receptors on disease-site vascular endothelium, induce very rapid (ca. 3-minute) extravasation of the carrier and associated active agent, and then widely permeate throughout the underlying tissue matrix, forming a depot reservoir of the carrier-agent selectively at the site of disease (including tumors—even at sites up to several hundred micrometers distant from the typically irregularly spaced and perfused microvessels within the tumor matrix), and thirdly, bind to complementary receptors on the final target cells (including tumor cells), leading to induced tumor-cell internalization of GAG-actives (including DS-actives) (see Examples below). The new special class of dermatan sulfates (described just above and more extensively below) appears to perform this complementary binding function via their selectively enriched oversulfated saccharide sequences, which correlate with an enriched heparin cofactor II activity of at least about 220 U/mg, and which appear to bind the positively charged, cationic and/or structurally complementary receptors or lectins that are selectively induced on disease-site endothelium, tissue matrix and target cells (including in tumors). For the new dermatan sulfates, these binding and targeting functions and potencies occur without either the overall high sulfation/polysulfation or the incumbent toxicity and safety disadvantages thereof (as otherwise described herein).

The biological address of a disease site can be viewed in a fashion similar to that of a postal address, wherein effective carrier substances must (1) first recognize the "state" address of the signal endothelium induced by proximal tissue disease; (2) next extravasate and load the "city" address of the extracellular tissue matrix with locally effective doses of the diagnostic and therapeutic actives; and (3) finally bind and load the "street" address of the target cells and antigens. Previous approaches to site delivery have attempted to recognize the "street" address without first recognizing the "state" and "city" addresses.

The reason that acidic saccharide and sulfated glycosaminoglycan systems work substantially better than previous antigen-recognition approaches, is that they recognize the newly induced signals which the body uses to attract and target white blood cells into sites of tissue disease. When disease strikes at a local site, it initiates a cascade of local mediators within the tissue matrix and at the endothelial-blood interface which signal the blood cells and central body systems that inflammatory and immune cells are required within the tissue site. These mediators include cytokines, chemoattractants, cytotoxins, induced cell-surface adhesins, selectins and integrins, and various tissue-derived and blood-borne, soluble and cell-surface procoagulants. White cell accumulation begins within minutes and continues over days to weeks, depending on the nature, severity and persistence of local disease and the continued generation of tissue mediators and trans-endothelial signals.

As has now been reported and reviewed in detail [Ranney (1990); Ranney (1992); Bevilaqua et al. (1993); Bevilaqua et al. (1993); Travis (1993); Sharon et al. (1993), all incorporated herein by reference], tumors, infarcts, infections, inflammatory diseases, vascular disorders, and other focal diseases, characteristically induce the release of such host mediators, or cytokines, from resident macrophages and local tissue matrices. In certain diseases, alien mediators such as bacterial lipopolysaccharides (LPS), viral RNA, and tumor-derived inducers, including EMAP II, and chemoattractants may also be released. Although additional mediators remain to be elucidated, the principal ones have now been defined and include: interleukin 1 (IL-1), tumor necrosis factor (TNF), vascular endothelial growth factor/vascular permeability factor (VEGF/VPF), transforming growth factor beta (TGF-beta), Lipopolysaccharide (LPS), single and double stranded nucleotides, various interferons, monocyte chemoattractant protein (MCP), interleukin 8 (IL-8), interleukin 3 (IL-3), interleukin 6 (IL-6), tumor-derived inducers and chemoattractant peptides (as above), various prostaglandins and thromboxanes. Certain ones of the preceding mediators induce the local generation and release of metalloproteinases, and these in turn, expose latent tissue binding sites, including intact and partially cleaved integrins, RDGS peptides, laminin, collagen, fibronectin, and cell-surface core-protein components of glycosaminoglycans.

Cytokines, including VEGF/VPF and monocyte chemoattractant protein (MCP); and tissue metalloproteinases and proteolytic tissue matrix fragments, directly induce the local endothelium to become adhesive for circulating white blood cells, including neutrophils, monocytes and lymphocytes. The induced endothelial adhesive molecules (adhesins) include: P-selectin (gmp-140), E-selectin (ELAM-1), intercellular cell adhesion molecule (ICAM-1), vascular cell adhesion molecule (VCAM-1), inducible cell adhesion molecule, (INCAM-110), von Willebrand's factor (vWF, Factor VIII antigen) (see below for disease states which activate these respective types of endothelial adhesins). Additional cascades become activated which indirectly amplify endothelial adhesiveness. These include (1) coagulation factors, especially fibronectin, tissue factor, thrombin, fibrinogen, fibrin, and their split products, especially fibronectin split products and fibrinopeptide A; (2) platelet-derived factors: platelet activating factor (PAF), glycoprotein IIb/IIIa complex; (3) white-cell (a) L-selectin, and (b) integrins, including VLA-4 (very late antigen 4); and (4) numerous complement factors.

The preceding pathologic processes and signals are involved, directly or indirectly as follows, in the binding and site localization of acidic carriers, including acidic saccharides (AC) and glycosaminoglycans (GAGs) (Note that in the following outline, potential tissue binding sites are designated as "GAGs" and "ACs").

1. Local tissue diseases induce local cytokines and mediators, as described above. In particular, it is reported recently that the cytokine, vascular endothelial growth factor/vascular permeability factor (VEGF/VPF), is selectively induced by many or most tumors of human and animal origin [Senger et al. (1994), incorporated by reference herein] and is a 34–42 kDa heparin-binding and GAG-binding glycoprotein that acts directly on endothelial cells by way of specific endothelial receptors [Jakeman et al. (1993), incorporated by reference herein], to cause endothelial activation and induce additional new endothelial receptors which can bind GAGs (see below). VEGF/VPF is a chemically basic growth factor which is quite highly selective for endothelial cells versus fibroblasts and other cell types [Senger et al. (1994); Nicosia et al. (1994), incorporated by reference herein]. It appears to be a key growth factor for stimulating the long-term endothelial angiogenesis in many or most human and animal tumors, and in AIDS-associated Kaposi's sarcoma [Connolly et al. (1989); Weindel et al. (1992), both incorporated by reference herein]. In certain instances, VEGF/VPF may also be important for the more transient and anatomically restricted angiogenic processes of wound healing and vascular restenosis [Senger et al. (1994); Miller et al. (1994); Nicosia et al. (1994); Berse et al. (1992), all incorporated by reference herein]. VEGF/VPF and platelet-derived growth factor, PDGF-BB, are reported recently to be the only species of the group of basic, GAG-binding growth factors which have significant angiogenic potency in vitro, i.e., ones which are directly active in the absence of in vivo cofactors [Nicosia et al. (1994), incorporated by reference herein]. The effects of VEGF/VPF are inhibited by antibodies directed against certain peptides on the external surface of the molecule [Sioussat et al. (1993), incorporated by reference herein], and importantly, such inhibition suppresses the growth of animal tumors in vivo [Kim et al. (1993), incorporated by reference herein]. Hence, VEGF/VPF both provides and induces receptor targets for binding of GAG carrier substances in tumors and potentially in other pathologic lesions.

2. These cytokines and mediators induce tissue chemoattractants, including VEGF/VPF, MCP (Yamashiro et al., 1994) and IL-8, which comprise a family of arginine-rich, 8Kd, heparin-binding proteins reported to bind GAGs/ACs [Huber et al. (1991), incorporated by reference herein];
3. The cytokines and mediators of No. 1, above, induce the local endothelium to express P-selectin, the vascular cell adhesion molecule (VCAM-1), inducible cell adhesion molecule (INCAM-110), and von Willebrand's factor (vWF, Factor VIII antigen), which are reported binding determinants for GAGs/ACs [Bevilaqua et al. (1993); Bevilacqua et al.(1993)]; P-selectin is reported to bind GAGs [Bevilacqua et al.(1993)];
4. Integrins, including but not limited to VLA-4, are induced on circulating white blood cells, including lymphocytes, during various disease processes (see below); VLA-4 has a distinct binding site on the (induced) endothelial selectin, VCAM-1 (see No. 3, above); fibronectin, which is abundantly present in plasma and also available from tissue sites, has a distinct and separate binding site on VLA-4 [Elices et al. (1990)]; since fibronectin has specific binding sites for GAGs/ACs [Bevilaqua et al. (1993)], these amplification steps provide a strong additional mechanism for site localization of GAGs/ACs;
5. The chemoattractants, MCP and IL-8, lymphocyte integrin, VLA-4, platelet factor, PAF, and coagulation factors, thrombin, fibronectin and others, diffuse from local tissue and blood, respectively, bind to the induced endothelial selections, and amplify adhesiveness and activation at the initial endothelial P-selectin sites for GAGs/ACs [Elices et al. (1990); Lorant et al. (1993)];
6. Tissue metalloproteinases become activated and expose new binding sites for GAGs/ACs in the tissues which underlie the activated endothelia. These new tissue binding sites include as follows [Ranney (1990); Ranney (1992); Travis (1993); Bevilaqua et al. (1993)]:
   a. fibronectin fragments;
   b. collagen fragments;
   c. laminin fragments;
   d. RGDS peptides;
   e. Exposed core proteins of GAGs;
7. White blood cells are attracted to the site, become activated and release additional proteolytic enzymes, thereby amplifying No. 6 and increasing the exposure of binding sites for GAGs/ACs in the tissue matrix.
8. GAG/AC carriers selectively bind the induced and exposed determinants listed in Nos. 1–7, above, giving immune-type localization which is specific for induced binding sites (lectins) at the lectin-carbohydrate level characteristic of white-cell adhesion;
9. In cases where the carrier substance has multivalent binding to the target binding substance, including for example, cases in which the carrier is an acidic oligosaccharide or polysaccharide or an acidic glycosaminoglycan, multivalent binding of the endothelial surface induces rapid extravasation of the carrier and bound active, and results in substantially increased loading of the underlying tissue matrix, relative to that achieved by antibodies, liposomes, and monovalent binding substances, such as hormones and monovalent-binding sugars;
10. Adhesion of GAGs/ACs to induced and exposed tissue binding sites, reduces plasma backdiffusion of GAGs/ACs and their bound actives, thereby giving sustained retention within the tissue site;
11. Controlled release of the diagnostic or drug activity from carriers comprising GAGs/ACs occurs gradually within the diseased site, thereby resulting in targeted controlled release;
12. Tumor cells, microbial targets and damaged cellular targets within the tissue site, may selectively take up the GAG/AC plus bound diagnostic or drug active, based respectively, on: induced tumor anion transport pathways, microbial binding sites for GAGs/ACs, and proteolytically exposed cell-surface core proteins [Ranney Ser. Nos. 07/880,660, 07/803,595 and 07/642, 033]—Fe uptake by hepatomas, $Cr_4S$ uptake by prostatic adenocarcinomas; [Kjellen et al. (1977)]
13. In cases where the carriers are hydrophilic or essentially completely hydrophilic, these carriers cause their bound actives to migrate (permeate) deeply into and throughout the tumor mass even at microanatomic sites distant from the tumor's typically irregularly spaced microvessels; and also to migrate out (permeate) into a small rim of normal tissue around each focus of disease, typically comprising a rim about 30–75 um thick; however, such carriers and/or their associated active substances (diagnostics or therapeutics) undergo selective uptake (internalization) by abnormal cells within tissue site and preferentially avoid uptake by normal cells within the site, thereby giving:
    a. In cases of diagnostic imaging applications: very sharp definition of the boundary between tumors or infarcts and the surrounding normal tissues;
    b. In cases of therapeutic applications:
       (1) protection against spread of disease at the rim;
       (2) relative protection of normal cells within and adjacent to the site of disease, from uptake of cytotoxic drugs.
14. In the case of hydrophilic carriers, including but not limited to GAGs/ACs, the non-targeted fraction of active is cleared rapidly and non-toxically, thereby minimizing:

a. in imaging uses, background signal intensity;
b. in all uses:
  (1) normal organ exposure; and
  (2) systemic side effects.

Regarding the above outline, the tumor-selective GAG-binding cytokines, VEGF/VPF and MCP, are now known to be present in all three of the following microanatomic locations: tumor-cell surface, tumor extracellular matrix, and local tumor neovascular endothelium. Hence, these cytokines provide receptor targets for GAG-agents at all three of the key tumor sites: tumor endothelium, tumor extracellular matrix, and tumor cells proper. The presence of these cytokines selectively on tumor endothelium, allows for site-selective binding of intravascularly administered GAG-agents to tumor microvessels and very rapid (ca. 3-minute) selective extravasation of GAG-agents across the VEGF/VPF-"permeabilized" endothelium. Note: such "permeabilization" is recently shown to actually (a) comprise rapid transport by vesicular endosomes which are markedly enlarged (over the standard 120 nm Palade vesicles characterizing normal endothelium) and markedly increased in number (over normal vascular endothelium) [Senger et al. (1993), incorporated by reference herein]; and (b) comprise anatomically non-porous vascular endothelium, as assessed by macromolecular and particulate markers of true microfiltration porosity. The presence of VEGF/VPF and MCP cytokines on tumor cell surfaces may account for selective tumor-cell internalization of GAG-agents, as shown in certain of the Examples below. Importantly, the presence of these cytokines plus the GAG-binding peptides of No. 6 (above) in the large extracellular volumes of the tumor matrix, accounts in part, for the large tumor-tissue reservoirs of GAG-associated agents (including metal chelates) which are observed by MRI contrast enhancement (see Examples below). The relatively slow (ca. 7-hour) backdiffusion of such agents into the bloodstream, further corroborates the presence of such extracellular tissue-matrix receptors. Importantly, the combination of: (1) prolonged tumor retention of Gag-agents as an extracellular reservoir (depot); (b) tumor-cell internalization of a portion of this extracellular agent; and (c) very rapid blood and body clearance of the non-targeted portion, provides the following surprising and unexpected advantages for in vivo imaging (including MRI contrast enhancement) and therapy: (a) enhanced tumor selectivity; (b) prolonged, high "areas under the curve" (AUC's) in tumor; (c) short, low AUC's in blood; (d) minimization of local and systemic toxicities. Additionally, involving the above outline, the following (A) cytokines and mediators; and (B) selectins, integrins and adhesins are reported to be induced by various disease states in addition to that reported for tumors, above [Bevilaqua et al. (1993)]. Representative non-oncologic induction also occurs as follows.

A. Cytokines and mediators.
  1. MCP: Experimental autoimmune encephalomyelitis in mice [Ransohoff et al. (1993)];
  2. IL-8: Neovascularization: [Strieter et al. (1992)];
  3. PAF: Reperfused ischemic heart [Montrucchio et al. (1993)].

B. Selectins, Integrins and Adhesins.
  1. ELAM-1:
    a. Liver portal tract endothelia in acute and chronic inflammation and allograft rejection [Steinhoff et al. (1993)];
    b. Active inflammatory processes, including acute appendicitis [Rice et al. (1992)].
  2. VCAM-1:
    a. Simian AIDS encephalitis [Sasseville et al. (1992)].
    b. Liver and pancreas allograft rejection [Bacchi et al. (1993)].
  3. INCAM-110: Chronic inflammatory diseases, including sarcoidosis [Rice et al. (1991)].
  4. Integrin, beta 1 subunit cell adhesion receptor: inflammatory joint synovium [Nikkari et al. (1993)].

It is apparent from the above, that broad categories and many specific types of focal tissue disease may be addressed by the carriers and actives of the present invention, both for diagnostic and therapeutic uses, including tumors, cardiovascular disease, inflammatory disease, bacterial and viral (AIDS) infections, central nervous system degenerative disorders, and allograft rejection. It will also be obvious to those skilled in the art, that numerous additional disease states may be selectively addressed by the carriers disclosed in this invention.

The site selectivity of glycosaminoglycans (GAGs) appears to mimic an immune mechanism at the level of white-cell targeting rather than antibody targeting. Because antibodies have extremely high specificities, they characteristically miss major subregions of disease foci (typically as great as 60% of tumor cells are nonbinding). Recently, one of the GAG-binding determinants of endothelial P-selectin has been identified as sialyl Lewis x. Others are in the process of identification. Notably, the available nonvalent oligosaccharides specific for sialyl Lewis x suffer from two critical problems:

1. They are exceedingly expensive materials, available only by synthetic or semi-synthetic means, and hence, are not cost effective;
  2. They do not bind effectively at diseased sites under in vivo conditions, apparently due to the inability as monomeric binding substances to displace endogenous interfering substances which are pre-bound at these sites.

There are two apparent benefits of the relatively broader range of GAG specificities and redundancy of GAG binding sites present on diseased endothelium, tissue matrix and cells:

1. GAGs allow a broader range of tumors and diseases to be targeted than that possible with antibodies (which typically target only a subset of histologic types—even within a given class of tumor, and hence, are typically ineffective from both a medical and cost/development standpoint);
  2. GAGs are projected to be effective over a greater time interval, from early onset of disease to progression and regression.

Despite the broader targeting specificity of GAGs over antibodies, their favorable clearance and avoidance of uptake by normal cells reduce systemic and local toxicities, even though more than one type of disease site may undergo targeted accumulation of the diagnostic/drug within its extracellular matrix.

The polymeric and multivalent binding properties of GAGs both are very important for optimal site localization of the attached diagnostic/drug. GAG molecular weights of generally ca. 8,000 to 45,000 MW, preferably 10,000 to 23,000 MW and more preferably 13,000 to 19,000 MW, are important in order to:

1. Restrict initial biodistribution of the diagnostic/drug to the plasma compartment and thereby maximize the quantity of agent available for site targeting;
  2. Displace endogenous interfering substances which are pre-bound to diseased endothelium;

3. Induce active endothelial translocation of the GAG-diagnostic/drug into the underlying tissue matrix;

4. Afford rapid clearance and markedly reduced side effects of the attached actives.

SUMMARY OF THE INVENTION

In all of the following descriptions, the paramagnetic metal-ion chelates and images obtained therewith, are intended to be demonstrative of agent localizations in sites of disease, including in tumor sites, and to be generally reflective of the disease-site levels, distributions and residence times, as well as of the blood and organ clearance patterns and kinetics, all of which may be useful in interpreting the targeting, localization, accumulation, cellular internalization, and blood and body clearance of therapeutic agents, including agents useful in treating tumors, infection, cardiovascular diseases and other local sites of disease, as described herein.

In certain embodiments, the invention comprises compositions and methods for delivering, localizing and retaining therapeutic actives selectively to sites of local disease, while clearing the non-targeted dose effectively, rapidly and/or non-toxically from the body, so as to minimize local and systemic toxicities and side effects. These therapeutic actives and methods of treatments may be for any type and location of local disease site, provided it has a vascular or other access route, and that it has any form of induced vascular receptors, adhesins, or other signals capable of recognition by the carrier substances described herein. In particular, such actives for tumor treatment may include but are not limited to: doxorubicin, adriamycin, taxanes (i.e. paclitaxel, docetaxel, taxol, taxotere) vincristine, vinblastine, bleomycin, idarubicin, epirubicin, and also to amsacrine, azacitidine, dideoxyinosine, dihydro-5-azacytidine, ethanidazole, ethiofos, methotrexate, misonidazole, porfiromycin, pyrazoloacridinek, terephthalamidine, taxotere and other taxane derivatives, topotecan, trimetrexate, N-formyl-met-leu-phe-lys, arginine bradykinin, poly-L-lysine, other chemoattractants, biological response modifiers, cytokines, interferons, lymphokines and other agents useful in treating tumors or neoplastic disease, with any of the above used singly or in combination. Further, in particular, such actives and methods for treating infection may include but are not limited to: gentamicin, amikacin, tobramycin, and other amine, basic, basic peptide, basic polypeptidic, hydrophobic or amphoteric antibiotics or agents for treating bacterial, fungal, mycobacterial, viral or other microbial or microbiological diseases.

The present invention may be described in certain embodiments as a drug carrier composition comprising a drug in combination with essentially purified dermatan sulfate with a sulfur content of up to 9% (w/w) and with selective oligosaccharide oversulfation, wherein said composition has a non-embolizing size of less than about 500 nm. In certain embodiments the drug may be a chelator. In certain embodiments the composition may have a size of less than about 250 nm or even less than about 25 nm. The drug carrier composition may also be defined further wherein binding to disease induced endothelia causes the endothelia to totally or partially envelop bound drug carrier composition in less than 10 to 15 minutes, and wherein said essentially purified dermatan sulfate with sulfur content of up to 9% (w/w) and with selective oligosaccharide oversulfation, contains Ido-GalNAc4SO$_3$, and further comprises IdoA2SO$_3$-GalNAc4SO$_3$ and IdoAGalNAc4,6SO$_3$.

The drug carrier composition of the present invention may also be defined in certain embodiments as being a nanoparticle, and the drug may preferably be an oncotherapeutic drug. The oncotherapeutic drug is preferably selected from the group consisting of adriamycin, doxorubicin, epirubicin, daunorubicin, idarubicin or salts thereof, with doxorubicin being the most preferred. The oncotherapeutic drug may alternatively be selected from the group consisting of bleomycin, taxanes (i.e. paclitaxel, docetaxel, taxol, taxotere), vinblastine and vincristine, amsacrine, azacytidine, dideoxyinosine, dihydro-5-azacytidine, ethanidazole, ethiofos, methotrexate, misonizadole, porfiromycin, pyrazoloacridinek, terephthalamidine, taxotere, topotecan, trimetrexate and carboplatin or salts thereof.

A particular embodiment of the present invention is a drug carrier composition comprising a drug selected from the group consisting of doxorubicin, epirubicin, daunorubicin and idarubicin or salts thereof in combination with essentially purified dermatan sulfate or with essentially purified dermatan sulfate having a sulfur content of up to 9% (w/w) and with selective oligosaccharide oversulfation, wherein said composition has a non-embolizing size of less than about 500 nm, preferably less than 250 nm, most preferably less than 25 nm.

Embodiments of the present invention also include drug carrier compositions wherein the drug is an antiinfective (antiviral, antimicrobial, antifungal or antitubercular) drug, with gentamycin, tobramycin or amikacin being preferred, or the drug is a biological response modifier (modifying an endogenous biological response), a biologically active peptide or polypeptide, or in certain embodiments a white cell chemoattractant, bradykinin or poly-L-lysine. The white cell chemoattractant is preferably N-formyl-met-leu-phe-lys (SEQ ID NO:1).

The drug carrier compositions of the present invention may be further defined as being in a pharmaceutically acceptable solution suitable for intravascular or other parenteral injection, and may be formed by paired-ion charge interactions, amphoteric or hydrophobic interactions between the carrier and drug.

In certain embodiments, the present invention is a method of treating an animal for a tumor responsive to an oncotherapeutic drug, the method comprising the steps of preparing a drug carrier composition comprising an oncotherapeutic drug in combination with essentially purified dermatan sulfate having a sulfur content of up to 9% (w/w) and with selective oligosaccharide oversulfation, wherein said carrier has a non-embolizing size of 500 nm or less; containing said drug carrier composition in a pharmaceutically acceptable carrier; and administering the drug carrier composition in the pharmaceutically acceptable carrier to an animal. In the preferred drug carrier compostions and methods, it is understood that the drug is in a controlled release form and preferably wherein binding of a sample of said drug carrier composition to disease induced endothelia produces an induction of the endothelia to totally or partially envelop the bound sample in less than 10 to 15 minutes.

In embodiments involving treatment of various diseases, the drug carrier composition may be administered by selected arterial perfusion, to obtain high-efficiency uptake in proximal target organs, tissues or tissue lesions, or it may be administered intravenously to obtain semiselective, medium-efficiency uptake in tissue lesions located at widely distributed systemic sites.

The present invention is also a method of treating an animal for tumors responsive to an oncotherapeutic agent, the method comprising the steps of preparing a drug carrier composition comprising an oncotherapeutic drug in combination with essentially purified dermatan sulfate with a sulfur content of up to 9% (w/w) and with selective oligosaccharide oversulfation, wherein the drug carrier composition may be further defined as a nanoparticle or wherein said carrier has a non-embolizing size of 500 nm or less; containing said drug carrier composition in a pharmaceutically acceptable carrier; and administering the drug carrier composition in the pharmaceutically acceptable carrier to an animal; wherein said oncotherapeutic drug is selected from the group consisting of adriamycin, doxorubicin, epirubicin, daunorubicin, idarubicin, bleomycin, taxanes (paclitaxel, docetaxel, taxol, taxotere, vinblastine and vincristine or salts thereof.

Alternatively, the invention may be described as a method of treating an animal for tumors responsive to an oncotherapeutic agent, the method comprising the steps of preparing a drug carrier composition comprising an oncotherapeutic drug in combination with essentially purified dermatan sulfate with a sulfur content of up to 9% (w/w) and with selective oligosaccharide oversulfation, wherein said carrier has a non-embolizing size of 500 nm or less; containing said drug carrier composition in a pharmaceutically acceptable carrier; and administering the drug carrier composition in the pharmaceutically acceptable carrier to an animal; wherein said oncotherapeutic drug is selected from the group consisting of amsacrine, azacytidine, dideoxyinosine, dihydro-5-azacytidine, ethanidazole, ethiofos, methotrexate, misonizadole, porfiromycin, pyrazoloacridinek, terephthalamidine, topotecan, trimetrexate and carboplatin or salts thereof.

In certain of the methods of treatment of the present invention, the binding of a sample of said drug carrier composition to disease induced endothelia may produce an induction of the endothelia to totally or partially envelop the bound sample in less than 10 to 15 minutes, or the drug carrier composition is administered by selected arterial perfusion, to obtain high-efficiency uptake in proximal target organs, tissues or tissue lesions, or the drug carrier composition is intravenously administered to obtain semiselective, medium-efficiency uptake in tissue lesions located at widely distributed systemic sites.

In another embodiment, the invention is a method of treating vascular disease, comprising administering to a subject a therapeutically effective amount of an agent of the present invention, and preferably an agent which comprises a metal ion.

Administration of the composition of the present invention may involve any mode of administration resulting in contact of the therapeutic agent with the target tumor, disease site or site of infection. This may include intravenous, intraarterial, intracisternal, intraperitoneal, oral or other administration modes.

The compositions or formulations of the present invention may be prepared dissolved or dispersed in a pharmaceutically acceptable carrier or diluent or in any other pharmaceutically acceptable form. Such pharmaceutically acceptable formulations will generally comprise an effective amount of the compositions, such as doxorubicin:essentially purified dermatan sulfate in a pharmacological preparation.

The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may thus be formulated for parenteral administration, such as for intravenous, subcutaneous or intramuscular injection; for oral administration, where the compositions may be formulated into tablets, caplets, or other solids; and the compositions may also be formulated into time release capsules and any other form of pharmaceutical currently used, including cremes, lotions, mouthwashes, inhalents and the like, depending upon location of targeted sites.

The present invention encompasses novel agents comprising cationic or chemically basic, amphoteric or hydrophobic therapeutic agents, including peptides, polypeptides and proteins, and metal chelators and metal-ion chelates in association with hydrophilic carriers of anionic or chemically acidic saccharides, sulfatoids and glycosaminoglycans. In certain embodiments of the invention, the agents also comprise chelated metals and metal ions. The binding of the metal chelators to the carriers is stabilized by covalent or non-covalent chemical and physical means. In some embodiments, novel non-covalently bound compositions give uniquely high payloads and ratio of metal chelator to carrier, ranging from a low of about 15% metal chelator by weight, to a characteristic range of 70% to 90% metal chelator by weight. Specific embodiments comprise deferoxamine, ferrioxamine, iron-basic porphine, iron-triethylenetetramine, gadolinium DTPA-lysine, gadolinium N-methyl-1,3-propanediamine (N-MPD)-DTPA, gadolinium DOTA-lysine and gadolinium with basic derivatives of porphyrins, porphines, expanded porphyrins, Texaphyrins and sapphyrins as the basic or cationic metal chelators, which are in turn, bound to acidic or anionic carriers, including one or more of acidic or anionic saccharides, and including sulfated sucrose, pentosan polysulfate, dermatan sulfate, essentially purified dermatan sulfate with a sulfur content of up to 9% (w/w) and with selective oligosaccharide oversulfation, heparan sulfate, beef heparin, porcine heparin, non-anticoagulant heparins, and other native and modified acidic saccharides and glycosaminoglycans.

Methods of magnetic resonance image (MRI) contrast enhancement are a particular embodiment of the present invention which confirm very rapid, carrier-mediated, site-selective in vivo localization and sustained site retention of metal-chelator compositions, based on stable binding of the metal chelator and carrier during in vivo plasma transit, allowing site localization following intravenous administration. Rapid and selective endothelial-site binding, facilitated rapid extravasation into underlying tissue sites, site accumulation, sustained site retention, together with rapid clearance of the non-site-localized fraction are also demonstrated by the use of the compositions of the present invention in the selective MRI contrast enhancement of tumors and cardiovascular infarcts.

Surprising and unexpected improvements of selectivity, mechanism of localization and cellular uptake, and MRI contrast sensitivity are shown for metal chelates having standard paramagnetic potencies. Further advantages of the use of the compositions and methods of the present invention are delineated in the examples (infra) including special histologic staining evidence which confirms the site-selective endothelial binding, extravasation, tissue matrix accumulation and cellular uptake mechanism. Selective localization and MRI imaging efficacy are also shown to occur when paramagnetic metal chelator actives are administered in carrier-bound form but not in free form.

In certain embodiments, the present invention may be an agent comprising a chelator for metal ions, said chelator having a cationic group and being bound to an anionic, hydrophilic carrier. In alternate embodiments, the chelator for metal ions which has a cationic group is bound to an anionic, hydrophilic carrier by non-covalent electrostatic binding. And, in certain alternate embodiments the invention comprises an agent comprising a basic chelator for metal ions, said chelator having a cationic group and being covalently bound to an anionic, hydrophilic carrier. In certain embodiments of the invention in which the chelator is not covalently bound to the carrier for example, the said chelator may be basic.

The agent which comprises a chelator for metal ions and having a cationic group bound to an anionic hydrophilic carrier may further comprise a chelated metal ion, and in particular it may further comprise a paramagnetic metal ion. The agents of the present invention, in particular those which comprise the chelator for metal ions non-covalently bound to the carrier may be further defined as being at least about 15 weight percent chelator. Preferably, the chelator has a formation constant for paramagnetic metal ions of at least about $10^{14}$.

Those agents of the present invention which comprise a metal ion will preferably comprise a metal ion selected from the group consisting of iron, manganese, chromium, copper, nickel, gadolinium, erbium, europium, dysprosium and holmium. In certain embodiments, the agents of the present invention may even comprise a metal ion selected from the group consisting of boron, magnesium, aluminum, gallium, germanium, zinc, cobalt, calcium, rubidium, yttrium, technetium, ruthenium, rhenium, indium, iridium, platinum, thallium, samarium, tin and strontium. In certain embodiments, non-radioactive or radioactive phosphorous, sulfur or iodine may be bound directly to the carrier (below). It is understood that other metal ions which are functionally equivalent to the listed metal ions are also included and would fall within the scope and spirit of the presently claimed invention.

The agents may also comprise a carrier wherein said carrier is an acidic saccharide, oligosaccharide, polysaccharide or glycosaminoglycan. The carrier may also be an acidic glycosaminoglycan or sulfatoid. In particular, the carrier may be, but is not limited to heparin, desulfated heparin, glycine-conjugated heparin, heparan sulfate, dermatan sulfate, essentially purified dermatan sulfate with a sulfur content of up to 9% (w/w) and with selective oligosaccharide oversulfation, hyaluronic acid, pentosan polysulfate, dextran sulfate, sulfated cyclodextrin or sulfated sucrose.

The chelator may also be defined as a chelator of iron ions. Preferably the chelator is a hydroxamate, and more preferably it is deferoxamine. In certain preferred embodiments the chelator together with the metal ion is ferrichrome, ferrioxamine, enterobactin, ferrimycobactin or ferrichrysin. In a particularly preferred embodiment, the chelator is deferoxamine, the carrier is heparin, or a heparin fragment and the agent further comprises iron(III). In an alternate embodiment, the chelator is deferoxamine and the carrier is dermatan sulfate or a dermatan sulfate fragment and the agent may further comprise chelated iron(III).

The invention may also be defined as comprising deferoxamine bound to a carrier selected from the group consisting of heparin, heparan sulfate, dermatan sulfate, essentially purified dermatan sulfate with a sulfur content of up to 9% (w/w) and with selective oligosaccharide oversulfation or chondroitin sulfate, and may further comprise a metal ion. The agents of the present invention may also comprise a chelator which is a porphine, porphyrin, sapphyrin or texaphyrin and which may further comprise a metal ion, and preferably an iron ion or a gadolinium ion.

The agent of the present invention may comprise a chelator which is 5,10,15,20-Tetrakis(1-methyl-4-pyridyl)-21H,23-porphine, a carrier which is heparin and a chelated iron ion. In certain embodiments, the chelator may also be a polyaminocarboxylate or macrocyclic, and preferably a basic or amine derivative of diethylenetriaminetetraacetate, or more preferably a basic or amine derivative of 1,4,7,10-tetraazacyclododecane-N,N',N'',N'''-tetraacetate (DOTA). In the agents of the present invention, the carrier may also be defined further as being complementary to endothelial determinants selectively induced at disease sites.

The present invention may also be defined as an image-enhancing agent or spectral-enhancing agent to enhance images arising from induced magnetic resonance signals, the agent comprising ferrioxamine covalently conjugated to heparin by 1-ethyl-3-(3-dimethylaminopropyl) carbodiimide, N-ethoxycarbonyl-2-ethoxy-1,2-dihydroquinoline, or carbonyldiimidazole. Alternatively, the invention is a spectral-enhancing agent to enhance images arising from induced magnetic resonance signals, the agent comprising Gd(III)diethylenetriaminepentaacetate covalently conjugated to one of heparin, dermatan sulfate or essentially purified dermatan sulfate with a sulfur content of up to 9% (w/w) and with selective oligosaccharide oversulfation. In another alternative, the invention is an agent for in vivo imaging, the agent comprising a basic chelator for metal ions and chelated metal ion, said chelator being bound by non-covalent electrostatic binding to a hydrophilic carrier selected from the group consisting of heparin, desulfated heparin, glycine-conjugated heparin, heparan sulfate, dermatan sulfate, essentially purified dermatan sulfate with a sulfur content of up to 9% (w/w) and with selective oligosaccharide oversulfation, hyaluronic acid, pentosan polysulfate, dextran sulfate, sulfated cyclodextrin or sulfated sucrose. The agent for enhancing body imaging preferably comprises deferoxamine, chelated Fe(III) and a glycosaminoglycan carrier bound to said deferoxamine and more preferably the glycosaminoglycan carrier is dermatan sulfate, and/or the Fe(III) is a radiopharmaceutical metal ion, and most preferably the radiopharmaceutical metal ion is $^{59}$iron or $^{67}$gallium.

The invention may also comprise an agent for enhancing body imaging, the agent comprising diethylenetriaminepentaacetate-lysine or N-methyl-1,3-propanediamine DTPA, chelated Gd(III) and a glycosaminoglycan carrier bound to said diethylenetriaminepentaacetate-lysine. Alternatively, the invention is an agent for enhancing body imaging, the agent comprising DOTA-lysine, chelated Gd(III) and a glycosaminoglycan carrier bound to said 1,4,7,10-tetraazacyclododecane-N,N',N'',N'''-tetraacetate-lysine (DOTA-lysine). In a particular embodiment, the invention is an agent comprising ferrioxamine bound by non-covalent electrostatic binding to dermatan sulfate or essentially purified dermatan sulfate with a sulfur content of up to 9% (w/w) and with selective oligosaccharide oversulfation.

The invention may also comprise an agent for enhancing body imaging, including MRI imaging and spectral shift, the agent comprising gadolinium (III) chelated to N-methyl-1, 3-propanediamine-diethylenetriaminepentaacetate (N-MPD-DTPA), the N-MPD-DtPA being bound or in association most preferably by paired-ion or other non-covalent means or alternatively preferably bound by covalent means to a glycosaminoglycan, preferably dermatan sulfate, and most preferably the new special class of dermatan sulfate, and most preferably the new special class of dermatan sulfates containing selectively oversulfated oligosaccharide sequences.

It is understood that any of the agents of the present invention as described in the above paragraphs or in the appended claims may be defined further as being in a combination with at least one of a buffer, saccharide, sulfated saccharide, or salt, to produce an osmotic strength suitable for parenteral administration, and as being an aqueous solution or a lyophilized or dry preparation suitable for aqueous reconstitution having the desired osmotic strength, and wherein said agent is aseptic or sterile.

A certain aspect of the invention is a method of enhancing magnetic resonance images or spectra in vertebrate animals comprising administering to said animal an effective amount of an agent of the invention which comprises the metal ion chelator, the carrier as described and a paramagnetic ion. In particular, the invention is a method of enhancing in vivo images arising from induced magnetic resonance signals, comprising the steps of administering to a subject an effective amount of an agent of the present invention which comprises a paramagnetic ion, exposing the subject to a magnetic field and radiofrequency pulse and acquiring an induced magnetic resonance signal to obtain a contrast effect.

Alternatively, the invention may be described as a method of enhancing in vivo images, comprising the steps of administering to a subject an effective amount of an agent of the present invention which comprises a chelated metal ion, exposing the body to ultrasound or X-rays and measuring signal modulation to obtain a contrast effect.

Further, the invention may be a method of obtaining in vivo body images comprising administering to a subject an effective amount of an agent of the invention which comprises a metal ion wherein the metal ion is a radioisotope and measuring scintigraphic signals to obtain an image.

BRIEF DESCRIPTION OF THE DRAWINGS

The following drawings and figures are presented to illustrate preferred embodiments of the present invention and their uses in MRI contrast enhancement. These examples are purely illustrative, and do not in any way delimit the full scope of the present invention.

FIG. 1A is a control infrared spectrum of diethylenetriaminetetraacetate (DTPA) substrate (see Example 3).

For the following Figures (FIG. 2A–FIG. 13D), the dermatan sulfate carrier is of the new special class of dermatan sulfates with selectively oversulfated oligosaccharide sequences but without overall oversulfation ($SO_3$—/COO— ratio=1:1 and sulfur content=6.3 wt %; supplied by Opocrin S.P.A., Corlo Di Formigine, Italy, as "435 type").

FIG. 2A, FIG. 2B, FIG. 3A, FIG. 3B, FIG. 4A, FIG. 4B, FIG. 4C, FIG. 4D and FIG. 8A, FIG. 8B and FIG. 8C show T1-weighted MRI images (TR/TE=800/45, 550/23 and 600/45) performed at 1.0 and 1.5 Tesla, before (Pre) and after (Post) intravenous (i.v.) injection of Ferrioxamine:Dermatan Sulfate Selective Paramagnetic Contrast Agent, prepared as in Examples 2 and 5, and injected i.v. at a Ferrioxamine dose of 0.155 mmol/Kg into Fisher 344 female rats, with syngeneic breast adenocarcinoma inoculated previously into the liver, such that tumor diameters at the time of imaging are between 1.0 cm and 2.5 cm.

Figure 1B:
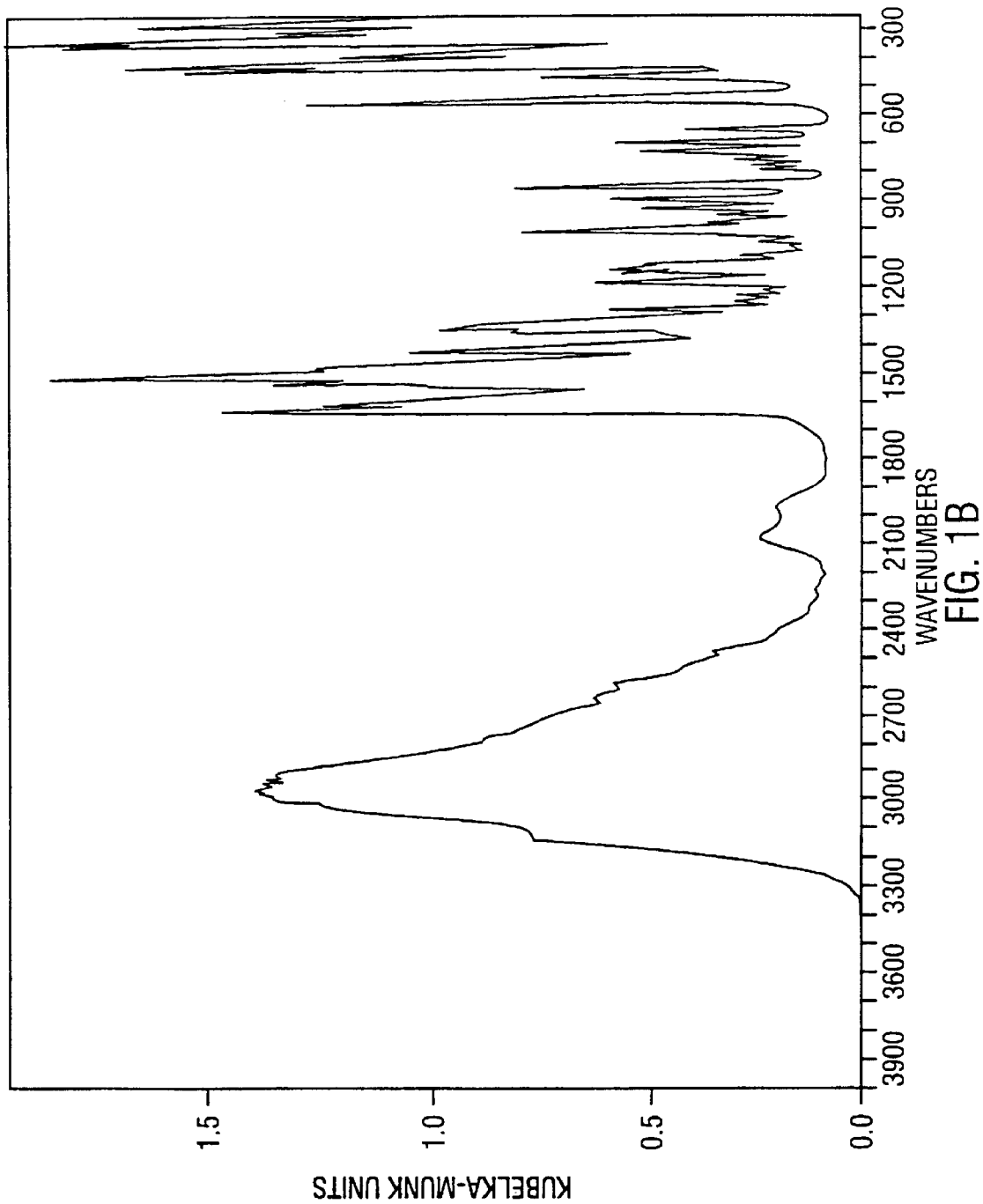
FIG. 1B is a control infrared spectrum of L-lysine.HCl substrate (see Example 3).
Figure 1C:
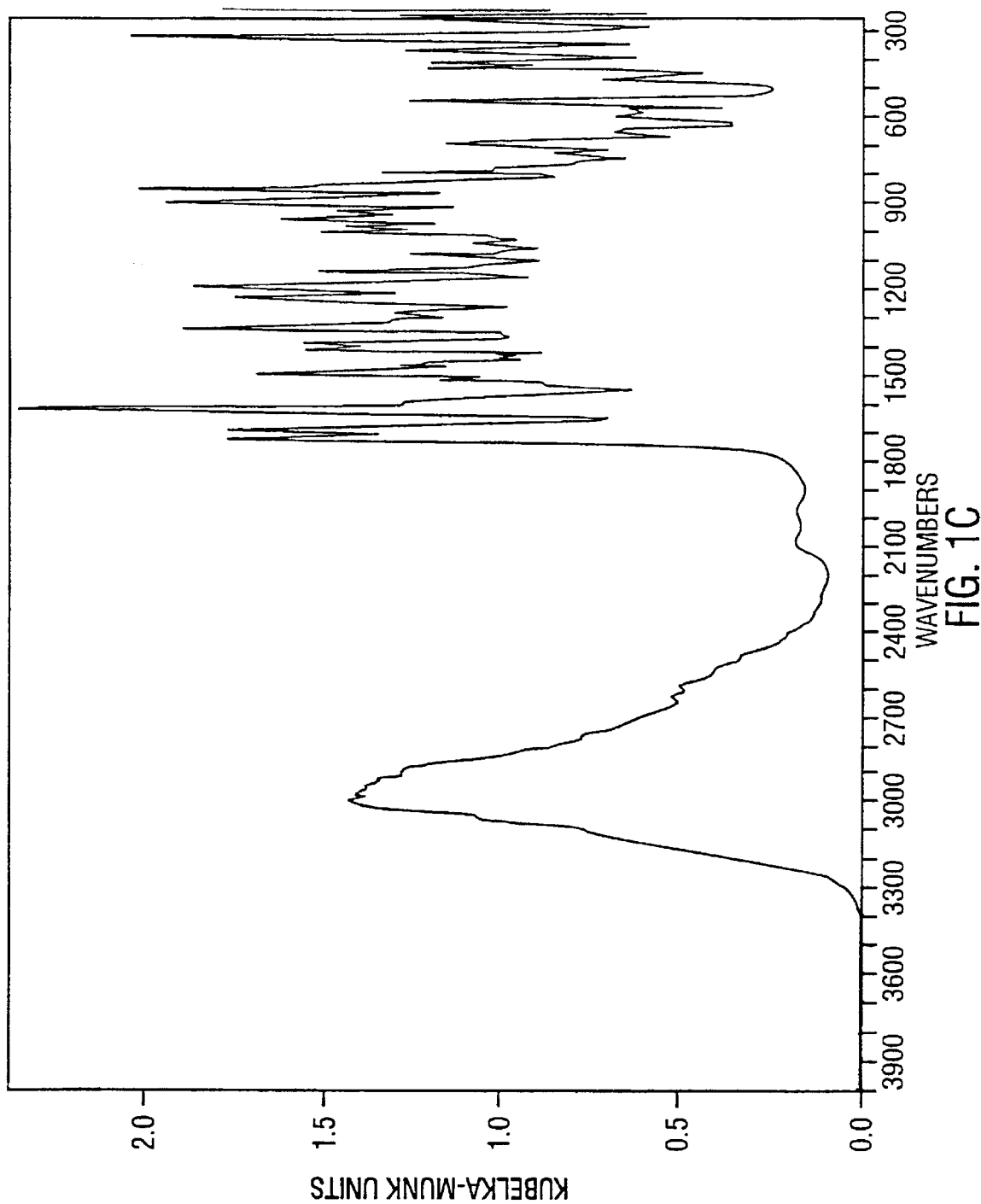
FIG. 1C is a control infrared spectrum of a physical mixture of these DTPA and L-lysine.HCl substrates without any chemical covalent linkage of the two substrates (see Example 3).
Figure 1D:
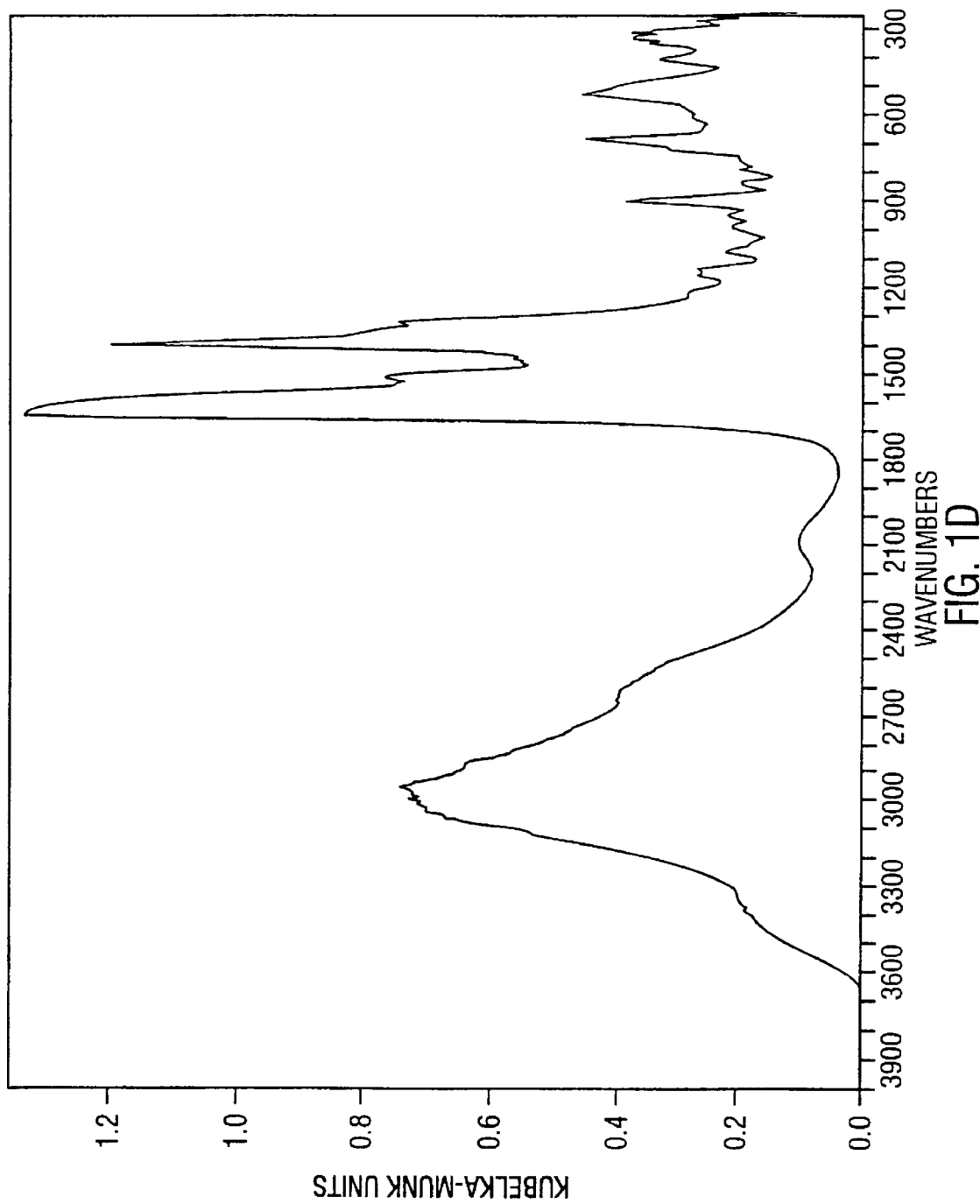
FIG. 1D is the experimental infrared spectrum of L-lysine covalently conjugated to DTPA by 1-ethyl-3-(3-dimethylaminopropyl) carbodiimide (EDC) linkage (see Example 3). Note the changes (height, width and loss of splitting) in signature peaks in the range of 1250–1700 wavenumbers, which indicate covalent conjugate formation.
Figure 2A:
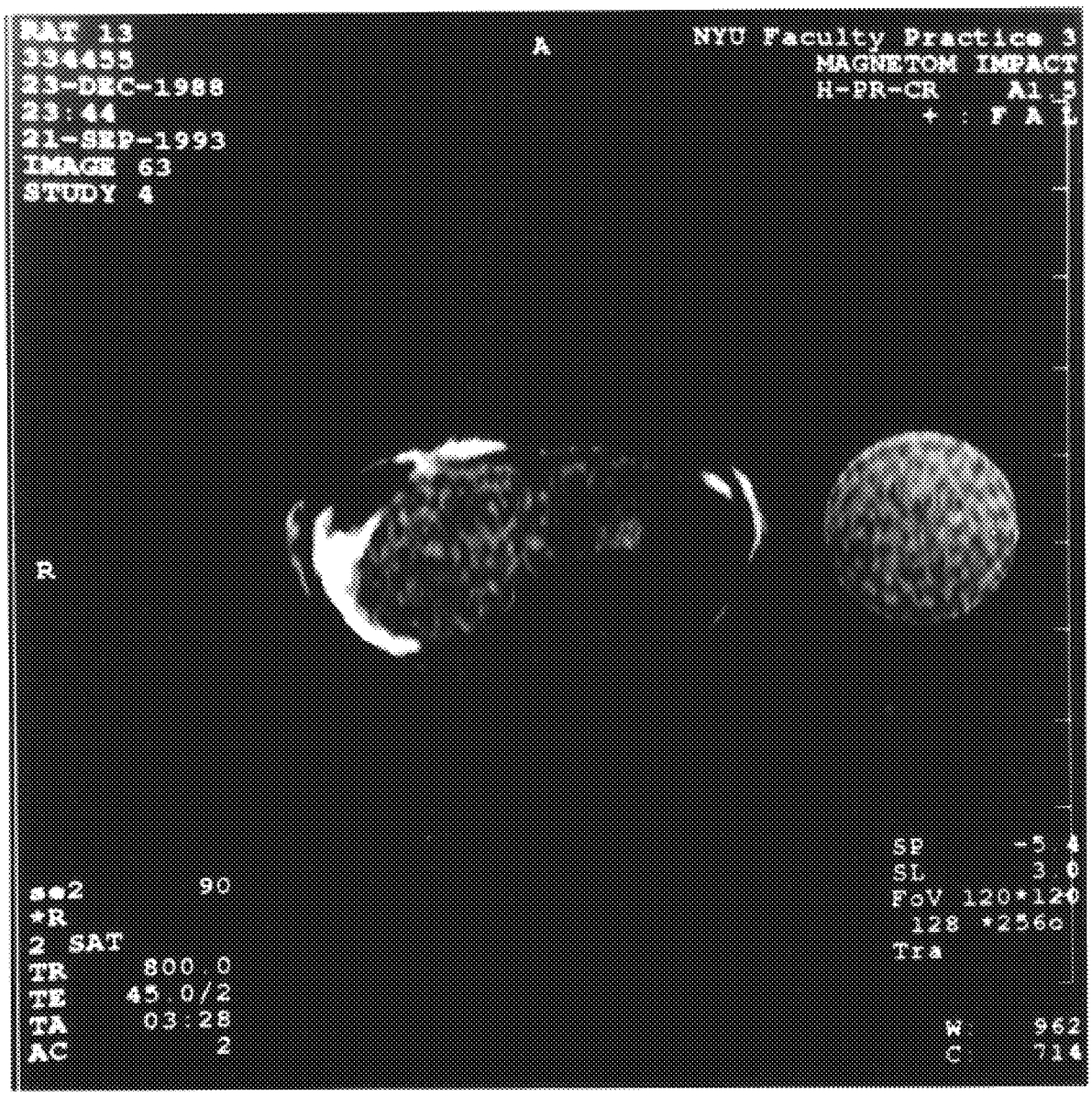

FIG. 2A. Precontrast image of liver (tumor not conspicuous).

Figure 2B:

FIG. 2B. Liver image at 7 min postinjection (MPI) of the Selective Paramagnetic Contrast Agent, Ferrioxamine:Dermatan Sulfate (0.155 mmol/Kg) i.v., showing marked contrast enhancement of tumor in right lobe of liver, very sharp tumor boundaries against surrounding liver, and discretely demarcated darker central region of tumor necrosis—allowing tumor perfusion and function to be spatially resolved and assessed within different, very small anatomical subregions.

Figure 3A:
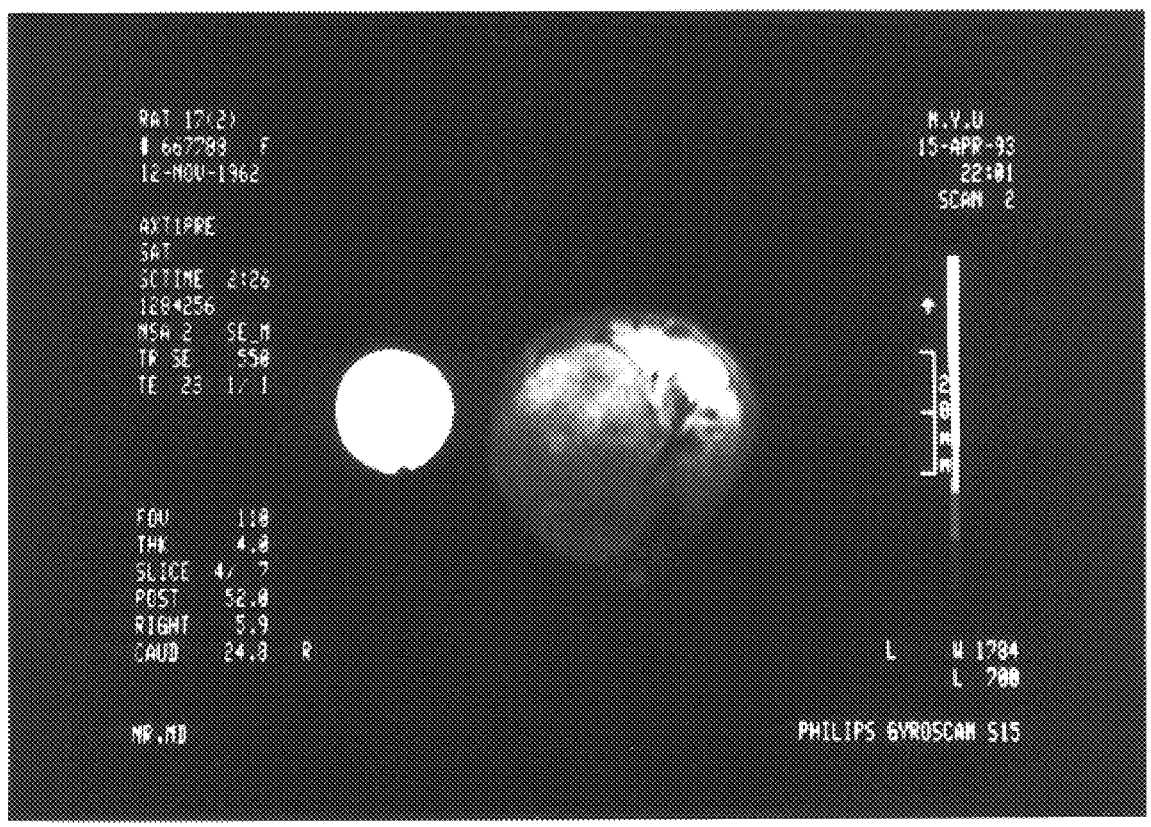

FIG. 3A. Precontrast image of liver (tumor is present but not conspicuous).

Figure 3B:
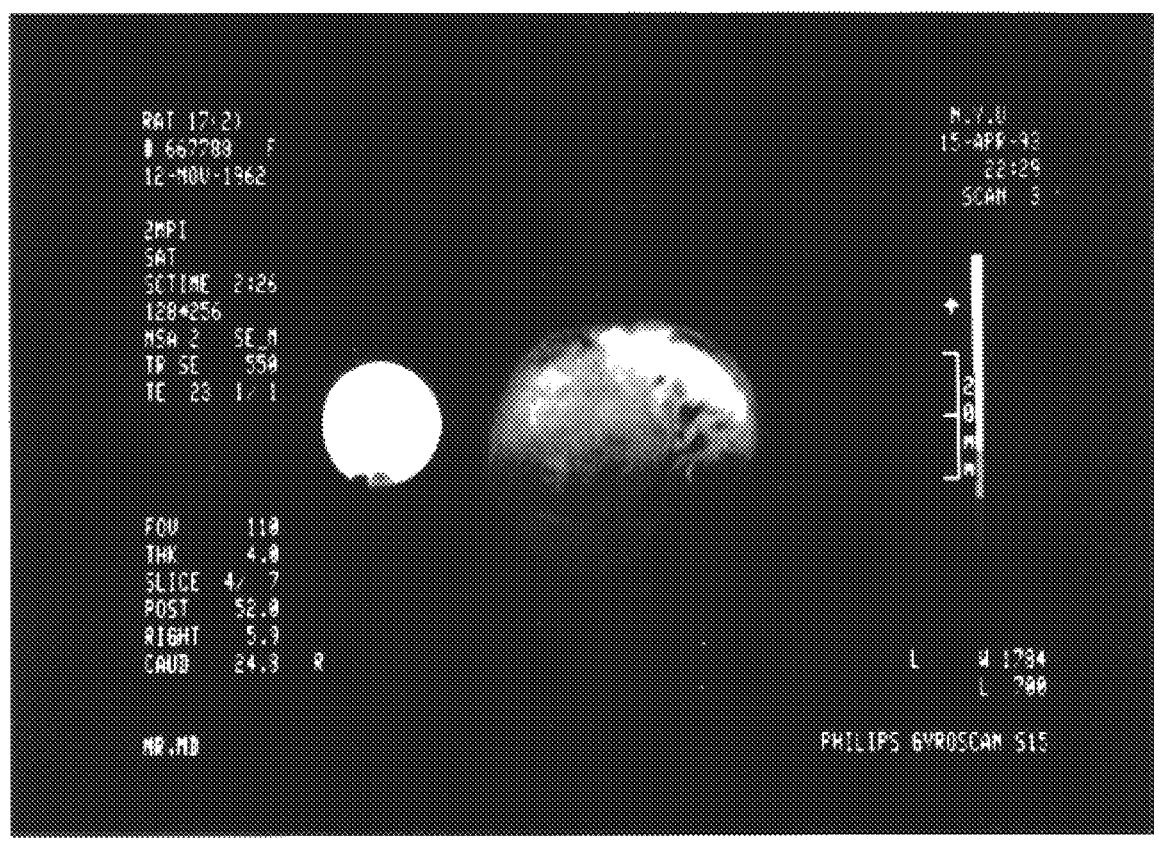

FIG. 3B. Liver image at 7 MPI of Ferrioxamine Active Alone (without any Dermatan Sulfate Carrier). Note that acute contrast enhancement is only very slight or nonexistent. This differs markedly from the pronounced tumor enhancement seen in FIG. 2B; and it indicates that binding of the Ferrioxamine active by the Dermatan Sulfate carrier is a requirement for tumor-site localization and tumor uptake of Ferrioxamine active.

Figure 4A:
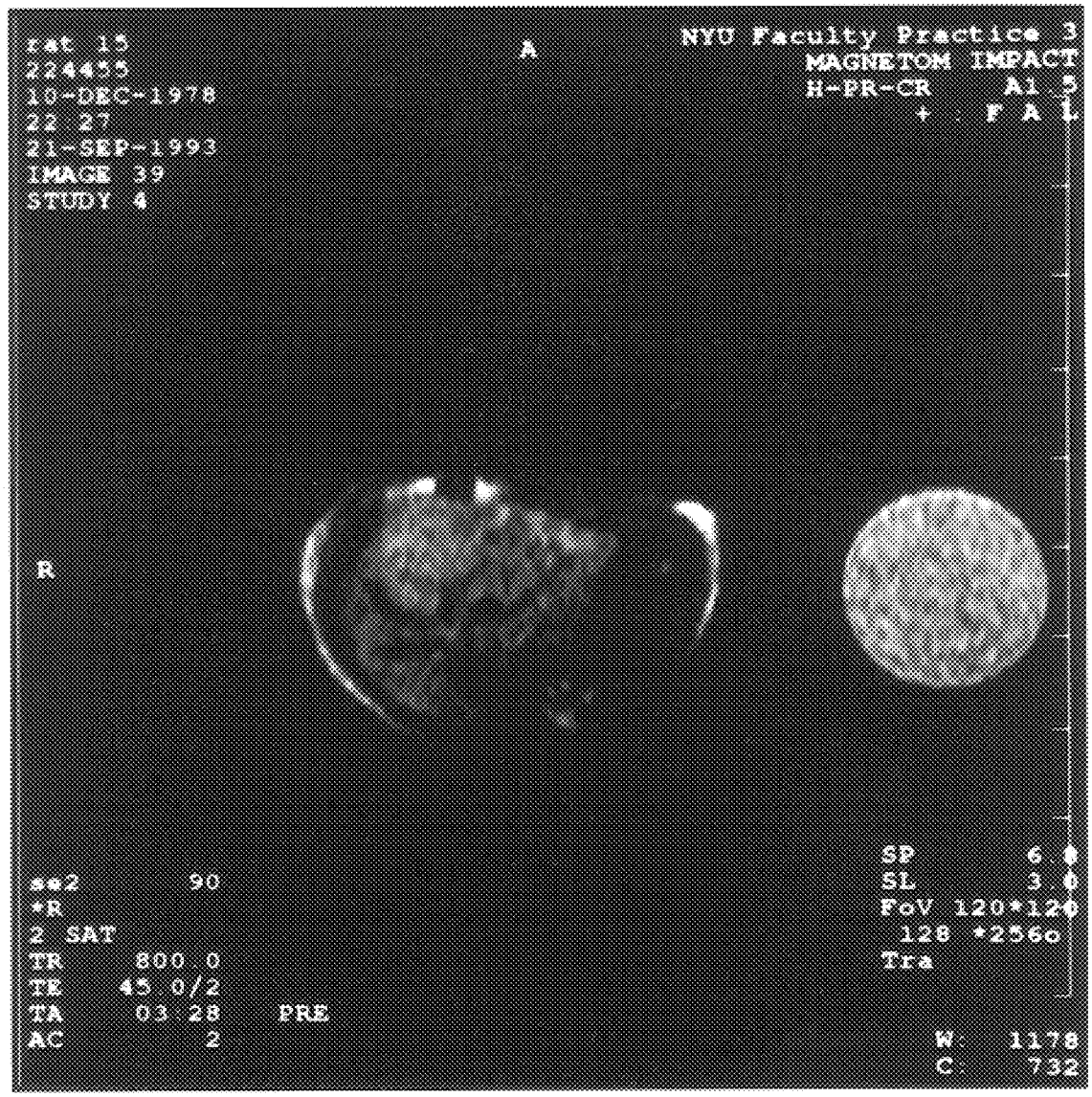

FIG. 4A. Precontrast T1 image (TR/TE=800/45) of liver (breast tumor is present but not conspicuous).

Figure 4B:

FIG. 4B. Liver image at 21 MPI of Ferrioxamine:Dermatan Sulfate Selective MRI Contrast Agent. Note the marked enhancement of main tumor mass and distinct tumor borders. Also note the small, 2-mm, bright enhancement of tumor metastasis in left lobe of liver. This metastasis is completely non-visualized in the Precontrast T1 images.

Figure 4C:
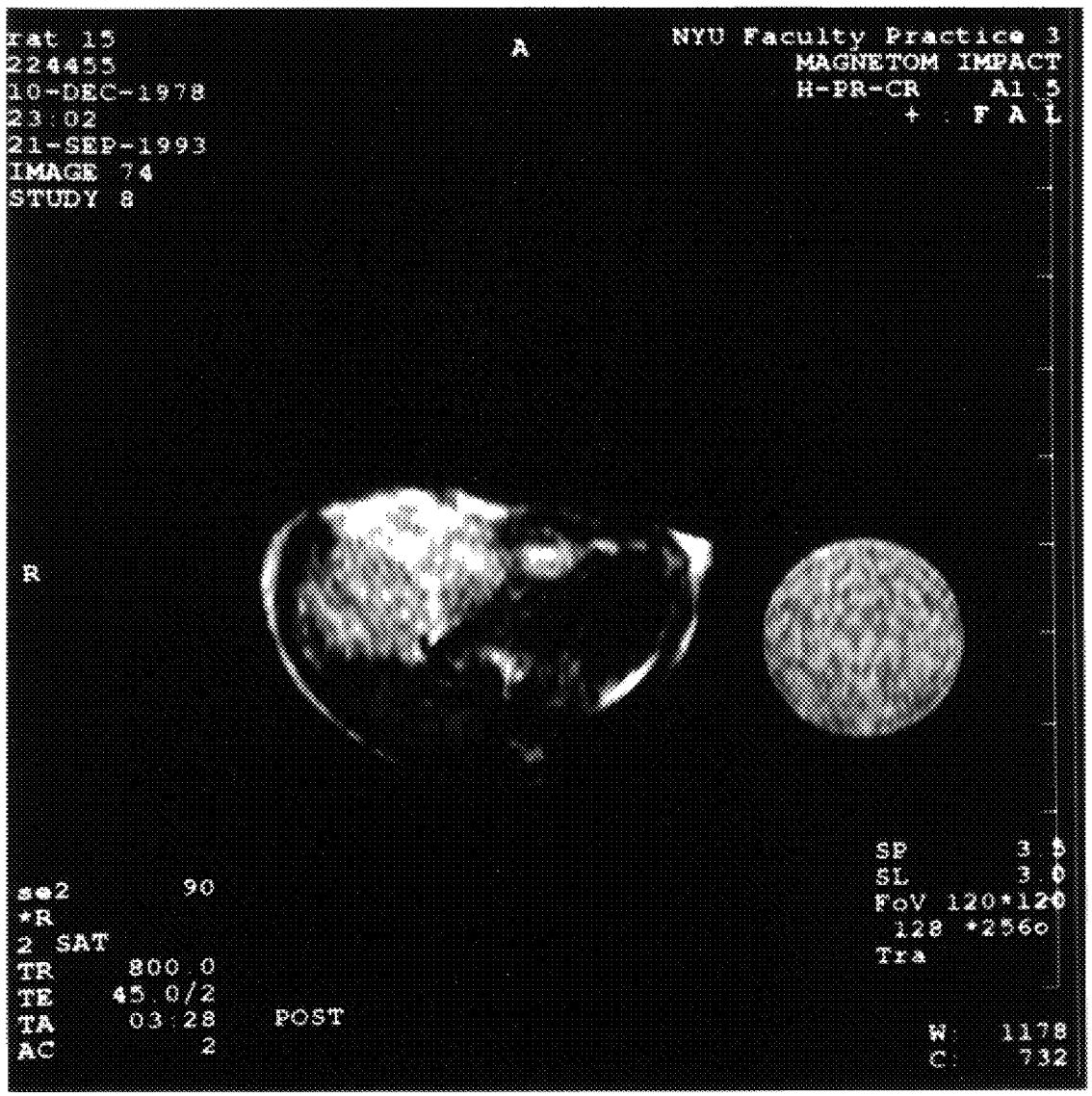

FIG. 4C. Liver image at 30 MPI of Ferrioxamine:Dermatan Sulfate Selective MRI Contrast Agent. Note the sustained enhancement of main tumor and metastasis.

Figure 4D:
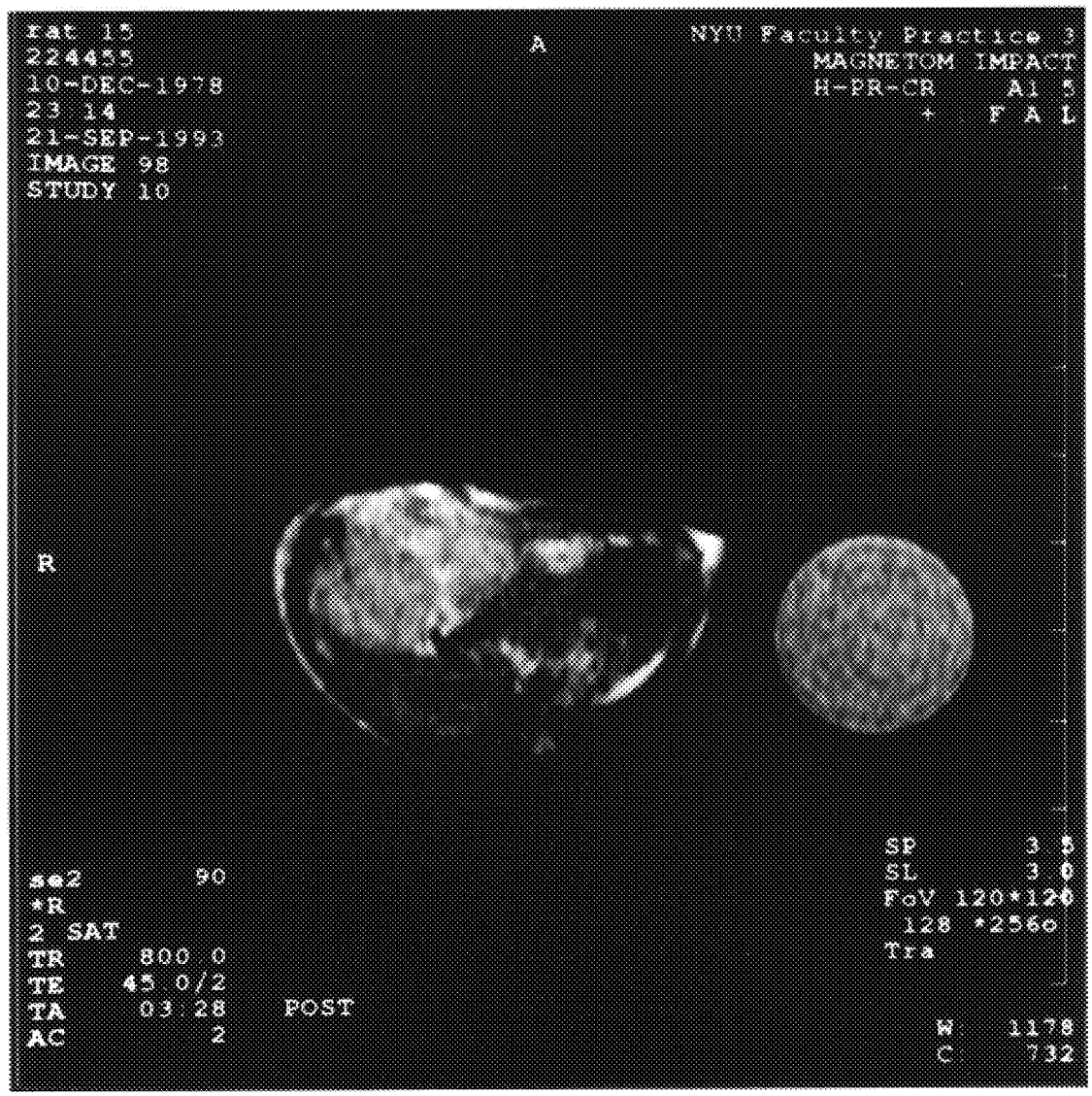

FIG. 4D. Liver image at 42 MPI of Ferrioxamine:Dermatan Sulfate Selective MRI Contrast Agent. Note: continued strong enhancement of main tumor and metastasis at prolonged post-contrast interval, at high, sustained sensitivity, and with continued delineation of tumor boundaries in both nodules (selectivity), plus delineation of the very small non-perfused region centrally within the 2-mm liver metastasis.

FIG. 5. Region-of-interest (ROI) analyses of MRI image intensities from a tumor animal analogous to that shown in FIG. 4A, FIG. 4B, FIG. 4C and FIG. 4D. Upper line=tumor ROI's; Lower line=liver ROI's; time points=Precontrast; and 12, 27, 44 and 64 MPI of Ferrioxamine:Dermatan Sulfate Selective MRI Contrast Agent. Note the Intensity Ratios of Tumor to Liver are: (a) at the Peak time of 12 MPI=11:1; (b) as an average over the 27–64 MPI=3.2:1—both (a) and (b) additionally indicating very good selectivity for tumor versus liver. Intensity fades only very gradually with time, unlike the kinetics reported for Gd:DTPA, which are very rapid and have a t1/2 at the site of ca. 12–20 min (images not shown).

Figure 6:
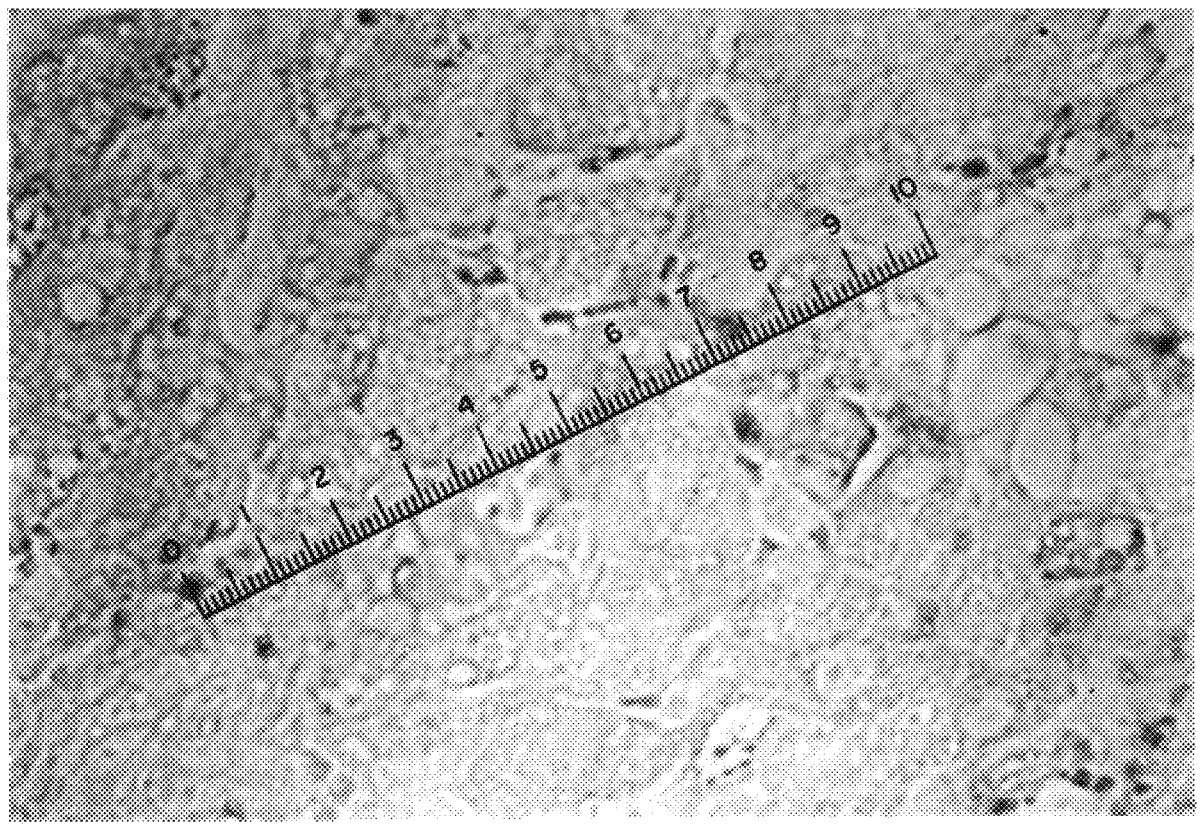

FIG. 6. Special histologic stain (heated ferroferricyanide reaction) of formalin-fixed section of syngeneic breast adenocarcinoma excised from liver inoculation site of Fisher 344 female rats: Outer Tumor Rim 7–10 MPI of Ferrioxamine:Dermatan Sulfate Selective MRI Contrast Agent. Note selective staining for ferrioxamine iron (a) strongly positive on and within tumor endothelium, (b) strongly positive in the subendothelia, (c) moderately positive in the extracellular matrix of tumor, and (d) lightly to moderately positive within tumor intracellular sites.

Figure 7A:
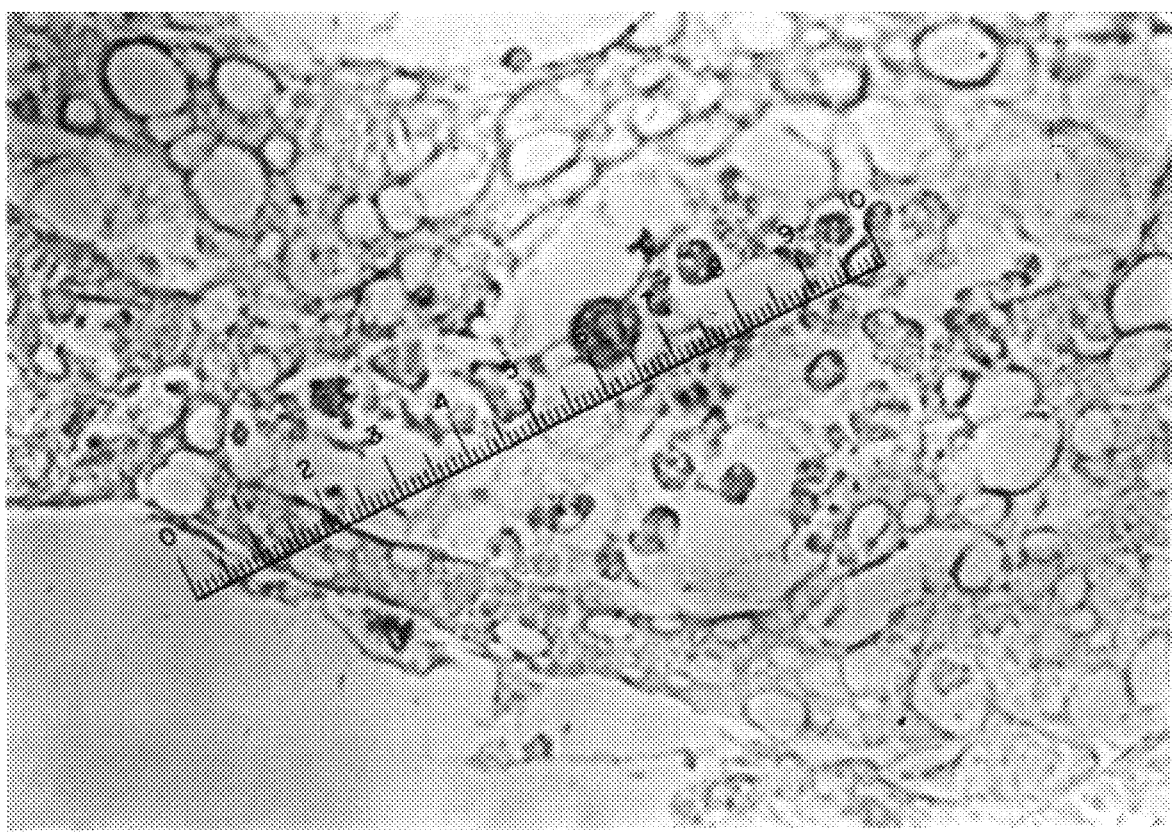

FIG. 7A. Same tumor, stain, conditions, and post-contrast time as FIG. 6, except tissue section is taken from Central Tumor, 7–10 MPI of Ferrioxamine:Dermatan Sulfate Selective MRI Contrast Agent. Significant staining positivity is present at all sites as in FIG. 6.

Figure 7B:
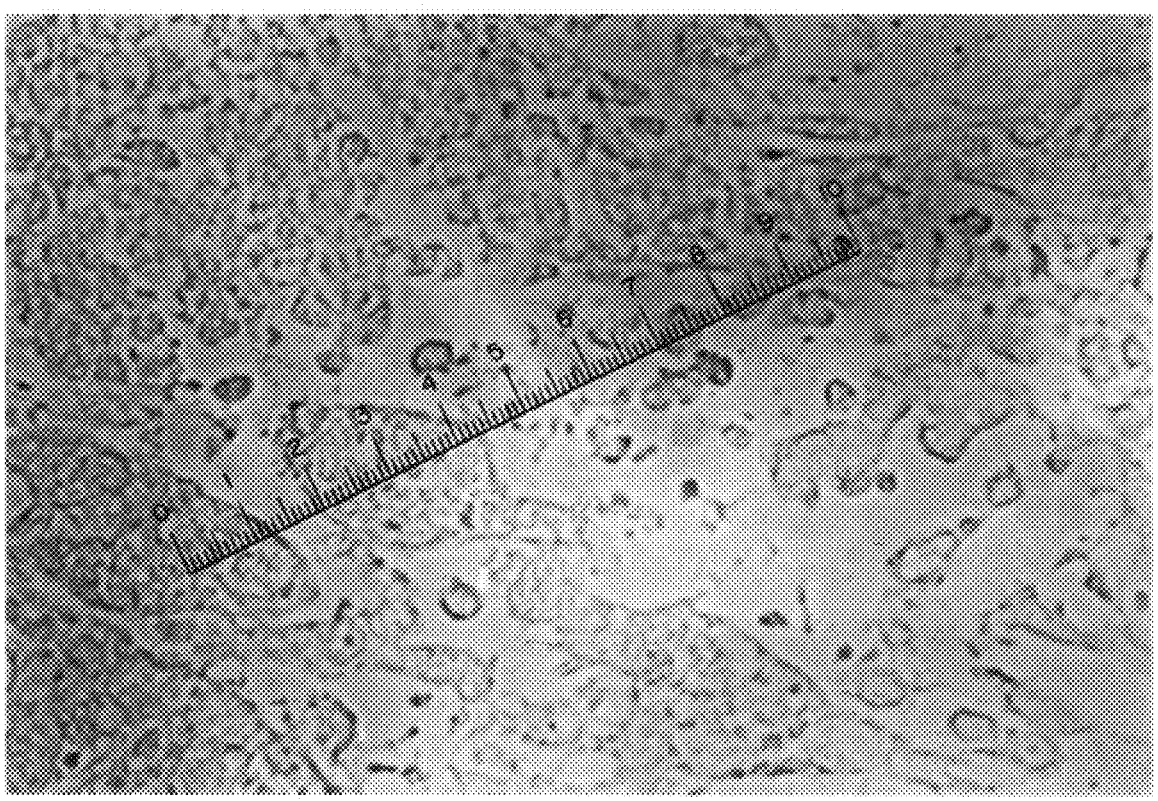

FIG. 7B. Identical to FIG. 7A, except a different animal with identical type and site of breast tumor, 7–10 MPI after i.v. Ferrioxamine Active Alone at a Ferrioxamine dose identical to FIG. 6 and FIG. 7A. Note the complete absence of staining positivity. This correlates directly with the results of MRI imaging with the full Agent (Active bound to Carrier) versus that with Active Alone (Active in free form)—(refer to FIG. 2A and FIG. 2B versus 3).

Figure 8A:
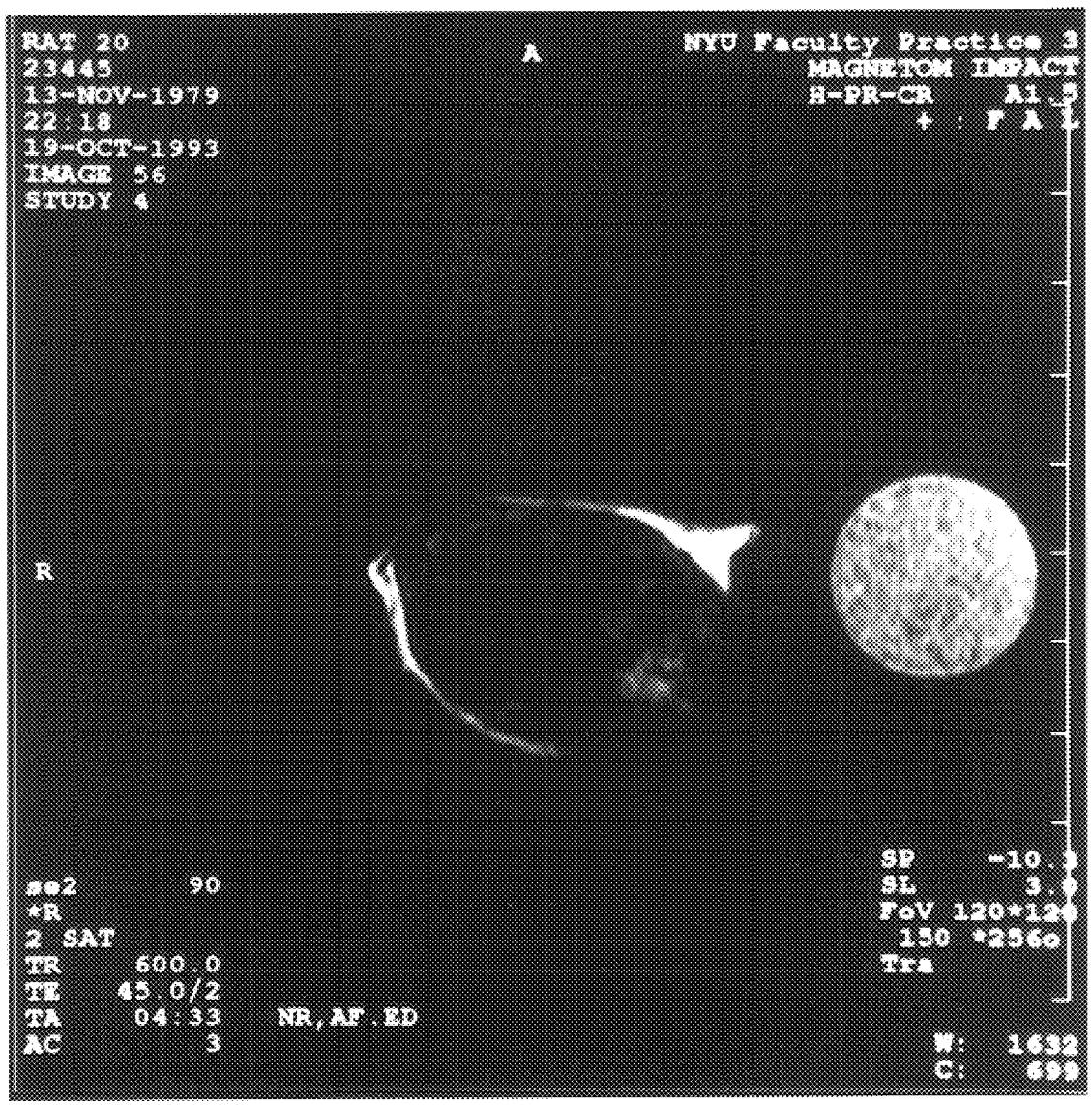

FIG. 8A. T1-weighted (TR/TE=600/45) image of Lung Field in rat with primary liver breast tumor. Note that the lung metastases (2-mm to 3-mm nodules) are only faintly conspicuous Precontrast.

Figure 8B:
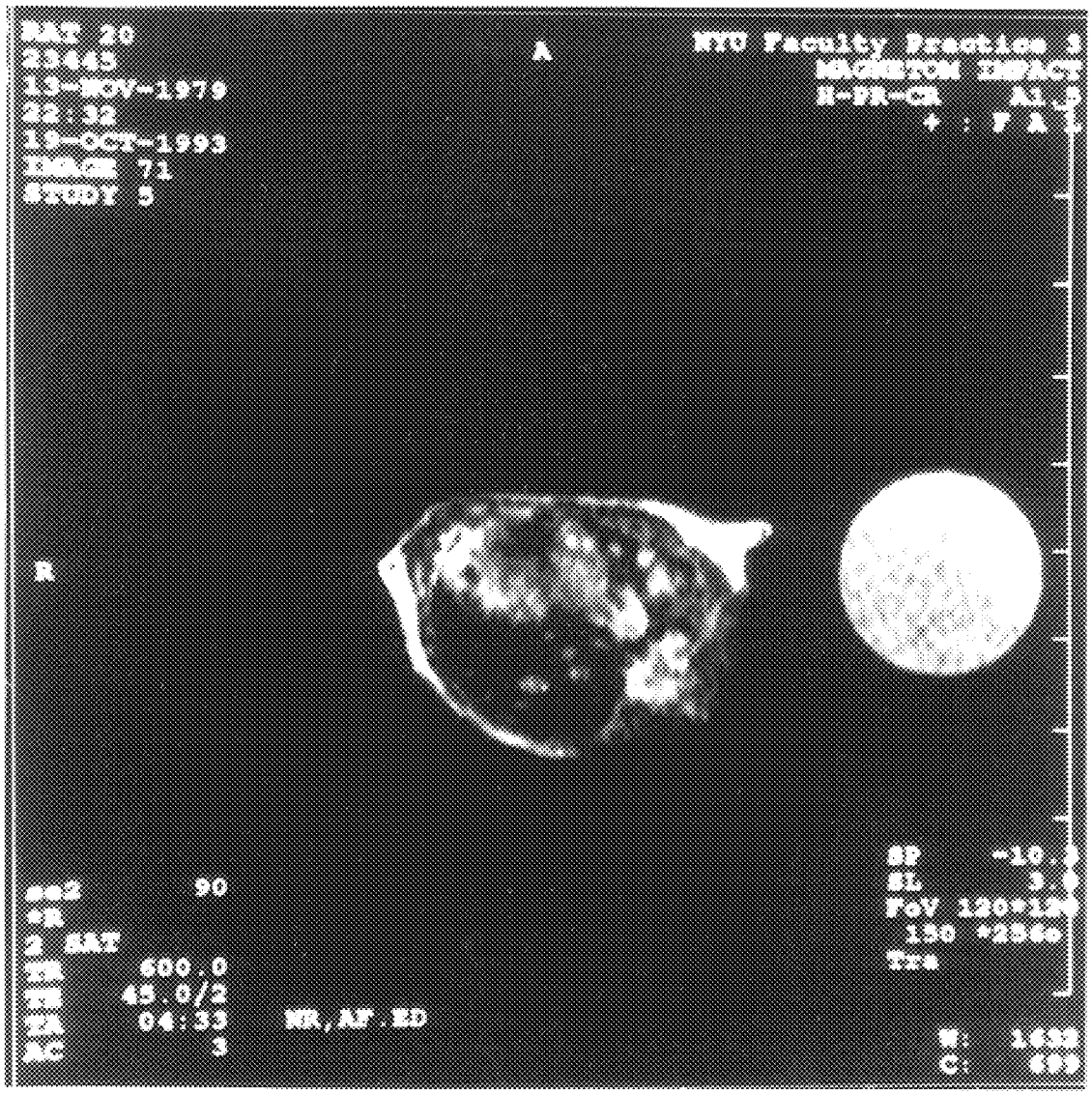

FIG. 8B. Lung Field of same rat at 12 MPI. Note the marked improvement in sensitivity of tumor detection (conspicuity) due to selective, bright enhancement of the lung metastases. Also note the sharpness of tumor boundaries.

Figure 8C:
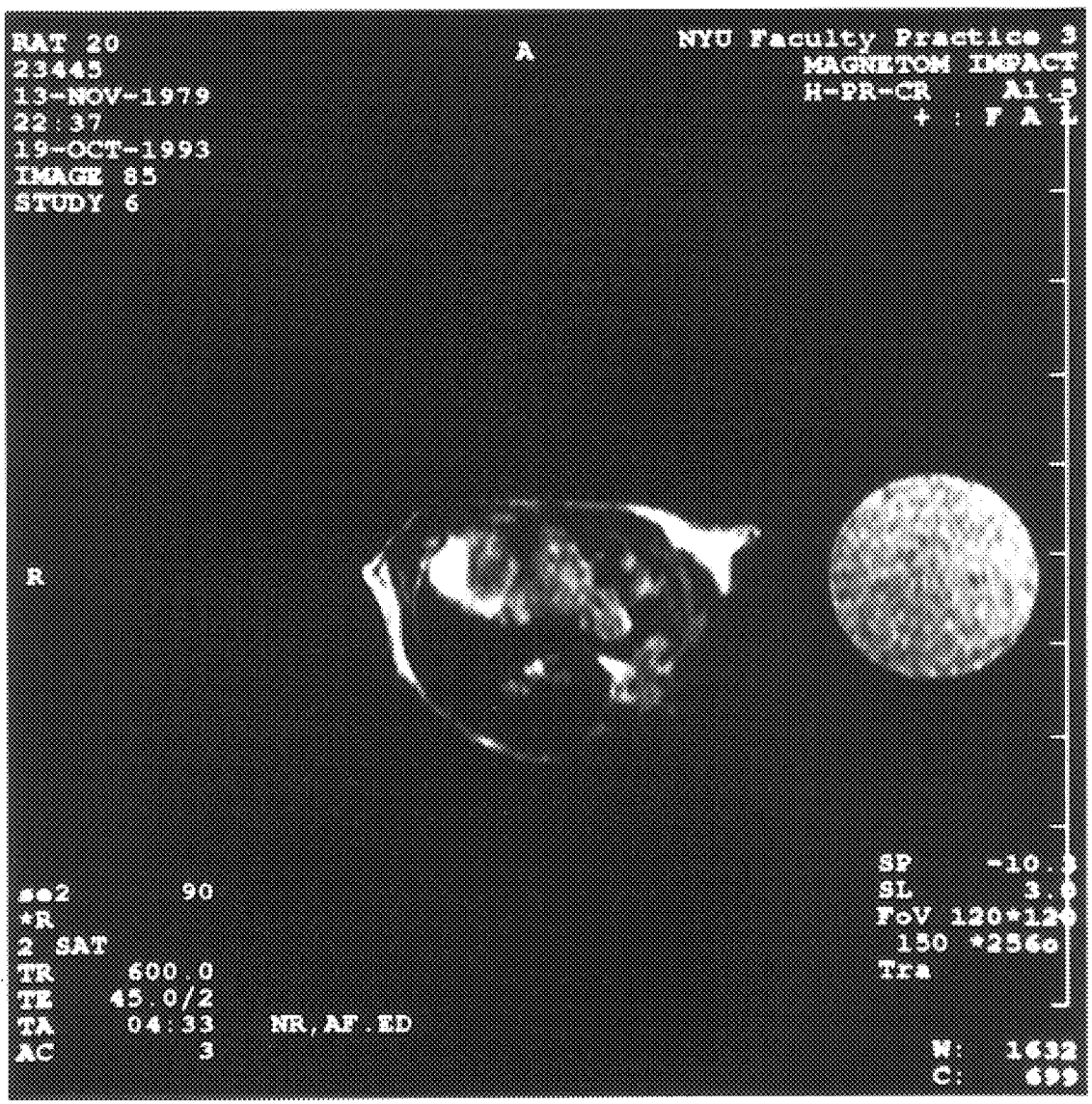

FIG. 8C. Same Lung Field at 17 MPI—showing sustained enhancement and sustained sharpness of tumor boundaries. By comparison, the rapid diffusion rates of Gd:DTPA lead to rapidly fuzzy boundaries at early times; and thereby also decrease the sensitivity of detecting pulmonary metastases.

FIG. 9A, FIG. 9B, FIG. 9C, FIG. 9D, FIG. 9E, FIG. 10A, FIG. 10B, FIG. 10C, FIG. 10D and FIG. 10E show T1-weighted MRI images (TR/TE=250/8) performed at 4.7 Tesla, before (Pre) and after (Post) intravenous (i.v.) injection of Ferrioxamine:Dermatan Sulfate Selective Paramagnetic Contrast Agent (FIG. 9A, FIG. 9B, FIG. 9C, FIG. 9D, FIG. 9E) prepared as in Examples 2 and 5, and injected i.v. at an Iron(III) dose of 0.155 mmol/Kg; compared to Gadolinium DTPA dimeglumine (FIG. 10A, FIG. 10B, FIG. 10C, FIG. 10D, FIG. 10E), injected i.v. at a Gd(III) dose of 0.100 mmol/Kg; each of these agents being administered to Copenhagen rats with syngeneic AT-1 prostate adenocarcinoma inoculated into previously prepared skin pouches [Hahn et al. (1993)], such that tumor diameters at the time of imaging are between 1.0 cm and 2.5 cm.

Figure 9A:
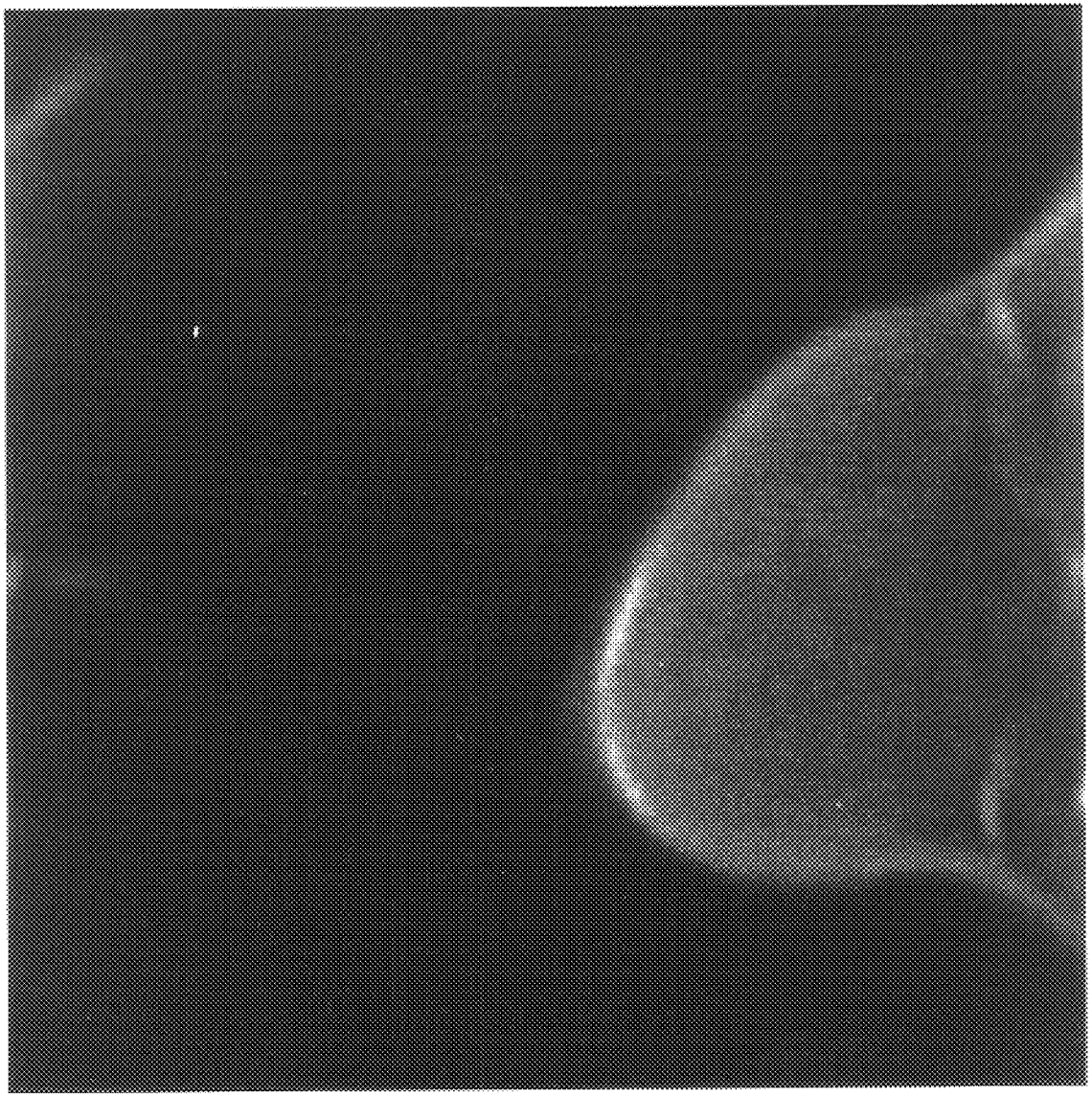

FIG. 9A. Precontrast image for Ferrioxamine:Dermatan Sulfate Selective Contrast Agent.

Figure 9B:
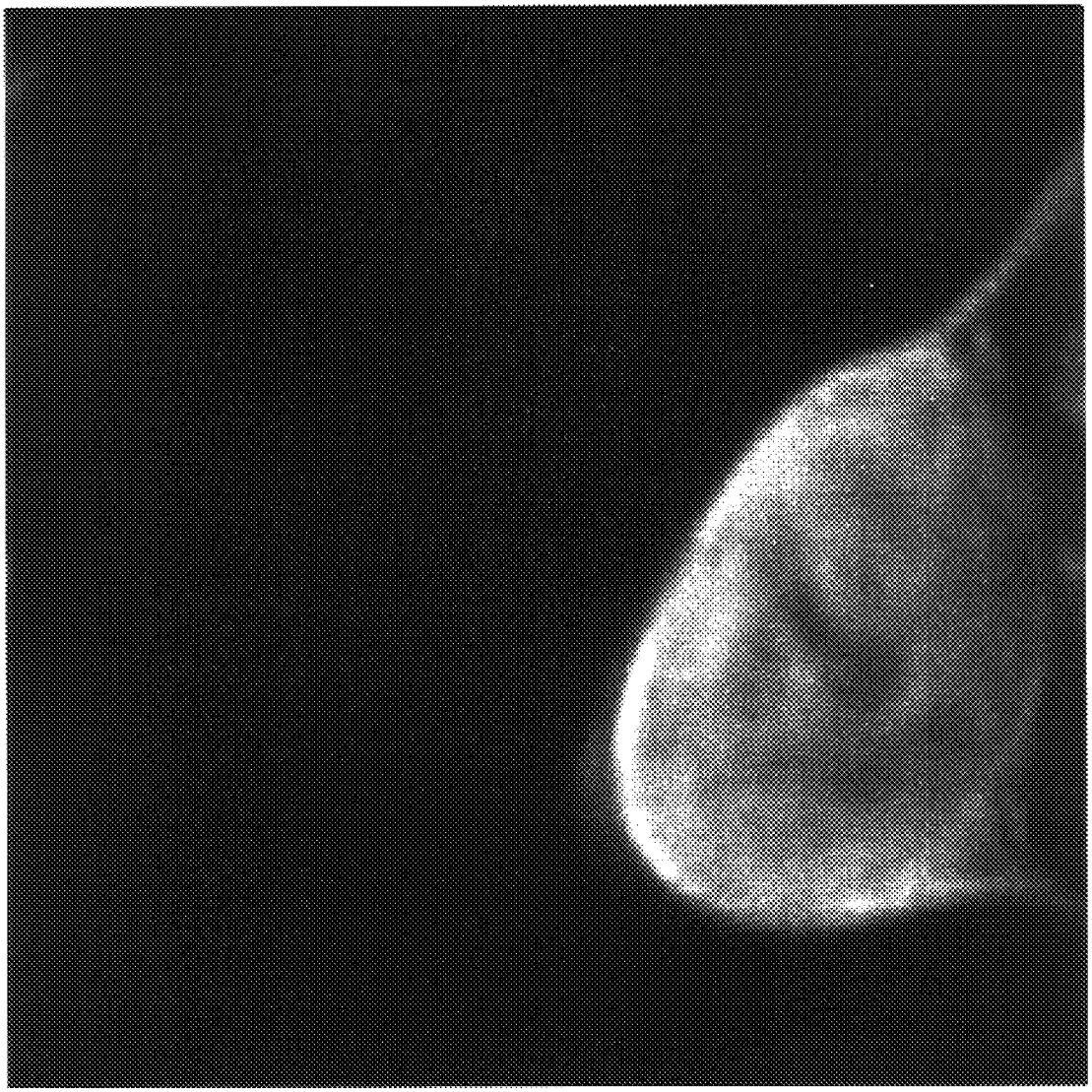

FIG. 9B. 7 MPI of Ferrioxamine:Dermatan Sulfate, liquid form at a ferrioxamine concentration of 0.166 mmol/mL. Note the strong enhancement of Outer Rim and Vascular array which fans out from the tumor pedicle.

Figure 9C:
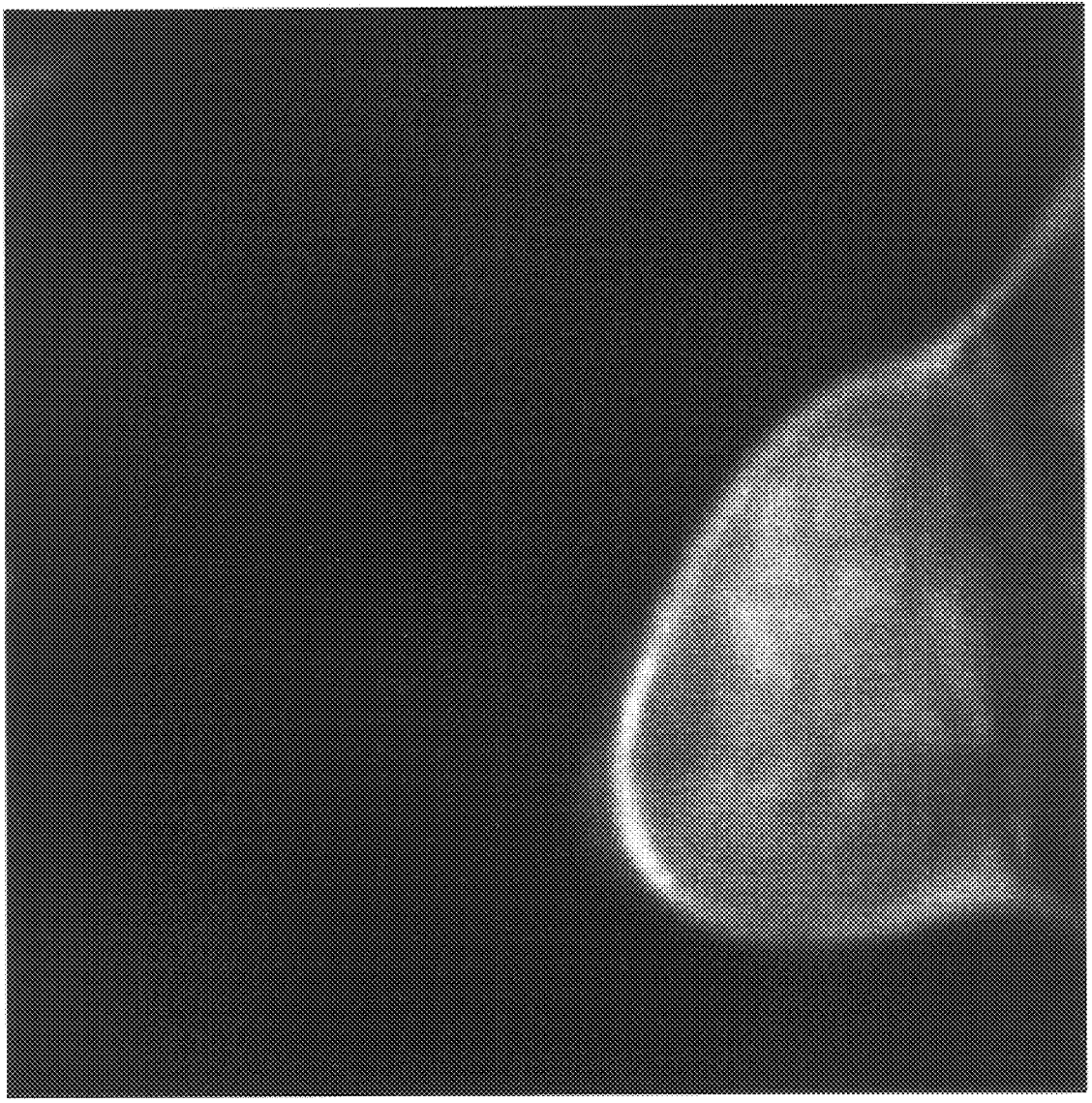

FIG. 9C. Same as FIG. 9B, except 20 MPI. Note the sustained, discrete enhancement of elements in FIG. 9B.

Figure 9D:
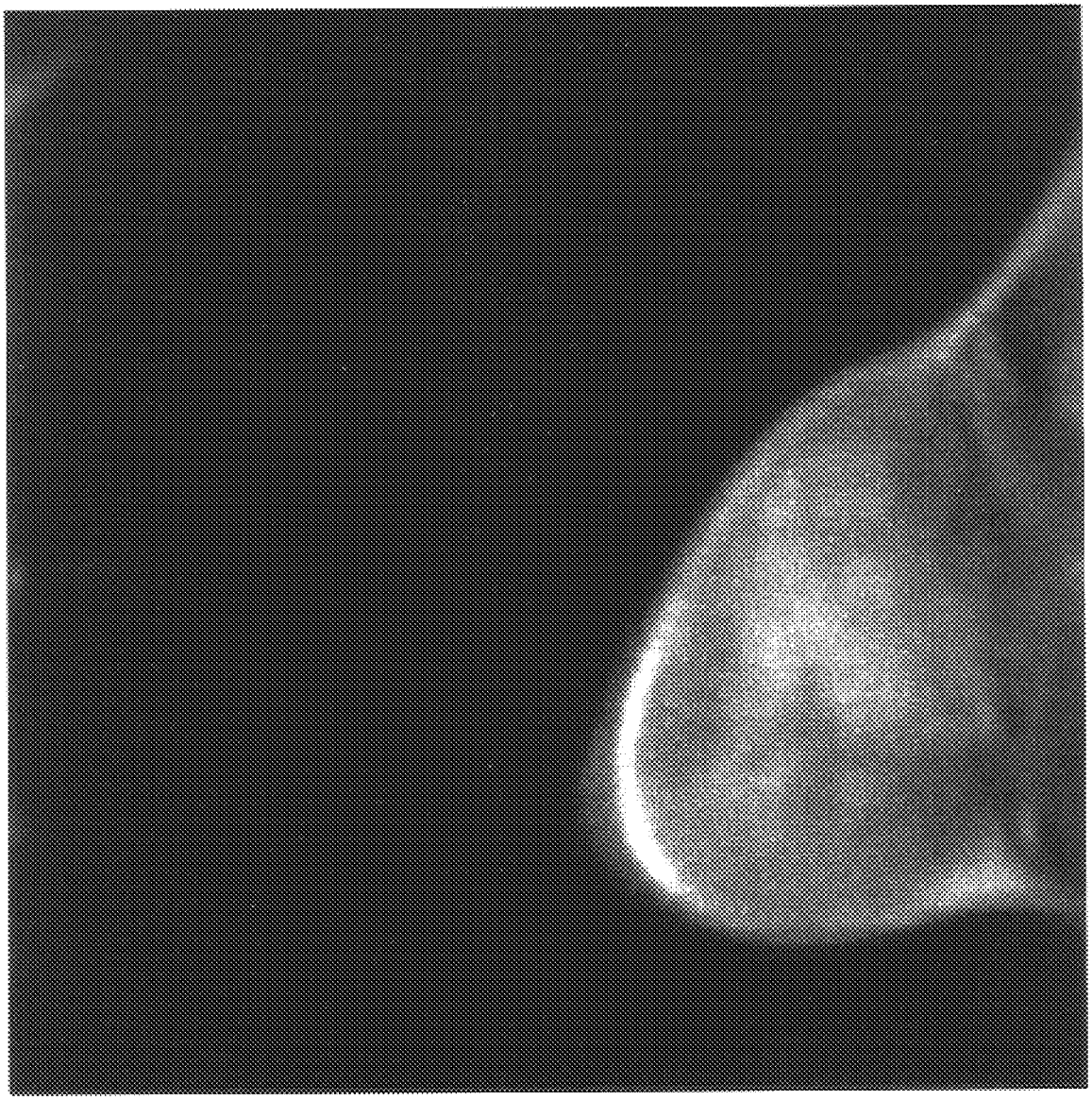

FIG. 9D. Same as FIG. 9C, except 40 MPI. Note the sustained contrast and delineation of Outer Rim.

Figure 9E:
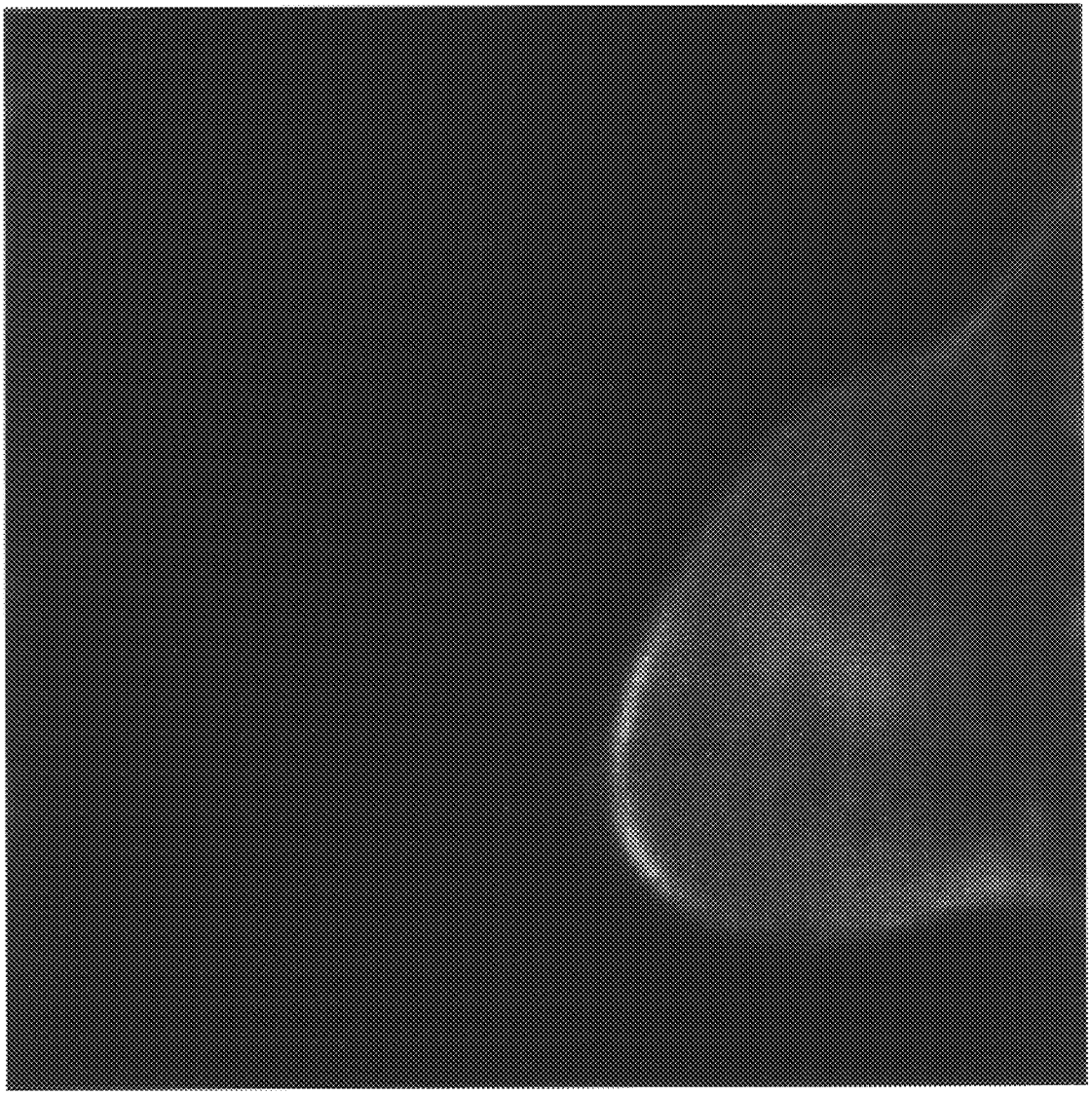

FIG. 9E. Same as FIG. 9D, except 60 MPI. Note the onset of contrast fading.

Figure 10A:
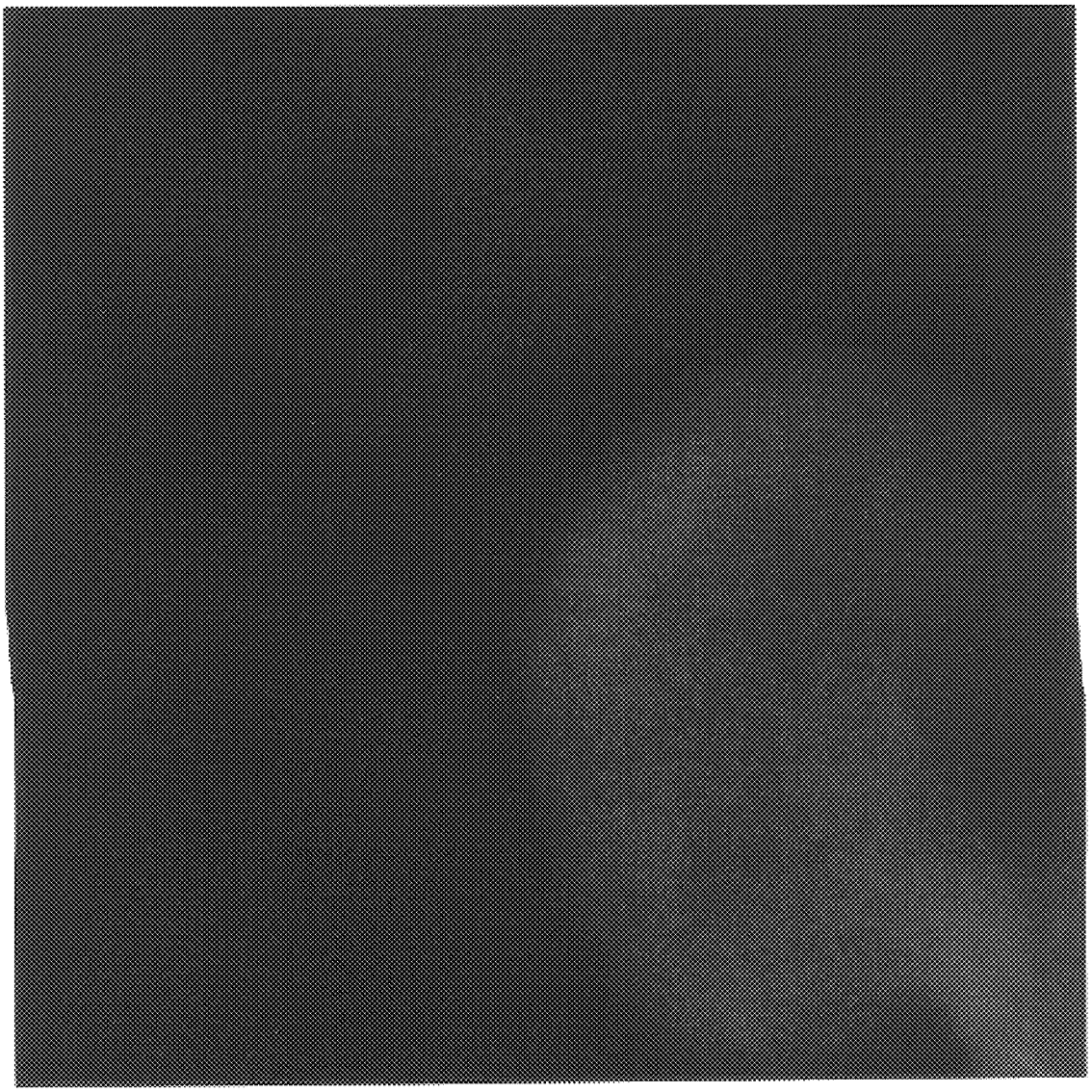

FIG. 10A. Precontrast image for Gd:DTPA dimeglumine Nonselective Contrast Agent.

Figure 10B:

FIG. 10B. 7 MPI of Gd:DTPA dimeglumine. Note that the Outer Rim is not well delineated, even at this very early post-contrast interval.

Figure 10C:
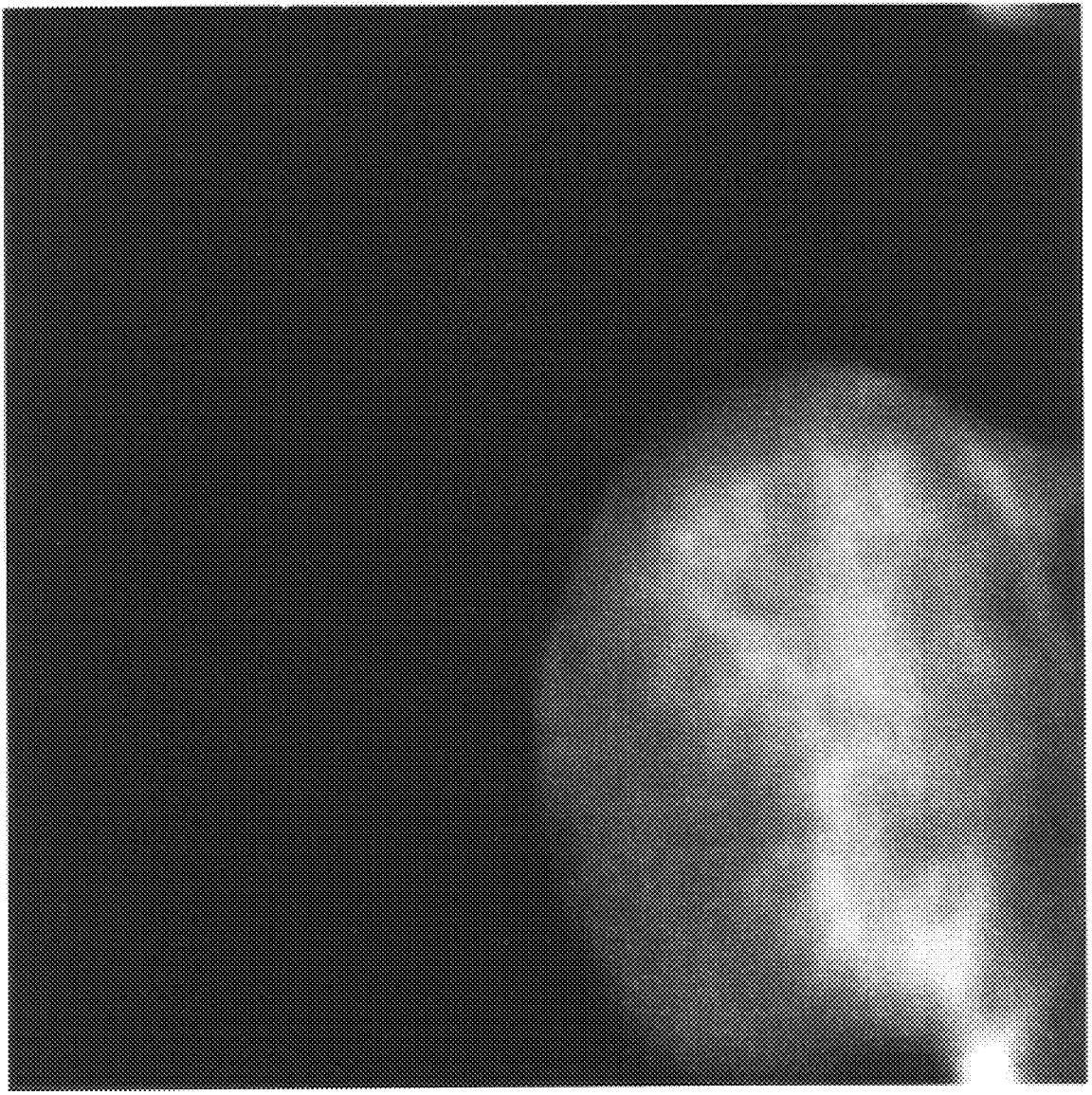

FIG. 10C. Same as FIG. 10B, except 20 MPI. Note the marked early contrast fading overall, with some agent sequestration seen at the central, poorly perfused (cystic) regions of tumor (as is typically reported for Gd:DTPA when used for imaging at body sites).

Figure 10D:
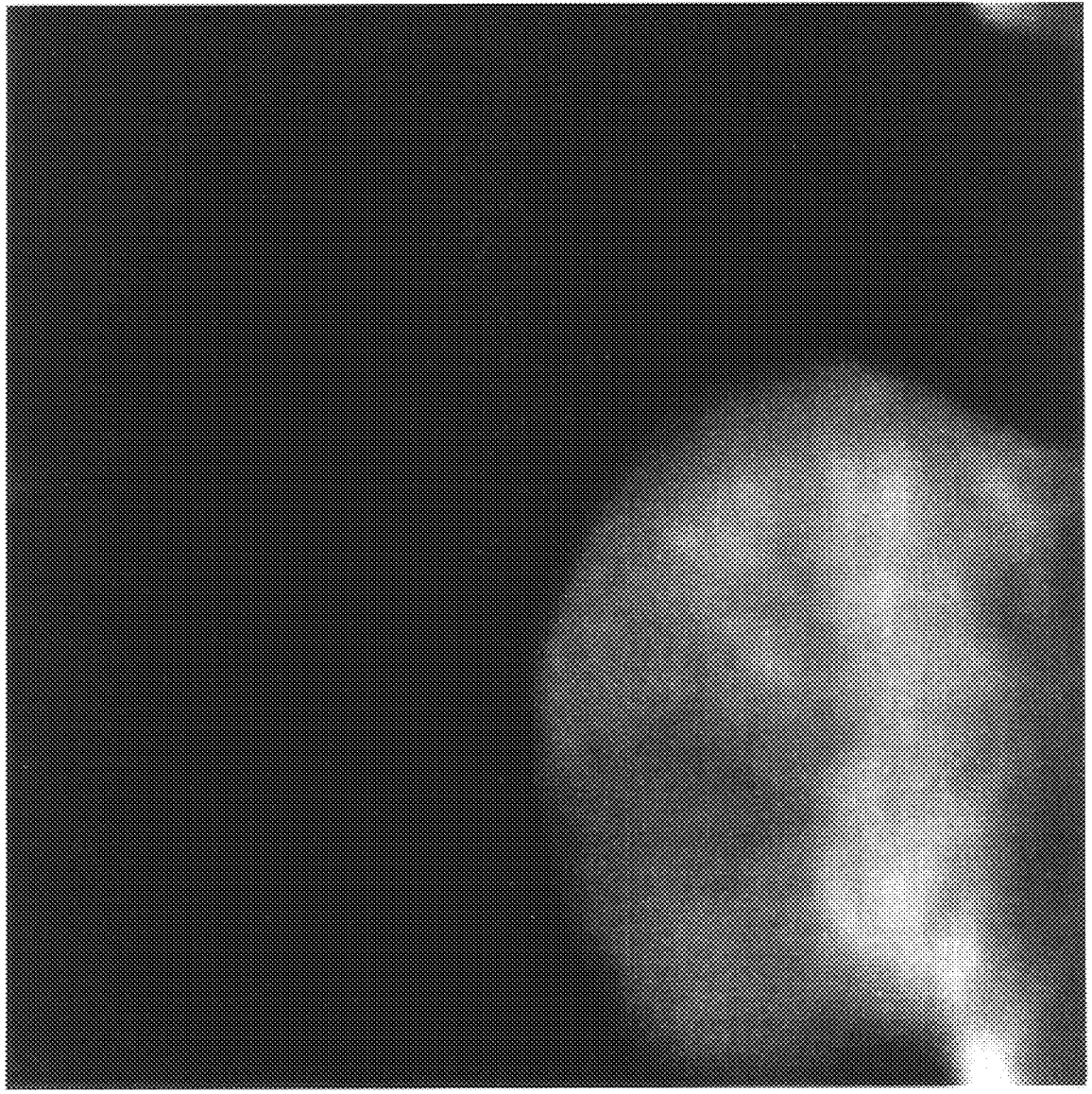

FIG. 10D. Same as FIG. 10C, except 40 MPI. Note that enhancement is nearly reverted to background levels.

Figure 10E:

FIG. 10E. Same as FIG. 10D, except 60 MPI. No residual contrast, except for central cystic regions.

FIG. 11A, FIG. 11B, FIG. 11C and FIG. 11D show T1-weighted MRI ECG-gated cardiovascular images performed at 0.5 Tesla, before (Pre) and after (Post) rapid intravenous (i.v.) infusion of Ferrioxamine:Dermatan Sulfate Selective Paramagnetic Contrast Agent prepared as in Examples 2 and 5, and injected i.v. at an Iron(III) dose of 0.155 mmol/Kg into German Shepherd dogs with acute, 90-min myocardial infarcts (ligature of proximal left anterior descending coronary artery) followed by reperfusion for ca. 90 minutes prior to contrast agent infusion.

Figure 11A:
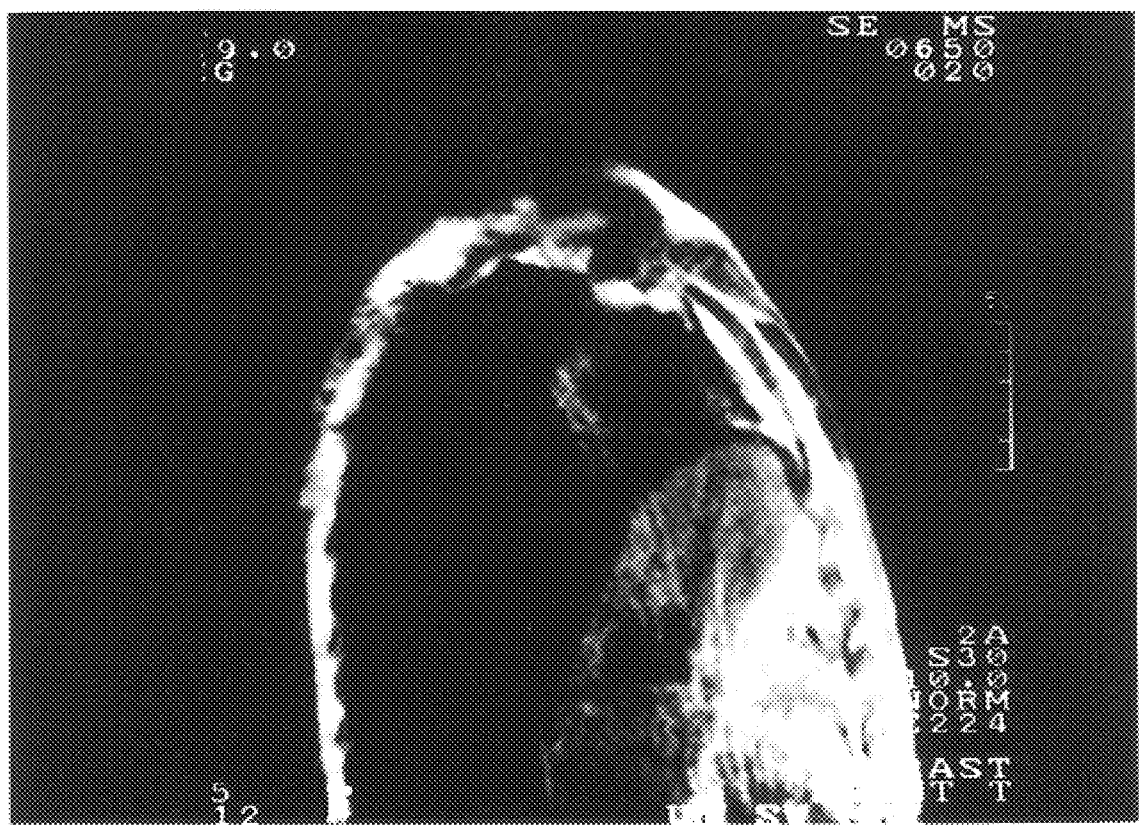

FIG. 11A. Precontrast image.

Figure 11B:

FIG. 11B. 7 MPI, showing strong enhancement of infarct by Ferrioxamine:Dermatan Sulfate Agent, and in particular delineating the boundary of the infarct—putatively the boundary of the marginal zone. Note the central darker region—putatively the irreversible central infarct zone.

Figure 11C:
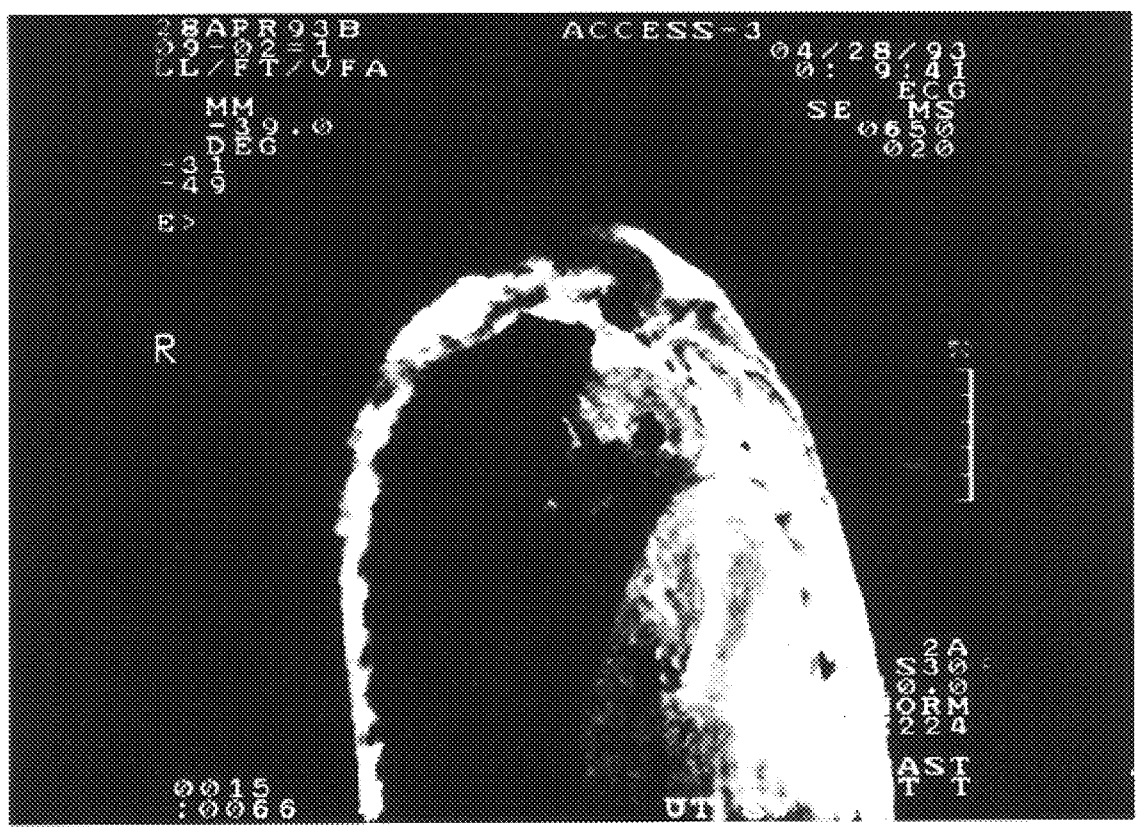

FIG. 11C. 20 MPI, showing sustained strong enhancement and zones as above.

Figure 11D:

FIG. 11D. 40 MPI, same as FIG. 11C, except filling in of central zone; absence of significant overall contrast fading. NOTES: (1) injection of Ferrioxamine Agent Alone at 0.155 mmol/Kg, gives no detectable enhancement (images not shown); (2) infarct sizes and positions are documented by double dye infusion methods immediately after imaging.

FIG. 12A, FIG. 12B, FIG. 12C and FIG. 12D show MRI 4.7 Tesla, T1-weighted images of Copenhagen rats with the AT-1 prostate tumor model (as in FIG. 9A, FIG. 9B, FIG. 9C, FIG. 9D, FIG. 9E, FIG. 10A, FIG. 10B, FIG. 10C, FIG. 10D and FIG. 10E), but rats are injected i.v. with Ferrioxamine:Dermatan Sulfate Selective Contrast Agent in the lyophilized (versus liquid) form, and the Agent is reconstituted with water just prior to administration at a higher concentration of 0.415 mmol/mL Fe(III) and administered at the usual dose of 0.155 mmol of Fe(III) per Kg.

Figure 12A:

FIG. 12A. Precontrast image for Ferrioxamine:Dermatan Sulfate Selective Contrast Agent.

Figure 12B:
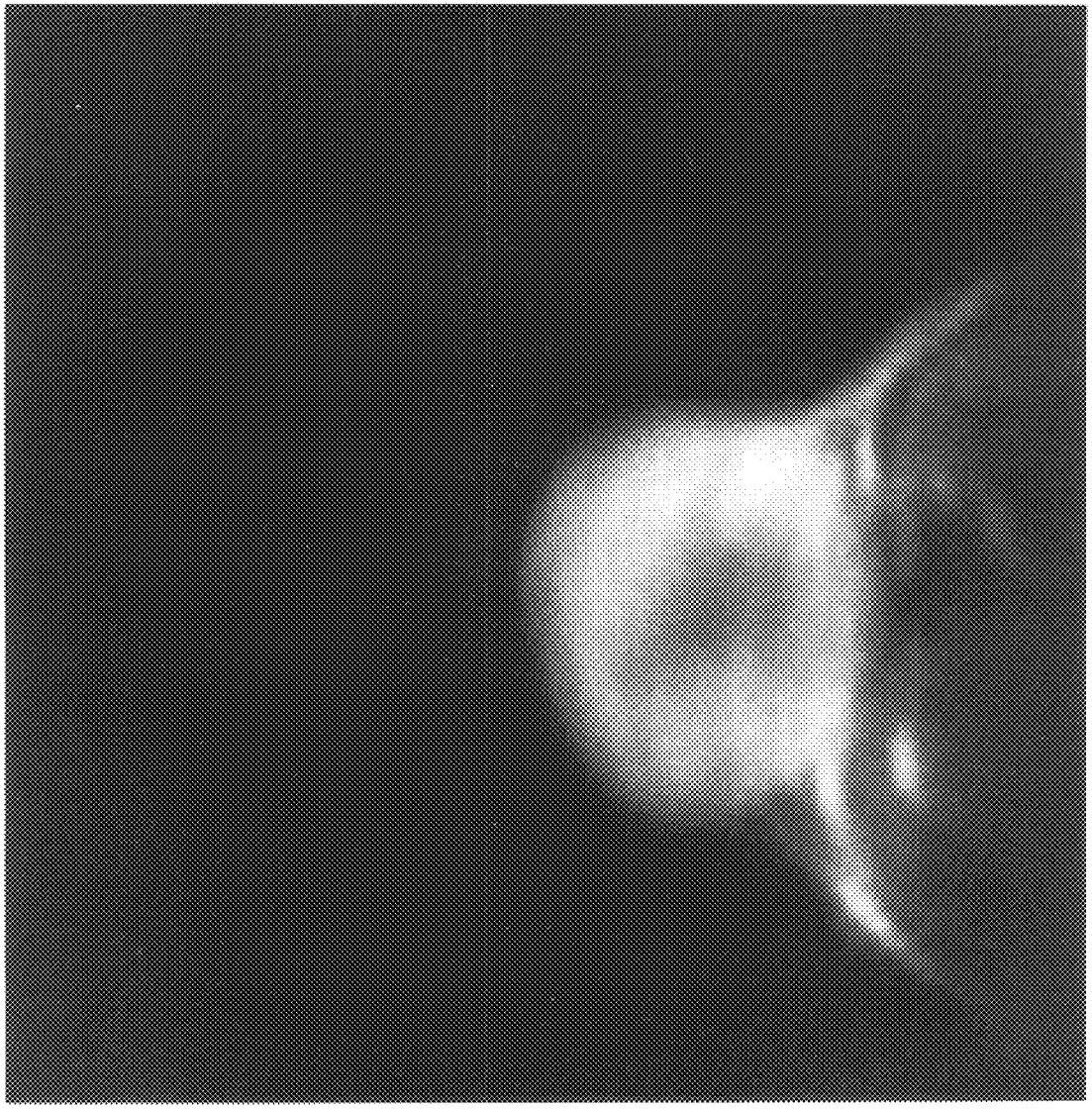

FIG. 12B. 7 MPI of Ferrioxamine:Dermatan Sulfate, lyophilized reconstituted to a Fe(III) concentration of 0.415 mmol/mL. Note the very strong enhancement of the entire Outer Rim of tumor.

Figure 12C:
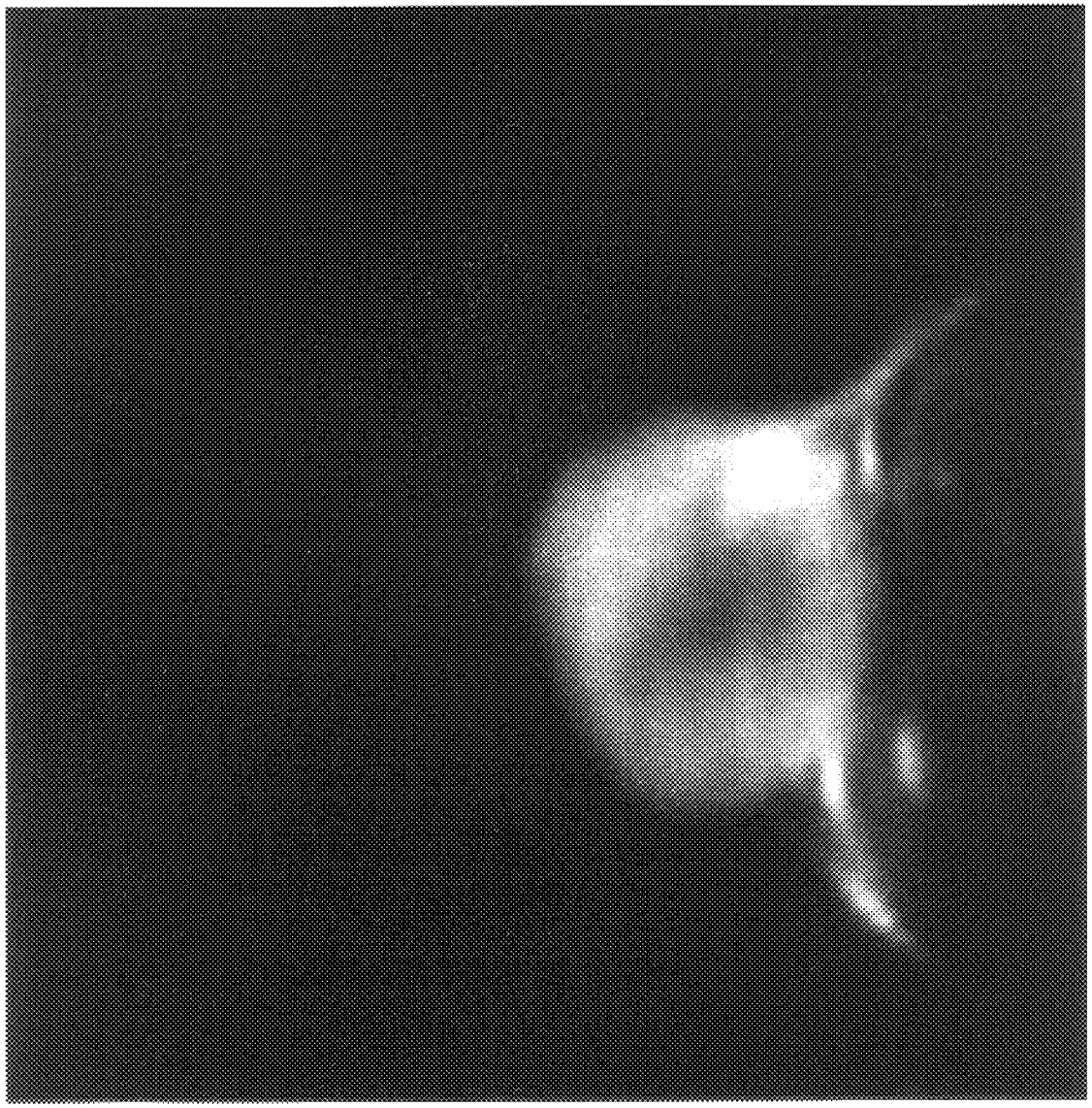

FIG. 12C. Same as FIG. 12B, except 20 MPI. Note the sustained, very strong enhancement and delineation of Outer Rim.

Figure 12D:
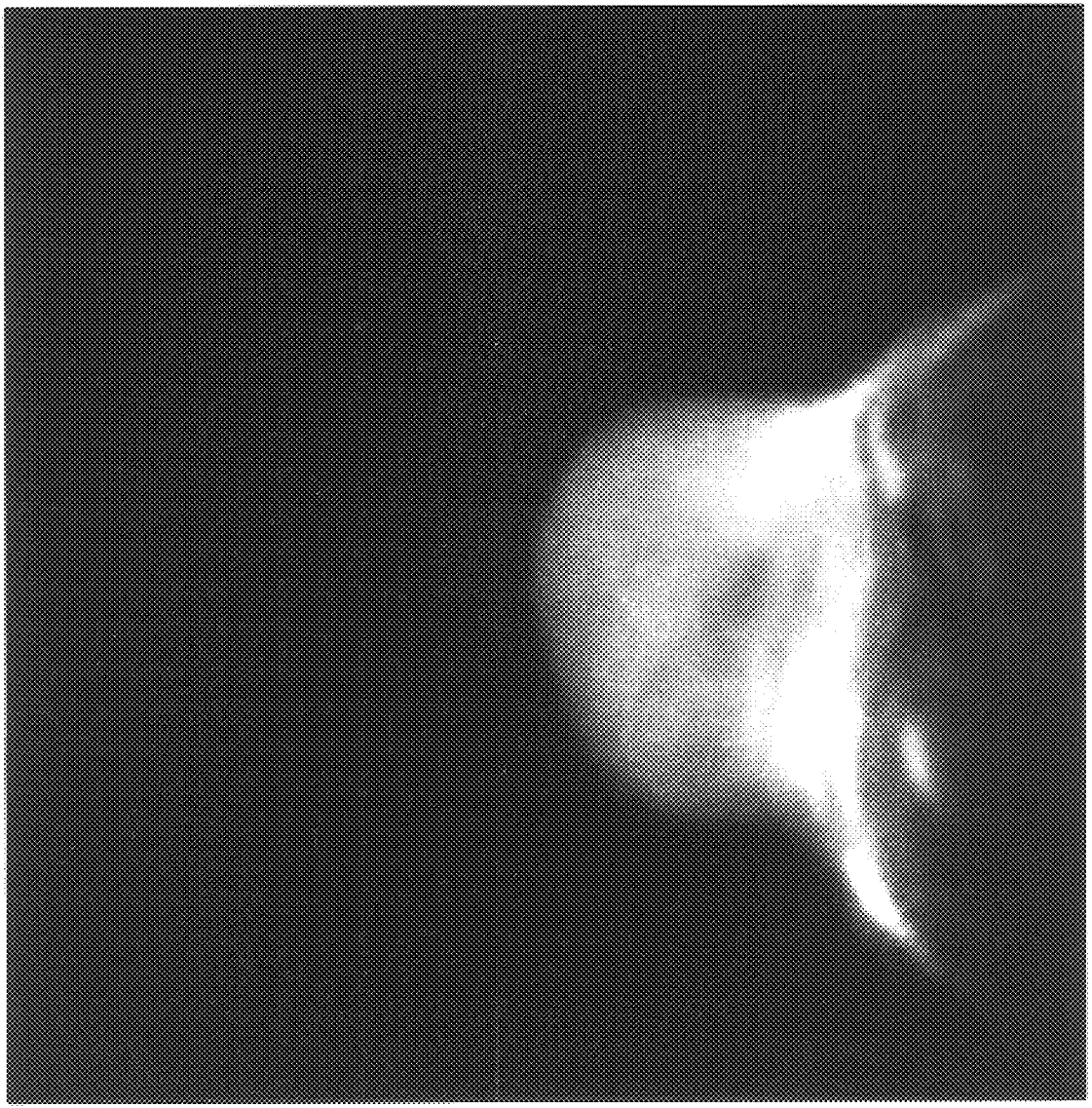

FIG. 12D. Same as FIG. 12C, except 40 MPI. Note the sustained very strong enhancement of Outer Rim with the Central Tumor now also starting to enhance brightly. Also note there is virtually no contrast fading at 40 minutes.

FIG. 13A, FIG. 13B, FIG. 13C, FIG. 13D show MRI 4.7 Tesla, T1-weighted images of Copenhagen rats with the AT-1 prostate tumor model (as in FIG. 12A, FIG. 12B, FIG. 12C and FIG. 12D), but rats are injected i.v. with Gd(III):DTPA-Lys:Dermatan Sulfate Selective Contrast Agent in liquid form pre-concentrated to 0.415 mmol/mL Gd(III) and administered at the usual dose of 0.155 mmol of Gd(III) per Kg.

Figure 13A:
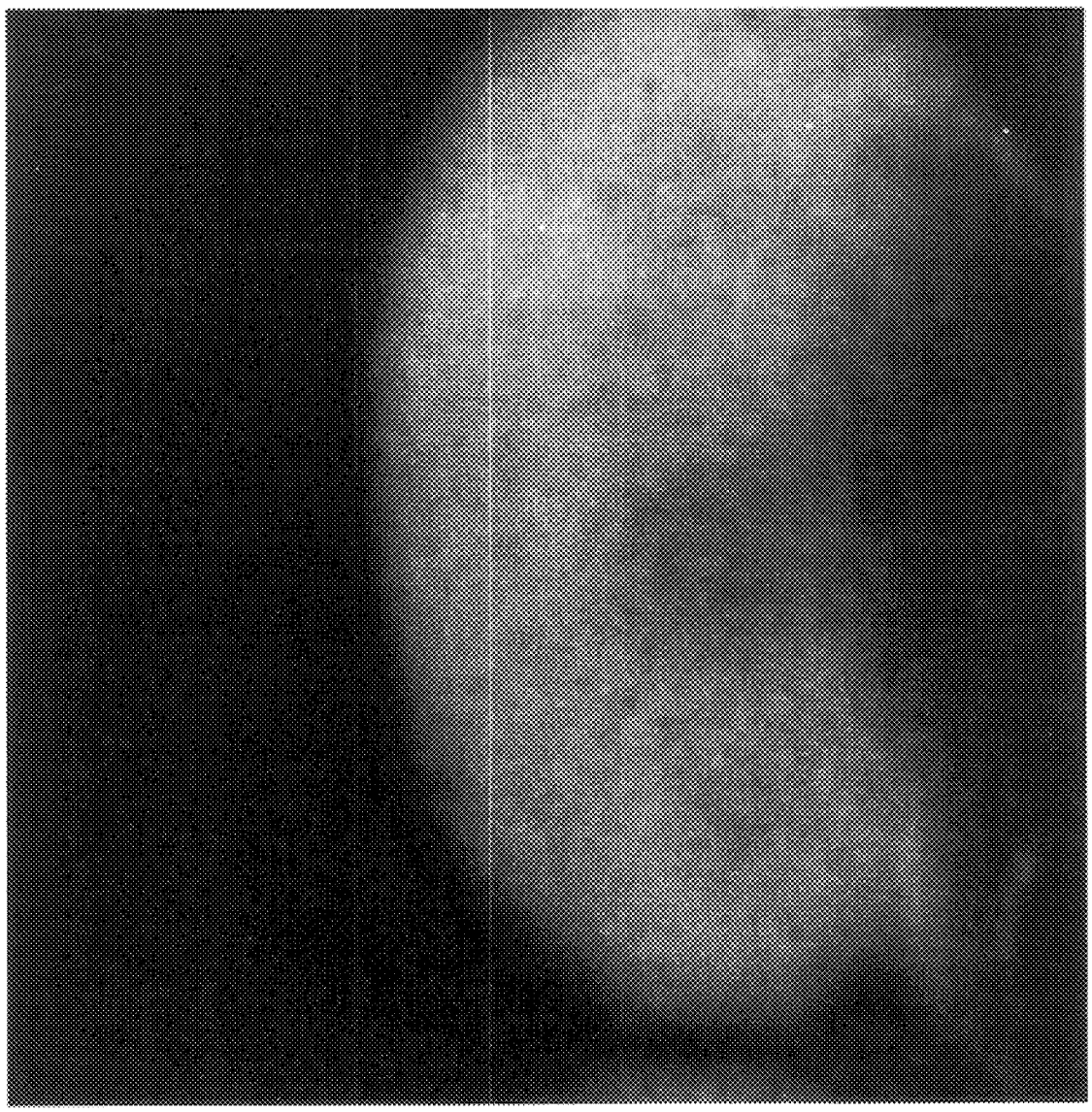

FIG. 13A. Precontrast image for Gd(III):DTPA-Lys:Dermatan Sulfate Selective Contrast Agent.

Figure 13B:

FIG. 13B. 7 MPI of Gd(III):DTPA-Lys:Dermatan Sulfate, at 0.415 mmol/mL. Note the exceedingly strong enhancement of the entire Outer Rim as well as Central Tumor. This is consistent with the higher paramagnetic potency of Gd:DTPA chelate, R1=4.3 [mmol.sec]−1, relative to ferrioxamine chelate, R1=1.5−1.8 [mmol.sec]−1.

Figure 13C:
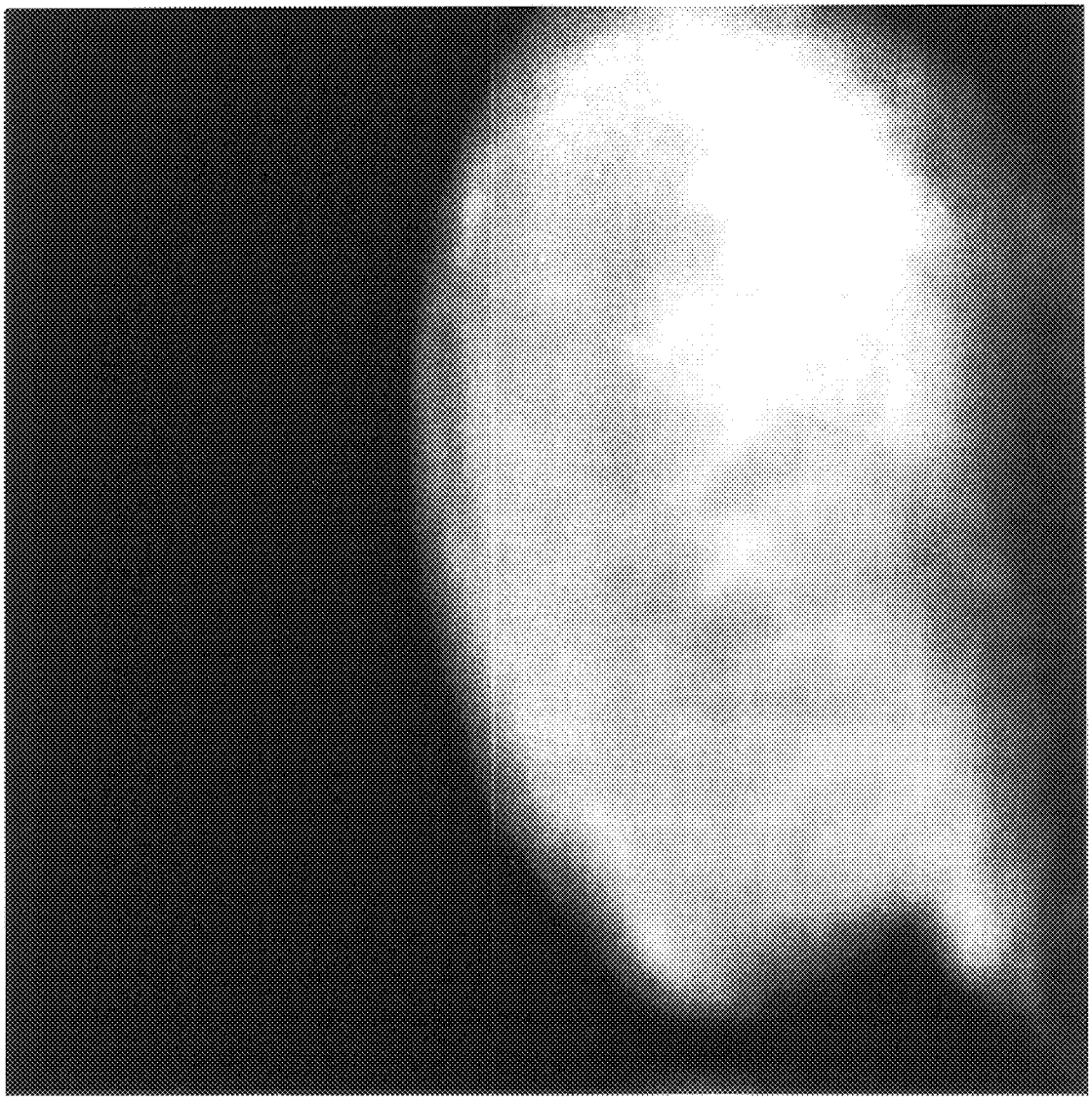

FIG. 13C. Same as FIG. 13B, except 20 MPI. Note the sustained, very strong absolute enhancement Outer Rim. Also note additionally strong enhancement of the central vascular array (as differentiated from cystic sequestration).

Figure 13D:
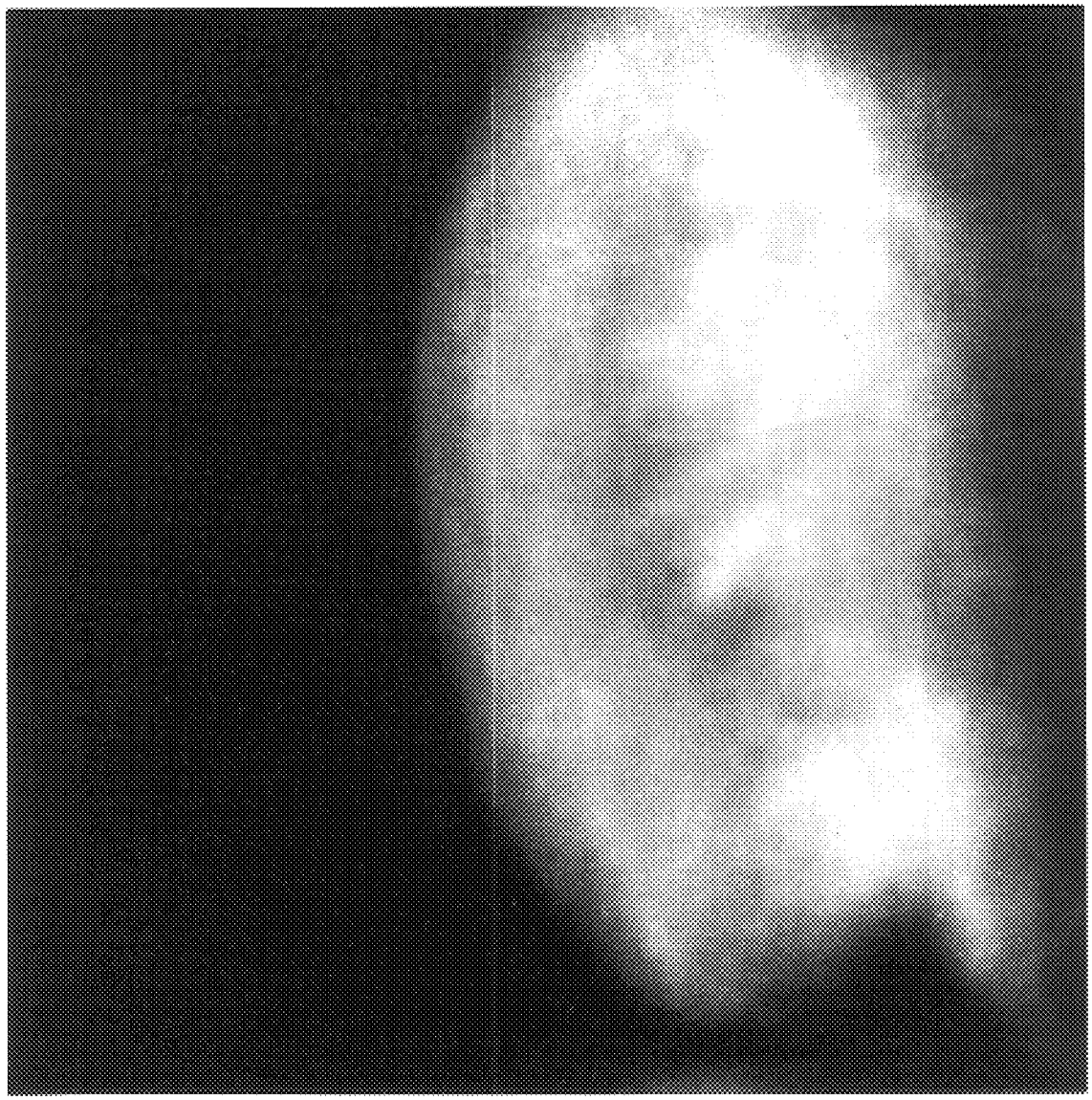

FIG. 13D. Same as FIG. 13C, except 40 MPI. Note sustained enhancement of Outer Rim, with overall enhancement just beginning to fade at 40 minutes, but absolute enhancement remaining as bright or brighter in all regions relative to Ferrioxamine:Dermatan Sulfate.

FIG. 14A, FIG. 14B, FIG. 14C and FIG. 14D show MRI 4.7 Tesla, T1-weighted images of Copenhagen rats with the AT-1 prostate tumor model (as in FIG. 13A, FIG. 13B, FIG. 13C and FIG. 13D), but rats are injected i.v. with Ferrioxamine Selective Contrast Agent, wherein the Active is non-covalently bound to Oversulfated Dermatan Sulfate, the Agent lyophilized and reconstituted with water just prior to administration at a concentration of 0.332 mmol/mL Fe(III) and administered at the usual dose of 0.155 mmol of Fe(III) per Kg.

Figure 14A:
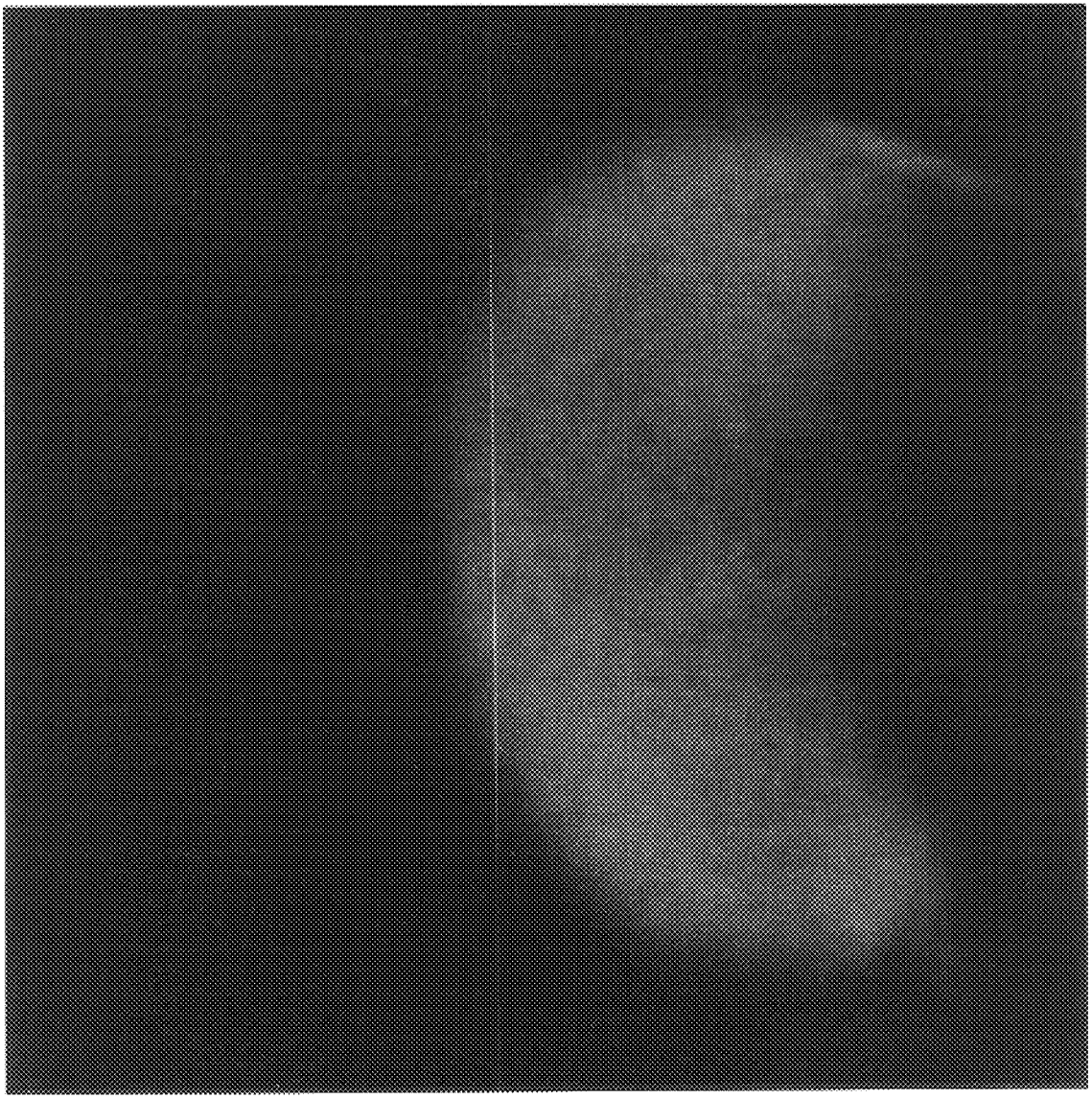
Figure 14B:
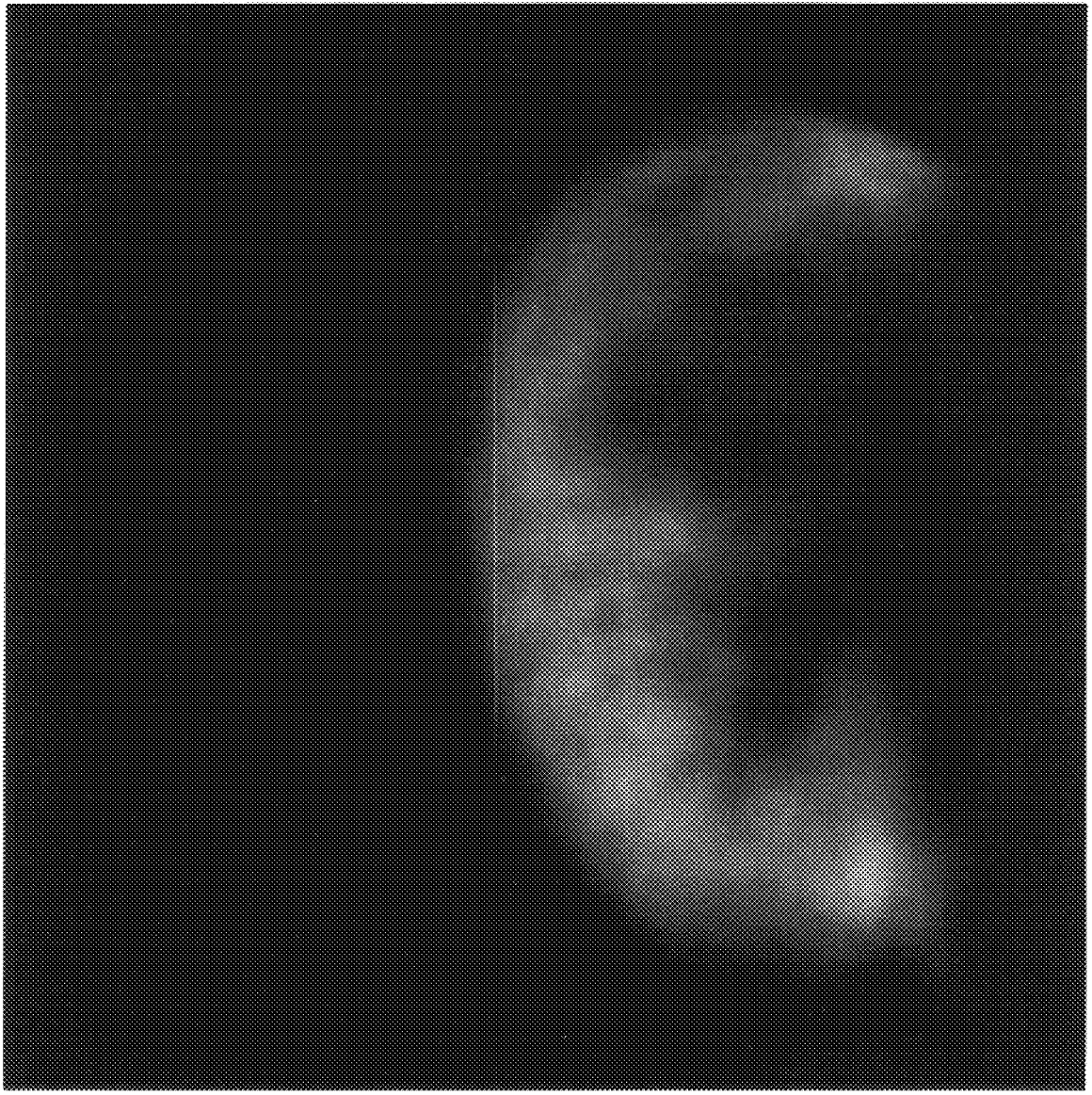
Figure 14C:
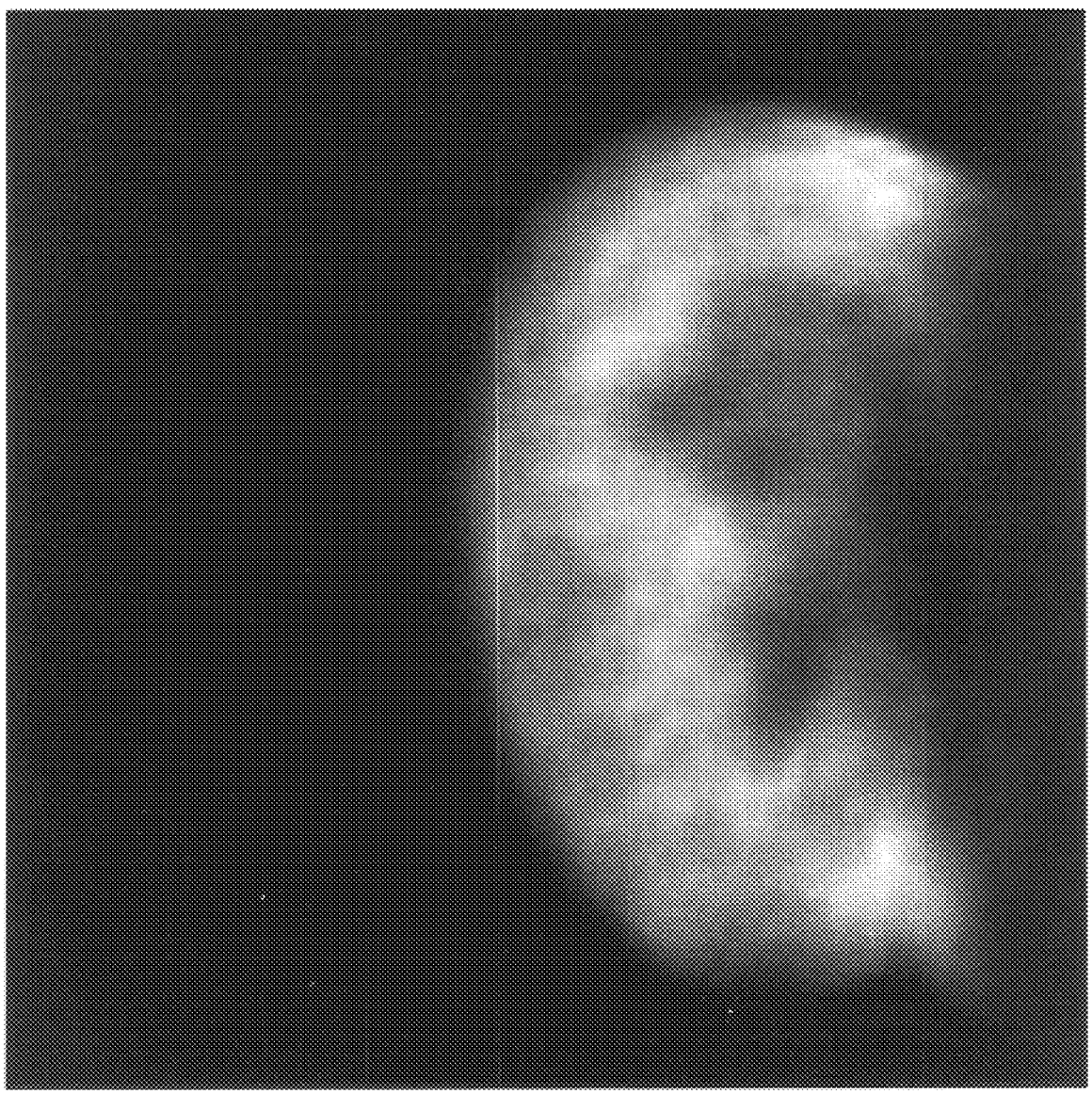

FIG. 14A. Precontrast.

FIG. 14B. 7 MPI.

FIG. 14C. 20 MPI.

Figure 14D:

FIG. 14D. 40 MPI. Note the equivalent to slightly greater enhancement of Tumor Rim and greater definition of the vascular array at all times, in relation to Ferrioxamine bound to Native Dermatan Sulfate (above).

FIG. 15A, FIG. 15B, FIG. 15C and FIG. 15D show MRI 4.7 Tesla, T1-weighted images of Copenhagen rats with the AT-1 prostate tumor model (as in FIG. 13A, FIG. 13B, FIG. 13C and FIG. 13D), but rats are injected i.v. with Ferrioxamine Selective Contrast Agent, wherein the Active is non-covalently bound to Oversulfated Chondroitin Sulfate, the Agent lyophilized and reconstituted with water just prior to administration at a concentration of 0.332 mmol/mL Fe(III) and administered at the usual dose of 0.155 mmol of Fe(III) per Kg.

Figure 15A:
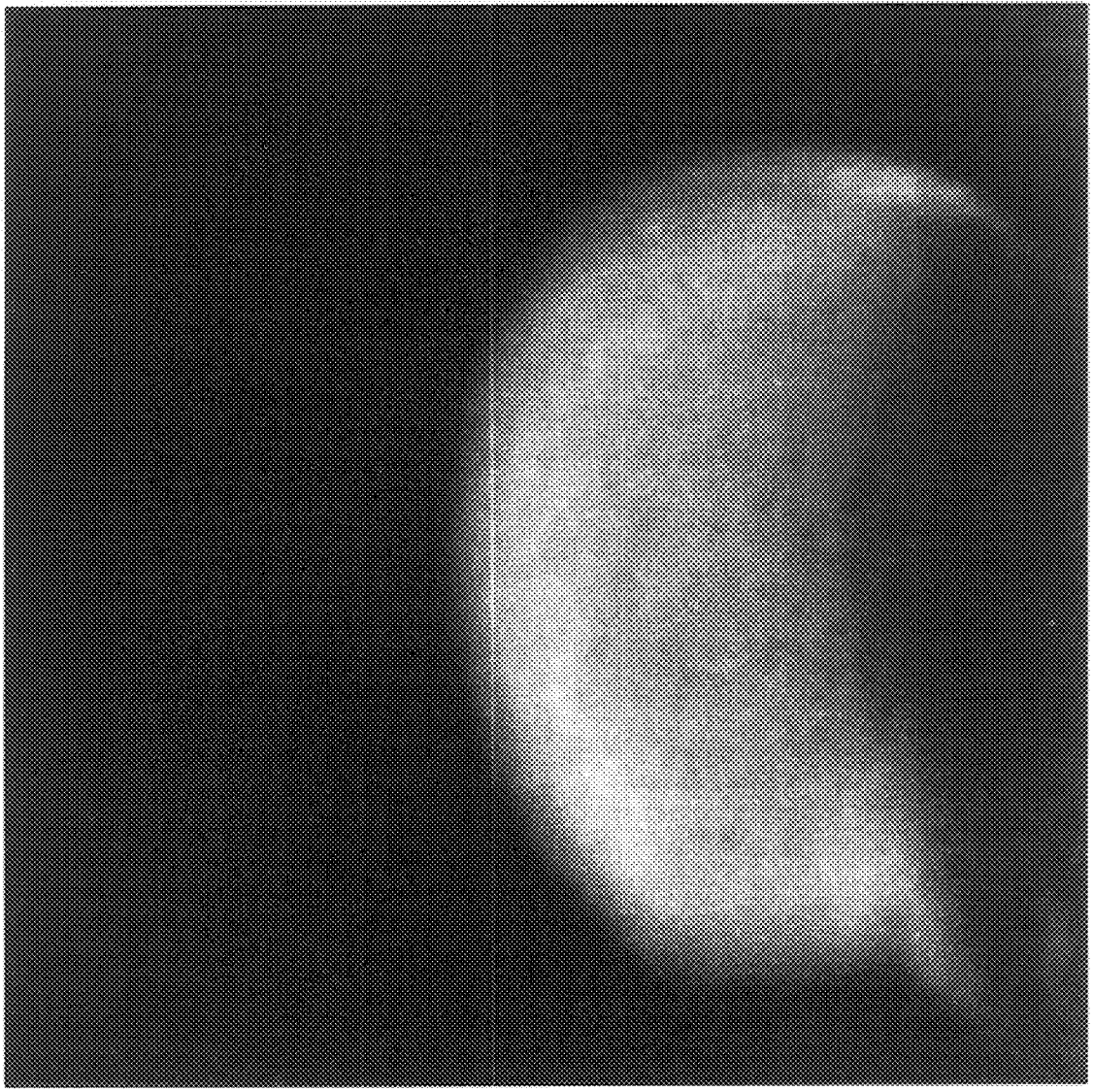
Figure 15B:
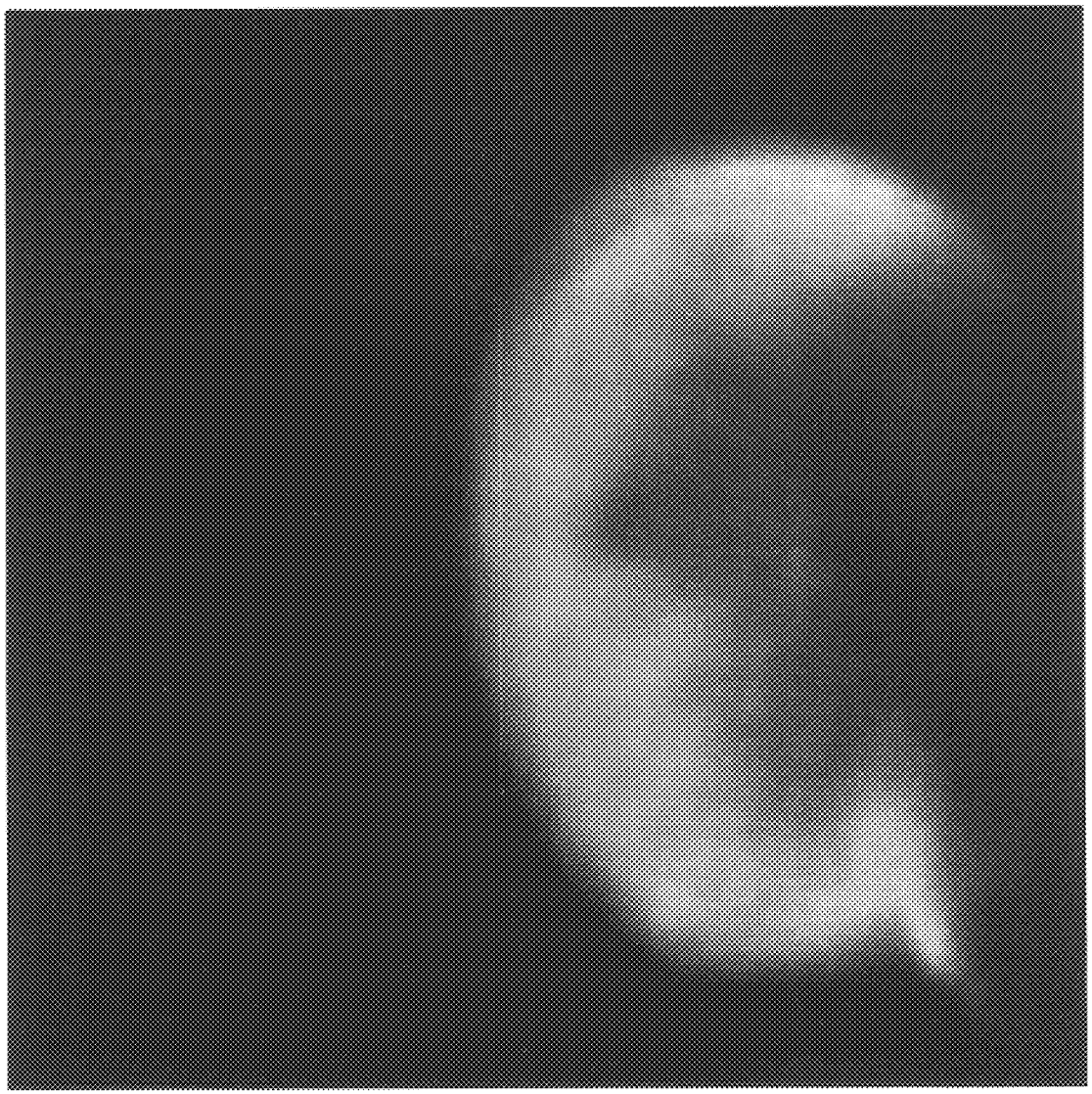
Figure 15C:
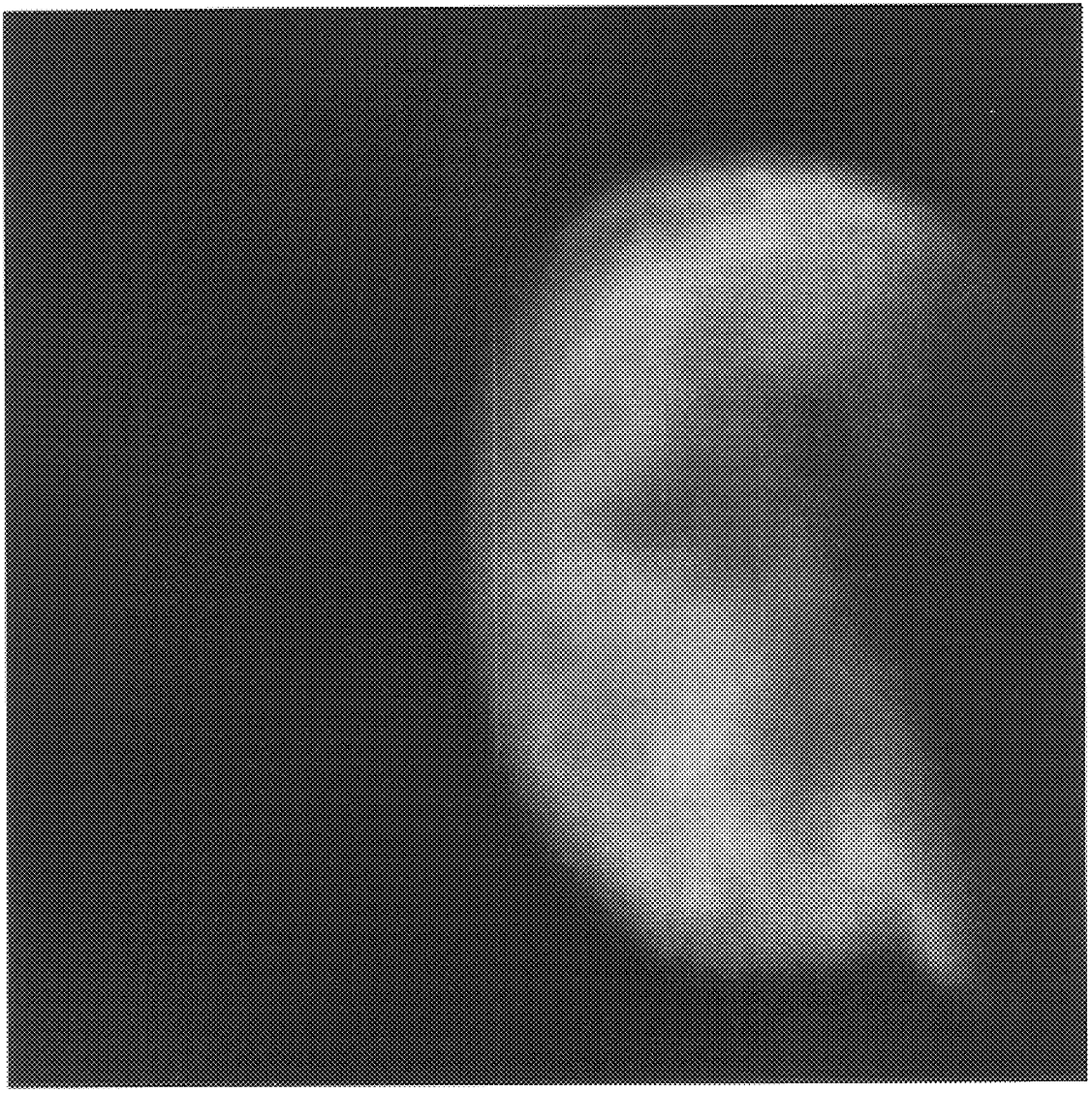

FIG. 15A. Precontrast.

FIG. 15B. 7 MPI.

FIG. 15C. 20 MPI.

Figure 15D:
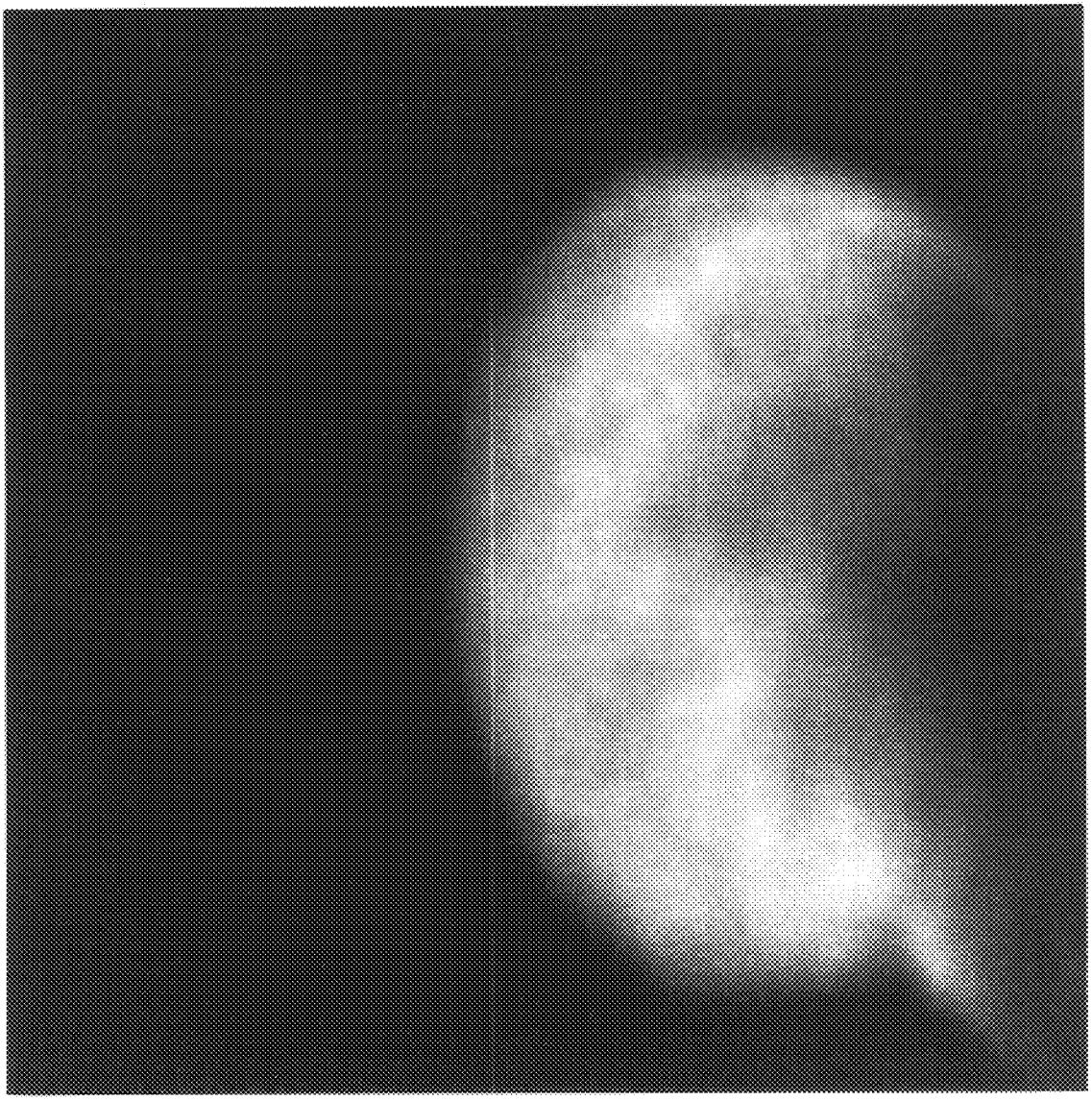

FIG. 15D. 40 MPI. Note the moderately greater enhancement of Tumor Rim and greater definition of the vascular array at 7 MPI, and the only slightly greater enhancement at the two later times, in relation Ferrioxamine bound to Native Dermatan Sulfate (above).

FIG. 16A, FIG. 16B, FIG. 16C and FIG. 16D show MRI 4.7 Tesla, T1-weighted images of Copenhagen rats with the AT-1 prostate tumor model (as in FIG. 13A, FIG. 13B, FIG. 13C and FIG. 13D), but rats are injected i.v. with Ferrioxamine Selective Contrast Agent, wherein the Active is non-covalently bound to a non-anticoagulant GAG, Heparan Sulfate, the Agent lyophilized and reconstituted with water just prior to administration at a concentration of 0.332 mmol/mL Fe(III) and administered at the usual dose of 0.155 mmol of Fe(III) per Kg.

Figure 16A:
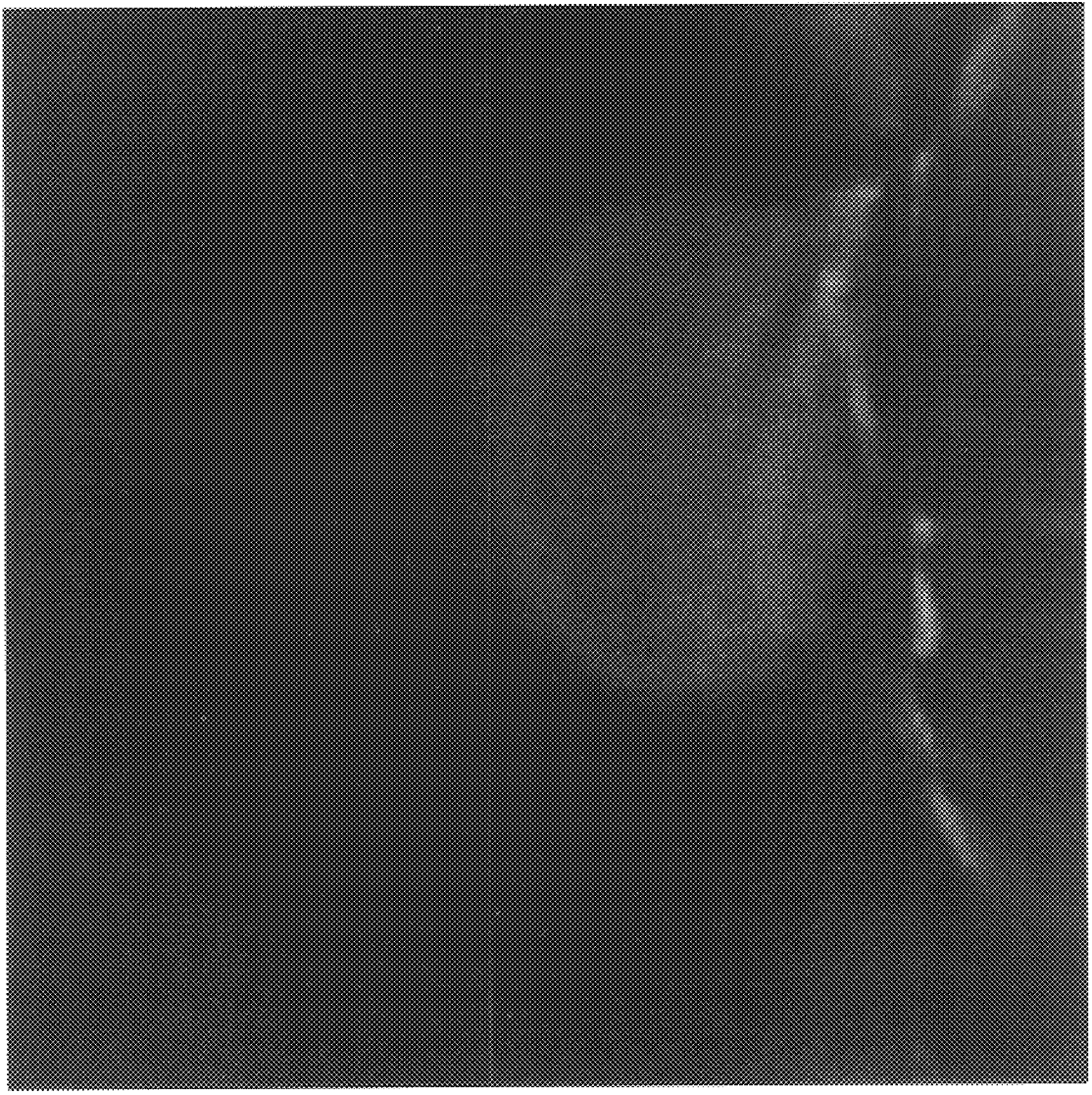
Figure 16B:
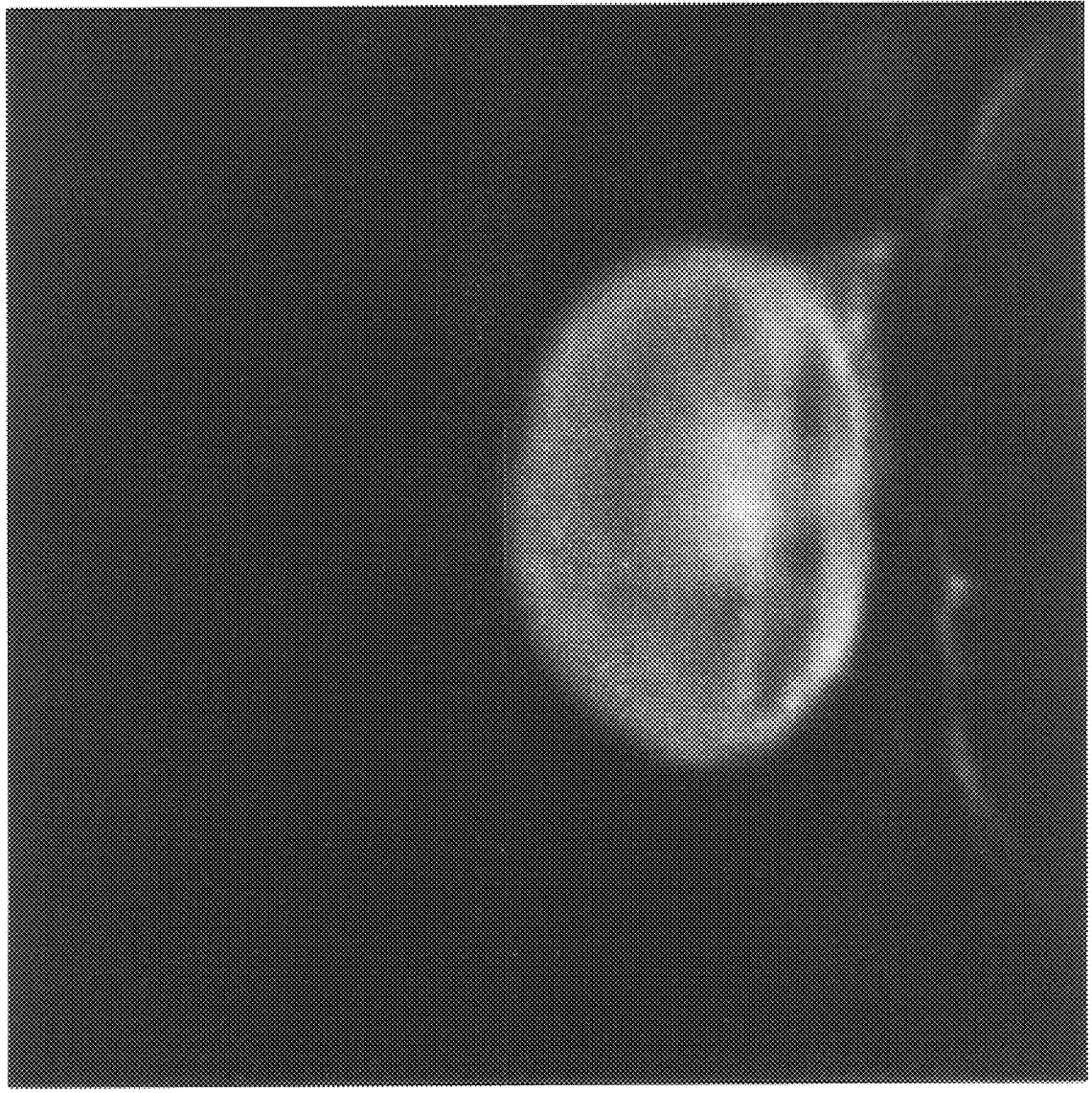
Figure 16C:
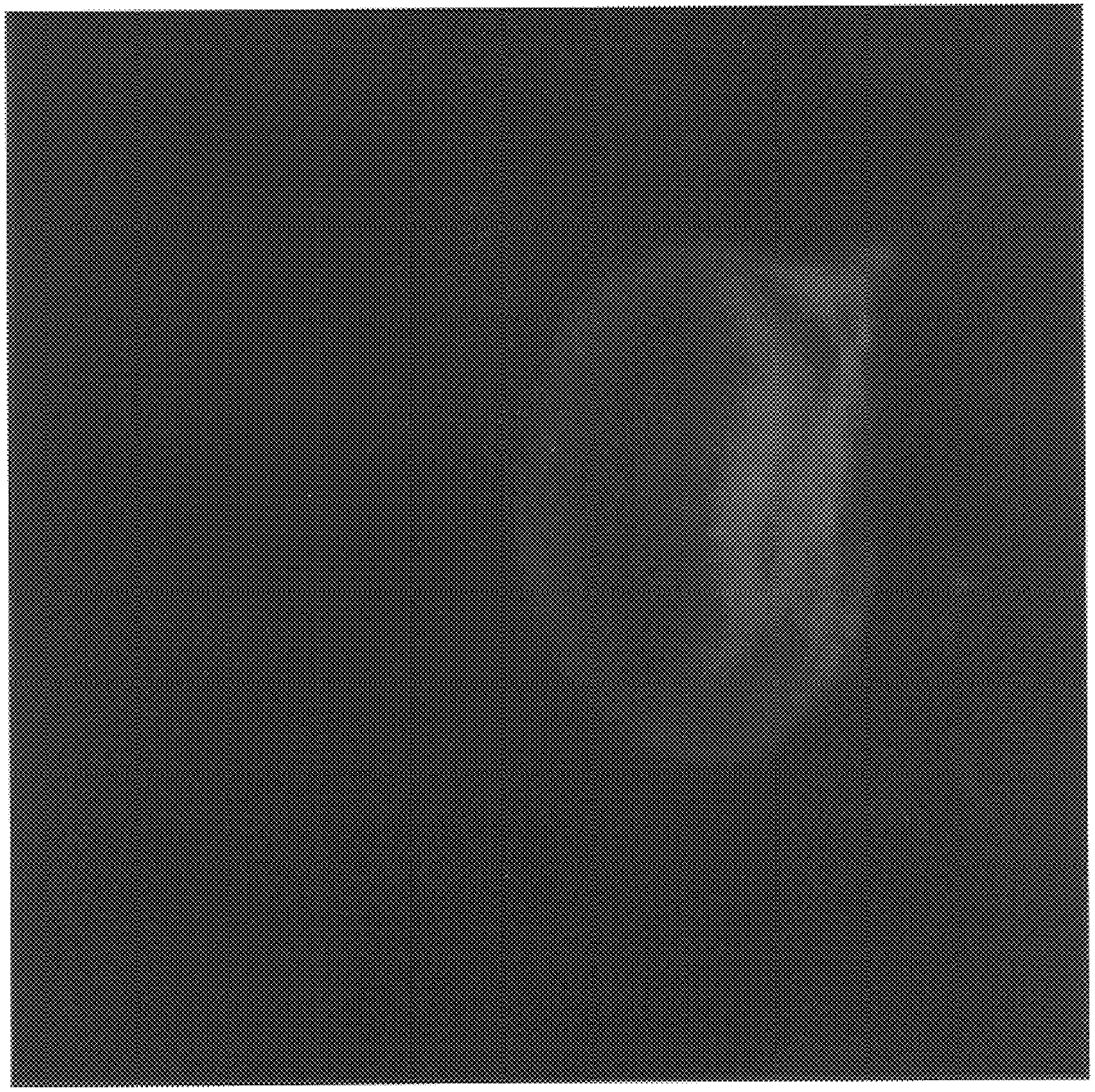

FIG. 16A. Precontrast.

FIG. 16B. 7 MPI.

FIG. 16C. 20 MPI.

Figure 16D:

FIG. 16D. 40 MPI. Note the very homogeneous enhancement of Outer Rim and Central Tumor at virtually all post-contrast times, in relation to the differential Rim enhancement achieved by essentially all of the other GAG carriers. This property may be useful in certain diagnostic and/or therapeutic applications.

Figure 17A:
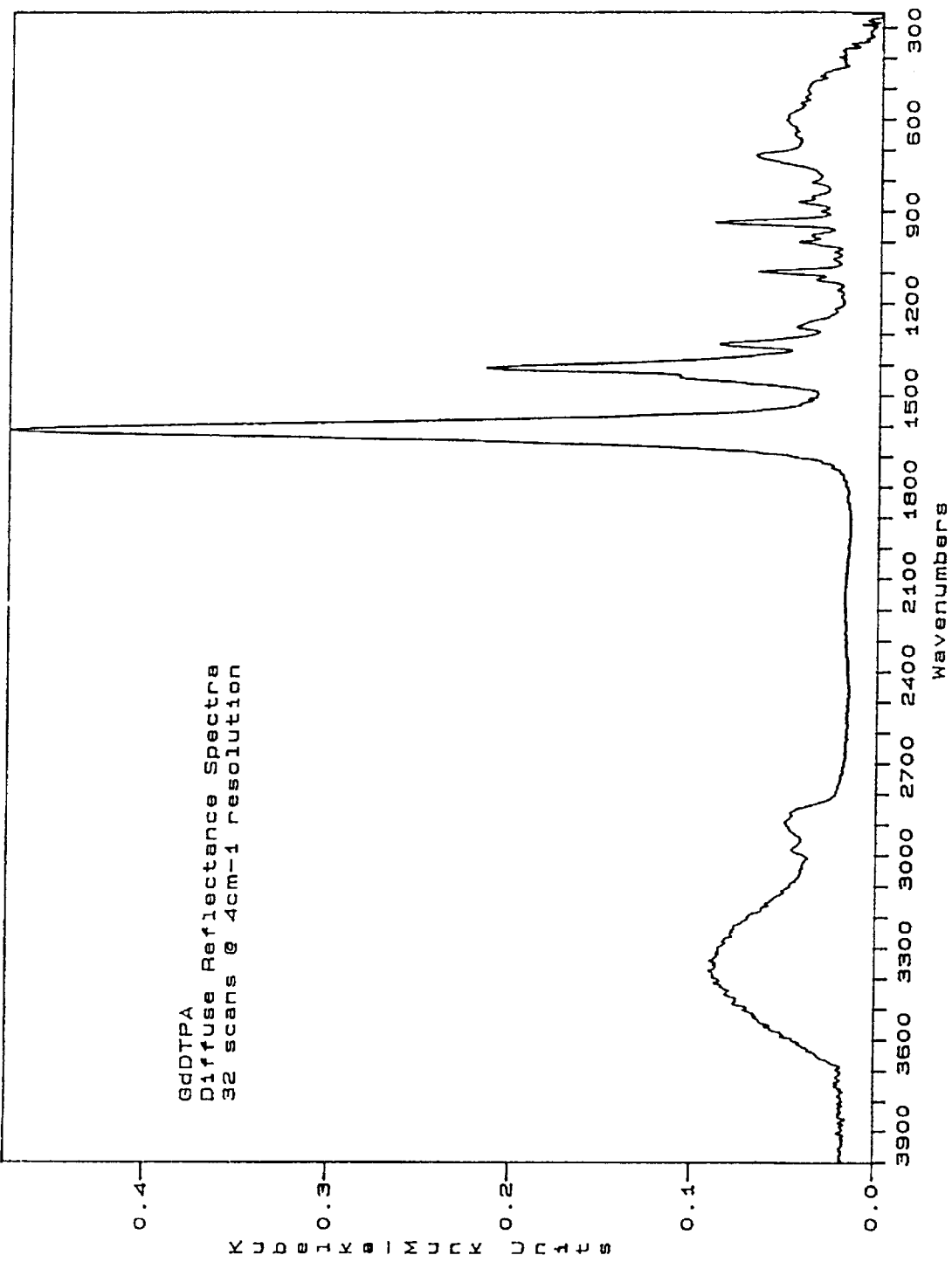

FIG. 17A is a control infrared (IR) spectrum of gadolinium diethylenetriaminepenaacetate (Gd:DTPA) (see Example 21).

Figure 17B:
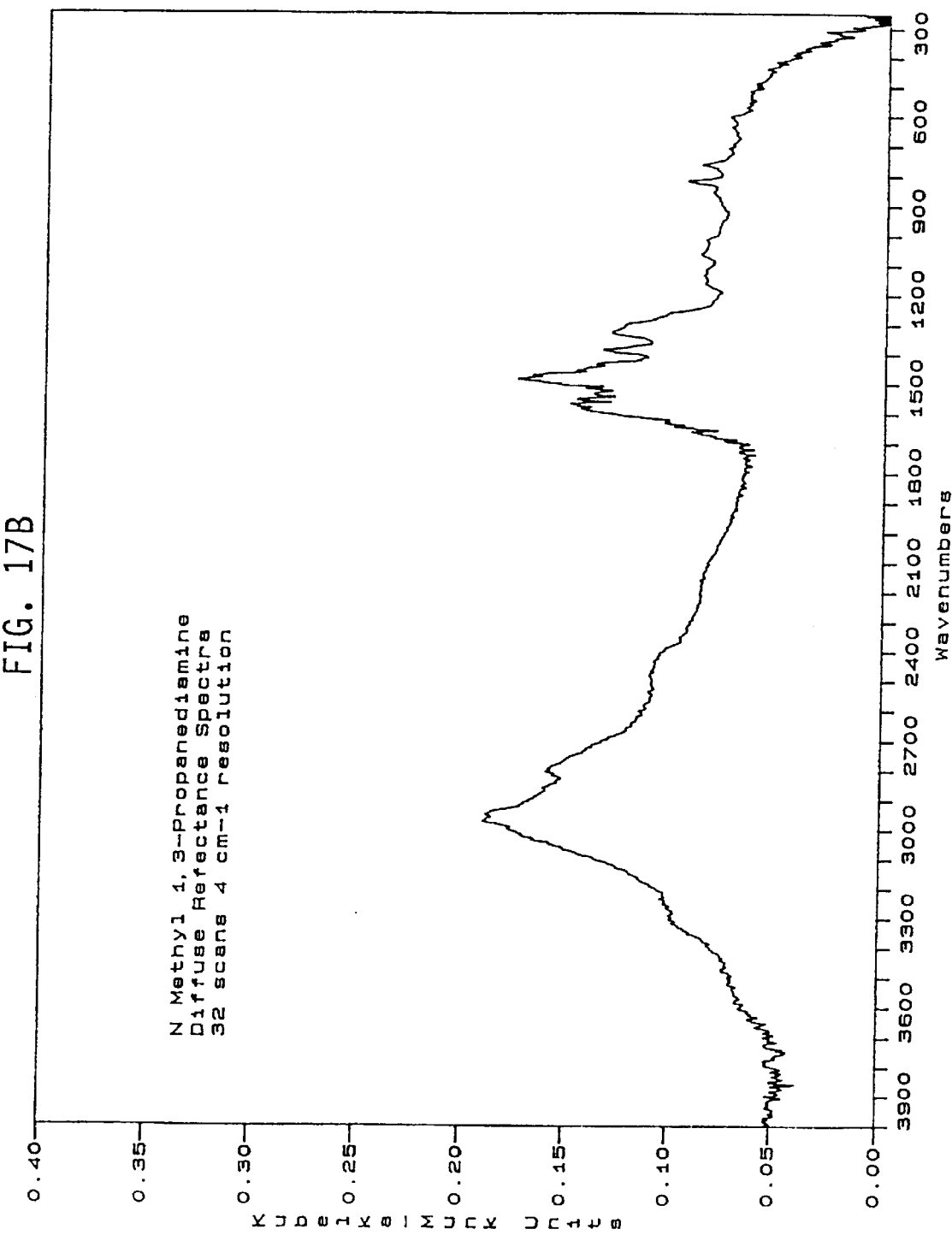

FIG. 17B is a control IR spectrum of N-methyl-1,3-propanediamine (MPD) (see Example 21).

Figure 17C:
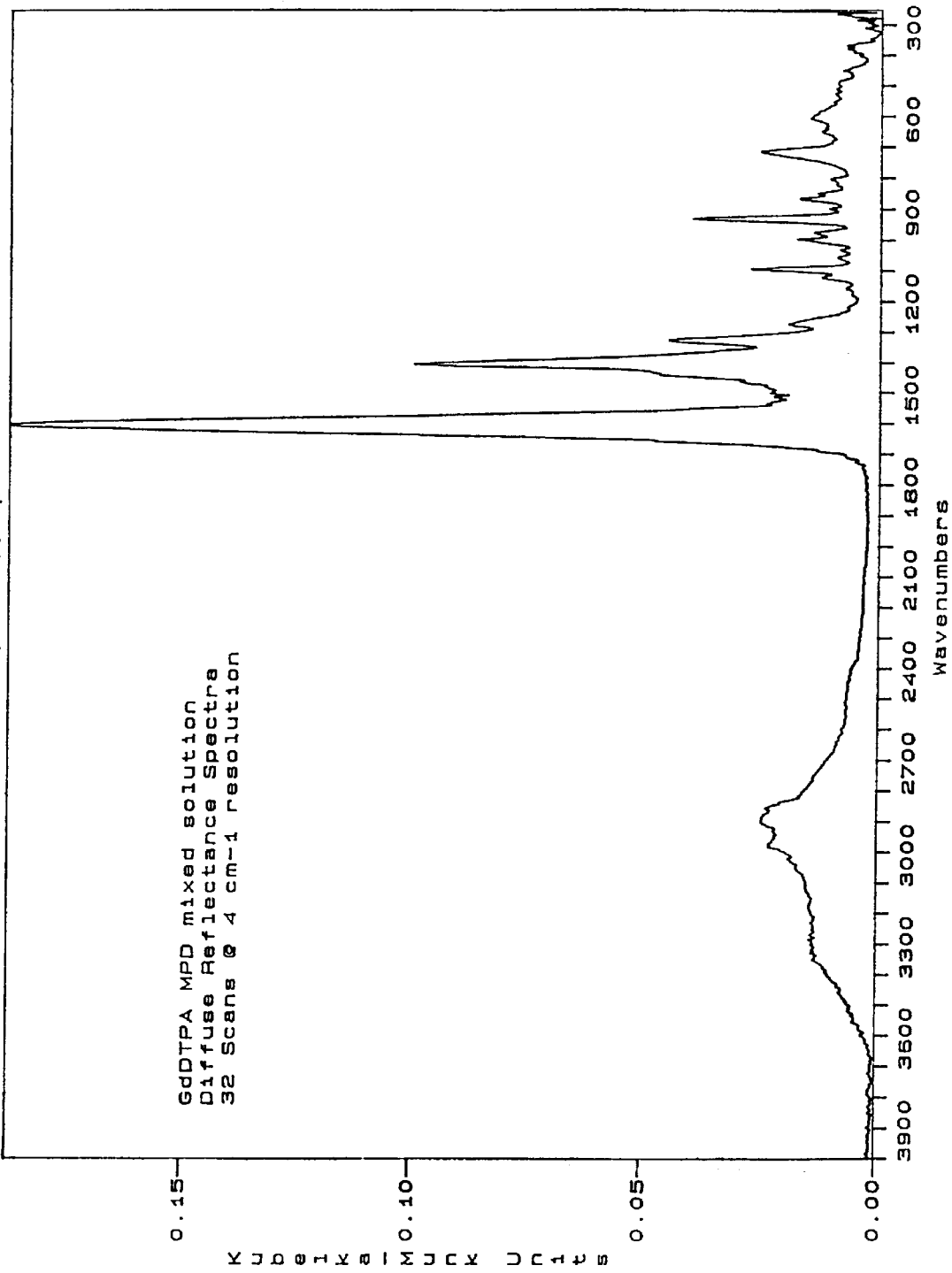

FIG. 17C is a control IR spectrum of a mixed (and dried) solution of the individual chemical components, Gd:DTPA and MPD (1:1 molar ratio).

Figure 17D:
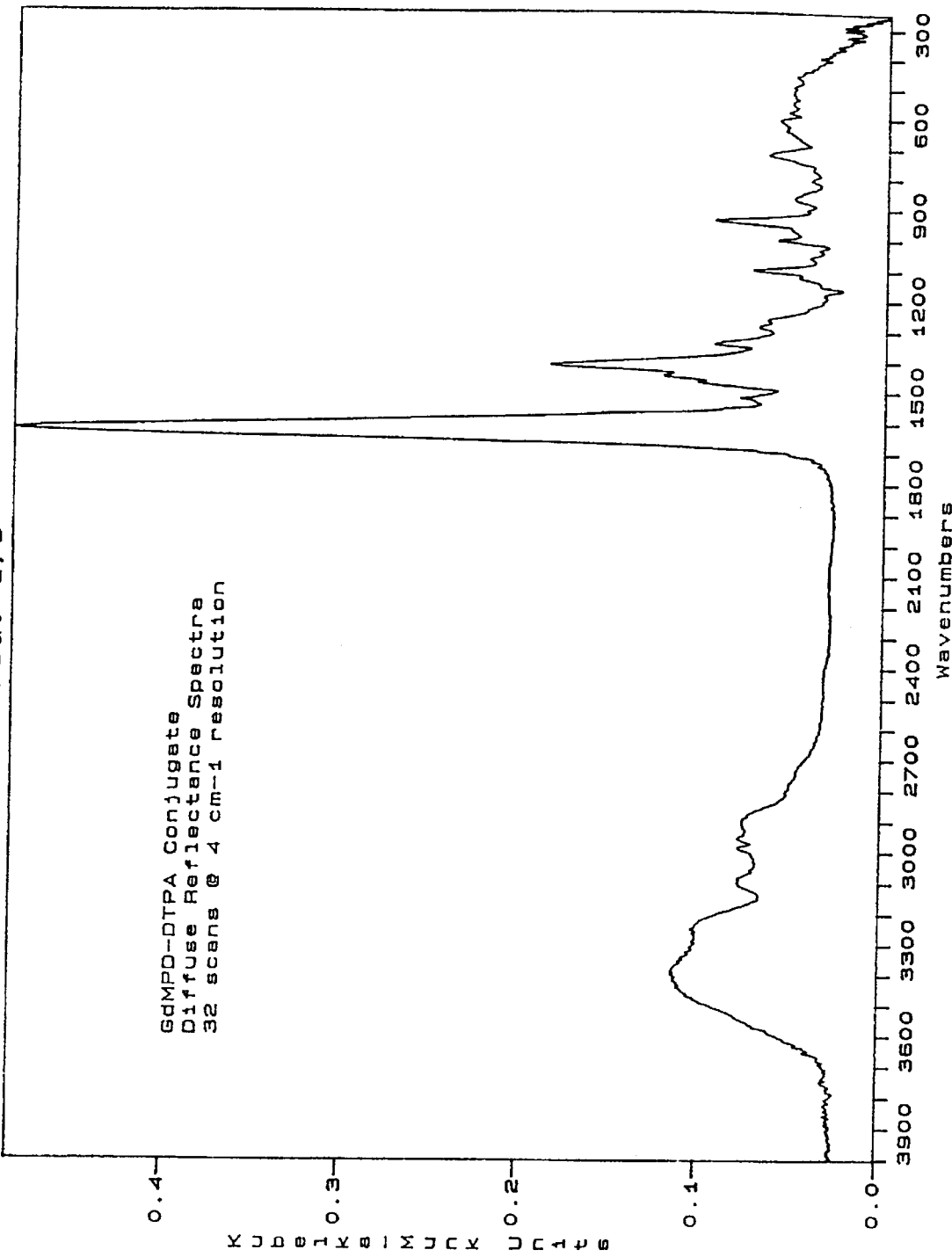

FIG. 17D is the experimental IR spectrum of MPD covalently conjugated at a 1:1 molar ratio to DTPA (as described in Example 21). Note the change in the height and splitting of the signature peak at 1400 wavenumber, and the change in the height and configuration of the broader stretching bands at 3300–3600 wavenumbers, which are indicative of covalent conjugate formation.

Figure 18A:
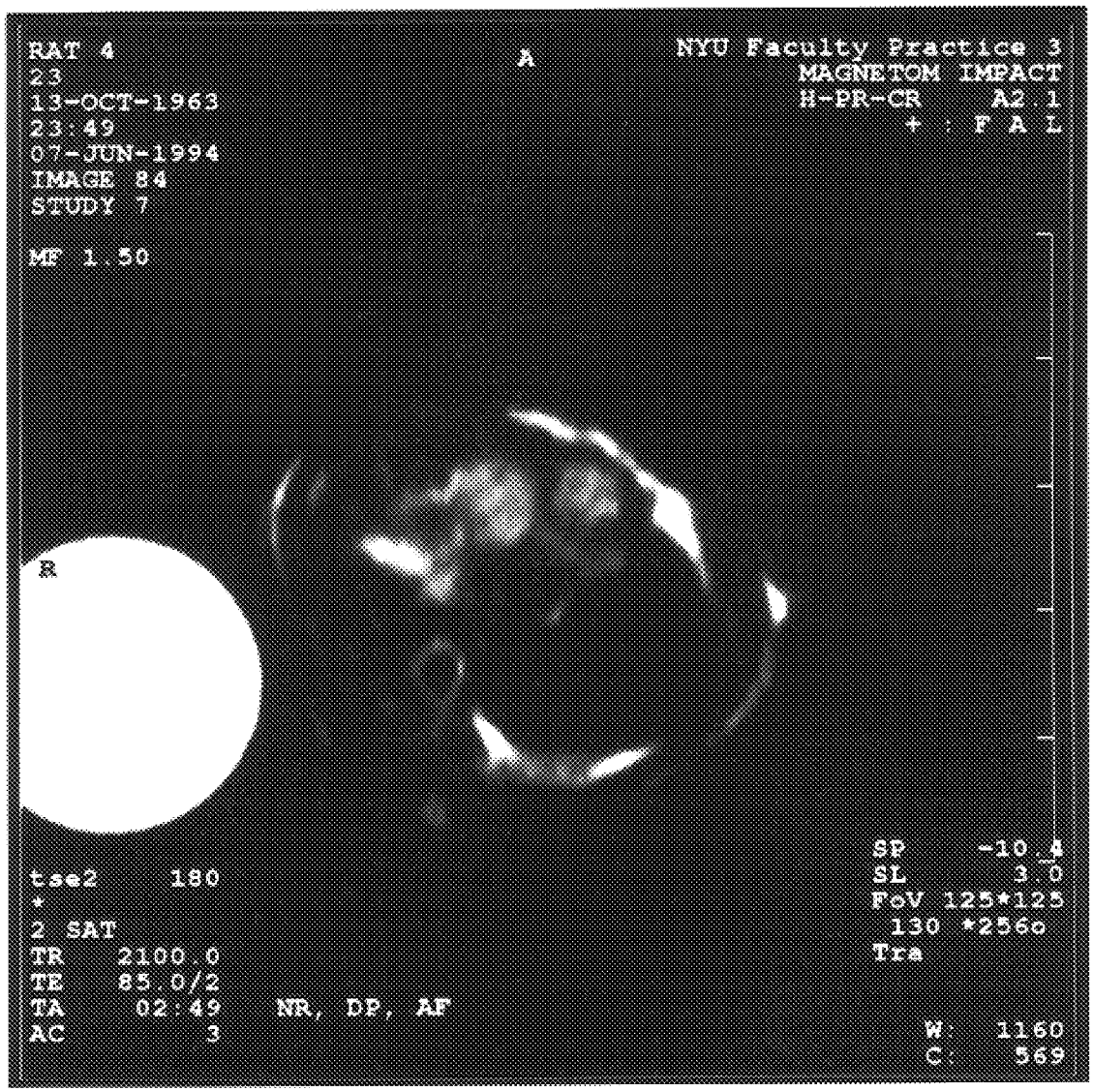

FIG. 18A shows a T2-weighted MRI scout image (TR/RE 2100/85) of the liver regions of Fisher 344 female rats with syngeneic breast adenocarcinomas inoculated previously into the liver, such that tumor diameters at the time of imaging are between 1.0 and 2.5 cm, with the image acquired at 1.0 Tesla, just before performing the T-1 weighted series of images (shown below). This T2 image is performed in order to identify the approximate locations of 2 tumor nodules (right posterior liver) and 1 tumor infiltrate (central liver region), all tumor growths being confirmed at necropsy by gross visual inspection.

FIG. 18B, FIG. 18C, FIG. 18D, FIG. 18E and FIG. 18F show T-1 weighted images (TR/TR=800/45) performed at 1.0 Tesla, before (Precontrast) and at various minutes after intravenous (i.v.) injection (Post-contrast, MPI) of Gd:MPD-DTPA:dermatan sulfate selective contrast agent, prepared as in Examples 21 and 22, and injected per Example 25, at a dose of 0.155 mmol/Kg into Fisher 344 female rats with syngeneic breast adenocarcinomas inoculated previously into the liver, such that the tumor diameters at the time of imaging are between 1.0 and 2.5 cm.

Figure 18B:
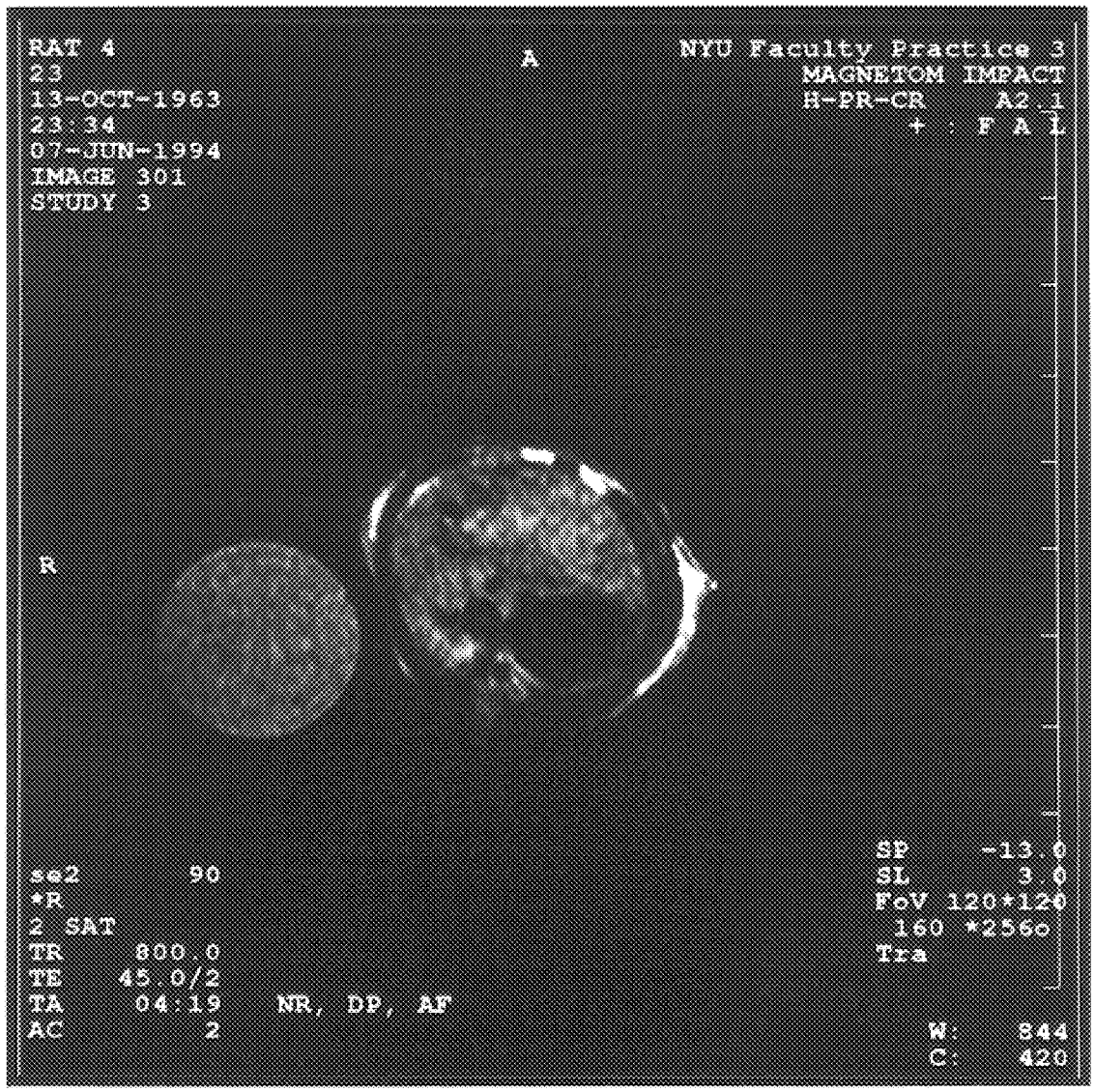

FIG. 18B. T1 Precontrast image of liver (tumor not conspicuous).

Figure 18C:
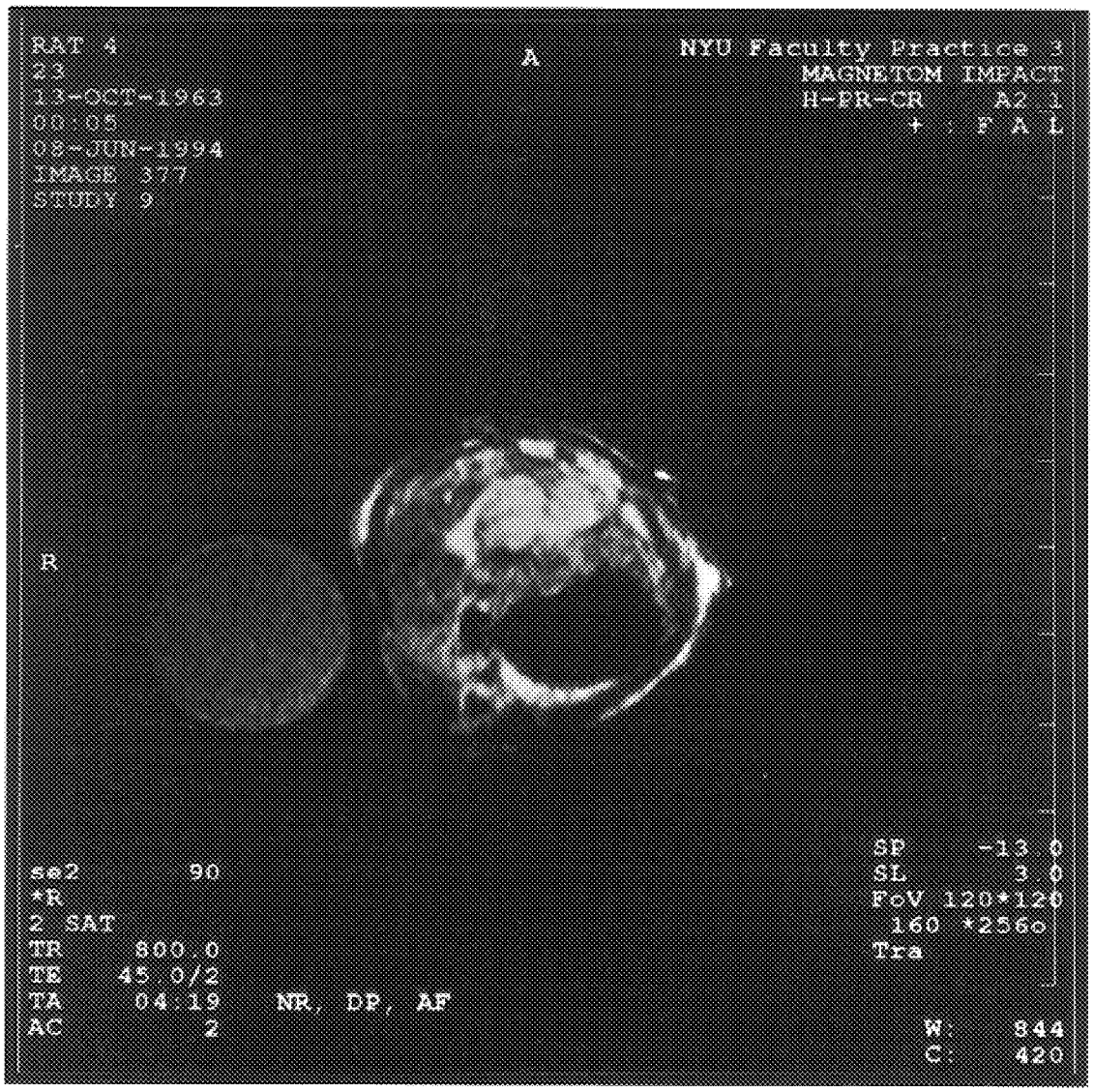

FIG. 18C. T1 liver image a 7 MPI, Gd:MPD-DTPA:dermatan sulfate selective contrast agent (0.155 mmol/Kg), showing extremely strong contrast enhancement of 2 solid tumor nodules (right posterior liver) and 1 irregular tumor infiltrate (central liver region), in the identical locations as those indicated by the T2-weighted scout image (FIG. 18A), but with much better definition of the tumor margins and much higher contrast gradients at the tumor margins. Note the moderately smaller size of tumor nodules and improved definition of the central tumor infiltrate, both due to an absence in the T1 mode of T2 imaging artifacts, namely an additional rim (corona) of water outside the actual tumor margin, which appears in the T2 pulse mode but not in the preferred T1 mode.

Figure 18D:
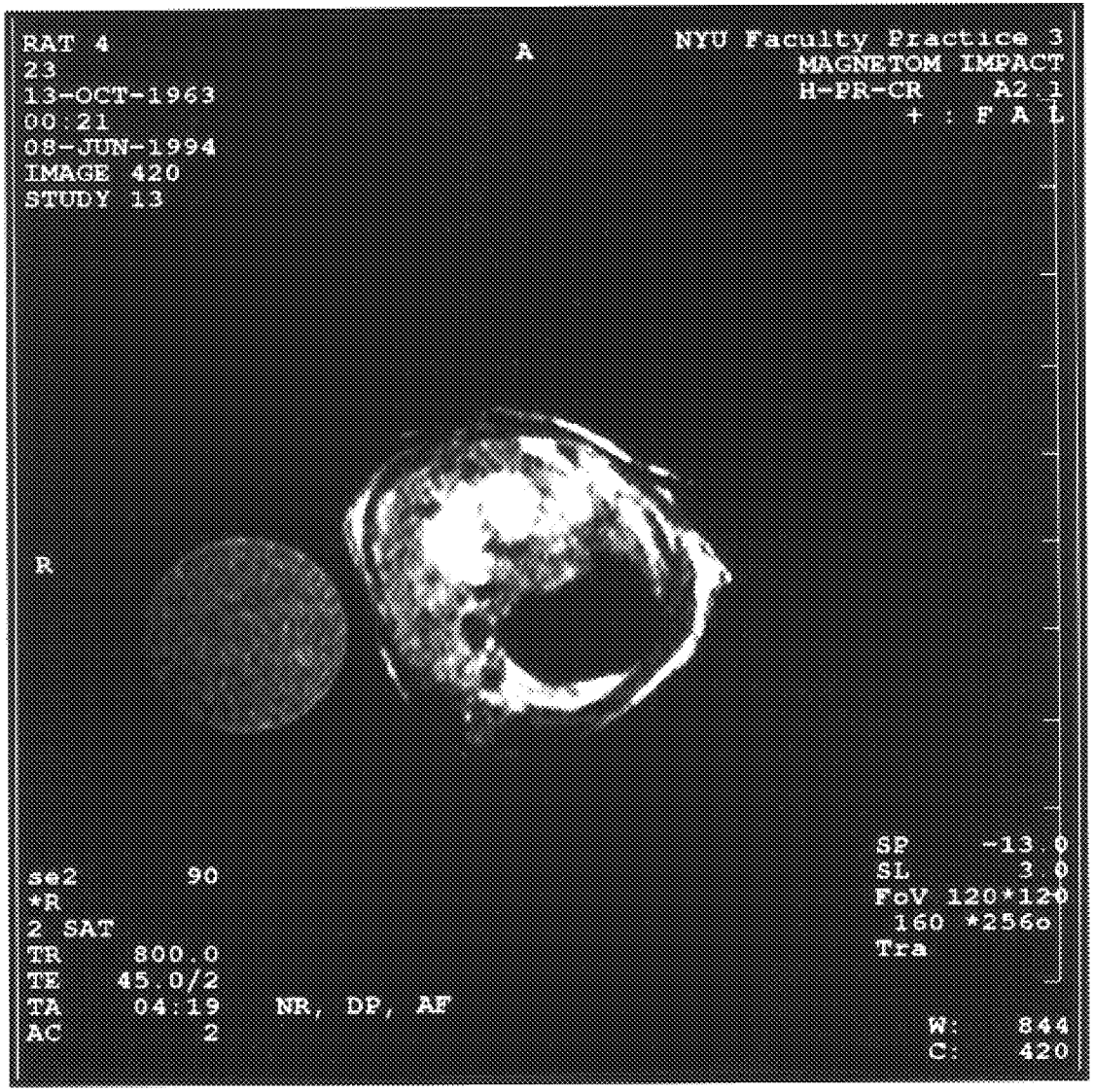
Figure 18E:
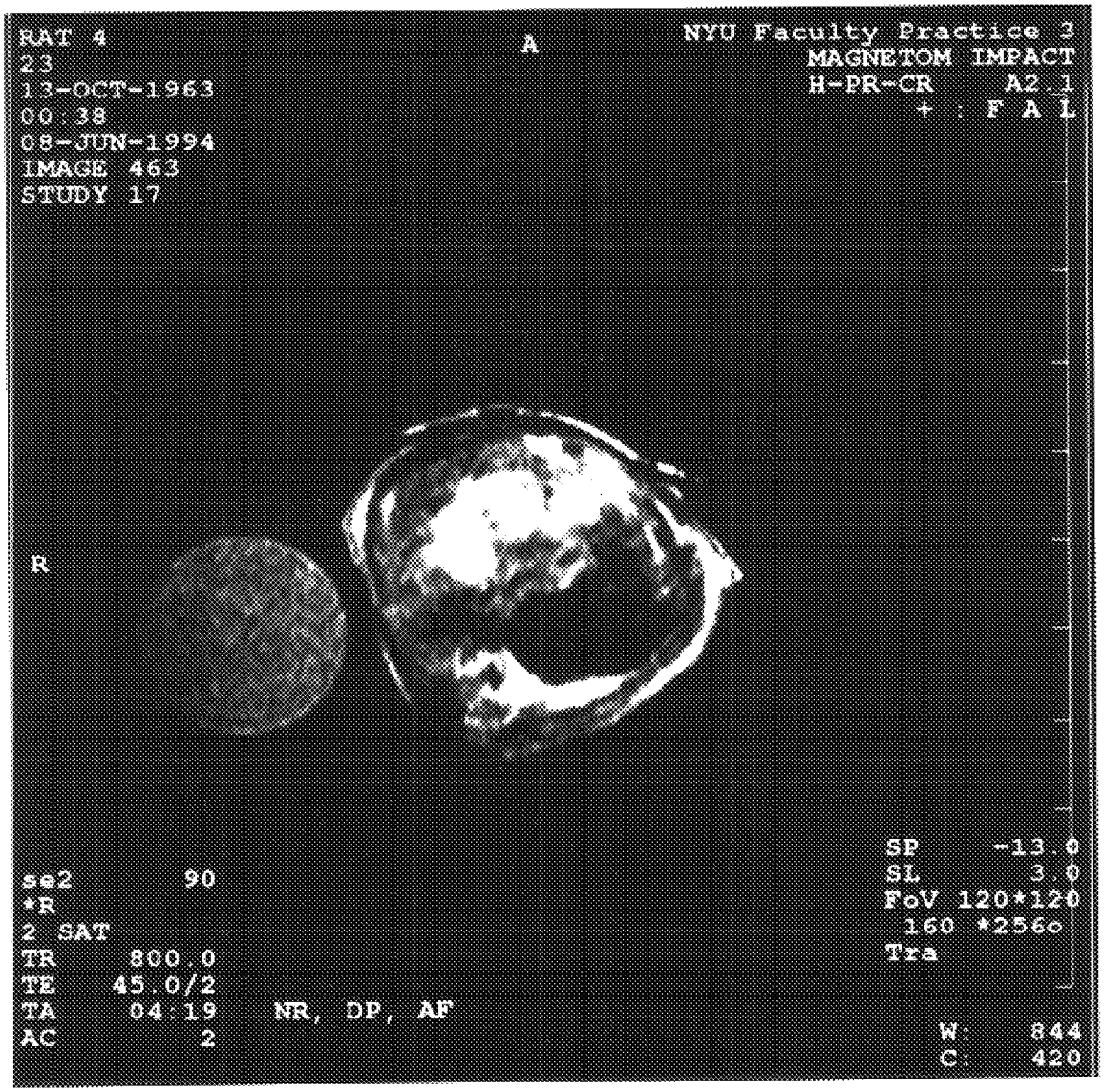

FIG. 18D and FIG. 18E. T1 Liver image at 20 and 40 MPI, Gd:MPD-DTPA:dermatan sulfate selective contrast agent (0.155 mmol/Kg), showing continued very marked contrast enhancement of the 2 solid tumor nodules (right posterior liver) and the 1 irregular tumor infiltrate (central liver region), with continued very highly demarcated tumor margins and essentially no contrast fading.

Figure 18F:
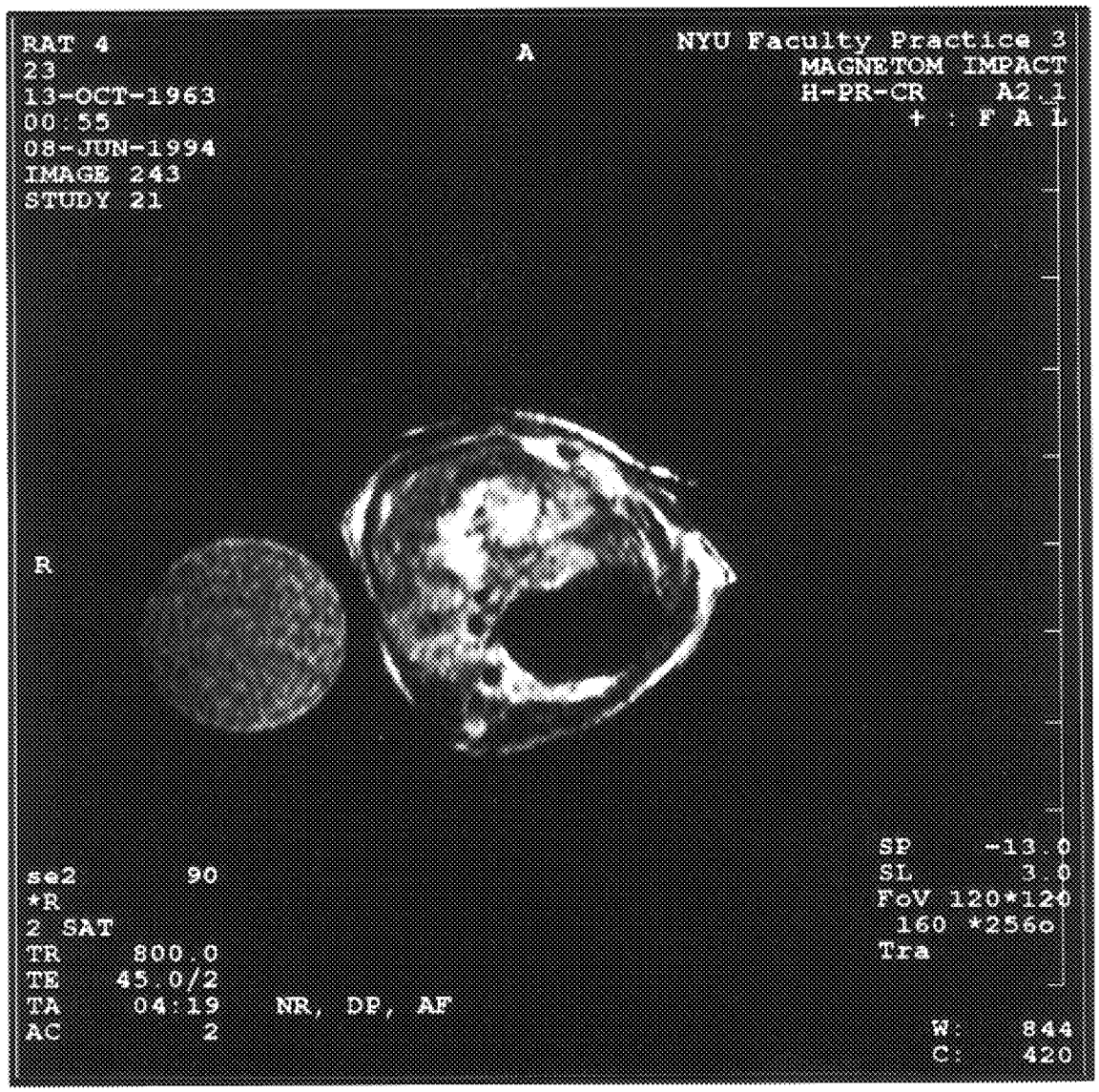

FIG. 18F. T1 Liver image at 20 and 40 MPI, showing continued very marked contrast enhancement of the 2 solid tumor nodules (right posterior liver) and 1 irregular tumor infiltrate (central liver region), with only a very slight degradation in the sharpness of tumor margins over 40 MPI, only a very minimal decrease (fading) of tumor contrast intensity in the 2 solid nodules (right posterior liver), a further brightening of the tumor infiltrate (central liver region), and a very slight background brightening of surrounding uninvolved liver.

FIG. 19A, FIG. 19B, FIG. 19C, FIG. 19D and FIG. 19E show T1-weighted images at 4.7 Tesla (TR/TE=250/8) of Copenhagen rats with syngeneic AT-1 prostate adenocarcinomas inoculated into previously prepared skin pouches [Hahn et al. (1993)], and imaged at diameters of 1.0–2.5 cm.

Figure 19A:
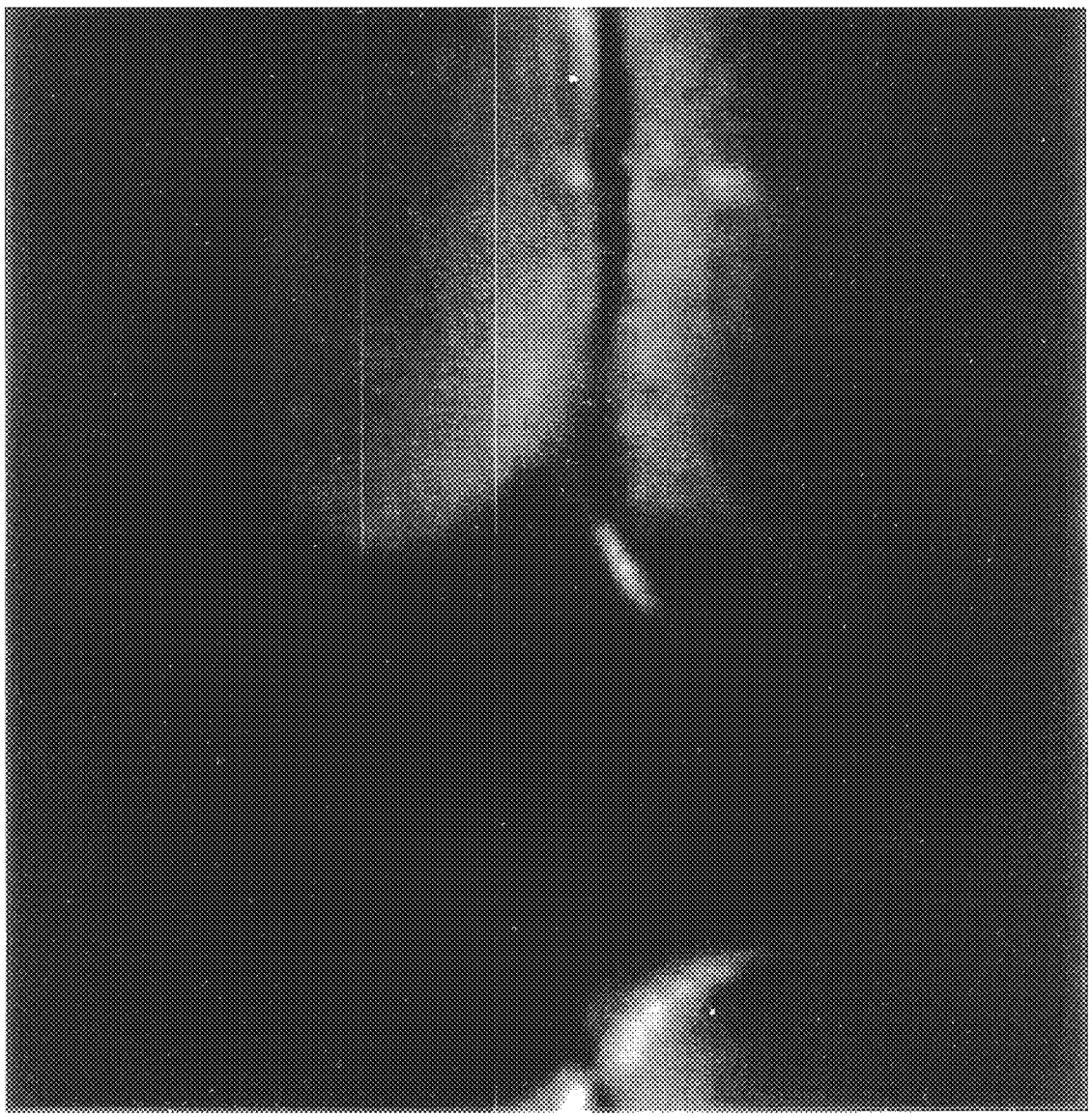

FIG. 19A. Precontrast image for Gd:MPD-DTPA:dermatan sulfate selective contrast agent, showing only the tumor and superficial back fat and back muscle, because a surface coil is used and not a whole body coil.

Figure 19B:

FIG. 19B. Post-contrast image, 7 MPI i.v. of Gd:MPD-DTPA:dermatan sulfate selective contrast agent, liquid form. Note the extremely strong enhancement of the entire tumor mass and the extremely strong gradient at the boundary between tumor and underlying normal tissue (image right).

Figure 19C:

FIG. 19C. Post-contrast image, 20 MPI i.v. of Gd:MPD-DTPA:dermatan sulfate selective contrast agent, liquid form. Note the extremely strong enhancement of the entire tumor mass and the extremely strong contrast gradient at the boundary between tumor and underlying normal tissue. Contrast has decreased slightly in the central tumor region, such that the tumor neovascular array is now very well visualized.

Figure 19D:
Figure 19E:

FIG. 19D and FIG. 19E. Post-contrast image, 40 and 60 MPI, of Gd:MPD-DTPA:dermatan sulfate selective contrast agent, liquid form. Note the still very strong enhancement of the tumor, and particularly the retention of an extremely strong contrast gradient at the boundary between tumor and underlying tissue. Contrast intensity in the central tumor and outer rim (image left, away from the animal) has decreased moderately, apparently due to progressive tumor accumulation in these regions, of such a high local concentration of the highly potent Gd:MPD-DTPA:dermatan sulfate [R1=7.8 (mmol.sec)$^{-1}$], that T2* effects are starting to produce competitive darkening of the central and outer tumor regions (image left; see also Example 26). The basal rim (image right), is relatively protected from this T2* darkening artifact, due to more rapid backdiffusion of the agent into plasma at this basal site. Hence, moderately lower doses are indicated.

Figure 20:
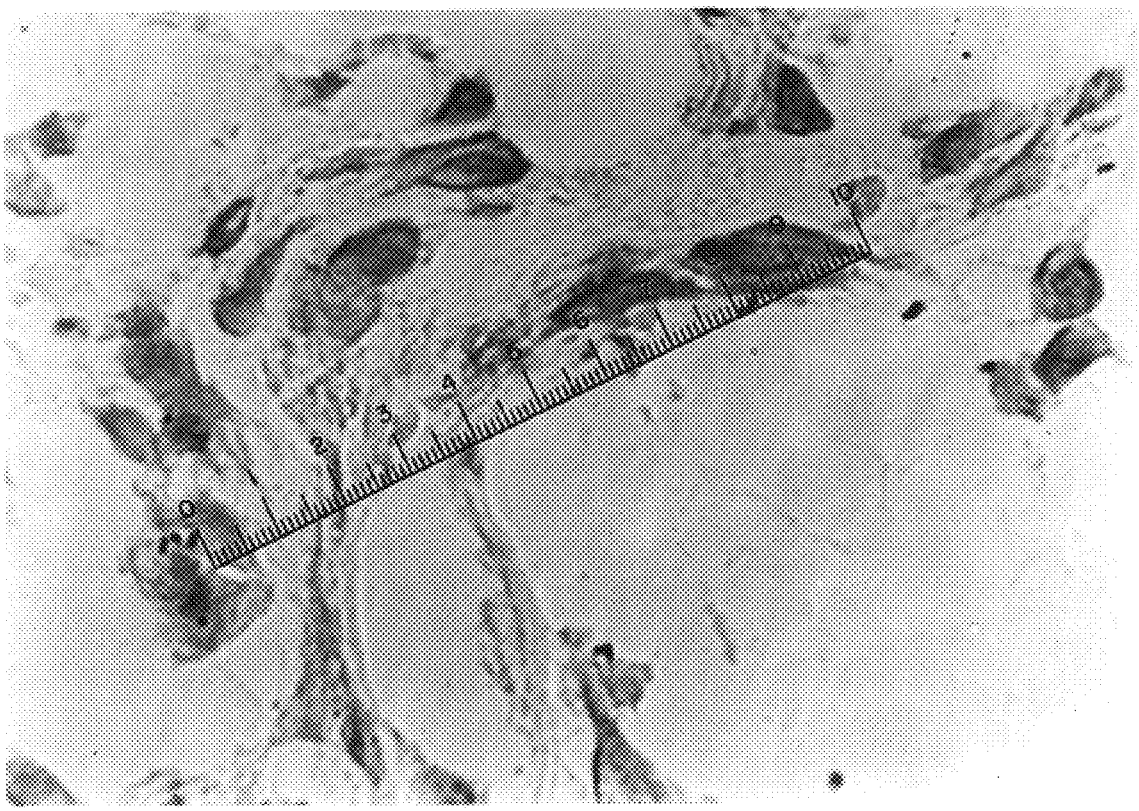

FIG. 20 shows a special histochemical stain (microwave augmented Prussian blue metal-ion stain) of AT-1 prostate adenocarcinoma (from Copenhagen rat), with the tumor tissue removed at 60 MPI just following the completion of MRI imaging, freshly frozen, sectioned and stained as above and as in Example 26 and FIG. 6 and FIG. 7. Note the selective staining positive for Gd(III) metal ion as follows: (a) very strongly positive within almost all tumor cells (tumor intracellular sites); (b) strongly positive at tumor-cell nuclei—for many but not all tumor cells (e.g., see tumor cells underlying grid marker "9" and directly to the left of grid marker "10" at image left); (c) moderately positive neovascular endothelial cells (e.g., see directly above grid marker "8" at image top—appearing as "railroad tracks": and directly under grid marker "2"); and (d) weakly positive to negative in subendothelial and extracellular matrix sites (=the spaces between tumor cells and endothelial ribbons). The low 60-minute staining of extracellular matrix may result from either or both of: (a) a more diffuse distribution of metal ions at 60 minutes (versus 7 minutes in FIG. 6 and FIG. 7A), diffuse metal ions being more difficult to visualize (due to their smaller optical staining niduses); or (b) plasma backdiffusion of a portion of the initially localized metal. These findings of metal-ion positivity in tumor endothelium, tumor matrix, tumor cells proper and tumor-cell nuclei, provide the basis for selectively localizing MRI and radionuclide diagnostic and therapeutic agents, and indeed, other types of active substances.

Figure 21A:
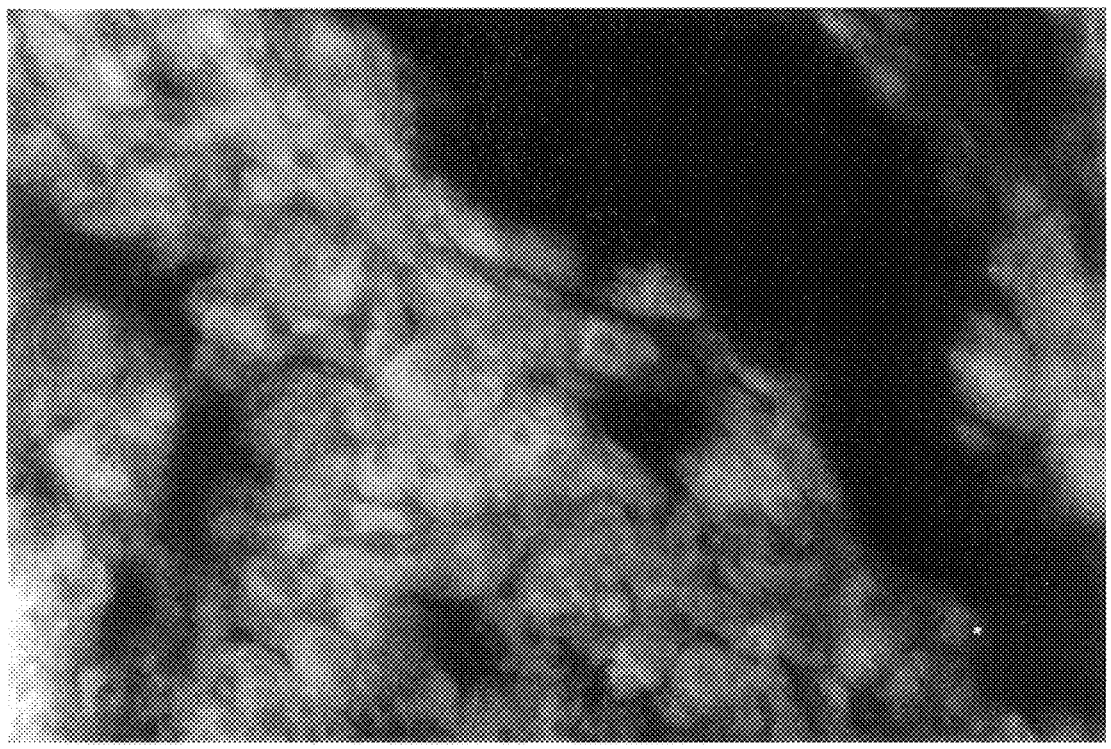

FIG. 21A. Frozen 8-micron thick section of prostate adenocarcinoma (outer 2/3 of tumor of ca. 4 cm diameter), excised from its host rat (Copenhagen strain, syngeneic) 3 hours after intravenous injection of 5 mg/Kg doxorubicin:DS (doxorubicin in association with essentially purified dermatan sulfate, 435 Type, Opocrin) at a weight ratio of 60:40 (doxorubicin to dermatan sulfate), and fluorescence microscopy performed using a rhodamine-type filter to elicit direct fluorescence of the doxorubicin drug substance (see also Example 29). Note the very bright direct drug fluorescence in almost all tumor cells which are packed into a relatively dense sheet throughout the tissue section. This is indicative of high tumor-cell internalization of the doxorubicin drug substance. Note also the endothelial cytoplasmic and nuclear positivity, indicative that endothelium, as well as tumor cells proper, constitute a target of doxorubicin:DS (but not of standard doxorubicin—see below).

Figure 21B:
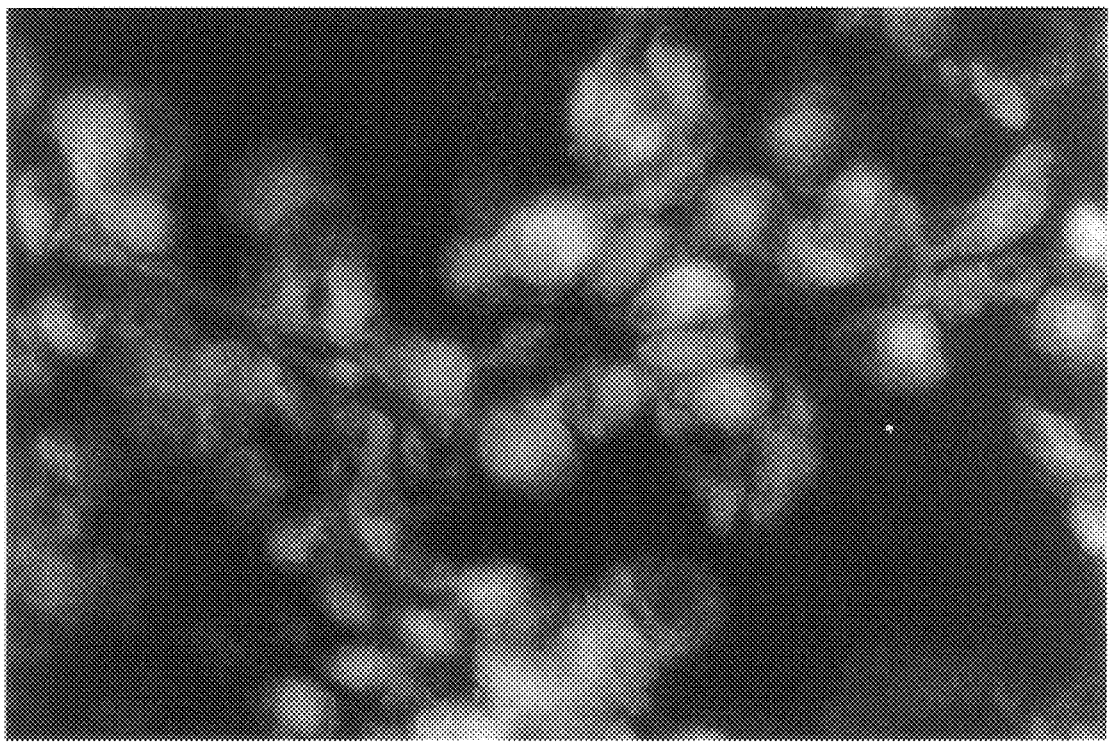

FIG. 21B. Section of same tumor as in FIG. 21A, but in a subregion with looser clusters of tumor cells which are located and arranged around an endothelial stalk (oriented horizontally across the image). Note the very bright staining of almost all cells, plus the strikingly bright fluorescence of doxorubicin now localized at nuclear sites, as well as in the tumor-cell cytoplasm. Also note the strong fluorescence of endothelial cells and endothelial-cell nuclei.

Figure 21C:
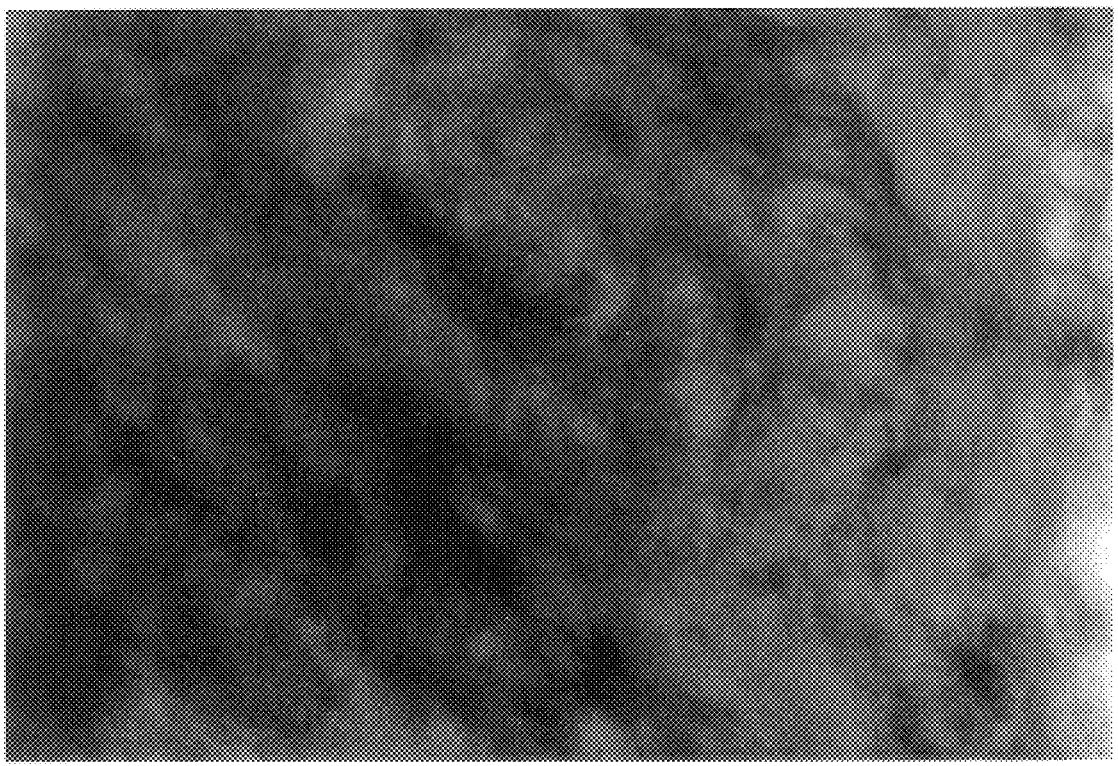

FIG. 21C. Section of the same tumor type and size, but from a different Copenhagen rat, which was sacrificed 3 hours after intravenous injection of 5 mg/Kg of standard doxorubicin (Adriamycin PFS liquid). Note the dense sheets of cells at upper right and the looser clusters at lower left—all of which exhibit markedly lower fluorescence (indicative of overall tumor and intracellular drug levels), as well as the general lack of fluorescence in and around the large tumor microvessel (image center) and no identifiable fluorescence in the tumor-cell nuclei. The latter finding is strongly suggestive of lower drug levels at a key intracellular site and target of drug action, namely the nucleus and nuclear DNA.

DESCRIPTION OF THE PREFERRED EMBODIMENTS

The present invention involves nontoxic, biodegradable small molecules, particles or microspheres (less than about 0.2–100 micrometers (um) in size) and microaggregates (1–200 nanometers, nm) comprising endothelial-binding substances and in particular, dermatan sulfate. These substances induce the following serial steps upon intravenous injection of particles into test rodents:

1) endothelial bioadhesion; 2) rapid (2-minute) endothelial envelopment (partial or total) of the substances; 3) a facilitated (accelerated) migration of intact drug-carrier particles across microvessels into the tissue compartment; (which is largely complete within 10 to 20 minutes of injection); and 4) delayed release of drug from a microsphere formulation of envelopment carrier which is known to correlate with controlled bioavailability of drug within the target tissue (lesion) in vivo.

The examples presented herein include compositions of matter serving as formulation carriers for efficient, nonmagnetic drug localization in normal and diseased tissues, including microspheres or nanospheres comprising a special class of dermatan sulfate as described herein which binds to the complementary heparins and heparan sulfates present on normal endothelium throughout the body.

This invention is not considered to be constrained by prior art involving the formulation of microcarrier matrices from any of the presently proposed materials providing that the said materials were not previously recognized and documented in vivo as undergoing multiple endothelial binding and inducing rapid endothelial envelopment, and producing accelerated extravasation of macromolecules, microaggregates and microparticles in either the first microvascular bed encountered, or potentially (as proposed) semiselectively at foci of disease following systemic intravenous administration.

Endothelial-envelopment carriers may be formulated and stored in either the dry or fluid state, to which may be added, for example, pharmaceutically acceptable appropriate stabilizers, osmotic agents, colorings, flavorings and physiologic solutions which render them appropriate for intravascular and intracavitary injection. The present invention is envisioned as most particularly applying to the vascular targeting phase of any future device (see below) which is developed for the efficient first-step transit across the external body barriers (e.g., gastrointestinal tract; oral, nasal, rectal, bladder or vaginal mucosa; skin, cornea or sclera).

The present disclosure documents that drug carriers which comprise microencapsulation spheres with surface adhesion properties were selectively taken up into tissues by endothelial bioadhesion and by induced transendothelial migration, into the tissue interstitium. The present application additionally documents that drugs controlled by such carriers, are deposited in selected target tissues, such as lung, in exact proportion to the deposition of drug carriers. It is now further established that soluble drug-carrier complexes (as well as formally microencapsulated drugs) give comparable tissue uptake of drugs, under conditions in which the drug alone is not taken up. It is now further established that the same and similar carriers are taken up by the transepithelial route in the lungs, gastrointestinal tract and bladder. Finally, it is established that the same and similar carriers undergo preferential lesional concentration in tumors and niduses of pulmonary infection.

The unique aspect of drug carrier technologies established by the present application are that these novel carriers afford high-efficiency tissue uptake and localization of drugs, in particular, when the drugs are controlled by nonembolizing (less than 3–4 $\mu$m) carriers. The carriers are preferably of a non-embolizing size of less than 500 nm and more preferably less than about 250 nm. Other unique features are that these carriers a) are formulated of water-soluble, biocompatible and biodegradable materials, and b) afford widespread percolation throughout tissue interstitium (and lesional gels) in a fashion which is not possible for hydrophobic carriers (e.g., liposomes). Finally, the carriers of the principal embodiments interact with their initial sites of cellular uptake (endothelial and epithelial cells) based on carbohydrate-carbohydrate binding and they do so in such a fashion as to produce multivalent binding, which leads to an induced, active endothelial (or epithelial) envelopment and transendothelial (or transepithelial) transport of both the carriers and drugs controlled by the carriers. This preferably involves transcytosis (process occurring across one endothelial or epithelial cell) or may involve endothelial (epithelial) migrational overgrowth of the carriers, leading to envelopment.

In the practice of preferred embodiments of the invention, multivalent binding to cells (or adjacent matrix substances) must occur, in order to induce active extravasation (or epithelial transport) of the drug-carrier couple, wherein such transport is significantly accelerated relative to that obtained for uncoated (uncontrolled) particles or drug-carrier complexes; this acceleration being of such a degree that transcellular transport of nonembolizing as well as embolizing particles (complexes) is completed within twelve minutes of endothelial/epithelial contact (typically in less than 5 minutes), under in vivo conditions of microvascular blood flow and/or cavitary fluid flow, air flow, or enteric flow (in microvessels, bladder, lungs, bowel, or other body cavities, respectively).

The carriers preferably control the delivery of multiple (at least two) molecules of drug, and are thus more clearly distinguished from naturally transported simple hormones, proteins, peptides, and hybrid conjugates of two low-molecular-weight drugs.

Although certain preferred embodiments describe a surface coating of dermatan sulfate, alternative carriers (and surface coatings and drug-complexing agents), such as dermatan sulfate fragments, heparin fragments, tridodecyl methylammonium chloride heparin, hereinafter referred to as TDMAC heparin, and other glycosaminoglycans (GAG's), and preferably the new class of dermatan sulfates with a sulfur content of up to 9% (w/w) and with selective oligosaccharide oversulfation, also serve to bind to constitutive and induced heparin cofactor II. The 8–12 unit fragment of dermatan sulfate binds heparin cofactor II without activating it. Unlike native heparin, neither dermatan sulfate nor its 8–12 unit fragment inhibits the constitutive endothelial surface coagulant, antithrombin III. This is also true of the shorter, semisynthetic fragments of heparin. Hence, dermatan sulfate and the short fragments of both heparin and dermatan sulfate, are envisioned as having even less anticoagulant activity than does native heparin (whose minimal anticoagulant activities are still acceptably low in this regard, when the heparin is incorporated into drug microspheres and complexes).

Endothelial uptake is described for a new physical formulation, namely a macromolecular complex between dermatan sulfate and doxorubicin (an antitumor drug). It is understood in the present application that doxorubicin is preferably provided as doxorubicin HCl in order to promote ion pair binding or complexation with the sodium salt form (preferably) of dermatan sulfate. Therefore, doxorubicin and doxorubicin HCl are used interchangeably when describing the active agent in the drug carrier compositions of the present disclosure. Selective high-efficiency uptake of this drug and carrier complex is documented in the present application following administration of the complexed agent. The absence of endothelial injury by dermatan sulfate-doxorubicin is also documented. This novel result established the rationale for reformulating existing drugs using dermatan sulfate and related kits (as devices), which can be performed by hospital pharmacists on-site, just prior to drug administration. This new approach can allow localized tissue (lesional) uptake of drugs controlled by nonembolizing carriers, as follows:

a) by intravenous administration to the lungs (high efficiency delivery) and systemic lesional sites (moderate efficiency delivery); or b) by selective arterial perfusion to liver, kidney, brain, pelvis, extremities and other body sites (high efficiency delivery).

The present application describes that secondary tissue percolation of these hydrophilic drug-carriers occurs in normal target tissues for dermatan sulfate-coated microspheres (interstitium, lymphatic and epithelial). In the present application, additional examples are presented, which establish the general principal that, unlike the situation for lipid microemulsions, liposomes and other hydrophobic carriers, the present hydrophilic spheres percolate extensively through the interstitium of a tumor and the lesional gel of a spontaneous pneumonitis, to reach both the outer spreading rims and the inner necrotic cores of these lesions. This provides new rationale for improved lesional penetration, cellular (microbial) access and uptake of drug carriers, and their entrapped (controlled) drugs. It is envisioned as allowing improved drug access to tumor cells and microorganisms lying in sequestered sites.

The present invention describes new entrapments of substances such as:

a) doxorubicin HCl; and b) other antitumor drugs such as taxol, vincristine or peptide onco agents that are amenable to coating with dermatan sulfate and its derivatives.

The present invention includes formulations which employ additional detergents as excipients for preparing the internal drug nanoparticles, nanoemulsions, or other internally entrapped, controlled-release subcapsules, complexes or agents for formulation and entrapment of the internal drug emulsions. Such detergents include:

a) preferably, sodium deoxycholate;

b) alternatively, cholesterol, TWEEN 80, zwitterionic detergents, or other biocompatible nonionic, polysulfated or positively charged detergents, as needed to formulate stable drug emulsions.

The present invention teaches that cancers (and drugs) can potentially be treated (and localized) in an improved fashion by using the described technology. The bioadhesion carriers set forth in the present application are envisioned as being preferred for the delivery of drugs which are highly toxic (certain antitumor drugs); drugs which are highly labile; agents which experience inappropriate biodistribution or poor tissue access due to their large molecular size or the presence of disseminated, competing receptors in the body; and anti-adhesion pharmaceuticals (as depot formulations, for the prevention of cancer-cell metastasis, prophylaxis of atherosclerosis, and inhibition of white-cell and platelet adhesion to vascular endothelium).

The present invention includes the use of additional methods for matrix stabilizing and controlling the release of drugs. These include addition of thickening agents, such as polylactic and polyglycolic acids, polyaminoacids, poly-L-lysine, polyethyleneimine, glycerol, polyglycerols or polyalchols (with or without heating or chemical reaction), polyethylene oxides, biodegradable poloxamers or poloxamines (pluronics or tetronics), poly-COOH compounds (polycarbols), or polyamines.

Additional methods of microparticle formulation are envisioned as including (particularly for the purposes of product scale-up): preferably, extrusion of matrix (and/or surface) components through single (and/or coaxial), sonified or air-stream-fractured micro-orifices (single or multiport); alternatively, aerosolization using hybrid, homogenization-spray drying apparatus.

The present invention includes additional methods of extracting the solvents used for phase emulsification and simultaneously crystallizing the matrices, surfaces and/or entrapment materials): preferably, hexanes; alternatively, ethanol or methanol.

Additional methods of sterilization (and/or particle sizing) of the final (or subfinal) preparations, include: preferably, for heat-stable agents: autoclaving at 120° C. for 10–20 minutes; preferably, for heat-labile agents: submicron filtration of complexes and nanoparticles; and irradiation of particles larger than 0.22 um; alternatively, ultrasonification.

The many innovative teachings of the present invention will be described with particular reference to the presently preferred embodiments, wherein these innovative teachings are advantageously applied to the particular issues of in vivo T1-Type MRI image contrast enhancement by site-selective localization and sustained site retention of paramagnetic metal chelates according to optimal spatial and kinetic profiles at the site, while simultaneously enhancing clearance and minimizing toxicity of the non-localized dose fraction. However, it should be understood that this principal embodiment is only one example of the many advantageous uses of the innovative teachings herein. For example, the various types of innovative compositions and methods disclosed herein can alternatively be used to selectively localize and enhance clearance of radionuclide imaging agents, X-ray contrast agents, ultrasound-acoustic image enhancing agents and a wide spectrum of therapeutic agents which are based on site delivery of metal chelates and in situ chelation of endogenous body metals of special interest to the therapeutic agents and uses embodied herein, are actives and indications useful in oncotherapy, cardiovascular infarcts, restenosis, atherosclerosis, acute thrombosis, microvascular disease, inflammation, and any other tissue diseases which have as part of their development or progression, a vascular component amenable to binding, adhesion, transport and/or modulation by the novel teachings, compositions and uses described herein. Hence, it will be obvious to those skilled in the art, that numerous additional compositions and uses are uniquely enabled by the present invention.

The present invention includes but is not limited to the preparation and utilization of novel contrast agents for magnetic resonance imaging. These novel contrast agents consist of paramagnetic metal chelates, as distinguished from metal-atom complexes, wherein the presently disclosed chelates are bound to glycosaminoglycans (GAG). Binding of the metal complex to the GAG may take the form of, but is not limited to, electrostatic interactions (ion-paired), hydrogen-bonding, Van der Waals interactions, covalent linkages, or any combination of these interactions. Following parenteral administration of these metal complex-glycosaminoglycan formulations, the technology described herein utilizes a biocompatible carrier molecule to deliver an associated biologically active substance to sites of vascular injury.

The present invention provides substantially improved MRI image and spectral enhancement compositions and methods, whereby the capacity of MRI hardware systems to detect tumors, cardiovascular diseases, and other diseases with a vascular or endothelial adhesive component are greatly enhanced. These improvements are presently accomplished by introducing a chelated paramagnetic metal ion selectively into tissue sites of interest, inducing selective (local) modulation of T1-Type, paramagnetic relaxation of water protons or other diffusible nuclei present within the site which are susceptible to orientation by fixed and gradient magnetic fields and to pulsed re-orientation by radiofrequency fields of appropriate resonant frequencies, thereby giving rise to detectable modulations of induced magnetic resonance signals, in the forms of either image contrast enhancement or spectral enhancement.

Past disclosures (Ranney: U.S. Ser. No. 07/880,660, filed May 8, 1992, U.S. Ser. No. 07/803,595 filed Apr. 3, 1992, and U.S. Ser. No. 07/642,033 filed Jan. 1, 1991] have dealt with the binding of magnetic agents which required: (a) magnetic potencies greater than that of the most potent single metal ion, gadolinium(III); (b) intramolecularly coupled, polyatomic metal-atom complexes stabilized by non-bridged ligands which have a stronger potential for chemical and physical instability than the stably, bridged-ligand chelated metal ions disclosed herein; and (c) divalent cationic charge on the "superparamagnetic" active for binding to anionic carriers, versus the presently disclosed requirement for only a monovalent cationic charge on paramagnetic metal chelator actives. It is understood, that for MRI uses, the metal chelator will also comprise an appropriate paramagnetic metal ion, for example, preferably iron (III) or gadolinium (III), however, for certain other diagnostic and therapeutic compositions and uses, the presently disclosed metal chelators may either comprise or avoid an appropriate metal ion. For the presently preferred MRI applications, basic metal chelators and metal chelators with electrophilic properties at formulation pH's are preferred, for example, ferrioxamine [Crumbliss, 1991], basic or amine derivatives of the polyaminocarboxylate chelator, diethylenetriaminepentaacetate (DTPA), and basic or amine derivatives of the macrocyclic chelator, 1,4,7,10-tetraazacyclododecane-N,N',N",N'''-tetraacetate (DOTA) [Li et al. 1993; Brechbiel et al. 1986]. In certain instances and with certain potent carriers bound to these and related actives, site localization may be so pronounced that the inherent potency (in vitro paramagnetic R1) of the paramagnetic metal ion may not be crucial to obtaining optimal site-localized image contrast or spectral enhancement effects. Hence, the present invention discloses pronounced T1 image contrast effects for the basic metal chelate, ferrioxamine, which by virtue of chelated Fe(III) ions, has a potency, or R1 relaxivity, of about 1.6–1.8 $[mmol.sec]^{-1}$. Alternatively, basic metal chelates of Gd(III) maybe expected under certain but not all in vivo conditions, to have a potentially greater relaxivity, due to its greater in vitro R1 of about 4.0–4.3 $[mmol.sec]^{-1}$ when chelated by DTPA, and potentially moderately higher when chelated by DOTA [Geraldes et al. 1985], and as high as $R1 \geq 7.5$ $[mmol.sec]^{-1}$ when Gd(III) is chelated to certain DTPA derivatives, including N-methyl-1,3-propane diamine-DTPA as one preferred embodiment of a group of preferred DTPA-amine and DTPA-basic derivatives which can both (a) allow accelerated water diffusion and relaxation above that of DTPA; and (b) bind non covalently to acidic saccharides, including, preferably, glycosaminoglycans. Alternative metal ions may preferably include the divalent or trivalent cations, manganese, chromium and dysprosium; and less preferably, those ions of copper, nickel, erbium, europium, and holmium.

Preferred chelators of the present invention include those with a formation constant of at least about $10^{14}$ for strongly paramagnetic metal ions disclosed above, and including a basic or cationic group. These chelators preferably include ferrioxamine, basic or amine derivatives of DOTA, DTPA, porphines, porphyrins, sapphyrins or texaphyrins, which can preferably chelate Fe(III) and most preferably chelate Gd(III), as well as bind by principally paired-ion (electrostatic) means to the acidic groups of acidic carriers. For example, certain texaphyrins have an expanded macrocyclic ring which may, in certain instances, stably chelate Gd(III) [Sessler et al. '065; Sessler et al. '720; Sessler et al. '498, incorporated by reference herein]. Whereas texaphyrins and sapphyrins are not exemplified in the present invention, it will be obvious to those skilled in the art, from the references cited just above, and from the presently disclosed and exemplified Fe(III) chelator, 5,10,15,20-Tetrakis(1-methyl-4-pyridyl)-21-23-porphine, that the related texaphyrins and sapphyrins and their basic, cationic and amine derivatives, as well as the presently disclosed porphine derivative and its analogues and basic, cationic and amine derivatives, would be included under the disclosures and teachings of the present invention, and may be used in combination with the presently disclosed acidic carriers. There are hybrid considerations of, among others: (a) paramagnetic potency of the metal chelate; (b) binding stability to the acidic carrier; (c) formulation compatibility; and (d) biocompatibility and clearance in vivo. Hydrophilic chelators and carriers are usually, but not always preferred, due to their typically favorable formulation properties (absence of aggregation), biodistribution properties (absence of generalized binding to hydrophobic plasma and cell-membrane constituents during the process of localization); and clearance plus toxicity advantages. Alternative chelators may include the hydroxamates, ferrichrome, enterobactin, ferrimycobactin, ferrichrysin, and their basic or amine derivatives, all derivatives being defined as subsumed under the parent chelators listed above.

Preferred carriers include monomeric, oligomeric and polymeric substances which contain or comprise anionic or acidic groups defined at the pH's used for formulation. These typically contain or comprise groups of carboxylate, and more preferably, the even more strongly acidic groups of phosphate, and most preferably, sulfate. Preferred carriers include, but are not limited to an acidic saccharide, oligosaccharide, polysaccharide, glycosaminoglycan or sulfatoid, typically of bacterial or semisynthetic origin, or derivatives, modifications or fragments of the preceding substances, all defined herein as being subsumed under the names of the parent substances and categories. Hence, preferred carriers include the following: heparin, desulfated heparin, glycine-conjugated heparin, heparin sulfate, dermatan sulfate, chondroitin sulfate, pentosan polysulfate, and sulfated sucrose, including sucrose octasulfate, and any derivative, modification or modified form thereof, with the most preferred being the essentially purified dermatan sulfate as described herein. Less preferably for typical MRI formulations and uses, are included the carriers of sulfated cyclodextrin, dextran sulfate and hyaluronic acid, although any of these may be particularly suitable for certain specific diagnostic or therapeutic formulations and uses.

In all cases reported and tested, non-covalent binding of the basic amine chelator to the acidic carrier gives payloads of active agent which are markedly higher than those afforded by covalent conjugation. For example, preferred basic chelators, ferrioxamine and Gd(III) DTPA-lysine, and most preferred, N-methyl-1,3-propane diamine-DTPA (N-MPD-DTPA), are bound to their acidic glycosaminoglycan carriers at weight ratios of $\geq 70\%$. Alternative covalent active-carrier conjugates may be preferred in certain instances, and preferred examples thereof are shown for MRI applications.

Specific embodiments of the present invention which have been tested in vivo, include, but are not limited to the presently exemplified preferred embodiments of: (a) deferoxamine, (b) ferrioxamine, (c) Gd(III):DTPA-lysine, (d) N-methyl-1,3-propane diamine-DTPA, and (e) other basic metal chelates bound most preferably by non-covalent means, and also preferably by covalent means, as exemplified below, to acidic glycosaminoglycans, including preferably, dermatan sulfate, essentially purified dermatan sulfate having a sulfur content of up to 9% (w/w) and with selective oligosaccharide oversulfation, heparan sulfate, and heparin, which include by definition, any derivative or modification thereof, including oversulfation and modification undertaken to reduce anticoagulant activities or provide improved site binding, enhanced clearance or other desired formulation or in vivo properties. In particular, however, the preferred carrier substances from the standpoint of low toxicity and optimal safety margins at the higher doses which typify MRI contrast agent administrations, are the dermatan sulfates with relatively low $SO_3$—/$COO$— ratios of preferably between 0.7:1 and 1.8:1, most preferably between 0.9:1 and 1.5:1, and typically 1:1; and additionally with relatively low sulfur content of preferably less than 9% (w/w), most preferably between 4% and 7% (w/w/), and typically 6.3–6.4% (w/w); and the most preferred carrier substances under the high-dose administration conditions employed just above, comprise the new special class of dermatan sulfates with oversulfation of only selected oligosaccharide sequences but without overall oversulfation of the entire molecule (as described and defined above). Alternative preferred Agents obvious from the present disclosures, to those skilled in the art, may induce arginine and histidine basic derivatives of DTPA and DOTA, and also of the various texaphyrins, sapphyrins, porphines, porphyrins, EHPG, and by definition, most preferably for MRI applications, comprising their Gd(III) and Fe(III) metal-ions, and also preferably comprising their alternative paramagnetic metal ion chelates, as disclosed above.

The carrier substance most preferably used in the present invention is the new class of essentially purified dermatan sulfates, enriched in uronic (L-iduronic) acid content and, in addition to its major monosulfated disaccharide sequence, (Ido-GalNAc4$SO_3$), also characterized by an oligosaccharide sequence with a selectively high degree of sulfation, including the oversulfated saccharide sequences, (IdoA2$SO_3$-GalNAc4$SO_3$) and (IdoAGalNAc4, 6$SO_3$) (as assessed by disaccharide analysis and as uniquely correlated with $^1H$ and $^{13}C$ magnetic resonance spectra), enriched in heparin cofactor II activity, preferably greater than 220 Units/milligram, but low in factor Xa and antithrombin III activity and in overall anticoagulant activity (preferably less than 10% and most preferably less than 5% of standard heparin by USP anticoagulant assay), low in $SO_3$—/$COO$— ratio, preferably in the range of 0.7:1 to 1.8:1 and most preferably in the range of 0.9:1 to 1.5:1, and low in sulfur content, preferably less than 9% and most preferably in the range of 4 to 7%; and preferably having a modal molecular weight of between 10,000 and 23,000 daltons, and most preferably between 13,000 and 19,000 daltons—the lower end of this molecular weight bracket generally being important in order for the carrier to be highly retained within the vascular compartment of normal organs after intravenous administration; and the higher end of this molecular weight bracket generally being important for effective disease site binding and uptake, while still affording the very rapid blood clearance by the renal route, which is important for rapidly achieving low blood imaging backgrounds and low body residua at early post-injection times.

The dermatan sulfates of the preceding paragraph may, in one case, be prepared by the methods of: (a) grinding and treating animal organs or tissues, including beef mucosa, swine skin or lung, and preferably for certain of the present uses, beef mucosa, with proteolytic enzymes including papain, at pH 5 to 7 for the shortest possible time to remove proteins; (b) passage over a strong anion (basic) exchange resin including a macroreticular styrene-divinylbenzene matrix functionalized with quaternary ammonium groups and having a particle size range of 0.3 to 1.3 mm; (c) eluting the sulfated polysaccharides with a neutral salt solution between of 0.7 and 2.0 molarity; (d) crystallization of the dermatan sulfate as a low-solubility salt of a bivalent or trivalent metal including copper, iron and calcium, and preferably copper; (e) reconversion to sodium salt via cation exchange resin including chelex 100 type (Bio-Rad 143-5852); selectively enriching for the oversulfated oligosaccharide sequences (above) by chromatography on a strongly basic anion exchange resin functionalized with quaternary ammonium groups, wherein the resin typically has a particle size of less than or equal to 10 micrometers and a cross-linkage of 2–8%; (f) concentrating the eluate by reverse osmosis; and (g) lyophilizing the resulting liquid to form a fine white powder. One example of the above dermatan species, which is not intended in any way to limit the scope of the present invention, comprises a subspecies of these dermatan sulfates (sulphates), as described [Mascellani, et al. WO 93/05074 (1993), incorporated herein by reference; Mascellani, et al. (1994), incorporated herein by reference]. One of most preferred examples of this subspecies of dermatan sulfate is the Type 435 beef mucosal dermatan sulfate (sulphate) manufactured and supplied by Opocrin S.P.A., Via Pacinotti, 3, I-41040 Corlo Di Rormigine, Italy. It has a modal molecular weight of approximately 17,500 to 18,000 daltons, as determined by charge suppressed molecular sieve chromatography with UV absorbance analysis, and a sulfur content of approximately 6.2 to 6.6% weight percent—this low sulfur content occurring despite the selective enrichment in these dermatan sulfates of certain oligosaccharide sequences with a high degree of sulfation, including the oversulfated saccharide sequences, (IdoA2$SO_3$-GalNAc4$SO_3$) and (IdoAGalNAc4, 6$SO_3$) whose enrichment correlates with high heparin cofactor II activity.

In the descriptions of the two preceding paragraphs, (a) enrichment for uronic (L-iduronic) acid content plus the preceding 2,4-disulfated disaccharide sequences in combination with (b) the preferred molecular weights in the range of 10,000 to 23,000 and most preferably 13,000 to 19,000 daltons, and (c) low $SO_3$—/$COO$— ratio, corresponding to a low overall sulfur content, typically in the range of 4.5 to 7% by weight, correlates with the surprising and unexpected advantages of: (a) in vivo potency of rapid disease-site binding, localization, uptake and deep penetration, e.g., of tumor endothelium, tumor extracellular matrix and tumor cells; and (b) low side effects of induced platelet aggregation, anticoagulation and bleeding—which are characteristically induced by the more highly sulfated and/or longer-chain (higher molecular weight) carriers, including sulfated, oversulfated and polysulfated glycosaminoglycans and natural and synthetic sulfated, oversulfated and polysulfated polysaccharides and sulfatoids—most specifically those with a sulfur content of 10% or greater, and those with a USP heparin-type anticoagulant activity ranging from 15 to 145 USP units per milligram or greater.

The preferred dermatan sulfates (above) and the most preferred new special dermatan sulfate subspecies, essentially purified as prepared by the special processes described above, when used as site-selective diagnostic or drug carrier substances, are clearly distinguished from all of the previous, older dermatan sulfates, i.e., those (a) not having the special structures described above; (b) not prepared according to the above isolation and purification processes; or (c) not prepared by such alternative processes as would give comparable enrichment of the preferred oligosaccharide sequences and selective sulfations described above. These preferred essentially purified dermatan sulfates are also clearly distinguished, when used as above, from all of the prior older dermatan sulfates in that they are not only structurally different, but they are also essentially free of the contaminating heparins, heparan sulfates and heparinoids which bind normal endothelium, undergo various degrees of in vivo metabolism, and interfere with rapid and complete blood and body clearance [Dawes, et al. (1989), incorporated herein by reference]. It will be further obvious to those skilled in the art, that the new special dermatan sulfates described above, are, when used as site-selective diagnostic or drug carrier substances, even more distantly distinguished from the non-dermatan sulfate classes of glycosaminoglycans, namely: (a) chondroitin sulfates A and C—which do not share the uronic (L-iduronic) acid sugars of dermatan sulfate [Walton, et al., US Pat. No. 4,489,065; Maeda, et al. (1993), both incorporated herein by reference]; (b) heparin—which does share uronic (L-iduronic) acid structure but which has high anticoagulant activity and high binding to normal endothelium [Cremers, et al. (1994); Kalishevskaya, et al. (1988), both incorporated by reference herein]; (c) hyaluronic acid—which is a non-sulfated glycosaminoglycan; (d) all of the polysulfated glycosaminoglycans and oversulfated sulfatoids, e.g., bacterial polysulfates including pentosan polysulfate—all of which characteristically have sulfur contents of 10% or greater that create significant in vivo safety issues due to polysulfate-induced platelet aggregation and cell membrane perturbation/lysis, or act as cofactors for such cellular lysis and which can affect normal body cells as well as tumor cells and other pathological cells/organisms, such as that specifically described as direct toxic cofactor "opening" of tumor cells produced by chondroitin polysulfate, resulting from chondroitin polysulfate-induced membrane damage [Landsberger (1984)]. Hence, the new special dermatans preferred in the present invention are ones which do not themselves cause significant direct cellular or membrane damage, but instead induce rapid (3- to 7-minute) selective binding of disease-site endothelium, rapid (10 to 5-minute) endothelial cell transport, tumor uptake, deep matrix permeation and tumor-cell internalization of the attached diagnostic or drug active without the dermatan sulfate carrier itself or alone, damaging either the intermediate (e.g., endothelial) or final (e.g., tumor) target cells.

This new special class of dermatan sulfate is clearly distinguished from chondroitin sulfate Types A and C by its high content of L-iduronic (uronic) acid relative to the low or absent content in chondroitin sulfates A and C; and by its relatively lower modal molecular weight, most typically less than 25,000 daltons versus the chondroitin sulfates A and C, which typically equal or exceed 25,000 daltons modal molecular weight. The relatively lower molecular weight of the new special dermatan sulfates has at least three surprising and unexpected advantages when used as a carrier substance for bound or associated active substances: (a) very rapid blood clearance of the carrier and active, predominantly by the renal route, with a blood t ½ of typically about 20 to 120 minutes, increasing only very gradually as a function of increasing dose; (b) minimal to absent in vivo metabolism—in major contrast to standard heparins, heparan sulfates and chondroitin sulfates A and C—thereby giving extremely low residual in vivo deposition or retention of the carrier material; and (c) maximal, rapid vascular egress across disease-site endothelium—including across induced and "permeabilized" endothelium, e.g., induced by Vascular Endothelial Growth Factor/Vascular Permeability Factor (VEGF/VPF) for maximal disease-site and tumor access, uptake and tumor-cell internalization of the bound or associated active substance.

Whereas, this new class of dermatan sulfates has been recognized as useful for conferring antithrombosis in the absence of (heparin-type) anticoagulant activity and bleeding side effects, it has not previously been recognized, nor would it be obvious to one skilled in the art, that this new special class of dermatan sulfates could confer the surprising and unexpected advantages of acting as a highly potent and effective in vivo carrier of noncovalently or covalently bound amine or chemically basic chelators or metal chelates, furthermore, to selectively localize them in sites of disease, including tumors, across non-permeabilized as well as "permeabilized" vascular endothelium and simultaneously to promote very rapid clearance of the non-targeted fraction of carrier plus active, highly preferentially by the renal route, in a fashion which increases only very gradually with increasing dose—thereby conferring not only reduced side effects and low in vivo retention, but also the additional advantages of: (a) very low imaging backgrounds at very early times post-injection upon intravenous administration for the purpose of in vivo contrast enhancement by associated paramagnetic metal chelate; and (b) pronounced capacity for dose escalation with acceptable safety. These surprising and unexpected advantages are particularly important for use in paramagnetic enhancement of in vivo magnetic resonance images (MRI) because of low sensitivity of the imaging equipment and detection method, and hence, the need for injecting high intravenous doses of paramagnetic metal chelate (typically in the range of 0.1 to 0.3 mmol/kg) in order to deposit sufficient local-site concentrations of paramagnetic agent (ca. 50–100 micromolar). This further emphasizes the advantage of using a carrier material, including the new special dermatan sulfates, which can preferable allow a noncovalent method of binding the active to the carrier, and hence, can enable a high quantity of active to be bound per unit of carrier, preferably greater than 70% (weight % of active to [active+carrier]) versus typically 7 to 12% (w/w) for most covalently bound active-polymer systems, including antibody systems. Hence, the self-assembling, noncovalent formulation (as well as covalent formulation) properties of the new special dermatan sulfates provide an additional surprising and unexpected advantage of minimizing the quantity of dermatan sulfate carrier required to administer and selectively localize an effective in vivo dose of paramagnetic chelate.

The present invention describes the preparation and utilization of a novel MRI contrast agent for enhancement of solid tumors and cardiovascular infarcts. The contrast agents consist of cationic or basic paramagnetic metal complexes in association with strongly acidic, including polysulfated carriers, and including preferably glycosaminoglycans. It would be obvious to those skilled in the art that any acidic glycosaminoglycan can be used. Of the paired-ion systems described below, most notable are those consisting of ferrioxamine with glycosaminoglycans, DTPA-lysine with glycosaminoglycans, N-methyl-1,3-propanediamine-DTPA with glycosaminoglycans, and most preferably, N-methyl, 3-propanediamine-DTPA with the new special subspecies of dermatan sulfates described above.

In one particularly preferred embodiment, essentially purified dermatan sulfate (435 Type of 17,000 to 19,000 modal MW, with selectively oversulfated oligosaccharides and a heparin cofactor II activity at least about 220 U/mg, Opocrin), is used in noncovalent (or covalent) association with the following oncology actives to localize them in sites of disease and facilitate their clearance from the rest of the body: doxorubicin, adriamycin, taxol, docetaxel, paclitaxel, vincristine, vinblastine, bleomycin, idarubicin, epirubicin, amsacrine, azacitidine, dideoxyinosine, dihydro-5-azacytidine, ethanidazole, ethiofos, methotrexate, misonidazole, porfiromycin, pyrazoloacridinek, terephthalamidine, taxotere and other taxane derivatives, topotecan, trimetrexate, carboplatin, N-formyl-met-leu-phe-lys, arginine bradykinin, poly-L-lysine, other chemoattractants, biological response modifiers, cytokines, interferons and lymphokines.

In another particularly preferred embodiment, essentially purified dermatan sulfate (435 Type of 17,000 to 19,000 modal MW, with selectively oversulfated oligosaccharides and a heparin cofactor II activity at least about 220 U/mg, Opocrin), is used in noncovalent (or covalent) association with the following anti-infectives: gentamicin, amikacin, tobramycin, and other amine, basic, basic peptidic, basic polypeptidic, hydrophobic or amphoteric antibiotics or bacterial, fungal, mycobacterial, viral or other microbial or microbiological diseases.

It is envisioned that alternative diagnostic and therapeutic compositions and applications may be carried out using compositions substantially similar to those disclosed above. For example, alternative metal ions may be chelated for purposes of metal-ion exchange at the site. Hence, the present formulations may contain or comprise metal ions of manganese, aluminum, germanium, zinc, cobalt, calcium, platinum, or others. Alternatively, for purposes of radiation and radionuclide therapy, such compositions may contain or comprise metal ions of boron, cobalt, rubidium, yttrium, technetium, ruthenium, rhenium, indium, iridium, thallium, samarium or others. Specifically, and in some cases preferably, $^{59}$Fe and $^{67}$Ga [Hashimoto et al. 1983; Janoki et al. 1983] may be substituted as radionuclide forms of the non-radioactive metal ions, for purposes of nuclear medical imaging of tumors, thrombi, and other biomedical imaging purposes.

The preceding discussion is presented to specify major aspects of the invention and their use in in vivo diagnostic and therapeutic applications, however, to those skilled in the art many additional and related compositions and methods of use will be obvious from this preceding discussion and are encompassed by the present invention.

TABLE 1

Advantages of Metal Ion Chelator and Anionic, Hydrophilic Carrier

| Technology | Selective MRI Agent | Antibodies | PEG | Liposomes |
|---|---|---|---|---|
| Property | | | | |
| Drug Payload | High *60–90%; **77.5% | Very Low 5% | Low 10–30% | Low 15–20% |
| Localization in Tissue Sites | Yes | Very Low | No | No |
| Selectivity | Broad Immune (CHO-lectin) | Narrow Immune (Ab-antigen) | None | None |
| Time to Target | Very Rapid (several mins) | Slow (several hrs) | Slow (many hrs) | Very Slow (hrs-days) |
| Time to Clear Plasma & Body | Rapid | Very Slow | Very Slow | Extremely Slow (RES) |
| Applications | Broad (Tissue Sites) | Narrow (Intravascular) | Narrow (Enzymes) | Narrow (RES) |

*preferred
**most preferred

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In all of the following Examples, except as otherwise stated, all references to dermatan sulfate and native dermatan sulfate refer to the new special class of dermatan sulfates with oversulfation of only selected oligosaccharide sequences but without overall oversulfation (hypersulfation) of the entire molecule (as described and defined herein), and in particular refer to the new special "435 Type" of dermatan sulfate as supplied by Opocrin S.P.A., Via Pacinotti, 3, I-41040 Corlo Di Formigine, Italy.

EXAMPLE 1

Preparation of Deferoxamine Free Base and Use in Formulation of Ferrioxamine

The free base of deferoxamine is used in certain instances, in order to minimize the residual salt content present in final formulations which utilize deferoxamine as a basic metal chelator. In these instances, deferoxamine is precipitated out of aqueous salt solutions by the addition of 2 N $KHCO_3$, as previously reported [Ramirez et al. (1973), incorporated by reference herein]. A saturated solution of deferoxamine (320 mg/mL at 25° C.) is prepared by dissolving 4.0 g of deferoxamine mesylate salt in 12.5 mL of pharmaceutical-grade water. The solution is cooled to 4° C. in an ice bath and 2.5 mL of 2.0 N $KHCO_3$ added. The glass container is scratched with a stainless steel spatula to initiate precipitation. The precipitate is collected by centrifugation, washed repeatedly with ice cold water, and filtered. The crude deferoxamine free base is purified by sequential recrystallization from hot methanol. The resulting pure deferoxamine free base is dried under a stream of nitrogen. The infrared spectrum of the deferoxamine as prepared is consistent with that referenced above.

Ferrioxamine is formulated from the deferoxamine free base by addition of ferric chloride at stoichiometric molar ratios of Fe(III) to deferoxamine free base. This results in chelated iron and minimizes residual mesylate and chloride ions.

EXAMPLE 2

Preparation of Ferrioxamine-Iron (III) Chelate

Batch quantities of the Fe(III) chelate of deferoxamine are prepared as follows. Deferoxamine mesylate (methanesulfonate) (Ciba-Geigy Limited, Basel, Switzerland), 390 g, is dissolved in pharmaceutical-grade water. Alternatively, the chloride salt of deferoxamine may be used. A highly purified slurry of ferric iron in the form of Fe(O)OH (13.44% w/v of Fe(O)OH particles, Noah Technologies Corporation, San Antonio, Texas), 372.9 g is suspended in 1899 mL of water and added to the deferoxamine with constant stirring. The resulting suspension is heated to 60° C. for between 1 and 24 hours and the pH adjusted periodically to between 6.5 and 7.9 by addition of 0.10 N NaOH. Formation of the ferrioxamine complex is evidenced by development of an intense, deep reddish-brown color to the solution. Stoichiometric chelation of Fe(III) with deferoxamine is confirmed by in-process UV-Visible absorbance spectroscopy at 430 nm, against stoichiometrically chelated ferrioxamine standards. The batch solution is cooled to room temperature and centrifuged at 4500 rpm (≈2500 g) for 15 minutes to remove any unreacted or aggregated Fe(O)OH. This final batch volume is adjusted as desired, typically to a final volume of 2600 mL. Any remaining trace amounts of unreacted Fe(O)OH are removed and the solution also made aseptic, by passing the supernatant through a 0.22 $\mu$m Millipore GV-type filter in a Class 100 laminar flow hood. The resulting batch is stored at 4° C. in an autoclaved, sealed glass container until further use (see Examples below). The final concentration of ferrioxamine (DFe) is determined once again by UV-Visible absorbance spectrophotometry at 430 nm. The R1=1.6 $(mmol.sec)^{-1}$, based on ICP-AA measurement of Fe(III).

EXAMPLE 3

Preparation of the Basic Amine Chelator: Diethylenetriaminepentaacetate-Lysine (DTPA-Lys)

DTPA, 500 mg, is dissolved in 20 mL of pharmaceutical-grade water and heated to 60° C. L-Lysine hydrochloride powder, 931 mg, is added with constant stirring until dissolved. Alternatively, N-epsilon-t-BOC-L-lysine can be used to prevent reaction of the carbodiimide intermediate at the lysine epsilon amino group (see below), and when used, is dissolved in dimethylformamide:water (50:50, w/v). The solution pH is adjusted to 4.75 by addition of 0.1 N HCl. The water-soluble carbodiimide, 1-ethyl-3-(3-dimethylaminopropyl)carbodiimide HCl (EDC), 732.5 g, is dissolved in 2 mL water and its pH also adjusted as above. This EDC solution is added dropwise to the DTPA+lysine solution mixture (above) over 1 hour at 22° C. with constant stirring and periodic adjustment of pH to 4.75, and the reaction allowed to proceed to completion over 2 more hours. When N-epsilon-t-BOC-L-lysine is used (see above), the N-epsilon-t-BOC group is hydrolyzed at this step, by acidification with hydrochloric acid to a pH of between 1.0 and 2.0, and stirring for 30–60 min. The pH is readjusted to 4.75 as needed, and the reaction solution is concentrated down to 5 mL by rotary evaporation at 60° C., and the DTPA-lysine (DTPA-Lys) derivative is precipitated by addition of 3 volumes of ethanol. Note: under these conditions, the ethanol:water ratio used, maintains the solubility of all individual substrates (above). The resulting precipitate is harvested by centrifugation at 2,500× g, washed with ethanol, re-centrifuged, and dried over a stream of dry nitrogen. Covalent conjugation of lysine to DTPA is confirmed by infrared (IR) spectroscopy. The resulting reaction product has a faint yellow color.

EXAMPLE 4

Preparation of the Gadolinium(III) Metal Chelate of DTPA-Lys: gadolinium:DTPA-Lys [Gd(III):DTPA-Lys]

The gadolinium(III) chelate of DTPA-Lys, namely Gd(III):DTPA-Lys, is prepared by dissolving a known quantity of DTPA-Lys in water and adding a stock solution of gadolinium chloride, prepared at 0.1–1.0 M, as needed, until a stoichiometric quantity of Gd(III) has been added. The pH is adjusted to 7.0 by addition of 1.0 N NaOH. Alternatively, gadolinium oxide can be added and the reaction mixture stirred for 24 hours. In the case of gadolinium oxide, neutralization with 1.0 N NaOH is not needed. Each batch of Lys-DTPA conjugate is pre-titrated and the final chelation product checked for stoichiometric addition of Gd(III), using a standard xylenol orange titration method [Lyle et al. (1963)], and further confirmed by quantitative ICP atomic absorption spectroscopy for gadolinium. The resulting Gd(III):DTPA-Lys is precipitated by addition of ethanol (3 volumes per volume of water), and the precipitate collected by centrifugation. This precipitate is rewashed with ethanol and centrifuged (as above), washed with acetone plus centrifuged, and the collected precipitate dried over a stream of dry nitrogen. The resulting product continues to have the same faint yellow color as noted in Example 3. The R1 of aqueous product=4.2$(mmol.sec)^{-1}$ based on ICP-AA measurement of Gd(III).

EXAMPLE 5

Preparation of Paired-ion Agents of Ferrioxamine bound to Dermatan Sulfate Carriers; and Ferrioxamine to Depolymerized Dermatan Sulfate Carrier Ferrioxamine:dermatan sulfate paired-ion agents are prepared by mixing appropriate ratios of the water solutions of ferrioxamine (see Example 2, above) with either: (a) dermatan sulfate of modal MW between approximately 5,000 daltons and 45,000 daltons (Opocrin, S.p.A., Modena, Italy, 435 type from beef mucosa modal MW=18,000 daltons; and Scientific Protein Laboratories, Waunake, Wis., from porcine mucosa, modal MW=19,600 daltons); or (b) depolymerized dermatan sulfate of modal MW between approximately 2,000 daltons and 5,000 daltons (Opocrin S.p.A., Modena, Italy, 370 type from beef mucosa, depolymerized from 435 type starting material). A range of ratios of ferrioxamine to dermatan sulfate are prepared between a low of 1:99 (wt %) of ferrioxamine:dermatan sulfate or depolymerized dermatan sulfate; and a high of 30:70 (wt %) of ferrioxamine: dermatan sulfate or depolymerized dermatan sulfate). Using 0.1 to 1.0 N NaOH, the pH of the mixture is adjusted to between 5.5 and 8, the mixture is stirred continuously for 0.5 to 72 hours and the pH re-adjusted between 5.5 and 8, and typically to 7.5. This ferrioxamine:dermatan mixture is passed through a 0.22 μm filter to remove any residual insoluble iron oxides and hydroxides, and to render the liquid agent aseptic. The aseptic agent is stored either as a liquid at 4° C., or as a lyophilized powder (see below). Further processing is carried out on the liquid, by filling into glass vials and autoclaving at 120° C. for 15 minutes. Alternatively, further processing is carried out on the liquid by filling into glass vials, freezing at −50° C., and lyophilization to give an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and dermatan sulfate are measured and vial quantities confirmed by standard reverse-phase HPLC and macromolecular size exclusion HPLC methods, respectively.

Multiple batches of Ferrioxamine:Dermatan Sulfate Agent have been prepared. In vitro test results for a representative batch are as follows: ferrioxamine:dermatan sulfate ratio: 77.5:22.5 (w/w); solubility of agent, 550 mg/mL; water:octanol partition, 17,600 (±2,750):1; concentration of ferrioxamine, 0.166 mmol/mL; concentration of dermatan sulfate, 32 mg/mL; molecular weight of dermatan sulfate, Opocrin type 435, MN=18,000 daltons; sulfate/carboxylate ratio of dermatan sulfate, 1.0±0.15; ferrioxamine and dermatan purities, nominal±10%; pH, 6.5–7.9; viscosity, 3.8–4.2 centipoise; osmolality, 475–525 mOsm/Kg; R1, 1.5–1.8 [mmol.sec]$^{-1}$; oversized particles, within USP guidelines for small-volume parenterals; Anticoagulant activity, less than 4.5 U.S.P. Units/mg (modified USP XXII assay); binding of ferrioxamine active to dermatan carrier, at least 92% retained (dialysis for 3 hours against 200 volumes, 500 daltons molecular weight cutoff).

In vitro stability of Ferrioxamine:Dermatan Sulfate Agent under accelerated conditions, indicate the following. (a) The liquid form is stable, by the preceding physicochemical and HPLC parameters for longer than 6 months at 4° C., 22° C. and 40° C.; is slightly unstable at 2 to 6 months at 60° C., and degrades significantly within 1 to 3 days at 80° C. (b) The liquid form can be autoclaved as above, with less than 3% degradation of ferrioxamine. (c) The lyophilized form is stable with respect to all parameters (above), including oversized particles; and is projected to be stable over storage periods of multiple years.

EXAMPLE 6

Preparation of Paired-ion Agents of Ferrioxamine bound to Heparin

Ferrioxamine:dermatan sulfate paired-ion agents are prepared by mixing appropriate ratios of water solutions of ferrioxamine (as in Example 5, above) with (a) beef lung heparin of modal MW between approximately 8,000 daltons; and (b) porcine heparin of modal MW between approximately 10,000 daltons and 20,000 daltons. A range of ratios of ferrioxamine to heparin or heparin fragment are prepared between a low of 1:99 (wt/wt) of ferrioxamine:heparin or heparin fragment; and a high of 30:70 (wt %) of ferrioxamine:fragment. Using 0.1 to 1.0 N NaOH, the pH of the mixture is adjusted to between 5.5 and 8, the mixture is stirred continuously for 0.5 to 72 hours and the pH re-adjusted between 5.5 and 8. This ferrioxamine:heparin mixture is passed through a 0.22 μm filter to remove any residual insoluble iron oxides-hydroxides and render the liquid agent aseptic. The aseptic agent is stored at 4° C. As indicated, further processing is carried out by filling the aseptic liquid in glass vials, followed by freezing and lyophilizing, to render the agent as an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and heparin are measured and vial quantities confirmed by standard reverse-phase HPLC and macromolecular size exclusion HPLC methods, respectively.

EXAMPLE 7

Preparation of Non-anticoagulant Heparin Carrier by Glycine Derivatization

The anticoagulant activity of heparin can be reduced to almost negligible activity by derivatizing its carboxylate groups with glycine residues as reported [Danishefsky et al. (1971); Danishefsky et al. (1972)]. This non-anticoagulant heparin (Nac-heparin) can then be utilized as a modified glycosaminoglycan carrier. According to one present method of glycine conjugation, 0.75 g of heparin is weighed into a 100 mL beaker and dissolved in 25 mL of pharmaceutical-grade water. Glycine, 0.75 g, is added and the pH of the resulting solution adjusted to 4.75 with 0.10 N HCl. 1-ethyl-3-(3-dimethylaminopropyl)carbodiimide HCl (EDC), 0.75 g, is weighed into a separate vial, solubilized by adding a minimum amount of water, and the pH adjusted to 4.75 with 0.10 M HCl. Aliquots of the EDC solution are added to the mixture of glycine-glycosaminoglycan over a one hour period. After each addition of EDC, the pH is adjusted to maintain it at 4.75. After addition of all EDC, the reaction is allowed to proceed for an additional two hours with constant stirring and periodic pH adjustment. The glycine-heparin conjugate (Gly-HEP) is then precipitated by addition of 3 volumes of absolute ethanol. The precipitate is collected by centrifugation at 4500 rpm (≈2500× g) for 15 minutes; and washed three times with 20-mL aliquots of ethanol with re-centrifugation.

EXAMPLE 8

Preparation of Paired-ion Agents of Ferrioxamine Bound to Glycosaminoglycans, Modified and Derivatized Glycosaminoglycans of: Heparan Sulfate, Non-Anticoagulant Heparin Oversulfated Dermatan Sulfate Chondroitin Sulfate, Oversulfated Chondroitin Sulfate and the Bacterial Sulfatoid, Pentosan Polysulfate Ferrioxamine paired-ion agents are prepared with various glycosaminoglycan carriers by mixing appropriate ratios of water solutions of ferrioxamine (as in Example 5, above) with the following glycosaminoglycans: (a) heparan sulfate of MN=8,500 daltons; (b) non-anticoagulant heparin SPL, ++of MN=10,500 daltons; (c) oversulfated dermatan sulfate of MN=19,000 daltons; (d) chondroitin sulfate of MN=23,400 daltons; (e) oversulfated chondroitin sulfate of MN=14,000 daltons; and (f) pentosan polysulfate of MN=2,000 daltons. The ratios of ferrioxamine to glycosaminoglycan and sulfatoid carriers are prepared to give a payload of [77.5:22.5% (w/w) of ferrioxamine to carrier] (adjusted) by a scaling factor of [(mEq sulfates/mg of carrier as above)/(mEq sulfates/mg of beef lung heparin*)]. Using 0.1 to 1.0 N NaOH, the pH of the mixture is adjusted to between 5.5 and 8, the mixture is stirred continuously for 0.5 to 72 hours and the pH re-adjusted between 5.5 and 8. This ferrioxamine:heparin mixture is passed through a 0.22 µm filter to remove any residual insoluble iron oxides-hydroxides and render the liquid agent aseptic. The aseptic agent is stored at 4° C. As indicated, further processing is carried out by filling the aseptic liquid in glass vials, followed by freezing and lyophilizing, to render the agent as an aseptic lyophilized powder. The lyophilized vials are reconstituted by adding sterile water and hand mixing for 1 to 5 minutes, to give a reconstituted liquid of desired concentration which is ready for injection. The resulting concentrations of ferrioxamine and heparin are measured and vial quantities confirmed by standard reverse-phase HPLC and macromolecular size exclusion HPLC methods, respectively.

*For beef lung heparin, mEq $SO_3^-$/g carrier=4.4.

Although not prepared in the present application, it is apparent that by combining the teaching of the present Example with those of previous disclosures Ser. Nos. 07/880,660, 07/803,595, and 07/642,033, ferrioxamine complexes can be similarly prepared with additional acidic saccharides, including sucrose octasulfate and sulfated cyclodextrins; with additional glycosaminoglycans, including keratan sulfate and hyaluronate; and with additional sulfatoids, including the bacterial sulfatoid, dextran sulfate.

EXAMPLE 9

Preparation of Paired-ion Agents of Gd(III):DTPA-Lys Bound to Dermatan Sulfate Carrier Gd(III):DTPA-Lys:Dermatan Sulfate paired-ion agents are prepared by mixing the water solutions of Gd(III):DTPA-Lys with dermatan sulfate of modal MW between approximately 5,000 daltons and 45,000 daltons (as in Example 5, above), and in particular, dermatan sulfate of MN=18,000 (Opocrin, S.p.A., Modena, Italy, 435 type), to form a final solution ratio of 75:25% (w/w) of the Gd(III):DTPA-Lys active to the Dermatan Sulfate carrier. Several stable Agent variations of the resulting liquid have been prepared, wherein the concentration of Gd(III):DTPA-Lys ranges from 0.166 to 0.415 mmol/mL, and the respective concentration of dermatan sulfate ranges from 35 to 87.5 mg/ml. The T1 relaxivity (RI) of Gd (III):DTPA-Lys=4.2.

EXAMPLE 10

Preparation of a Basic Iron-porphine Chelate; and Paired-ion Binding to Heparin

The soluble, tetra-basic porphine, 5,10,15,20-tetrakis(1-methyl-4-pyridyl)-21H-23H-porphine, 40 mg as the tetra-p-tosylate salt, is refluxed with Fe(II) chloride, 30 mg, for 2 hours in 20 mL of dimethylformamide. Evidence of iron complexation is observed in the form of a red to dark green color. Solvent was removed by evaporation, the solid product dissolved in water. The pH is adjusted to 7.5 to insolubilize excess ferric iron, followed by filtration of the iron-porphine product. A 2 mg/mL solution of iron-porphine complex and ca. 100% product yield is confirmed by inductively coupled plasma atomic absorption. A comparable reaction in water gives ca. 70% yield.

This iron-porphine complex is added to beef lung heparin dissolved in water, ca. 8 Kd, at ratios ranging from 1:20 to 20:1 (iron-porphine:heparin). This resulted in clear solutions without precipitates. Binding of iron-porphine to heparin is nearly 100% as evaluated by dialysis against water for 16 hours, using bags with molecular weight cutoffs of 3.5 Kd and 12 Kd. Iron-porphine alone is nearly completely dialyzed. UV-Visible spectrophotometric titration indicates maximum binding occurs at a molar ratio of 18:1 (iron-porphine:heparin). Since the beef lung heparin used is known to have approximately 18 available strongly acidic (sulfate) groups per mole (and per heparin chain), these results indicate strong ionic interaction and stable (to dialysis) binding of the basic tetraamine porphine complex to the sulfate groups of heparin.

EXAMPLE 11

Preparation of a Basic Triethylenetetraamine-iron Chelate; and Paired-ion Binding to Heparin and Sucrose Octasulfate Soluble complexes of triethylenetetraamine and iron(III) are formed by dissolving 1.0 g of triethylenetetraamine.2HCl (Syprine™) (Merck, West Point, Pa.) in water and adding a 1:1 mole ratio of iron chloride under acidic conditions (pH=2) to give a clear yellow solution. Using 0.1 N NaOH, the pH is adjusted to 6.8, giving a red solution indicative of iron complexation. This solution develops a feathery red precipitate, indicative of intermolecular aggregation of the iron-triethylenetetraamine complex.

(a) To this resulting aqueous dispersion of complex is added beef lung heparin, to give final complex-to-heparin ratios of between 95:5 and 5:95 (by weight). At a ratio of 65:35 (complex:heparin) and higher ratios of heparin, heparin completely solubilizes the complex. This apparent solubilization is indicative of paired-ion binding between triethylenetetraamine-iron and heparin.

(b) To the aqueous dispersion of triethylenetetraamine-iron complex is added sucrose octasulfate (SOS), to give final complex-to-SOS ratios of between 95:5 and 5:95 (by weight). At a ratio of 65:35 (complex:SOS) and higher ratios of SOS, SOS causes the dispersion to become very much finer, indicative of paired-ion binding between triethylenetetraamine-iron complex and SOS. The absence of complete clarification of this SOS paired-ion system relative to that with heparin (above), is due to the much higher density of sulfates on SOS relative to heparin, which confers substantially increased intermolecular hydrogen bonding on the SOS system.

Although not directly exemplified, it will be apparent that polyamines with the homologous series $C_xH_{x+y}N_{x-z}$, which also form stable complexes with Iron(III), can also be used in place of triethylenetetraamine-iron complex and SOS in the present invention.

Preparation of Covalent Conjugates of Deferoxamine Glycosaminoglycan Carriers

Substrates with electrophilic amine groups may be covalently conjugated reagents to nucleophilic carboxylate groups of acidic carriers, acidic saccharides and acidic glycosaminoglycans as reported [Danishefsky et al. (1971); Danishefsky et al. (1972); Janoki et al. 1983); Axen (1974); Bartling et al. (1974); Lin et al. (1975)]. The coupling reagents described in these references activate carboxylate groups toward nucleophilic attack. The mechanism involves formation of an activated intermediate resulting from reaction of the coupling reagent with the carboxylate residues on the carrier. The intermediate undergoes nucleophilic attack, typically by an amine functional group. This results in formation of a stable covalent conjugate, typically via an amide bond between the active and the carrier. Examples 12, 13, and 14 (below) describe the synthesis of ferrioxamine-heparin covalent conjugates, wherein the ferrioxamine is covalently bound to heparin via three different coupling reagents.

EXAMPLE 12

Preparation of a Covalent Ferrioxamine-Heparin Conjugate by 1-ethyl-3-(3-dimethylaminopropyl) Carbodiimide (EDC) Linkage Aqueous ferrioxamine, 2.0 g, as prepared in Example 1, is adjusted to pH 4.75 by addition of 0.10 M HCl. Beef-lung heparin (Hepar-Kabi-Pharmacia, Franklin, Ohio), 0.75 g, is dissolved 5.0 mL of pharmaceutical-grade water and added to the ferrioxamine with constant stirring. The pH of the resulting solution is re-adjusted to 4.75 with 0.10 M HCl. The water-soluble carbodiimide, 1-ethyl-3-(3-dimethylaminopropyl) carbodiimide HCl (EDC), 2 g, is weighed into a scintillation vial, solubilized in a minimum amount of water, and the pH adjusted to 4.75 with 0.10 M HCl. Aliquots of EDC solution are pipetted into the mixture of ferrioxamine-heparin over a one hour period. After each addition of EDC the 0.10 M HCl is added to maintain the pH at 4.75. After addition of all EDC, the reaction is allowed to proceed for an additional two hours with constant stirring. The ferrioxamine-heparin conjugate is precipitated by addition of 3 volumes of absolute ethanol. This precipitate is collected by centrifugation at 4500 rpm ($\approx$2500× g) for 15 minutes and washed three times with 20 mL aliquots of ethanol plus centrifugation. The complex is further purified by redissolving in water and reprecipitating with 3 volumes of ethanol plus centrifugation. The final product is collected and dried over nitrogen. Ferrioxamine derivatization of heparin is confirmed by UV-visible absorbance spectroscopy of the ferrioxamine chelate at 430 nm and heparin analysis by size-exclusion HPLC chromatography.

EXAMPLE 13

Preparation of a Covalent Ferrioxamine-Heparin Conjugate by N-Ethoxycarbonyl-2-ethoxy-1,2-dihydroquinoline (EEDQ) Linkage Beef-lung heparin (Hepar-Kabi-Pharmacia, Franklin, Ohio), 0.50 g, is weighed into a 3-necked 100 mL round bottom flask fitted with an inlet and outlet for $N_2$ purge. Anhydrous dimethylformamide (DMF), 20 mL, is added with constant stirring and the resulting suspension warmed to 50° C. under a constant flow of nitrogen. A 30 mole excess ($\approx$463.7 mg) of N-ethoxycarbonyl-2-ethoxy-1,2-dihydroquinoline (EEDQ) is added and the resulting suspension stirred at 50° C. for 3 hours. The activated EEDQ-activated heparin is collected by centrifugation at 4500 rpm ($\approx$2500× g) for 10 minutes. The pellet is washed repeatedly with anhydrous DMF and then 3 times with acetone. The activated intermediate is dried under a stream of nitrogen.

An aliquot of ferrioxamine solution containing 766.3 mg of the iron complex, as prepared in Example 1, is pipetted into a 50 mL beaker and diluted to 25 mL with anhydrous DMF. In a separate 50 mL beaker, a known amount of EEDQ-activated heparin is suspended in 50 mL of anhydrous DMF with constant stirring. The DMF solution of ferrioxamine is pipetted slowly into the EEDQ-heparin suspension over a 5 minute period. The resulting suspension is stirred continuously for 3 hours at 40° C. After cooling to room temperature, the final product is collected by centrifugation, washed three times with anhydrous DMF, washed three times with acetone, and dried under nitrogen. Confirmation of conjugate formation is performed as in Example 12.

EXAMPLE 14

Preparation of a Covalent Ferrioxamine-Heparin Conjugate by Carbonyldiimidazole (CDI) Linkage An activated intermediate of beef-lung heparin (Hepar-Kabi-Pharmacia, Franklin, Ohio) is prepared by weighing 3.0 g of heparin into a 50 mL round bottom flask and adding 25 mL of anhydrous dimethylformamide (DMF) with constant stirring. Carbonyl-diimidazole (CDI), 608.1 mg, (10 mole excess relative to heparin) is weighed into a separate vial and dissolved in 20 mL of anhydrous DMF. The DMF solution of CDI is added to the DMF-heparin suspension and stirred at 300C for one hour. The CDI-activated heparin is collected by centrifugation, washed repeatedly with acetone to remove unreacted CDI and residual DMF, and dried under nitrogen.

The deferoxamine-heparin conjugate is prepared by weighing 1.0 g of the CDI-activated heparin into a 50 mL round bottom flask and suspending this in 25 mL of anhydrous DMF. Deferoxamine, 250 mg, prepared as in Example 1, is weighed into a separate round bottom flask and dissolved in 20 mL of anhydrous DMF. The deferoxamine free base solution is added slowly to the CDI-heparin suspension and stirred continuously for 16 hours at 75° C. The deferoxamine-heparin conjugate is collected by centrifugation at 4500 rpm ($\approx$2500× g) for 15 minutes, washed repeatedly with anhydrous DMF, washed repeatedly with acetone, and dried under nitrogen. The resulting product is dissolved in water, and its concentration determined by UV-Visible spectroscopy. A stoichiometric quantity of aqueous $FeCl_3$ is added and the resulting solution adjusted gradually to pH 6.5 and stirred for 2 hours. This results in a deep brown-red product. This ferrioxamine-heparin conjugate is separated from any residual substrates and intermediates by dialysis through a 2,000 MW cutoff bag against 150 volumes of water. The retentate is collected and concentrated by rotary evaporation. Confirmation of derivatization is performed as in Examples 12 and 13.

EXAMPLE 15

Preparation of a Covalent Heparin-Diethylenetriaminepentaacetate Conjugate (DTPA-heparin)

DTPA-functionalized carriers are prepared in aqueous media from the reaction of diethylenetriaminepentaacetic dianhydride (cDTPAA; Calbiochem-Bhering Corp.) and a molecule containing a nucleophilic functional group. Beef-lung heparin (Hepar-Kabi-Pharmacia, Franklin, Ohio), 1.5 g, is dissolved in 75.0 mL of 0.05 M HEPES buffer and the pH adjusted to 7.0 with 0.10 M NaOH. cDTPAA, 4.5 g ($\approx$100 mole excess relative to heparin), is weighed out and divided into 20 equal (225 mg) aliquots. An aliquot of cDTPAA is added to the heparin solution every 3–5 minutes until all cDTPAA has been added. The pH of the solution is monitored continuously throughout cDTPAA addition and maintained at pH 7.0 with 0.10 M NaOH. After addition of the last aliquot of cDTPAA, the solution is stirred for an additional 30 minutes. The DTPA-heparin solution is dialyzed through 1000 MW bags against 150 volumes to remove non-conjugated DTPA. The resulting conjugate is concentrated by nitrogen-evaporation at 37° C. and stored at 4° C.

EXAMPLE 16

Preparation of Gadolinium(III) and Iron(III) Chelates of DTPA-heparin Covalent Conjugate The DTPA-heparin conjugate of Example 15 is further prepared in the form of paramagnetic metal chelates of the DTPA group with gadolinium(III) or Fe(III), by pipetting the required volume of DTPA-heparin into a 125 mL Erlenmeyer flask, adding a 1.5-to-10 mole excess of the paramagnetic metal ion oxide, as $Gd_2O_3$ or $Fe(O)OH$, and stirring for 24 to 36 hours at 37° C. to obtain solubilization of the metal oxides sufficient for complete occupancy of the DTPA groups. The residual metal oxides are precipitated by centrifugation at 4500 rpm ($\approx$2500 g), and the product separated from unreacted metal oxides by filtration through a Millipore 0.22 $\mu$m GV-type filter, followed by dialysis against 150 volumes. The concentrations of chelated metal ion and heparin are determined by inductively coupled plasma (ICP) and size-exclusion HPLC, respectively. In the case of Gd(III), stoichiometric chelation is also confirmed by standard xylenol orange titration [Lyle et al. (1963)].

EXAMPLE 17

Toxicity Studies of Ferrioxamine:Dermatan Sulfate, 435 Type

Acute intravenous Toxicity Studies with 14-day recovery and necropsy are performed in male and female rats and male and female dogs. At standard i.v. injection rates of 0.075 mmol/Kg/min., significant signs generally occur only after 5–12.5 times the effective imaging dose of 0.155 mmol/Kg. The LD50 is much greater than 4.5 mmol/Kg and is limited by technical aspects of tail-vein infusion. At this rate, some rats can be infused with 10 mmol/Kg without untoward effects. At an artificially accelerated i.v. injection rate of 0.080 mmol/Kg, deaths in rats can be obtained, and the LD50 is between 2.5 and 3.0 mmol/Kg. Terminal necropsy reveals no abnormalities in any rats after i.v. injection of 2.2, 3.0 and 4.5 mmol/Kg (n=5 males and 6 females per dose level).

A pyramid acute i.v. toxicity study is performed in dogs at escalating doses of 0.5, 1.2 and 2.25 mmol/Kg and an infusion rate of 0.012 mmol/Kg/min in protocol studies. An acute symptom complex of hypotension can be obtained, which is minimal and reversible. No deaths occurred and terminal necropsy at 14 days revealed no abnormalities (n=2 males and 2 females, all administered each of the three dose levels, with a 72-hour rest interval).

EXAMPLE 18

Ferrioxamine:Dermatan Sulfate Selective Contrast Agent: MRI Imaging of Lactating Breast Adenocarcinomas in Syngeneic Fisher 344 Female Rats; Plus Correlation with Special Histochemical Studies As shown in FIG. 2A, FIG. 2B, FIG. 3A, FIG. 3B, FIG. 4A, FIG. 4B, FIG. 4C and FIG. 4D, T1-weighted MRI images (TR/TE—800/45 and 550/23) are performed at 1.0 and 1.5 Tesla, before (Pre) and after (Post) intravenous (i.v.) injection of Ferrioxamine:Dermatan Sulfate, 435 type Selective Paramagnetic Contrast Agent (Example 5), at a Ferrioxamine dose of 0.155 mmol/Kg into Fisher 344 female rats, with syngeneic breast adenocarcinomas inoculated by trocar into the livers, such that tumor diameters at the time of imaging are between 1.0 cm and 2.5 cm. Tumors are not conspicuous on standard T1-weighted Precontrast images. Following injection of Ferrioxamine:Dermatan Sulfate Agent, the tumors (a) become rapidly and markedly enhanced at an early post-injection time (7 mins) (FIG. 2A, FIG. 2B); (b) display very sharp tumor boundaries against surrounding liver (FIG. 2A, FIG. 2B, FIG. 4A, FIG. 4B, FIG. 4C and FIG. 4D), and discretely demarcated, darker central region of tumor necrosis (FIG. 2A, FIG. 2B) (allowing tumor perfusion and function to be spatially resolved and assessed within different, very small anatomical subregions); (c) exhibit sustained contrast for longer than 64 minutes postinjection (MPI) (FIG. 4A, FIG. 4B, FIG. 4C, FIG. 4D, MRI images; FIG. 5, quantitative region-of-interest, ROI, analysis) with continued very well defined tumor borders at prolonged imaging intervals. Correlation of these MRI images with microwave augmented iron stains of the freshly excised, 7 MPI tumors, indicate that tumor-site localization of the Ferrioxamine active occurs only when it is bound (non-covalently) to carrier (FIG. 6 and FIG. 7A) and not when administered in free form (Active alone) (FIG. 3A, FIG. 3B). As shown in FIG. 8A, FIG. 8B and FIG. 8C, lung metastases of the liver tumor are rapidly and sensitively enhanced in very small 2-mm to 3-mm nodules at an early post-contrast interval; and this enhancement of the tumor at lung sites is also sustained for a prolonged period with high sensitivity plus retention of very sharp tumor boundaries against normal lung. The sustained intervals shown in FIG. 8A, FIG. 8B and FIG. 8C are much longer than those typically reported for Gd:DTPA dimeglumine contrast enhancement at body organ sites.

EXAMPLE 19

Ferrioxamine:Dermatan Sulfate Selective Contrast Agent: MRI Imaging of Prostate AT-1 Carcinomas in Syngeneic Copenhagen Rats and Comparison with Gd(III)DTPA As shown in FIG. 9A, FIG. 9B, FIG. 9C, FIG. 9D, FIG. 9E, FIG. 10A, FIG. 10B, FIG. 10C, FIG. 10D and FIG. 10E, T1-weighted MRI images (TR/TE—250/8) performed at 4.7 Tesla, before (Pre) and after (Post) intravenous (i.v.) injection of Ferrioxamine:Dermatan Sulfate, 435 type Selective Paramagnetic Contrast Agent prepared as in Examples 2 and 5, and injected i.v. at an Iron(III) dose of 0.155 mmol/Kg (FIG. 9A, FIG. 9B, FIG. 9C, FIG. 9D, FIG. 9E); compared to Gadolinium DTPA dimeglumine, injected i.v. at a Gd(III) dose of 0.100 mmol/Kg (FIG. 10A, FIG. 10B, FIG. 10C, FIG. 10D, FIG. 10E); each of these agents being administered to Copenhagen rats with syngeneic AT-1 prostate adenocarcinomas inoculated into previously prepared skin pouches [Hahn, et al.], such that tumor diameters at the time of imaging are between 1.0 cm and 2.5 cm. Ferrioxamine-:Dermatan Sulfate produces a rapid large enhancement of the Outer Rim of tumor and also of the Vascular Array which fans out from the tumor pedicle which carries a high majority of the tumor vasculature. Sustained contrast and delineation of these elements remains present through kinetic time points of 40 minutes. By comparison, following Gd:DTPA dimeglumine, the outer rim is not well delineated, even at the earliest post-contrast interval (7 MPI). Marked early contrast fading occurs overall in the tumor at 20 MPI, and some agent sequesters in the central, poorly perfused (cystic) regions of tumor (as is typically reported for Gd:DTPA when used for imaging at body sites). At 40 MPI, enhancement reverts to essentially background levels, and at 60 MPI, there is no residual contrast, except for central cystic regions.

EXAMPLE 20

MRI Contrast Enhancement of Acute Dog Myocardial Infarcts by Ferrioxamine:Dermatan Sulfate As shown in FIG. 11A, FIG. 11B, FIG. 11C and FIG. 11D, T1-weighted MRI ECG-gated cardiovascular images are performed at 0.5 Tesla, before (Pre) and after (Post) rapid intravenous (i.v.) infusion of Ferrioxamine:Dermatan Sulfate, 435 type Selective Paramagnetic Contrast Agent injected i.v. at an Iron(III) dose of 0.155 mmol/Kg into German Shepherd dogs with acute, 90-min myocardial infarcts (ligature of proximal left anterior descending coronary artery) followed by reperfusion for ca. 90 minutes prior to contrast agent infusion. At 7 MPI, Ferrioxamine:Dermatan gives strong enhancement of the infarct zone, and in particular distinguishes the outer boundary of the infarct, which represents the putative marginal zone of the infarct amenable to potential recovery, from the central darker region, which represents the putative irreversible central infarct. Sustained strong enhancement and zonal demarcation is present through 40 MPI. Ferrioxamine injected without carrier at 0.155 mmol/Kg, gives no detectible enhancement. In these studies, infarct sizes and positions are documented by double dye infusion performed immediately after MRI imaging.

EXAMPLE 21

Comparison of MRI Tumor-imaging Potency In Vivo with Ferrioxamine Active Bound to Various Sulfated Glycosaminoglycans Based on low anticoagulant activity, safety and projected site-localization potential, certain alternative glycosaminoglycan carriers and certain alternative physical forms of the resulting Selective MRI Contrast Agents are compared for their relative in vivo potencies of carrier-mediated tumor localization of bound Ferrioxamine. Because of its high spatial resolution and capacity to detect subtle quantitative differences in agent localization, the AT-1 prostate tumor model of Example 19 is used.

TABLE 2

| FIG. No. | Agent | Form Liquid/Lyo | [metal] mmol/mL | Dose mmol/kg | Relative Potency (scale of 1–6) |
| --- | --- | --- | --- | --- | --- |
| 19 | Gd:MPD-DTPA Dermatan-$SO_3^-$ 435 type* | Liquid | 0.332 | 0.155 | 7 |
| 12 | Ferrioxamine Dermatan-$SO_3^-$ 435 type* | Lyo | 0.415 | 0.155 | 4.0 |
| 13 | Gd:DTPA-Lys Dermatan-$SO_3^-$ 435 type* | Liquid | 0.415 | 0.155 | 6 |
| 14 | Ferrioxamine Oversulfated Dermatan-$SO_3^-$ | Lyo | 0.332 | 0.155 | 4.0–4.5 |
| 15 | Ferrioxamine Oversulfated Chondroitin-$SO_3^-$ | Lyo | 0.332 | 0.155 | 5 |
| 16 | Ferrioxamine Heparan Sulfate | Lyo | 0.332 | 0.155 | 3.5 |
|  | Ferrioxamine Dermatan Sulfate** | Lyo | 0.332 | 0.155 | 1.5 |

Carriers of shorter chain length than the glycosaminoglycans, namely pentosan polysulfate, are found to be less potent (typically only ⅔ on the scale above) and remain at the tumor site for intervals of less than about 20 minutes, whereas the GAGs shown in the table above, are much more potent and have considerably longer tumor site localization intervals. In comparing these carriers, there is a slight-to-moderate trend towards increased carrier potency based on carrier sulfate charge density.
Lyo=Lyophilized powder form
$SO_3^-$=Sulfate (e.g. dermatan $SO_3^-$=dermatan sulfate)
* beef mucosa, purified, 18,000 daltons
** porcine mucosa, 19,600 daltons

EXAMPLE 22

Preparation of a N-Methyl-1,3 Propanediamine Derivative of DTPA (MPD-DTPA) and Chelation with Gadolinium (III)

The diethylenetriamine-pentaacetic acid anhydride (DTPA anhydride) solution is prepared by adding 180 ml of anhydrous dimethylformamide (DMF) into a 250 ml round bottom flask. The flask is fitted with a side arm addition funnel and contains a magnetic stir. While the DMF is stirring vigorously, 5 g (14 mmol) of DTPA anhydride (Sigma Chemical Co.) is added in 0.5 g portions over one hour. The resulting suspension is warmed to 60° C. to 15 minutes or until the solution clears. The flask is removed from the heat and placed in an ice bath until the solution has equilibrated to 4° C.

The MPD-DTPA derivative is prepared by mixing 15 ml of DMF with 1.46 ml (14 mmol) of N-methyl-1,3 propanediamine (Sigma Chemical Co.) in the addition funnel. The MPD-DMF mixture in the side arm addition funnel is added to the cold (4° C.), vigorously stirring DTPA anhydride solution, dropwise. A white precipitate forms throughout the addition. The suspension is allowed to stir overnight at room temperature. The MPD-DTPA derivative is collected by centrifugation at 2500 g for 10 minutes and washed repeatedly with acetone (5×300 ml).

The product at this stage, in concentrated solution has a pH of 3.5, additional purification requires a solution pH of 7.0. The product MPD-DTPA derivative is dissolved in water and the pH is adjusted to 7 with 5 N NaOH. The product is lyophilized for 16 hours to dryness. The lyophilized material is dissolved in a minimum amount (40 ml) of warm (50° C.) methanol for 15 minutes, cooled to room temperature, and precipitated with 10 volumes of acetone. The precipitate is collected by centrifugation at 2500 g for 10 minutes. This material is again dissolved in warm methanol for 15 minutes, precipitated with 10 volumes of acetone and collected by centrifugation at 2500× g. The precipitate is washed repeatedly with acetone, dried under nitrogen and stored in a vacuum desiccator.

Formation of the MPD-DTPA conjugate is confirmed by infrared (IR) Spectroscopy (see FIG. 17A, FIG. 17B, FIG. 17C) and HPLC chromatograph. HPLC characterization is carried out using a cation exchange column (Dionex IonPac CS14, 4×250 mm, 8 micrometer, carboxylic acid) with a mobile phase consisting of 20 mM methanesulfonic acid in acetonitrile-water (99:1) at pH 1.8 and with UV detection at 220 nm. This gives well separated, chromatographically pure (exceeding 99% purity) peaks for: (a) DTPA at 3.7 minutes; (b) N-methyl-1,1-propanediamine (20:1 molar ratio of MPD to DTPA required for detection, due to low UV absorbance of MPD) at 8.4 minutes; (c) the solution mixture of DTPA (or hydrolyzed DTPA anhydride) with MPD (1:1 molar ratio) at 3.7 minutes (only DTPA detected and MPD, due to very low extinction coefficient of MPD); and (d) MPD-DTPA conjugate (1:1 molar ratio) at 15.6 minutes. The product purity of (d) is greater than 93% by HPLC absorbance at 220 nm.

The chelating capacity of N-Methyl-1,3-propanediamine-DTPA (MPD-DTPA) is determined by titrating a small aliquot with 0.1 M $GdCl_3$ $5H_2O$ in 1 M ammonium acetate (pH 5.5) buffer, using Xylenol Orange (5%, w/v) as the colorimetric indicator of endpoint. Based on this titration, a stoichiometric quantity of 1 M $GdCl_3$ $5H_2O$ is added to a batch quantity of N-MPD-DTPA as follows: the bulk MPD-DTPA is dissolved in a minimum amount of water (ca. 300 mg/ml), 1M $GdCl_3$ $5H_2O$ is to the added while vigorously stirring, and the pH is adjusted from <4.0 to 7.0 with 5 N NaOH. The average chelating capacity is about 22% (by weight), with slight variation based on the extremely hygroscopic nature of the dry chelator.

EXAMPLE 23

Preparation of Paired-Ion Formulation of Gadolinium:MPD-DTPA:Dermatan Sulfate The paired-ion formulation of gadolinium(Gd):MPD-DTPA:dermatan sulfate (using the new, special 435 Type dermatan sulfate, Opocrin) is prepared over a range of weight ratios from 10:1 to 1:10 of Gd:MPD-DTPA to dermatan sulfate, and is particularly prepared at one of the preferred ratios of 60% Gd:MPD-DTPA to 40% dermatan sulfate (w/w)(=a mole ratio of 43:1). These paired-ion formulations are prepared by dissolving the desired amount of dermatan sulfate at a concentration of 400 mg/ml and stirring in the Gd:MPD-DTPA as prepared in Example 22. This results in a hydrophilic, completely clear solution without any detectable molecular aggregates by laser light scattering analysis (Nicomp Instrument). Strong paired-ion binding between GdMPD-DTPA and dermatan sulfate is confirmed and evaluated by dialysis through a 500 MW cutoff bag for 3 hours, 150 volumes, and is assessed by ICP atomic absorption analysis of the retained Gd (mass balance=95%). Very strong paired-ion binding is indicated by 73% retention of Gd within the bag for the Gd:MPD-DTPA:dermatan sulfate formulation prepared at 60:40% (Gd:MPD-DTPA to dermatan sulfate); compared to the much lower 23% retention within the bag for Gd:DTPA:dermatan sulfate when prepared at the same molar ratio of Gd:DTPA to dermatan sulfate.

Quantification of dermatan sulfate is performed by assessing the decrease in UV absorbance at 620 nm which occurs upon binding of the extremely strong binding (displacing) cationic dye, Azure A, as previously described [Klein et al. (1982: Grant et al. (1984), both incorporated by reference herein].

The R1 potencies (T1 relaxivities) of (a) Gd:MPD-DTPA alone and (b) the 60:40% (w/w) paired-ion formulation of Gd:MPD-DTPA:dermatan sulfate, are evaluated using an IBM PC20 Minispectrometer, and both are determined to be 7.8 $mmol^{-1}s^{-1}$ (based on parallel determinations of Gd concentration by ICP atomic absorption). The equality of R1's for the Gd chelate alone and Gd chelate bound to dermatan sulfate, indicate that binding of the chelate to dermatan sulfate does not interfere with water diffusion and paramagnetic relaxation. Furthermore, the absence of R1 prolongation indicates an absence of increase in rotational correlation time, and hence, further corroborates that the size of the Gd:MPD-DTPA-dermatan sulfate molecular complex is relatively small (likely less than about 50,000–60,000 daltons). This further confirms a basis for the surprising and unexpected advantages of high tumor accessibility across even the relatively more (anatomically and filtration) intact portions of tumor neovascular endothelium, and also the very rapid renal clearance, both of which are observed in intact animals (see below). This result correlates with the absence of detectible molecular aggregates by laser light scattering (above). The remarkably high R1 of this new formulation is repeated multiple times and appears to correlate with enhanced water diffusion of the new Gd:MPD-DTPA conjugate (and also for the full dermatan sulfate product) in relation to Gd:DTPA with the MPD side group (R1=ca. 4 [mmol. sec]$^{-1}$. The stability Kd of Gd:MPD-DTPA is greater than $10^{17}$.

EXAMPLE 24

Acute Murine Toxicity of Paired-Ion Formulation of Gadolinium:MPD-DTPA:Dermatan Sulfate One of the formulations of EXAMPLE 22, Gd:MPD-DTPA:dermatan sulfate (at a 60:40 wt % of Gd:MPD-DTPA to dermatan sulfate; 435 Type dermatan sulfate, Opocrin) was tested for acute toxicity by intravenous tail-vein injection into 20-gram, male Balb/c mice (n=6). When injections were performed over 10–12 minutes, the average LD50=

11.0 mmol/kg (of Gd and chelator), with 3 mice surviving at an average of 9.9 mmol/kg and 3 mice dying at an average of 12.2 mmol/kg. When injections were performed more rapidly, over a 2–3 minute interval, the LD50's were moderately lower in dose. These results compare favorably to those of Gd:DTPA (dimeglumine), for which LD50=4.0 mmol/kg.

EXAMPLE 25

Acute Blood Clearance of Radiolabeled Paired-Ion Formulations of: 67Ga-labeled Deferoxamine:Dermatan Sulfate; and 111In-labeled MPD-DTPA:Dermatan Sulfate In order to assess if dermatan sulfate carriers could confer their own very rapid and complete blood clearance properties to attached active substances (including non-covalently bound chelates), the formulations of Examples 2, 5, 21 and 22 (above) are modified such as to bind the radioactive single-photon-emitting (SPECT) metals, 67Ga or 111In, in place of the non-radioactive metal ions, Fe(III) or Gd(III).

For the 67Ga experiments, approximately 1.55 umole of deferoxamine (DFo)-dermatan sulfate (77.5:22.% wt %; DS Type 435, Opocrin) is labeled with approximately 800 uCi of 67Ga, by converting the 67Ga from a chloride to a citrate form and incubating it for 10 min at room temperature with DFo:dermatan sulfate at pH 5.5–6.5, injecting Copenhagen-strain rats intravenously in the tail vein with 0.39 umoles of DFo:dermatan sulfate to which is chelated ca. 200 uCi of 67Ga, obtaining serial gamma camera images over a 1-hour interval (and again at 24 and 48 hours), and analyzing the heart, upper abdominal region and pelvic regions of interest (ROI's) for blood, liver and renal clearances, respectively. The blood clearance t1/2 average=18 minutes, with a very rapid t1/2 alpha component of 8 minutes plus a t1/2 beta component of 35 minutes. No liver clearance is observed at all. Renal clearance is very rapid, accounting for all of the discernable clearance and leading to rapid bladder activity. There is no significant residual activity in the snout, skeletal axis or regions of bone or bone marrow. In a control experiment, injection of 67GaDFo alone (without dermatan sulfate) also results in very rapid blood clearance, however, a significant fraction of the agent (ca. 30%) cleared quite rapidly (10–30 minutes) into the liver and bowel, producing high organ backgrounds in the liver and colon.

In a separate experiment wherein the Copenhagen rats had AT-1 prostate adenocarcinomas (1.0–4.5 cm in diameter) implanted in the back of the neck, the tumors become very rapidly (ca. 5 minutes) active (bright) with radionuclide agent, and the tumor counts per pixel exceed those of the blood and liver at all times after 15 minutes of injection, resulting in rapid, sensitive detection of the tumors. This corroborates the MRI imaging results in the same tumor model (Example 19).

In another experiment, the dose of DFo:dermatan sulfate is increased 100× from 1.55 umole/kg to 155 umol/kg (0.155 mmol/kg) while maintaining the dose of radionuclide constant at 200 uCi per rat, in order to assess the effects of MRI doses, dose augmentation and potentially therapeutic doses, on clearance half times. By visual assessment, clearance is very nearly identical to the 100-fold lower dose of agent (above), with only a very minimal, ca. 5-minute prolongation.

In a further separate experiment, 111In is converted to the acetate form at pH 5.5–6.5, used to radiolabel MPD-DTPA:dermatan sulfate (60:40 wt % MPD-DTPA:dermatan sulfate, 435 Type, Opocrin). Clearance times and organ clearance patterns (renal versus liver) are comparable to those of 67GaDFo:dermatan sulfate (above); and when tested, tumor uptake is also rapid and distinct.

These surprising and unexpected advantages of: (a) very rapid clearance over a 100-fold (or greater) dose eschelation, for two different actives non-covalently bound (by paired-ion binding) to dermatan sulfate; and (b) avoidance of liver and bowel clearance in the presence but not the absence of dermatan sulfate carrier, provide major advantages for low MRI and radionuclide imaging backgrounds in the blood and especially additionally, in the critical and difficult body regions of liver and mid-abdomen. Upon bladder catheterization, the pelvic region is also observed without substantial background interferences. Additionally, significant therapeutic regimens are enabled because of the only very gradual increase in blood and body clearance times with major dose increments of at least 2 orders of magnitude. These clearance properties, coupled with the selective (tumor) uptake properties shown in this Example and above, provide even further surprising and unexpected advantages for augmenting the differential between selectivity versus body residual and systematic toxicity.

EXAMPLE 26

Gadolinium:N-methyl-1,3,propanediamine-DTPA:Dermatan Sulfate (Gd:MPD-DTPA:DS) Selective Contrast Agent: MRI Imaging of Lactating Breast Adenocarcinomas in Syngeneic Fisher 344 Female Rats T1-weighted MRI images (TR-TE=800/45) are performed at 1.0 Tesla, before (Pre) and after (Post) intravenous (i.v.) injection of Gd:MPD-DTPA:DS (DS=435 Type, Opocrin) at a dose of 0.155 mmol/kg into Fisher 344 female rats with syngeneic breast adenocarcinomas inoculated by trocar into the livers, as in Example 18 (above). A T2 scout image (TR/TE=2100/85) is performed in advance of the T1 image contrast series, in order to identify the approximate location(s) of tumor nodule(s) (FIG. 18A). This reveals 2 solid tumor nodules (right posterior liver) and one irregular tumor infiltrate (central liver region), all tumor sites subsequently being confirmed by gross visual inspection. These nodules are unidentifiable in the T1 (800/45) Precontrast (Pre) image (FIG. 18B), however following injection of Gd:MPD-DTPA:DS, all three tumor nodules: (a) become rapidly and exceedingly strongly enhanced at an early post-injection time of 7 minutes (FIG. 18C); (b) display rapid and prolonged (through 60 minutes) sharp tumor boundaries against the surrounding uninvolved liver (FIG. 18C, FIG. 18D, FIG. 18E), and exhibit prolonged (sustained) contrast through 60 minutes (FIG. 18F), with only a very slight degradation of the contrast gradient at the tumor boundaries at 60 minutes postinjection (MPI). In this animal model, the MRI contrast enhancement produced by Gd:MPD-DTPA:DS, is markedly greater (more potent on a dose basis) than that produced by the ferrioxamine:dermatan sulfate agent of Example 18; and is slightly to moderately greater (more potent on a dose basis) than that produced by Gd:DTPA-lysine:dermatan sulfate (prepared per Examples 3, 4 and 9; see also FIG. 13A, FIG. 13B, FIG. 13C, FIG. 13D, Example 21 and Table 2 for relative potency); both of the preceding agents containing less potent metal chelates, namely, with Rl's of 1.6 and 4.2, respectively, compared to an R1 of 7.8 [mmol.sec]$^{-1}$ for Gd:MPD-DTPA:DS of the present Example. Also, the images of the present Example show all the following, surprising and unexpected advantages over Gd:DTPA (dimeglumine), as well as over all the reported liver-specific T1 and T2 contrast agents: (a) uptake by tumor proper without substantial uptake by the surrounding uninvolved liver; (b) enhanced tumor selectivity and sensitivity; (c) prolonged as well as immediate tumor uptake, for improved clinical flexibility of multi-site and multi-image acquisition without contrast fading or need for multiple contrast-agent injections; (d) improved contrast sharpness and brightness gradient at the tumor boundaries, for improved tumor staging and improved detection of small tumors; (e) improved detection of small metastases; and (f) improved detection of small invasive outgrowths, for enhanced prognostic and therapeutic monitoring information. Note that there is a minor blood-pool enhancement in the surrounding normal liver at all post-contrast times, strongly suggesting that an even lower dose than 0.155 mmol/kg would be highly effective, indicated and appropriate for optimal T1 imaging of Gd:MPD-DTPA:DS. This is because the Gd:MPD-DTPA chelate is substantially more potent [R1=7.8 (mmol.sec)$^{-1}$] than all of the others described herein, and hence, gives more of T2* darkening, as well as T1 brightening effects, per micromole of agent deposited in the tumor.

EXAMPLE 27

Gadolinium:N-methyl1-1,3,propanediamine-DTPA:Dermatan Sulfate (Gd:MPD-DTPA:DS) Selective Contrast Agent: MRI Imaging of Prostate AT-1 Adenocarcinomas in Syngeneic Copenhagen Rats; Plus Correlation with Special Histochemical Stain T1-weighted images (TR/Te=250/80) are performed at 4.7 Tesla, before (Pre) and after (Post) intravenous (i.v.) injection of 0.155 mmol/Kg [Gd(III) dose] of the Gd:MPD-DTPA:DS (DS=435 Type, Opocrin) selective contrast agent, as prepared in Examples 21 and 22, into AT-1 prostate adenocarcinomas grown in skin pouches of syngeneic Copenhagen rats (described and referenced in Example 18). Gd:MPD-DTPA:DS produces a rapid, extremely strong T1 contrast enhancement of the entire tumor at 7 minutes (FIG. 19B) and 20 minutes (FIG. 19C) post-injection (MPI), and a continued strong contrast enhancement of the tumor at 40 MPI (FIG. 19D) and 60 MPI (FIG. 19E), especially at the tumor rim and most especially at the basal tumor rim (where tumor host staging is typically assessed). Upon further experimental evaluation, the apparent moderate contrast darkening of central tumor regions which appears at 40 and 60 MPI, actually represents an overconcentration of the agent within these tumor regions, leading to T2* effects, which compete with the strong T1 brightening effects and artifactually darken the T1 contrast in these central tumor regions. This T2* artifact is detected and assessed by utilizing a T2 pulse sequence of TR/TE=2500/250, (=selectively sensitive to T2* effects) and observing substantial contrast darkening at the more delayed post-contrast times. Hence, the very high R1 of Gd:MPD-DTPA:DS (relative to all of the preceding agents), in combination with an injected dose of 0.155 mmol/Kg, together with the very marked tumor uptake of agent and the paramagnetic response characteristics of the TR/TE=250/80 pulse sequence at a 4.7 Tesla field, leads to an overly high local paramagnetic activity within the tumor as Gd:MPD-DTPA:DS accumulates over time, especially in the central regions of the tumor. The rim, and especially the basal rim, is relatively protected from this T2* darkening artifact, due to more rapid backdiffusion of agent into plasma at this basal site. The preceding results and considerations lead to the conclusion that a lower dose than 0.155 mmol/Kg is indicated for optimal T1 imaging with Gd:MPD-DTPA:DS, because the Gd:MPD-DTPA chelate is a substantially more potent T1 paramagnetic active than all of the others described herein. Note that in Example 25, there appears to be a slight overdose, as evidenced by the very slightly enhanced blood-pool background in the uninvolved liver surrounding the 3 liver tumor nodules. Nevertheless, these nodules are still exceptionally well visualized at all post-contrast times (7–60 MPI).

Correlation of these MRI images with a microwave augmented Prussian blue stain for Gd(III) metal ion is performed (as described in Example 18), for the Gd(III) of Gd:MPD-DTPA:DS which becomes localized in the outer ⅔ of the tumor mass excised at 60 MPI (and freshly frozen for sectioning and staining). (See FIG. 20). This shows strongly positive histochemical staining of almost all tumor cells, with a significant number of the tumor cells having positive staining of the nucleus as well (i.e., nuclear localization of the metal-ion marker). This very strong staining of nearly all tumor cells at 60 minutes, compared to the lighter staining of fewer numbers of (breast) tumor cells at 7 minutes (Example 18), and the additional nuclear localization seen here at 60 minutes but not in the (breast) tumor at 7 minutes (Example 18), strongly suggests that tumor-cell internalization proceeds over a 1-hour interval, and likely over the entire interval of time during which the dermatan-sulfate bound metal chelates remain at significant concentrations within the extracellular matrix is initially and rapidly loaded via local microvessels, by extremely rapid and selective extravasation across tumor-induced neovascular MRI endothelium —see text above for tumor-selective induction and endothelial localization of GAG-binding receptors, including VEGF/VPF and others. The surprising and unexpected advantage of endothelial localization observed here for malignant prostate tumor, was also observed in Example 18 for malignant breast tumor. This corroborates the surprising and unexpected finding of Example 18 above, that tumor-induced neovascular endothelium, as well as tumor cells proper, are targets for binding, pumping, extravasation and tumor-cell internalization of the dermatan sulfate-bound (including non-covalently bound) classes of MRI contrast agents, and indeed for other active agents similarly bound to dermatan sulfates and GAGs. These findings of tumor endothelium, tumor matrix, tumor cell and nuclear localizations and accumulations, further provide the basis for selectively localizing therapeutic agents, whether metal chelates or other types of active substances.

EXAMPLE 28

Preparation of Doxorubicin Formulation as a Paired-Ion Complex with Essentially Purified Dermatan Sulfate Essentially purified dermatan sulfate (435 Type, Opocrin, modal MW=18,000 daltons) is dissolved in water at 10 mg/ml, and a 4 mg/ml solution of high-purity doxorubicin (Meiji Seika Kaisha, Ltd., Japan) is added dropwise while vigorously stirring, to give a 60:40 (w/w) ratio of doxorubicin to dermatan sulfate. (Other ratios are also tested between 10:90 and 90:10 (w/w) doxorubicin to dermatan sulfate.) The mixture is homogenized by sonication for 8 minutes at 4° C., using a macroprobe sonicator (Heat Systems). This effectively reduces the doxorubicin:dermatan sulfate complex to its limit (small) size of 11 nanometers, as assessed by laser light scattering (Nicomp system). The resulting liquid is filtered through a 0.22 um low binding filter (Millipore, Millex GV), 3 mL of a 500 mg/mL solution of saccharose (Boehringer Mannheim) is added and stirred, then 1.5 mL of a 10 mg/mL solution of polyethylene glycol (Hoechst, mean MW=3,350 daltons) is added, the resulting solution is sonicated once again (as above) and again filtered through 0.22 um GV filters for asepsis, filled into vials, and either saved as a liquid or frozen and lyophilized over a 17-hour primary drying cycle at appropriate shelf and chamber temperatures and conditions, to give a well-formed, brick-red cake with ca. 2.0% residual water (Karl Fisher method). The vials are stoppered and sealed. For use, the cakes are resuspended with sterile water (hand shaking for 15 seconds) at 2 mg/ml. The resulting Liquid is completely translucent and red-orange, with a pH of 6.8–7.1, an osmolality of ca. 210 mOsm/Kg, and a Zeta potential of −38 to −40 mV, indicating the presence of strongly bound dermatan sulfate in slight molar excess (the doxorubicin itself having a positive Zeta potential, due to its sugar amine group, which is effective to bind the sulfates of dermatan sulfate by strong paired-ion binding). The lyophilized cakes are stable (in both doxorubicin and dermatan components) for long intervals at room temperature as well as 4° C. (doxorubicin analysis by HPLC: C-18 Lichrosphere; mobile phase: acetonitrile:water (50:50), 20 mM phosphoric acid+5 mM sodium dodecylsulfate, pH 2.3; dermatan sulfate analysis by HPLC: TSK molecular sieve; mobile phase: 0.2M sodium sulfate for charge suppression, with Opocrin dermatan molecular weight standards of 1,800–17,250 daltons). The reconstituted cakes meet USP specifications for oversized particles above 10 and 25 um (by Hyac-Royco laser analysis).

Adriamycin (Adria Laboratories source of doxorubicin) is also similarly prepared in paired-ion couples with dermatan sulfate (Opocrin, as above).

EXAMPLE 29

Preparation of Doxorubicin Formulation as a Paired-Ion Complex with Beef Lung Heparin Beef lung heparin (Hepar-Kabi-Pharmacia) is solubilized, mixed with high-purity doxorubicin, over the ranges of 90:10 to 10:90 ratios (w/w, doxorubicin:heparin) and at one of the optimal ratios, namely 60:40 (w/w), and then subjected to the additional steps as described in EXAMPLE 28. A visually clear, 0.22 um filterable liquid results. However, this liquid has a larger limit size of 25 nanometers by laser light scattering, and the lyophilized cake is considerably more resistant to rapidly homogeneous reconstitution (requiring ca. 1–2 hours).

EXAMPLE 30

Preparation of Taxol Nanoparticle Formulations Coated with Essentially Purified Dermatan Sulfate and with Beef Lung Heparin These formulations are prepared in two steps, first by solubilizing and preparing the taxol in lecithin or lecithin-cholesterol nanodispersions, and second, by interacting the lecithin-coated nanodispersions with dermatan sulfate (435 Type, Opocrin) or beef lung heparin (Hepar-Kabi-Pharmacia) to produce and stabilize the final nanodispersions by paired-ion interaction at the nanoparticle surface, with binding of the glycosaminoglycan sulfate groups to the highly basic nitrogen groups of lecithin. Taxol (Sigma Chemical Co., St. Louis) is dissolved in methylene chloride, egg yolk lecithin in chloroform, and alternatively, soy lecithin+cholesterol in methylene chloride. The solubilized components are placed in a round bottom flask and the solvents evaporated under vacuum for 30 minutes, resulting in formation of a thin-film of taxol-lecithin (in one case, also with cholesterol). After sufficient drying, water is added (under nitrogen), the ingredients hydrated for 2 hours and probe sonicated for 10 minutes at 4° C. (Heat Systems). Dermatan sulfate, or alternatively beef lung heparin, is added over a range of 2–6% (w/w, to lecithin) and the mixture probe sonicated for 1 minute at 4° C. The resulting nanoparticles are observed by optical microscopy, and surface glycosaminoglycan (GAG) is confirmed by addition of the cationic dye, Azure A, which turns rapidly purple and produces particle aggregation upon binding to the surface GAG (uncoated formulations with lecithin only, =negative). The size and quantity of drug in dermatan sulfate-coated and heparin-coated nanoparticles are assessed by microfiltration and UV absorption analysis for solubilized taxol (230 nm), and size is further confirmed by laser light scattering (Nicomp). Formulations containing 4% glycosaminoglycans are optimal. Representative results for the quantities of taxol present before filtration ("None") and remaining after filtration through various pore sizes (5.0, 0.45 um and 0.22 um) are shown in Table 3 for dermatan sulfate formulations.

TABLE 3

Relative (%) Drug Remaining after Filtration

| | | Formulation with dermatan sulfate | |
| --- | --- | --- | --- |
| Filter | Taxol with Lecithin without DS | Taxol + Egg Yolk Lecithin | Taxol + Soy Lecithin and Cholesterol |
| None | 100% | 100% | 100% |
| 5.0 um | 90% | 98% | 97% |
| 0.45 um | 14% | 55% | 48% |
| 0.22 um | — | 23% | 15% |

The results of these analyses indicate that both lecithins interact effectively with dermatan sulfate and beef lung heparin, to form a glycosaminoglycan surface coating which stabilizes the nanoparticulate dispersion of taxol. However, for the optimal type of lecithin (egg yolk), the resulting nanoparticle size (by laser light scattering (see Table 4)) is smaller for dermatan sulfate (column a) than for heparin (column c), and only dermatan sulfate allows taxol to be formulated, filtered and obtained at acceptable recoveries through an aseptic cutoff filter (0.45 um), giving an aseptic, intravenously acceptable nanodispersion of taxol without the need for the standard taxol solubilizer, cremofor, and without its incumbent toxic and acute allergic side effects.

TABLE 4

Comparison of Nanoparticle Size by Laser Light Scattering (No filtration)

| Dermatan Sulfate Coating | | Heparin Coating |
| --- | --- | --- |
| (a) + Egg Yolk Lecithin | (b) + Soy Lecithin and Cholesterol | (c) + Egg Yolk Lecithin |
| 10.8 nm (98.7%) 281.8 nm (1.3%) | 31.4 nm (40.1%) 234.1 nm (18.4%) 908.4 nm (41.5%) | 45.5 nm (63.6%) 235.4 nm (36.4%) |

This smaller nanoparticle size with dermatan sulfate versus beef lung heparin, is similar to that observed for doxorubicin (Example 28). This corroborates the additional surprising and unexpected formulation advantages (above) of dermatan sulfate over heparin.

EXAMPLE 31

Preparation of Vincristine Paired-ion Formulation with Essentially Purified Dermatan Sulfate (435 Type)

Vincristine (Sigma Chemical Co., St. Louis) is dissolved in water and mixed with dermatan sulfate at ratios of between 90:10 and 30:70 (w/w) drug to dermatan sulfate. This results in clear solutions, with an optimal ratio occurring at 30–40% (w/w) of drug, with particles being undetectable (by laser light scattering). This result, in combination with retention of the paired-ion form, but not the drug alone, inside a 500 MW cutoff dialysis bag, is indicative of a strong paired-ion formation between the amine group of vincristine and the sulfate groups of dermatan sulfate.

EXAMPLE 32

Preparation of the Amine-containing Antibiotic Anti-infectives, Amikacin, Gentamicin and Tobramycin, as Paired-ion Formulations with Essentially Purified Dermatan Sulfate (435 Type) and with Beef Lung Heparin Amikacin, gentamicin and tobramycin (all obtained from Sigma Chemical Co., St. Louis) are dissolved in water and mixed with either dermatan sulfate (435 Type) or beef lung heparin (Hepar-Kabi-Pharmacia) at ratios of between 90:10 and 30:70 (w/w) drug to glycosaminoglycan. For the optimal range of 30–50% (w/w), strong paired-ion complexes form between drug and both glycosaminoglycans, as evidenced by laser light scattering (Nicomp), in the 100–200 nanometer range for beef lung heparin; or by 500 MW cutoff dialysis retention of the smaller dermatan sulfate formulations (undetectable to ca. 10 nanometers by laser light scattering).

EXAMPLE 33

Paired-ion Formulations of Basic Peptides with Essentially Purified Dermatan Sulfate (435 Type)

The basic, white-cell chemoattractant, and inflammatory peptides, (a) N-formyl-met-leu-phe-lys (acetate) (SEQ ID NO:1), (b) arginine bradykinin (arg-pro-pro-gly-phe-ser-pro-phe-arg, SEQ ID NO:2) and (c) poly-L-lysine (all 3 from Sigma Chemical Co., St. Louis), are dissolved in water and mixed with essentially purified dermatan sulfate (435 Type, Opocrin) at ratios of 90:10 to 10:90 (w/w of active substance to dermatan sulfate). Strong paired-ion binding occurs at optimal ratios of ca. 60:40 (active substance to dermatan sulfate), as evidenced by laser light scattering, retention in a 500 MW cutoff dialysis bag, and in the case of (a) N-formyl-met-leu-phe-lys, fluorescence enhancement at an emission wavelength of 518 nm (with excitation=257 nm).

These basic peptides, in formulation with essentially purified dermatan sulfate, provide a novel means for site-selective localization, accumulation, retention and action of biomodulatory peptides at sites of tumors and/or infections, in order to recruit and activate endogenous or transfused white blood cells for the purposes of local therapy, under conditions where the systemically circulating free form of agent could not be tolerated, due to marked system-wide inflammatory side effects. Hence, these new dermatan-sulfate formulations provide surprising and unexpected advantages for in vivo tumor and anti-infective therapies.

EXAMPLE 34

In Vitro Tests of Paired-Ion Doxorubicin:Dermatan Sulfate Formulation and Standard Doxorubicin for Comparative Activity against Wild-type and Doxorubicin-resistant Human Breast Carcinoma Cells The paired-ion doxorubicin:dermatan sulfate (essentially purified dermatan sulfate, 435 Type, Opocrin) of Example 28 (=doxorubicin:DS), is compared to standard doxorubicin liquid (Adria Laboratories), for tumor-cell killing potency in a clonigenic assay, using the following human breast cancer cell lines: parent MCF-7 cell line and adriamycin/doxorubicin-resistant MCF-7 cell line. For each group, five serial dilutions of each formulation were mixed on day 0, with an appropriate number of cells, growth medium and $^{14}C$-labelled glucose, the mixture then injected into serum vials pre-gassed with 5% $CO_2$, and the vials incubated at 37° C. (with cells continuously exposed to drug). The quantity of $^{14}C$-glucose $CO_2$ produced in control and drug-treated vials was determined using a Bactec machine (Bactec Corp.) on Days 6, 9 and 12 of incubation, and the data recorded and analyzed as percent survival values, IC50 and IC90 values, with percent survival values greater than 100 normalized to 100% against control cells (incubated without drug). Results are shown in Table 5 for the day of peak counts (day 9):

TABLE 5

| Cell Line & Test Substance | IC50 (uM) | IC90 (uM) |
| --- | --- | --- |
| A. Parent MCF-7 Line | | |
| 1. Doxorubicin:DS | 0.01–0.02 | 0.05–0.06 |
| 2. Standard doxorubicin (adriamycin liquid) | 0.02 | 0.06 |
| B. Doxorubicin-resistant MCF-7 Line | | |
| 1. Doxorubicin:DS | 0.81–0.89 | 3.15–13.33 |
| 2. Standard doxorubicin (adriamycin liquid) | 22.28 | not achieved |

The finding of comparably low IC50 and IC90 concentrations for the Parent MCF-7 line, but very different IC50 and IC90 concentrations for the Doxorubicin-resistant MCF-7 line, with the doxorubicin-dermatan sulfate formulation able to overcome (or bypass) resistance but standard doxorubicin unable to do so, strongly suggests that the dermatan sulfate combination overcomes the multi-drug resistant phenotype and may do so by bypassing the Pgp (P glycoprotein) pump. This might be predicted by the net negative charge of the dermatan sulfate formulation. Notwithstanding the specific mechanism, this result provides additionally important, surprising and unexpected advantages of the dermatan sulfate anti-tumor formulations, and in particular, doxorubicin dermatan sulfate doxorubicin, and most particularly, the essentially purified doxorubicin dermatan sulfate formulation (Example 28) in the treatment of tumors and neoplastic disease. Note, these test assays were performed by Donna Degen, M. S., and Daniel D. Von Hoff, M. D., of the Cancer Therapy and Research Center, Institute for Drug Development, San Antonio, Tex.

EXAMPLE 35

Acute In Vivo Toxicity Tests of Paired-Ion Doxorubicin:Dermatan Sulfate

Male Balb/c mice (n=4/group) are injected intravenously with 22.5 mg/Kg of either the paired-ion doxorubicin:dermatan sulfate (essentially purified dermatan sulfate, 435 Type, Opocrin) of Example 28 (=doxorubicin:DS), or standard doxorubicin liquid (Adria Laboratories) and then housed in cages with filter tops and observed for the day of death. Note that 22.5 mg/Kg is the reported LD90 in mice for standard doxorubicin, and it was chosen in order to minimize the time needed to observe the test endpoint; lower doses might be expected to widen any differences which may be observed in the present protocol. The days of death are: doxorubicin:DS: modal day=6, mean=5.5±0.9 SE; standard doxorubicin: modal day=day 5, mean=4.8±0.5 SE. Hence, doxorubicin has an acute murine toxicity which is at least comparable to and trending towards superior over standard doxorubicin, although the differences in this present test are not statistically significant. This result, in combination with the advantages of overcoming adriamycin/doxorubicin resistance in human tumor cells (Example 34) and localizing more effectively in vivo, on a constant-dose basis, in animal tumors and tumor intracellular sites (see Example 36, below), provide further surprising and unexpected advantages of the dermatan sulfate antitumor formulations, and in particular, doxorubicin dermatan sulfate doxorubicin and essentially purified doxorubicin dermatan sulfate (Example 28) in the treatment of tumors and neoplastic disease.

EXAMPLE 36

Acute In vivo Tumor Localization and Tumor-cell Internalization of Paired-Ion Doxorubicin:Dermatan Sulfate Compared to Standard Doxorubicin The paired-ion doxorubicin:dermatan sulfate (essentially purified dermatan sulfate, 435 Type, Opocrin) of Example 28 (=doxorubicin:DS) and standard doxorubicin liquid (Adria Laboratories) are injected at 5 mg/kg of doxorubicin i.v., into Copenhagen rats with AT-1 prostate carcinomas grown in a skin pouch (to mimic growth at deep organ sites). The rats are sacrificed at 3 hours after injection, the tumors and major organs removed, the cut tumors & organ pieces placed in OCT polymer and frozen at 4° C., and cryostat sections cut at 8 um and coverslipped. Fluorescence microscopy is performed by exciting the sections using a rhodamine-type bandpass filter (at ca. 485 nm—in order to selectively excite doxorubicin) and assessing direct doxorubicin fluorescence (at an emission wavelength greater than 530 nm) to determine the following:

relative tumor drug levels;

depth and homogeneity of drug penetration into tumor mass, at sites both proximal to and more distant from tumor microvessels;

tumor targets, i.e., endothelium cells as well as tumor cells proper;

normal organ fluorescence, as predictor of clearance and potential toxicities (see Table 6).

TABLE 6

Summary of results in Tumor
(on intensity scale of 0 to 4+)

| Property | Adriamycin PFS | Doxorubicin: essentially Purified Dermatan Sulfate |
|---|---|---|
| Overall fluorescence: Macropharmacology: | 0–1+ | 3–4+ |
| Near capillaries | 1+ (⅓ of regions) 0 (⅔ of regions) | 4+ (nearly all regions) |
| Away from capillaries | 0 (most regions) | 2–3+ (ca. 8/10 of regions) |
| Fluorescence at invading edge | 2+ | 4+ |
| Cellular Pharmacology: | | |
| Tumor-cell fluorescence | 1+ | 3+ |
| Nuclear | 1+ | 2–3+ |
| Endothelial fluorescence | 0 | 3+ |
| Nuclear | 0 | 2–3+ |

See FIG. 21A for doxorubicin:DS—dense sheet of tumor cells, with very bright fluorescence in almost all tumor cells (=tumor-cell internalization) and in neovascular endothelia. See FIG. 21B for doxorubicin:DS—looser clusters of tumor cells on an endothelial stalk. Looser tumor-cell clusters are most likely to be in growth phase or division (compared to the more dense tumor-cell sheets of FIG. 21A). Note the very bright staining of almost all cells, plus the strikingly bright nuclear fluorescence of doxorubicin now localized at this site, as well as in the cytoplasm. Also note the strong fluorescence of endothelial cells and endothelial-cell nuclei. See FIG. 21C for standard doxorubicin (dense sheets of cells at upper right and looser clusters at lower left)—all with markedly lower fluorescence and general lack of fluorescence in and around tumor microvessel (image center) and in tumor-cell nuclei.

Fluorescence intensities and pattern in other major organs, indicate that the clearance of doxorubicin:DS is shifted away from the kidneys (relative to standard doxorubicin) and caused to clear via the liver in an accelerated fashion (relative to standard doxorubicin), into the bile. No increment in cardiac or splenic red pulp is observed (which might be predictive of toxicities at these sites, and which are the major sites of toxicity for standard doxorubicin), and the fluorescence levels at these two sites, if anything, is slightly lower for doxorubicin:DS than for standard doxorubicin.

These results indicate a markedly higher tumor localization, depth and breadth of tumor extracellular matrix penetration, tumor-cell internalization and nuclear migration of doxorubicin (its key cellular site of action) when the drug is formulated as doxorubicin:DS (but not as doxorubicin alone); and they further indicate surprising and unexpected uptake by induced tumor endothelia and endothelial nuclei (for doxorubicin:DS). These surprising and unexpected advantages, taken together with those of the preceding Examples (29–35), clearly and completely distinguish the present formulation of doxorubicin with essentially purified dermatan sulfate, and other oncology and non-oncology therapeutic (and diagnostic) actives, when in association with the essentially purified dermatan sulfates of the present invention.

EXAMPLE 37

Preparation of Oncotherapeutic Drug Formulations as Paired-Ion Complexes with Essentially Purified Dermatan Sulfate Formulations containing water soluble oncotherapeutic drugs as paired-ion complexes with essentially purified dermatan sulfate (435 Type, Opocrin, modal MW=18,000 daltons) are prepared as in Example 28. These formulations are prepared in ratios of from 10:90 to 90:10 (w/w), with preferable ratios generally in the range of 60:40. Oncotherapeutic drugs that are less water soluble are prepared by the two step process as described in Example 30.

What is claimed is:

1. A drug carrier composition comprising a drug in combination with essentially purified dermatan sulfate having a sulfur content of up to 9% (w/w) and selective oligosaccharide oversulfation, wherein said composition has a non-embolizing size of less than about 500 nm.

2. The drug carrier composition of claim 1 wherein said composition has a size of less than about 250 nm.

3. The drug carrier composition of claim 1 wherein said composition has a size of less than about 25 nm.

4. The drug carrier composition of claim 1 defined further wherein binding to disease induced endothelia causes the endothelia to totally or partially envelop bound drug carrier composition in less than 10 to 15 minutes.

5. The drug carrier composition of claim 1 where the drug is an oncotherapeutic drug.

6. The drug carrier composition of claim 5 wherein the oncotherapeutic drug is selected from the group consisting of adriamycin, doxorubicin, epirubicin, daunorubicin, and idarubicin or salts thereof.

7. The drug carrier composition of claim 1 wherein the drug is doxorubicin or salt thereof.

8. The drug carrier composition of claim 5, in which the oncotherapeutic drug is selected from the group consisting of bleomycin, a taxane, paclitaxel, docetaxel, vinblastine and vincristine, amsacrine, azacytidine, dideoxyinosine, dihydro-5-azacytidine, ethanidazole, ethiofos, methotrexate, misonizadole, porfiromycin, pyrazoloacridinek, terephthalamidine, topotecan, trimetrexate and carboplatin or salts thereof.

9. The drug carrier composition of claim 1 wherein the drug is a chelator.

10. A drug carrier composition comprising a drug selected from the group consisting of doxorubicin, epirubicin, daunorubicin and idarubicin or salts thereof in combination with essentially purified dermatan sulfate having a sulfur content of up to 9% (w/w) and selective oligosaccharide oversulfation, wherein said composition has a non-embolizing size of less than about 500 nm.

11. The drug carrier composition of claim 1 wherein the drug is an antiinfective drug.

12. The drug carrier composition of claim 11, wherein the drug is gentamycin, tobramycin or amikacin.

13. The drug carrier composition of claim 1 in which the drug is a biological response modifier.

14. The drug carrier composition of claim 1, wherein the drug is a biologically active peptide or polypeptide.

15. The drug carrier composition of claim 14, wherein the biologically active peptide or polypeptide is selected from the group consisting of a white cell chemoattractant, bradykinin and poly-L-lysine.

16. The drug carrier composition of claim 15, wherein said white cell chemoattractant is N-formyl-met-leu-phe-lys (SEQ ID NO:1).

17. The drug carrier composition of claim 1, 7, or 10 further defined as being in a pharmaceutically acceptable solution suitable for intravascular or other parenteral injection.

18. The drug carrier composition of claim 1, having a sulfur content of 4% to 7% (w/w) and a $SO_3^-/COO$-ratio of 0.7:1 to 1.8:1.

19. The drug carrier composition of claim 1, wherein the dermatan sulfate further comprises an oversulfated saccharide sequence selected from the group consisting of $IdoA2SO_3$-GalNAC4$SO_3$ and IdoAGalNAc4,6$SO_3$.

20. The drug carrier composition of claim 10, having a sulfur content of 4% to 7% (w/w) and a $SO_3^-/COO$-ratio of 0.7:1 to 1.8:1.

21. The drug carrier composition of claim 10, wherein the dermatan sulfate further comprises an oversulfated saccharide sequence selected from the group consisting of $IdoA2SO_3$-GalNAC4$SO_3$ and IdoAGalNAc4,6$SO_3$.

22. The drug carrier composition of claim 1, wherein the drug is non-covalently bound to the dermatan sulfate.

23. The drug carrier composition of claim 12, wherein the drug is non-covalently bound to the dermatan sulfate.

* * * * *